US012807959B2

(12) United States Patent
Wilson et al.

(10) Patent No.: US 12,807,959 B2
(45) Date of Patent: Nov. 24, 2026

(54) COMPOSITIONS USEFUL IN TREATMENT OF CDKL5 DEFICIENCY DISORDER (CDD)

(71) Applicant: The Trustees of the University of Pennsylvania, Philadelphia, PA (US)

(72) Inventors: James M. Wilson, Philadelphia, PA (US); Ralf Schmid, Havertown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 860 days.

(21) Appl. No.: 17/997,301

(22) PCT Filed: Apr. 26, 2021

(86) PCT No.: PCT/US2021/029185
§ 371 (c)(1),
(2) Date: Oct. 27, 2022

(87) PCT Pub. No.: WO2021/222118
PCT Pub. Date: Nov. 4, 2021

(65) Prior Publication Data

US 2023/0167455 A1 Jun. 1, 2023

Related U.S. Application Data

(60) Provisional application No. 63/109,608, filed on Nov. 4, 2020, provisional application No. 63/091,032, filed on Oct. 13, 2020, provisional application No. 63/016,036, filed on Apr. 27, 2020.

(51) Int. Cl.
*C12N 15/52* (2006.01)
*A61P 43/00* (2006.01)
*C12N 15/86* (2006.01)

(52) U.S. Cl.
CPC .............. *C12N 15/52* (2013.01); *A61P 43/00* (2018.01); *C12N 15/86* (2013.01); *C12N 2750/14143* (2013.01); *C12N 2830/48* (2013.01)

(58) Field of Classification Search
CPC .................... C12N 15/52; C12N 15/86; C12N 2750/14143; C12N 2830/48; C12N 2830/008; C12N 2830/42; C12N 2830/50; C12N 9/12; A61P 43/00; A01K 2227/105; A01K 2267/0306; A61K 48/0058; C12Y 207/11022
See application file for complete search history.

(56) References Cited

U.S. PATENT DOCUMENTS

| | | | |
|---|---|---|---|
| 5,139,941 | A | 8/1992 | Muzyczka et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,660,514 | B1 | 12/2003 | Zolotukhin et al. |
| 7,282,199 | B2 | 10/2007 | Gao et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 8,323,653 | B2 | 12/2012 | Damschroder et al. |
| 8,524,867 | B2 | 9/2013 | Bernett et al. |
| 8,734,809 | B2 | 5/2014 | Gao et al. |
| 8,883,992 | B2 | 11/2014 | Damschroder et al. |
| 8,927,514 | B2 | 1/2015 | Chatterjee et al. |
| 9,290,746 | B2 | 3/2016 | Ciani et al. |
| 9,506,083 | B2 | 11/2016 | Arbetman et al. |
| 9,585,971 | B2 | 3/2017 | Deverman et al. |
| 9,587,282 | B2 | 3/2017 | Schaffer et al. |
| 9,611,302 | B2 | 4/2017 | Srivastava et al. |
| 9,725,485 | B2 | 8/2017 | Srivastava et al. |
| 9,803,020 | B2 | 10/2017 | Bernett et al. |
| 9,856,539 | B2 | 1/2018 | Schaffer et al. |
| 9,896,505 | B2 | 2/2018 | Damschroder et al. |
| 9,909,142 | B2 | 3/2018 | Yazicioalu et al. |
| 9,920,097 | B2 | 3/2018 | Zhong et al. |
| 10,011,640 | B2 | 7/2018 | Srivastava et al. |
| 10,081,659 | B2 | 9/2018 | Chiarini et al. |

(Continued)

FOREIGN PATENT DOCUMENTS

| | | |
|---|---|---|
| CN | 101287834 | 10/2008 |
| CN | 109069668 | 12/2018 |

(Continued)

OTHER PUBLICATIONS

Gao, Yunan, et al. "Gene replacement ameliorates deficits in mouse and human models of cyclin-dependent kinase-like 5 disorder." Brain 143.3 (2020): 811-832.) (Year: 2020).*

(Continued)

*Primary Examiner* — Ekaterina Poliakova-Georgantas
*Assistant Examiner* — John Charles McKillop
(74) *Attorney, Agent, or Firm* — Howson & Howson LLP; Cathy A. Kodroff

(57) ABSTRACT

Provided is a recombinant adeno-associated virus (rAAV) having an AAV capsid and a vector genome which comprises a nucleic acid sequence encoding a functional CDKL5 (hCDKLK5). Also provided are a production system useful for producing the rAAV, a pharmaceutical composition comprising the rAAV, and a method of treating a subject having CDD, or ameliorating symptoms of CDD, or delaying progression of CDD via administrating an effective amount of the rAAV to a subject in need thereof.

22 Claims, 28 Drawing Sheets

Specification includes a Sequence Listing.

(56) References Cited

U.S. PATENT DOCUMENTS

| | | | |
|---|---|---|---|
| 10,179,176 B2 | 1/2019 | Kav et al. | |
| 10,202,657 B2 | 2/2019 | Schaffer et al. | |
| 10,214,566 B2 | 2/2019 | Schaffer et al. | |
| 10,214,785 B2 | 2/2019 | Schaffer et al. | |
| 10,266,845 B2 | 4/2019 | Cronin et al. | |
| 10,294,281 B2 | 5/2019 | Srivastava et al. | |
| 10,301,648 B2 | 5/2019 | Vandenberahe et al. | |
| 10,385,320 B2 | 8/2019 | Kay et al. | |
| 10,392,632 B2 | 8/2019 | Wright et al. | |
| 10,918,451 B2 | 2/2021 | Inoue | |
| 2007/0036760 A1 | 2/2007 | Wilson et al. | |
| 2009/0197338 A1 | 8/2009 | Vandenberahe et al. | |
| 2012/0219528 A1 | 8/2012 | Sista et al. | |
| 2013/0045186 A1 | 2/2013 | Gao et al. | |
| 2014/0010861 A1 | 1/2014 | Bancel et al. | |
| 2014/0124086 A1 | 5/2014 | Jean et al. | |
| 2015/0079038 A1 | 3/2015 | Deverman et al. | |
| 2015/0344911 A1 | 12/2015 | Chatterjee et al. | |
| 2016/0067228 A1 | 3/2016 | Kishimoto | |
| 2017/0021114 A1 | 1/2017 | Vonarbura et al. | |
| 2018/0023070 A1 | 1/2018 | Kjellman et al. | |
| 2018/0037962 A1 | 2/2018 | Kjellman et al. | |
| 2019/0241633 A1* | 8/2019 | Fotin-Mleczek .. | A61K 31/7105 |

FOREIGN PATENT DOCUMENTS

| | | |
|---|---|---|
| EP | 1310571 | 5/2003 |
| WO | WO-2003/042397 | 5/2002 |
| WO | WO-2005/012493 | 2/2005 |
| WO | WO-2005/033321 | 4/2005 |
| WO | WO-2006/089133 | 8/2006 |
| WO | WO-2006/110689 | 10/2006 |
| WO | WO 2007/000668 A2 | 1/2007 |
| WO | WO-2007/002223 | 1/2007 |
| WO | WO-2007/076950 | 7/2007 |
| WO | WO-2007/082715 | 7/2007 |
| WO | WO-2008/022152 | 2/2008 |
| WO | WO-2008/031056 | 3/2008 |
| WO | WO-2009/052431 | 4/2009 |
| WO | WO-2009/054863 | 4/2009 |
| WO | WO-2010/053716 | 5/2010 |
| WO | WO-2010/095031 | 8/2010 |
| WO | WO-2010/102276 | 9/2010 |
| WO | WO-2011/097456 | 8/2011 |
| WO | WO-2011/126808 | 10/2011 |
| WO | WO-2011/139379 | 11/2011 |
| WO | WO-2011/147834 | 12/2011 |
| WO | WO-2012/010561 | 1/2012 |
| WO | WO-2012/057765 | 5/2012 |
| WO | WO-2013/004943 | 1/2013 |
| WO | WO-2015/074085 | 5/2015 |
| WO | WO-2015/164758 | 10/2015 |
| WO | WO-2016/033570 | 3/2016 |
| WO | WO-2016/049230 | 3/2016 |
| WO | WO-2016/081029 | 5/2016 |
| WO | WO-2017/015783 | 2/2017 |
| WO | WO-2017/055328 | 4/2017 |
| WO | WO-2017/066136 | 4/2017 |
| WO | WO 2017/106202 A2 | 6/2017 |
| WO | WO-2017/117530 | 7/2017 |
| WO | WO-2017/134274 | 8/2017 |
| WO | WO-2017/165859 | 9/2017 |
| WO | WO-2017/191274 | 11/2017 |
| WO | WO-2018/002031 | 1/2018 |
| WO | WO-2018/022905 | 2/2018 |
| WO | WO-2018/108106 | 6/2018 |
| WO | WO-2018/118102 | 6/2018 |
| WO | WO-2018/119163 | 6/2018 |
| WO | WO-2018/126369 | 7/2018 |
| WO | WO-2018/156654 | 8/2018 |
| WO | WO-2018/160582 | 9/2018 |
| WO | WO-2018/172795 | 9/2018 |
| WO | WO-2018/213786 | 11/2018 |
| WO | WO-2018/222503 | 12/2018 |
| WO | WO-2018/222926 | 12/2018 |
| WO | WO-2018/226602 | 12/2018 |
| WO | WO-2019/057100 | 3/2019 |
| WO | WO 2019/060454 A2 | 3/2019 |
| WO | WO-2019/075360 | 4/2019 |
| WO | WO-2019/168961 | 9/2019 |
| WO | WO-2019/191780 | 10/2019 |
| WO | WO-2020/016318 | 1/2020 |
| WO | WO-2020/023612 | 1/2020 |
| WO | WO-2020/118239 | 6/2020 |
| WO | WO-2020/132455 | 6/2020 |
| WO | WO-2020/154746 | 7/2020 |
| WO | WO-2020/159970 | 8/2020 |
| WO | WO-2020/214929 | 10/2020 |
| WO | WO 2020/219766 A1 | 10/2020 |
| WO | WO-2020/223231 | 11/2020 |
| WO | WO-2021/067598 | 4/2021 |
| WO | WO 2021/081217 A1 | 4/2021 |
| WO | WO-2021/163322 | 8/2021 |

OTHER PUBLICATIONS

Andersen et al., Herpesvirus-mediated gene delivery into the rat brain: specificity and efficiency of the neuron-specific enolase promoter, Cell. Mol. Neurobiol., vol. 13:503-15, Oct. 1993.

Bahi-Buisson et al., Key clinical features to identify girls with CDKL5 mutations, Brain, vol. 131:2647-2661, doi: 10.1093/brain/awn197, Oct. 2008.

Baltussen et al., Chemical genetic identification of CDKL5 substrates reveals its role in neuronal microtubule dynamics, EMBO Journal, vol. 37(24), Dec. 2018.

Buning et al., Recent developments in adeno-associated virus vector technology, J. Gene Med. 10:717-733, Jul. 2008.

Carter, Handbook of Parvoviruses (ed., P. Tijsser), CRC Press, pp. 155-168, Jan. 1990.

Dambal et al., The microRNA-183 cluster: the family that plays together stays together, Nucleic Acids Res, vol. 43:7173-7188, Sep. 2015.

Deverman et al,. Cre-dependent selection yields AAV variants for widespread gene transfer to the adult brain. Nat Biotechnol, vol. 34:204-209, Feb. 2016.

Fehr et al., The CDKL5 disorder is an independent clinical entity associated with early-onset encephalopathy, Eur J Hum Genet, vol. 21:266-273, Mar. 2013.

Fisher et al., Transduction with recombinant adeno-associated virus for gene therapy is limited by leading-strand synthesis, J. Virol., vol. 70:520-532, Jan. 1996.

Gao et al., Clades of Adeno-associated viruses are widely disseminated in human tissues, J Virol, vol. 78(12):6381-6388, Jun. 2004.

Gao, et al., Adeno-associated viruses undergo substantial evolution in primates during natural infections, Proc. Natl. Acad. Sci. U.S.A., vol. 100 (10):6081-6086, May 2003.

GenBank, cyclin-dependent kinase-like 5 isoform 1 [*Homo sapiens*], NP 001032420.1, Oct. 1996.

GenBank, cyclin-dependent kinase-like 5 isoform 1 [*Homo sapiens*], NP_003150.1, Oct. 1996.

GenBank, cyclin-dependent kinase-like 5 isoform 2 [*Homo sapiens*], NP 001310218.1, Oct. 1996.

GenBank, *Homo sapiens* cyclin dependent kinase like 5 (CDKL5), transcript variant II, mRNA, NM_001037343.1, Jul. 2020.

GenBank, *Homo sapiens* cyclin dependent kinase like 5 (CDKL5), transcript variant III, mRNA, NM_001323289.2, May 2019.

GenBank, *Homo sapiens* cyclin dependent kinase like 5 (CDKL5), transcript variant I, mRNA, NM_003159.2, Jul. 2020.

Grieger, Adeno-associated virus as a gene therapy vector: vector development, production and clinical applications, Adv. Biochem Eng Biotechnol, vol. 99:119-145, Feb. 2005.

Hector et al., Characterization of CDKL5 Transcript Isoforms in Human and Mouse, PloS one, vol. 11, e0157758, Jun. 2016.

Hinderer et al., Severe Toxicity in Nonhuman Primates and Piglets Following High-Dose Intravenous Administration of an Adeno-Associated Virus Vector Expressing Human SMN, Human Gene Therapy, vol. 29:285-298, Mar. 2018.

(56) References Cited

OTHER PUBLICATIONS

Kalscheuer et al., Disruption of the serine/threonine kinase 9 gene causes severe X-linked infantile spasms and mental retardation. American Journal of Human Genetics, vol. 72:1401-1411, Jun. 2003.
Molecular Cloning: A Laboratory Manual (2nd ed.), Cold Spring Harbor Laboratory, New York, Jan. 1989.
Munoz et al., Phosphoproteomic screening identifies physiological substrates of the CDKL5 kinase, EMBO Journal, vol. 37(24):e99559, Dec. 2018.
Nei and Kumar, Chp. 6.4: Neighbor Joining (NJ) Method in Molecular Evolution of Phylogenetics, Oxford University Press, New York, ISBN: 0-19-513584-9, pp. 103-110, Jan. 2000.
Nih-Ninds, Rett Syndrome, last reviewed Jan. 20, 2023, accessed on Mar. 17, 2023 from https://www.ninds.nih.gov/health-information/disorders/rett-syndrome (updated from archived source previously accessible at ninds.nih.gov/Disorders/Patient-Caregiver.
OMIM.org, #300203—Cyclin-Dependent Kinase-Like 5; CDKL5, Aug. 1999 (updated Apr. 2022), accessed Mar. 17, 2023 from https://www.omim.org/entry/300203.
OMIM.org, #312750—Rett Syndrome; RTT, Nov. 20, 2015 (updated Mar. 24, 2021), accessed on Mar. 17, 2023 from omim.org/entry/312750.
Piccioli et al., Neuroantibodies: ectopic expression of a recombinant anti-substance P antibody in the central nervous system of transgenic mice, Neuron, vol. 15:373-84, Aug. 1995.
Piccioli et al., Neuroantibodies: molecular cloning of a monoclonal antibody against substance P for expression in the central nervous system, Proc. Natl. Acad. Sci. USA, vol. 88:5611-5, Jul. 1991.
Tang et al., Altered NMDAR signaling underlies autistic-like features in mouse models of CDKL5 deficiency disorder, Nat Commun., vol. 10(1):2655, Jun. 2019.
Tao et al., Mutations in the X-linked cyclin-dependent kinase-like 5 (CDKL5/STK9) gene are associated with severe neurodevelopmental retardation, American Journal of Human Genetics, vol. 75(6):1149-1154, Dec. 2004.
Thiel et al., Characterization of tissue-specific transcription by the human synapsin I gene promoter, Proc Natl Acad Sci U S A, vol. 88:3431-3435, Apr. 1991.
Thompson et al., A comprehensive comparison of multiple sequence alignment programs, Nucl. Acids. Res., vol. 27(13):2682-2690, Jul. 1999.
UniProt.org, Q9W6R6 • Q9W6R6_TAKRU—Serine-threonine kinase 9 (STK9), Uniprot# 076039, Nov. 1999 (updated Feb. 2023).
Weaving et al., Mutations of CDKL5 cause a severe neurodevelopmental disorder with infantile spasms and mental retardation, American Journal of Human Genetics, vol. 75(6):1079-1093, Dec. 2004.
Zanta-Boussif et al., Validation of a mutated PRE sequence allowing high and sustained transgene expression while abrogating WHV-X protein synthesis: application to the gene therapy of WAS, Gene Therapy, vol. 16:605-619, May 2009.
Zhang et al., Adenovirus-adeno-associated virus hybrid for large-scale recombinant adeno-associated virus production, Human Gene Therapy, vol. 20(9):922-929, Sep. 2009.
Gao et al., Gene replacement ameliorates deficits in mouse and human models of cyclin-dependent kinase-like 5 disorder, Brain, vol. 143(3):811-832, Mar. 2020.
U.S. Appl. No. 63/023,593, filed May 12, 2020.
U.S. Appl. No. 63/038,488, filed Jun. 12, 2020.
U.S. Appl. No. 63/043,562, filed Jun. 24, 2020.
U.S. Appl. No. 63/065,616, filed Aug. 14, 2020.
U.S. Appl. No. 63/079,299, filed Sep. 16, 2020.
U.S. Appl. No. 63/091,032, filed Oct. 13, 2020.
U.S. Appl. No. 63/109,608, filed Nov. 4, 2020.
U.S. Appl. No. 63/109,734, filed Nov. 4, 2020.
U.S. Appl. No. 63/152,042, filed Feb. 22, 2011.
U.S. Appl. No. 63/016,036, filed Apr. 27, 2020.
International Search Report and Written Opinion issued on International Patent Application No. PCT/US2021/029185, dated Oct. 4, 2021.
International Preliminary Report of Patentability issued on International Patent Application No. PCT/US2021/029185, dated Nov. 22, 2022.
Communication pursuant to Rules 161(2) and 162 EPC, European Patent Application No. 21796098.8, dated Mar. 1, 2023.
Schmid et al., "Evaluation of CDKL5 Gene Therapy in CDD Mouse Models," CDKL5 Forum Presentation Poster, Nov. 2019, pp. 1.
Wilson, "Challenges of gene therapy and editing to the CNS," CDKL5 Forum Presentation, Nov. 5, 2019, pp. 1-14.
Gao et al., "Gene therapy with AAV-CDKL5 vectors in models of CDKL5 disorder," Human Gene Therapy, Oct. 2017, vol. vol. 28, in Selected Oral Presentations from ESGCT XXV Anniversary Congress in Collaboration with the German Society for Gene Therapy, pp. A6-A7.
Agius et al., "Safety and tolerability of inebilizumab (MEDI-551 ), an anti-CD19 monoclonal antibody, in patients with relapsing forms of multiple sclerosis: Results from a phase 1 randomised, placebo-controlled, escalating intravenous and subcutaneous dose study," Multiple Sclerosis Journal, Sep. 2017, pp. 1-11.
Amanna et al., "Duration of Humoral Immunity to Common Viral and Vaccine Antigens," NEJM, Nov. 2007, vol. 357(19):1903-15.
Bessis et al., "Immune responses to gene therapy vectors: influence on vector function and effector mechanisms," Gene Therapy, Oct. 2004, vol. 11:S10-S17.
Bhoj et al., "Persistence of long-lived plasma cells and humoral immunity in individuals responding to CD19-directed CART-cell therapy," Blood, Jul. 2016, vol. 128(3):360-370.
Brynjolfsson et al., "Long-lived plasma cells in human bone marrow can be either CD191 or CD19-" Blood Adv., Apr. 2017, vol. 1:835-838.
Chen et al., "Inebilizumab, a B Cell-Depleting Anti-CD19 Antibody for the Treatment of Autoimmune Neurological Diseases: Insights from Preclinical Studies," Journal of Clinical Medicine, Nov. 2016, vol. 5(107):1-12.
Choi et al., "AAV hybrid serotypes: improved vectors for gene delivery," Curr Gene Ther., Jun. 2005, vol. 5(3):299-310.
ClinicalTrials.gov, Clinical Trial No. NCT02240407 (Re-administration of Intramuscular AAV9 in Patients with Late-Onset Pompe Disease (AAV9-GAA IM)), Sep. 2014, 13 pages.
ClinicalTrials.gov, Clinical Trial No. NCT02525172 ("Immune Modulation Therapy for Pompe Disease"), Aug. 2015, 6 pages.
Collin et al., "Toward Clinical use of the IgG Specific Enzymes IdeS and EndoS against Antibody-Mediated Diseases," Bacterial Pathogenesis: Methods and Protocols, Methods in Molecular Biology, Dec. 2016, vol. 1535:339-351.
Corti et al., "B-cell depletion is protective against anti-AAV capsid immune response: a human subject case study," Molecular Therapy—Methods & Clinical Development, Aug. 2014, vol. 1, 14033, 7 pages.
Crotty et al., "Cutting Edge: Long-Term B Cell Memory in Humans after Smallpox Vaccination" The Journal of Immunology, Sep. 2003, vol. 171 :4969-4973.
Forsthuber et al., "B cell-based therapies in CNS autoimmunity: differentiating CD19 and CD20 as therapeutic targets," Ther Adv Neural Disord, Feb. 2018, vol. 11:1-13.
Gao et al., "New Recombinant Serotypes of AAV Vectors," Curr Gene Ther., Jun. 2005, vol. 5(3):285-297.
Jordan et al., "IgG Endopeptidase in Highly Sensitized Patients Undergoing Transplantation," The New England Journal of Medicine, Aug. 2017, vol. 377:442-453.
Lamphier et al., "Novel Small Molecule Inhibitors of TLR7 and TLR9: Mechanism of Action and Efficacy In Vivo," Mol Pharmacol., Mar. 2014, vol. 85(3):429-40.
Mei et al. "A unique population of IgG-expressing plasma cells lacking CD19 is enriched in human bone marrow" Blood, Mar. 2015, vol. 125(11):1739-1748.
Owczarczyk et al., "A Plasmablast Biomarker for Nonresponse to Antibody Therapy to CD20 in Rheumatoid Arthritis," Science Translational Medicine, Sep. 2011, vol. 3(101):ra92, 11 pages.
Schiopu et al., "Safety and tolerability of an anti-CD19 monoclonal antibody, MEDI-551, in subjects with systemic sclerosis: a phase I, randomized, placebo-controlled, escalating singledose study," Arthritis Research & Therapy, Jun. 2016, vol. 18:131, 14 pages.

(56) References Cited

OTHER PUBLICATIONS

Streicher et al., "Baseline Plasma Cell Gene Signature Predicts Improvement in Systemic Sclerosis Skin Scores Following Treatment With Inebilizumab (MEDI-551) and Correlates With Disease Activity in Systemic Lupus Erythematosus and Chronic Obstructive Pulmonary Disease," Arthritis Rheumatol, 2018, vol. 70(12):2087-2095.
Thaci et al., "The Challenge for Gene Therapy: Innate Immune Response to Adenoviruses," Oncotarqet, Mar. 2011, vol. 2(3):113-121.
Yazawa et al., "Immunotherapy using unconjugated CD19 monoclonal antibodies in animal models for B lymphocyte malignancies and autoimmune disease," PNAS, Oct. 2005, vol. 102(42):15178-15183.
Goncalves, I., et al., Development of a Stable Helper Virus Free Producer Cell Line for Scalable Adeno Associated Virus Vectors Production Based on Human Suspension Cells, 23rd Annual Meeting of the American Society for Gene and Cell Therapy, Virtual Format May 12-15, 2020, Molecular Therapy vol. 28 No 4S1, Apr. 28, 2020, Abstract 454, p. 201.
Hein, K., et al., Establishment of a Scalable Production Process Using Stable Helper-Virus Free AAV Producer Cell Lines Based on Human Suspension Cells, 23rd Annual Meeting of the American Society for Gene and Cell Therapy, Virtual Format May 12-15, 2020, Molecular Therapy vol. 28 No 4S1, Apr. 28, 2020, Abstract 464, p. 204.
Office Action dated Jan. 13, 2025 issued in corresponding Chinese Patent Application No. 202180045235.0, with unofficial English translation provided by local agent.
Office Action dated Nov. 3, 2025 issued in corresponding Chinese Patent Application No. 202180045235.0, with unofficial English translation provided by local agent.
Office Action dated Feb. 25, 2025 issued in corresponding United Arab Emirates Patent Application No. 202180045235.0.
Office Action dated Dec. 21, 2025 issued in corresponding Korean Patent Application No. 10-2022-7041749, with unofficial English translation provided by local agent.
Office Action dated Apr. 2, 2025 issued in corresponding Japanese Patent Application No. 2022-565789, with unofficial English translation provided by local agent.
Extended European Search Report dated Apr. 24, 2025 issued in corresponding European Patent Application No. 21796098.8.
Office Action dated Dec. 10, 2025 issued in corresponding Colombian Patent Application No. NC2022/0016956, with unofficial machine-generated translation provided.
Extended European Search Report dated Dec. 22, 2025 issued in related European Patent Application No. 22884659.8.
Office Action dated Aug. 25, 2025 issued in related United Arab Emirates Patent Application No. P2024-00976.

* cited by examiner

One-way ANOVA with Sidak's multiple comparison's test
*p<0.5

SEQUENCE LISTING

```
<160> NUMBER OF SEQ ID NOS: 48

<210> SEQ ID NO 1
<211> LENGTH: 4634
<212> TYPE: DNA
<213> ORGANISM: Artificial Sequence
<220> FEATURE:
<223> OTHER INFORMATION: Expression cassette
<220> FEATURE:
<221> NAME/KEY: repeat_region
<222> LOCATION: (1)..(130)
<223> OTHER INFORMATION: 5'ITR
<220> FEATURE:
<221> NAME/KEY: misc_feature
<222> LOCATION: (130)..(168)
<223> OTHER INFORMATION: AAV 2 seq upstream of 3'ITR
<220> FEATURE:
<221> NAME/KEY: promoter
<222> LOCATION: (213)..(678)
<223> OTHER INFORMATION: hSynapsin
<220> FEATURE:
<221> NAME/KEY: CDS
<222> LOCATION: (699)..(3581)
<223> OTHER INFORMATION: hCDKL5_1
<220> FEATURE:
<221> NAME/KEY: misc_feature
<222> LOCATION: (3596)..(4183)
<223> OTHER INFORMATION: WRPE
<220> FEATURE:
<221> NAME/KEY: polyA_signal
<222> LOCATION: (4201)..(4439)
<223> OTHER INFORMATION: SV40 polyA
<220> FEATURE:
<221> NAME/KEY: misc_feature
<222> LOCATION: (4467)..(44505)
<223> OTHER INFORMATION: AAV2 seq upstream of 3'ITR
<220> FEATURE:
<221> NAME/KEY: repeat_region
```

```
<222> LOCATION: (4505)..(4634)
<223> OTHER INFORMATION: 3'ITR

<400> SEQUENCE: 1

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctacgta gccatgctct     180

aggaagatcc tctagaacta tagctagcat gcctgcagag ggccctgcgt atgagtgcaa     240

gtgggtttta ggaccaggat gaggcggggt gggggtgcct acctgacgac cgaccccgac     300

ccactggaca agcacccaac cccattcccc caaattgcgc atcccctatc agagaggggg     360

aggggaaaca ggatgcggcg aggcgcgtgc gcactgccag cttcagcacc gcggacagtg     420

ccttcgcccc cgcctggcgg cgcgcgccac cgccgcctca gcactgaagg cgcgctgacg     480

tcactcgccg gtcccccgca aactcccctt cccggccacc ttggtcgcgt ccgcgccgcc     540

gccggcccag ccggaccgca ccacgcgagg cgcgagatag gggggcacgg gcgcgaccat     600

ctgcgctgcg gcgccggcga ctcagcgctg cctcagtctg cggtgggcag cggaggagtc     660

gtgtcgtgcc tgagagcgca gtcgaattcg ccgccacc atg aag atc ccc aac atc     716
                                         Met Lys Ile Pro Asn Ile
                                         1               5

ggc aac gtg atg aac aag ttc gag atc ctg ggc gtt gtc gga gaa ggc      764
Gly Asn Val Met Asn Lys Phe Glu Ile Leu Gly Val Val Gly Glu Gly
            10                  15                  20

gct tat ggc gtg gtg ctg aag tgc aga cac aaa gaa acc cac gag atc      812
Ala Tyr Gly Val Val Leu Lys Cys Arg His Lys Glu Thr His Glu Ile
        25                  30                  35

gtg gcc atc aag aag ttc aag gac agc gaa gag aac gag gaa gtg aaa      860
Val Ala Ile Lys Lys Phe Lys Asp Ser Glu Glu Asn Glu Glu Val Lys
    40                  45                  50

gag aca acc ctg cgc gag ctg aag atg ctg aga acc ctg aag caa gag      908
Glu Thr Thr Leu Arg Glu Leu Lys Met Leu Arg Thr Leu Lys Gln Glu
55                  60                  65                  70

aac atc gtg gaa ctg aaa gag gcc ttc cgg cgg aga ggc aag ctg tac      956
Asn Ile Val Glu Leu Lys Glu Ala Phe Arg Arg Arg Gly Lys Leu Tyr
                75                  80                  85

ctg gtg ttc gag tac gtg gaa aag aac atg ctc gag ctg ctg gaa gag     1004
Leu Val Phe Glu Tyr Val Glu Lys Asn Met Leu Glu Leu Leu Glu Glu
            90                  95                  100

atg ccc aat ggc gtg cca cct gag aaa gtg aag tcc tac atc tac cag     1052
Met Pro Asn Gly Val Pro Pro Glu Lys Val Lys Ser Tyr Ile Tyr Gln
        105                 110                 115

ctg atc aag gcc atc cac tgg tgc cac aag aac gac atc gtg cac aga     1100
Leu Ile Lys Ala Ile His Trp Cys His Lys Asn Asp Ile Val His Arg
    120                 125                 130

gac atc aag ccc gag aac ctg ctg atc tcc cac aac gac gtg ctg aag     1148
Asp Ile Lys Pro Glu Asn Leu Leu Ile Ser His Asn Asp Val Leu Lys
135                 140                 145                 150

ctg tgc gac ttc ggc ttc gcc aga aat ctg agc gag ggc aac aac gcc     1196
Leu Cys Asp Phe Gly Phe Ala Arg Asn Leu Ser Glu Gly Asn Asn Ala
                155                 160                 165

aac tac acc gag tat gtg gcc acc aga tgg tac aga agc cct gaa ctg     1244
Asn Tyr Thr Glu Tyr Val Ala Thr Arg Trp Tyr Arg Ser Pro Glu Leu
            170                 175                 180

ctg ctg gga gcc cct tac ggc aag tct gtg gat atg tgg tcc gtg ggc     1292
Leu Leu Gly Ala Pro Tyr Gly Lys Ser Val Asp Met Trp Ser Val Gly
        185                 190                 195
```

-continued

```
tgt atc ctg gga gag ctg tct gat ggc caa cct ctg ttt cct ggc gag     1340
Cys Ile Leu Gly Glu Leu Ser Asp Gly Gln Pro Leu Phe Pro Gly Glu
    200                 205                 210

tcc gag atc gac cag ctg ttc aca atc cag aag gtg ctg ggc cct ctg     1388
Ser Glu Ile Asp Gln Leu Phe Thr Ile Gln Lys Val Leu Gly Pro Leu
215                 220                 225                 230

cct agc gag cag atg aag ctg ttc tac agc aac ccc aga ttc cac ggc     1436
Pro Ser Glu Gln Met Lys Leu Phe Tyr Ser Asn Pro Arg Phe His Gly
                235                 240                 245

ctg aga ttc cct gcc gtg aat cac cct cag agc ctg gaa aga aga tac     1484
Leu Arg Phe Pro Ala Val Asn His Pro Gln Ser Leu Glu Arg Arg Tyr
            250                 255                 260

ctg ggc atc ctg aac agc gtg ctg ctg gac ctg atg aag aat ctg ctg     1532
Leu Gly Ile Leu Asn Ser Val Leu Leu Asp Leu Met Lys Asn Leu Leu
        265                 270                 275

aaa ctg gac ccc gcc gac aga tac ctg acc gag cag tgt ctg aac cat     1580
Lys Leu Asp Pro Ala Asp Arg Tyr Leu Thr Glu Gln Cys Leu Asn His
    280                 285                 290

cct acc ttt cag acc cag aga ctg ctg gat aga agc ccc agc aga agc     1628
Pro Thr Phe Gln Thr Gln Arg Leu Leu Asp Arg Ser Pro Ser Arg Ser
295                 300                 305                 310

gcc aag aga aag ccc tac cac gtg gaa agc agc acc ctg agc aat aga     1676
Ala Lys Arg Lys Pro Tyr His Val Glu Ser Ser Thr Leu Ser Asn Arg
                315                 320                 325

aac cag gcc gga aag agc act gcc ctg cag agc cac cac aga agc aac     1724
Asn Gln Ala Gly Lys Ser Thr Ala Leu Gln Ser His His Arg Ser Asn
            330                 335                 340

agc aag gac atc cag aac ctg agc gtg ggc ctg cct aga gct gat gaa     1772
Ser Lys Asp Ile Gln Asn Leu Ser Val Gly Leu Pro Arg Ala Asp Glu
        345                 350                 355

gga ctg cct gcc aac gag agc ttc ctg aat gga aat ctg gct ggc gcc     1820
Gly Leu Pro Ala Asn Glu Ser Phe Leu Asn Gly Asn Leu Ala Gly Ala
    360                 365                 370

tct ctg agc cct ctg cac aca aag aca tac cag gcc agc agc cag cct     1868
Ser Leu Ser Pro Leu His Thr Lys Thr Tyr Gln Ala Ser Ser Gln Pro
375                 380                 385                 390

ggc agc aca agc aag gac ctg acc aac aac aac atc cct cat ctg ctg     1916
Gly Ser Thr Ser Lys Asp Leu Thr Asn Asn Asn Ile Pro His Leu Leu
                395                 400                 405

agc ccc aaa gag gcc aag agc aag acc gag ttc gac ttc aac atc gac     1964
Ser Pro Lys Glu Ala Lys Ser Lys Thr Glu Phe Asp Phe Asn Ile Asp
            410                 415                 420

ccc aag cct agc gaa ggc cct ggc acc aag tac ctg aag tcc aac tcc     2012
Pro Lys Pro Ser Glu Gly Pro Gly Thr Lys Tyr Leu Lys Ser Asn Ser
        425                 430                 435

aga agc cag cag aac cgg cac tcc ttc atg gaa agc tct cag agc aag     2060
Arg Ser Gln Gln Asn Arg His Ser Phe Met Glu Ser Ser Gln Ser Lys
    440                 445                 450

gcc ggc aca ctg cag cct aac gag aag cag agc aga cac agc tac atc     2108
Ala Gly Thr Leu Gln Pro Asn Glu Lys Gln Ser Arg His Ser Tyr Ile
455                 460                 465                 470

gac aca atc cct cag tcc tct cgg agc ccc agc tac aga aca aag gcc     2156
Asp Thr Ile Pro Gln Ser Ser Arg Ser Pro Ser Tyr Arg Thr Lys Ala
                475                 480                 485

aaa tct cac ggc gcc ctg agc gat agc aag agc gtg tcc aat ctg tcc     2204
Lys Ser His Gly Ala Leu Ser Asp Ser Lys Ser Val Ser Asn Leu Ser
            490                 495                 500

gag gct aga gcc cag atc gcc gag cct agc acc agc aga tac ttc cct     2252
Glu Ala Arg Ala Gln Ile Ala Glu Pro Ser Thr Ser Arg Tyr Phe Pro
        505                 510                 515
```

```
agc agc tgc ctg gat ctg aac agc cct aca agc ccc aca cct acc agg     2300
Ser Ser Cys Leu Asp Leu Asn Ser Pro Thr Ser Pro Thr Pro Thr Arg
    520                 525                 530

cac agc gat acc aga aca ctg ctg tcc cca agc ggc cgg aac aac aga     2348
His Ser Asp Thr Arg Thr Leu Leu Ser Pro Ser Gly Arg Asn Asn Arg
535                 540                 545                 550

aat gag ggc acc ctg gac agc aga cgg acc acc aca aga cac agc aag     2396
Asn Glu Gly Thr Leu Asp Ser Arg Arg Thr Thr Thr Arg His Ser Lys
                555                 560                 565

acc atg gaa gaa ctg aag ctg ccc gag cac atg gac tct agc cac tct     2444
Thr Met Glu Glu Leu Lys Leu Pro Glu His Met Asp Ser Ser His Ser
            570                 575                 580

cat tct ctg agc gcc cct cac gag tcc ttt agc tac ggc ctg ggc tac     2492
His Ser Leu Ser Ala Pro His Glu Ser Phe Ser Tyr Gly Leu Gly Tyr
        585                 590                 595

aca agc cca ttt tcc agt cag cag cgg ccc cac aga cac tct atg tac     2540
Thr Ser Pro Phe Ser Ser Gln Gln Arg Pro His Arg His Ser Met Tyr
    600                 605                 610

gtg acc aga gac aaa gtc cgc gcc aaa ggc ctg gat ggc tct ctg tct     2588
Val Thr Arg Asp Lys Val Arg Ala Lys Gly Leu Asp Gly Ser Leu Ser
615                 620                 625                 630

att gga caa ggc atg gcc gcc aga gcc aat agc ctg caa ctt ctg tct     2636
Ile Gly Gln Gly Met Ala Ala Arg Ala Asn Ser Leu Gln Leu Leu Ser
                635                 640                 645

cct cag cct ggc gaa cag ctg cct cct gaa atg aca gtg gcc cgg tcc     2684
Pro Gln Pro Gly Glu Gln Leu Pro Pro Glu Met Thr Val Ala Arg Ser
            650                 655                 660

agc gtg aaa gaa acc agc aga gag ggc acc tcc agc ttc cac acc aga     2732
Ser Val Lys Glu Thr Ser Arg Glu Gly Thr Ser Ser Phe His Thr Arg
        665                 670                 675

cag aaa agc gaa ggc ggc gtg tac cac gat cct cac tct gat gat ggc     2780
Gln Lys Ser Glu Gly Gly Val Tyr His Asp Pro His Ser Asp Asp Gly
    680                 685                 690

aca gcc cct aaa gag aac aga cac ctg tac aac gac ccc gtg cct aga     2828
Thr Ala Pro Lys Glu Asn Arg His Leu Tyr Asn Asp Pro Val Pro Arg
695                 700                 705                 710

aga gtg ggc tcc ttc tac aga gtg cct tct cct aga cct gac aac tcc     2876
Arg Val Gly Ser Phe Tyr Arg Val Pro Ser Pro Arg Pro Asp Asn Ser
                715                 720                 725

ttc cac gag aac aac gtg tca acc cgg gtg tcc agc ctg cct tct gag     2924
Phe His Glu Asn Asn Val Ser Thr Arg Val Ser Ser Leu Pro Ser Glu
            730                 735                 740

agc agc tct ggc aca aac cac tcc aag agg cag ccc gcc ttc gat cct     2972
Ser Ser Ser Gly Thr Asn His Ser Lys Arg Gln Pro Ala Phe Asp Pro
        745                 750                 755

tgg aag tcc cct gag aat atc agc cac tcc gag cag ctg aaa gag aaa     3020
Trp Lys Ser Pro Glu Asn Ile Ser His Ser Glu Gln Leu Lys Glu Lys
    760                 765                 770

gag aag cag ggc ttt ttc cgg tcc atg aag aag aag aaa aag aag tcc     3068
Glu Lys Gln Gly Phe Phe Arg Ser Met Lys Lys Lys Lys Lys Lys Ser
775                 780                 785                 790

cag aca gtc ccc aac agc gac agc cct gat ctc ctg aca ctg cag aag     3116
Gln Thr Val Pro Asn Ser Asp Ser Pro Asp Leu Leu Thr Leu Gln Lys
                795                 800                 805

tcc atc cac agc gcc agc aca cct agc agc aga cct aaa gag tgg cgg     3164
Ser Ile His Ser Ala Ser Thr Pro Ser Ser Arg Pro Lys Glu Trp Arg
            810                 815                 820

cca gag aag atc agc gac ctg caa aca cag agc cag cct ctg aag tcc     3212
Pro Glu Lys Ile Ser Asp Leu Gln Thr Gln Ser Gln Pro Leu Lys Ser
```

```
        825                 830                 835

ctg agg aag ctg ctg cat ctg tcc tcc gcc tct aat cac cct gcc agc     3260
Leu Arg Lys Leu Leu His Leu Ser Ser Ala Ser Asn His Pro Ala Ser
    840                 845                 850

agc gat ccc aga ttt cag cca ctg aca gcc cag cag acc aag aac tcc     3308
Ser Asp Pro Arg Phe Gln Pro Leu Thr Ala Gln Gln Thr Lys Asn Ser
855                 860                 865                 870

ttc agc gag atc cgg att cac cca ctg tct cag gcc agc ggc ggc agc     3356
Phe Ser Glu Ile Arg Ile His Pro Leu Ser Gln Ala Ser Gly Gly Ser
                875                 880                 885

tct aat atc aga caa gag ccc gct cct aag ggc aga cct gct ctc caa     3404
Ser Asn Ile Arg Gln Glu Pro Ala Pro Lys Gly Arg Pro Ala Leu Gln
            890                 895                 900

ctg cct gga cag atg gat cct ggc tgg cac gtg tcc tct gtg aca aga     3452
Leu Pro Gly Gln Met Asp Pro Gly Trp His Val Ser Ser Val Thr Arg
        905                 910                 915

tct gcc acc gag gga cct agc tat tct gag cag ctg ggc gcc aag tct     3500
Ser Ala Thr Glu Gly Pro Ser Tyr Ser Glu Gln Leu Gly Ala Lys Ser
    920                 925                 930

ggc ccc aat gga cac ccc tac aac cgg acc aat cgg agc aga atg ccc     3548
Gly Pro Asn Gly His Pro Tyr Asn Arg Thr Asn Arg Ser Arg Met Pro
935                 940                 945                 950

aac ctg aac gac ctc aaa gaa aca gcc ctc tga gagcttatcg ataatcaacc   3601
Asn Leu Asn Asp Leu Lys Glu Thr Ala Leu
                955                 960

tctggattac aaaatttgtg aaagattgac tggtattctt aactatgttg ctccttttac   3661

gctatgtgga tacgctgctt taatgccttt gtatcatgct attgcttccc gtatggcttt   3721

cattttctcc tccttgtata aatcctggtt gctgtctctt tatgaggagt tgtggcccgt   3781

tgtcaggcaa cgtggcgtgg tgtgcactgt gtttgctgac gcaaccccca ctggttgggg   3841

cattgccacc acctgtcagc tcctttccgg gactttcgct ttccccctcc ctattgccac   3901

ggcggaactc atcgccgcct gccttgcccg ctgctggaca ggggctcggc tgttgggcac   3961

tgacaattcc gtggtgttgt cggggaaatc atcgtccttt ccttggctgc tcgcctgtgt   4021

tgccacctgg attctgcgcg ggacgtcctt ctgctacgtc ccttcggccc tcaatccagc   4081

ggaccttcct tcccgcggcc tgctgccggc tctgcggcct cttccgcgtc ttcgccttcg   4141

ccctcagacg agtcggatct ccctttgggc cgcctccccg catcgatacc gtcgatcgag   4201

gccgcttcga gcagacatga taagatacat tgatgagttt ggacaaacca caactagaat   4261

gcagtgaaaa aaatgcttta tttgtgaaat ttgtgatgct attgctttat ttgtaaccat   4321

tataagctgc aataaacaag ttaacaacaa caattgcatt cattttatgt ttcaggttca   4381

ggggagatg tgggaggttt tttaaagcaa gtaaaacctc tacaaatgtg gtaaaatcga   4441

taaggatctt cctagagcat ggctacgtag ataagtagca tggcgggtta atcattaact   4501

acaaggaacc cctagtgatg gagttggcca ctccctctct gcgcgctcgc tcgctcactg   4561

aggccgggcg accaaaggtc gcccgacgcc cgggctttgc ccgggcggcc tcagtgagcg   4621

agcgagcgcg cag                                                      4634

<210> SEQ ID NO 2
<211> LENGTH: 960
<212> TYPE: PRT
<213> ORGANISM: Artificial Sequence
<220> FEATURE:
<223> OTHER INFORMATION: Synthetic Construct

<400> SEQUENCE: 2
```

```
Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415
```

```
Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750

Gln Pro Ala Phe Asp Pro Trp Lys Ser Pro Glu Asn Ile Ser His Ser
        755                 760                 765

Glu Gln Leu Lys Glu Lys Glu Lys Gln Gly Phe Phe Arg Ser Met Lys
    770                 775                 780

Lys Lys Lys Lys Lys Ser Gln Thr Val Pro Asn Ser Asp Ser Pro Asp
785                 790                 795                 800

Leu Leu Thr Leu Gln Lys Ser Ile His Ser Ala Ser Thr Pro Ser Ser
                805                 810                 815

Arg Pro Lys Glu Trp Arg Pro Glu Lys Ile Ser Asp Leu Gln Thr Gln
            820                 825                 830

Ser Gln Pro Leu Lys Ser Leu Arg Lys Leu Leu His Leu Ser Ser Ala
```

```
        835                 840                 845

Ser Asn His Pro Ala Ser Ser Asp Pro Arg Phe Gln Pro Leu Thr Ala
    850                 855                 860

Gln Gln Thr Lys Asn Ser Phe Ser Glu Ile Arg Ile His Pro Leu Ser
865                 870                 875                 880

Gln Ala Ser Gly Gly Ser Ser Asn Ile Arg Gln Glu Pro Ala Pro Lys
                885                 890                 895

Gly Arg Pro Ala Leu Gln Leu Pro Gly Gln Met Asp Pro Gly Trp His
            900                 905                 910

Val Ser Ser Val Thr Arg Ser Ala Thr Glu Gly Pro Ser Tyr Ser Glu
        915                 920                 925

Gln Leu Gly Ala Lys Ser Gly Pro Asn Gly His Pro Tyr Asn Arg Thr
    930                 935                 940

Asn Arg Ser Arg Met Pro Asn Leu Asn Asp Leu Lys Glu Thr Ala Leu
945                 950                 955                 960
```

```
<210> SEQ ID NO 3
<211> LENGTH: 4750
<212> TYPE: DNA
<213> ORGANISM: Artificial Sequence
<220> FEATURE:
<223> OTHER INFORMATION: Expression Cassette
<220> FEATURE:
<221> NAME/KEY: repeat_region
<222> LOCATION: (1)..(130)
<223> OTHER INFORMATION: 5'ITR
<220> FEATURE:
<221> NAME/KEY: misc_feature
<222> LOCATION: (130)..(168)
<223> OTHER INFORMATION: AAV2 seq usptream of 3'ITR
<220> FEATURE:
<221> NAME/KEY: promoter
<222> LOCATION: (213)..(678)
<223> OTHER INFORMATION: hSynapsin
<220> FEATURE:
<221> NAME/KEY: CDS
<222> LOCATION: (699)..(3581)
<223> OTHER INFORMATION: hCDKL5-1
<220> FEATURE:
<221> NAME/KEY: misc_binding
<222> LOCATION: (3590)..(3705)
<223> OTHER INFORMATION: miR183
<220> FEATURE:
<221> NAME/KEY: misc_feature
<222> LOCATION: (3712)..(4299)
<223> OTHER INFORMATION: WRPE
<220> FEATURE:
<221> NAME/KEY: polyA_signal
<222> LOCATION: (4317)..(4555)
<223> OTHER INFORMATION: SV40 polyA
<220> FEATURE:
<221> NAME/KEY: misc_feature
<222> LOCATION: (4583)..(4621)
<223> OTHER INFORMATION: AAV2 seq upstream of 3'ITR
<220> FEATURE:
<221> NAME/KEY: repeat_region
<222> LOCATION: (4621)..(4750)
<223> OTHER INFORMATION: 3'ITR

<400> SEQUENCE: 3

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctacgta gccatgctct     180

aggaagatcc tctagaacta tagctagcat gcctgcagag ggccctgcgt atgagtgcaa     240

gtgggtttta ggaccaggat gaggcggggt gggggtgcct acctgacgac cgaccccgac     300
```

```
ccactggaca agcacccaac ccccattccc caaattgcgc atcccctatc agagaggggg    360

aggggaaaca ggatgcggcg aggcgcgtgc gcactgccag cttcagcacc gcggacagtg    420

ccttcgcccc cgcctggcgg cgcgcgccac cgccgcctca gcactgaagg cgcgctgacg    480

tcactcgccg gtcccccgca aactcccctt cccggccacc ttggtcgcgt ccgcgccgcc    540

gccggcccag ccggaccgca ccacgcgagg cgcgagatag gggggcacgg gcgcgaccat    600

ctgcgctgcg gcgccggcga ctcagcgctg cctcagtctg cggtgggcag cggaggagtc    660

gtgtcgtgcc tgagagcgca gtcgaattcg ccgccacc atg aag atc ccc aac atc    716
                                          Met Lys Ile Pro Asn Ile
                                          1               5

ggc aac gtg atg aac aag ttc gag atc ctg ggc gtt gtc gga gaa ggc      764
Gly Asn Val Met Asn Lys Phe Glu Ile Leu Gly Val Val Gly Glu Gly
            10                  15                  20

gct tat ggc gtg gtg ctg aag tgc aga cac aaa gaa acc cac gag atc      812
Ala Tyr Gly Val Val Leu Lys Cys Arg His Lys Glu Thr His Glu Ile
        25                  30                  35

gtg gcc atc aag aag ttc aag gac agc gaa gag aac gag gaa gtg aaa      860
Val Ala Ile Lys Lys Phe Lys Asp Ser Glu Glu Asn Glu Glu Val Lys
    40                  45                  50

gag aca acc ctg cgc gag ctg aag atg ctg aga acc ctg aag caa gag      908
Glu Thr Thr Leu Arg Glu Leu Lys Met Leu Arg Thr Leu Lys Gln Glu
55                  60                  65                  70

aac atc gtg gaa ctg aaa gag gcc ttc cgg cgg aga ggc aag ctg tac      956
Asn Ile Val Glu Leu Lys Glu Ala Phe Arg Arg Arg Gly Lys Leu Tyr
                75                  80                  85

ctg gtg ttc gag tac gtg gaa aag aac atg ctc gag ctg ctg gaa gag     1004
Leu Val Phe Glu Tyr Val Glu Lys Asn Met Leu Glu Leu Leu Glu Glu
            90                  95                  100

atg ccc aat ggc gtg cca cct gag aaa gtg aag tcc tac atc tac cag     1052
Met Pro Asn Gly Val Pro Pro Glu Lys Val Lys Ser Tyr Ile Tyr Gln
        105                 110                 115

ctg atc aag gcc atc cac tgg tgc cac aag aac gac atc gtg cac aga     1100
Leu Ile Lys Ala Ile His Trp Cys His Lys Asn Asp Ile Val His Arg
    120                 125                 130

gac atc aag ccc gag aac ctg ctg atc tcc cac aac gac gtg ctg aag     1148
Asp Ile Lys Pro Glu Asn Leu Leu Ile Ser His Asn Asp Val Leu Lys
135                 140                 145                 150

ctg tgc gac ttc ggc ttc gcc aga aat ctg agc gag ggc aac aac gcc     1196
Leu Cys Asp Phe Gly Phe Ala Arg Asn Leu Ser Glu Gly Asn Asn Ala
                155                 160                 165

aac tac acc gag tat gtg gcc acc aga tgg tac aga agc cct gaa ctg     1244
Asn Tyr Thr Glu Tyr Val Ala Thr Arg Trp Tyr Arg Ser Pro Glu Leu
            170                 175                 180

ctg ctg gga gcc cct tac ggc aag tct gtg gat atg tgg tcc gtg ggc     1292
Leu Leu Gly Ala Pro Tyr Gly Lys Ser Val Asp Met Trp Ser Val Gly
        185                 190                 195

tgt atc ctg gga gag ctg tct gat ggc caa cct ctg ttt cct ggc gag     1340
Cys Ile Leu Gly Glu Leu Ser Asp Gly Gln Pro Leu Phe Pro Gly Glu
    200                 205                 210

tcc gag atc gac cag ctg ttc aca atc cag aag gtg ctg ggc cct ctg     1388
Ser Glu Ile Asp Gln Leu Phe Thr Ile Gln Lys Val Leu Gly Pro Leu
215                 220                 225                 230

cct agc gag cag atg aag ctg ttc tac agc aac ccc aga ttc cac ggc     1436
Pro Ser Glu Gln Met Lys Leu Phe Tyr Ser Asn Pro Arg Phe His Gly
                235                 240                 245

ctg aga ttc cct gcc gtg aat cac cct cag agc ctg gaa aga aga tac     1484
Leu Arg Phe Pro Ala Val Asn His Pro Gln Ser Leu Glu Arg Arg Tyr
            250                 255                 260
```

```
ctg ggc atc ctg aac agc gtg ctg ctg gac ctg atg aag aat ctg ctg      1532
Leu Gly Ile Leu Asn Ser Val Leu Leu Asp Leu Met Lys Asn Leu Leu
        265                 270                 275

aaa ctg gac ccc gcc gac aga tac ctg acc gag cag tgt ctg aac cat      1580
Lys Leu Asp Pro Ala Asp Arg Tyr Leu Thr Glu Gln Cys Leu Asn His
    280                 285                 290

cct acc ttt cag acc cag aga ctg ctg gat aga agc ccc agc aga agc      1628
Pro Thr Phe Gln Thr Gln Arg Leu Leu Asp Arg Ser Pro Ser Arg Ser
295                 300                 305                 310

gcc aag aga aag ccc tac cac gtg gaa agc agc acc ctg agc aat aga      1676
Ala Lys Arg Lys Pro Tyr His Val Glu Ser Ser Thr Leu Ser Asn Arg
                315                 320                 325

aac cag gcc gga aag agc act gcc ctg cag agc cac cac aga agc aac      1724
Asn Gln Ala Gly Lys Ser Thr Ala Leu Gln Ser His His Arg Ser Asn
            330                 335                 340

agc aag gac atc cag aac ctg agc gtg ggc ctg cct aga gct gat gaa      1772
Ser Lys Asp Ile Gln Asn Leu Ser Val Gly Leu Pro Arg Ala Asp Glu
        345                 350                 355

gga ctg cct gcc aac gag agc ttc ctg aat gga aat ctg gct ggc gcc      1820
Gly Leu Pro Ala Asn Glu Ser Phe Leu Asn Gly Asn Leu Ala Gly Ala
    360                 365                 370

tct ctg agc cct ctg cac aca aag aca tac cag gcc agc agc cag cct      1868
Ser Leu Ser Pro Leu His Thr Lys Thr Tyr Gln Ala Ser Ser Gln Pro
375                 380                 385                 390

ggc agc aca agc aag gac ctg acc aac aac aac atc cct cat ctg ctg      1916
Gly Ser Thr Ser Lys Asp Leu Thr Asn Asn Asn Ile Pro His Leu Leu
                395                 400                 405

agc ccc aaa gag gcc aag agc aag acc gag ttc gac ttc aac atc gac      1964
Ser Pro Lys Glu Ala Lys Ser Lys Thr Glu Phe Asp Phe Asn Ile Asp
            410                 415                 420

ccc aag cct agc gaa ggc cct ggc acc aag tac ctg aag tcc aac tcc      2012
Pro Lys Pro Ser Glu Gly Pro Gly Thr Lys Tyr Leu Lys Ser Asn Ser
        425                 430                 435

aga agc cag cag aac cgg cac tcc ttc atg gaa agc tct cag agc aag      2060
Arg Ser Gln Gln Asn Arg His Ser Phe Met Glu Ser Ser Gln Ser Lys
    440                 445                 450

gcc ggc aca ctg cag cct aac gag aag cag agc aga cac agc tac atc      2108
Ala Gly Thr Leu Gln Pro Asn Glu Lys Gln Ser Arg His Ser Tyr Ile
455                 460                 465                 470

gac aca atc cct cag tcc tct cgg agc ccc agc tac aga aca aag gcc      2156
Asp Thr Ile Pro Gln Ser Ser Arg Ser Pro Ser Tyr Arg Thr Lys Ala
                475                 480                 485

aaa tct cac ggc gcc ctg agc gat agc aag agc gtg tcc aat ctg tcc      2204
Lys Ser His Gly Ala Leu Ser Asp Ser Lys Ser Val Ser Asn Leu Ser
            490                 495                 500

gag gct aga gcc cag atc gcc gag cct agc acc agc aga tac ttc cct      2252
Glu Ala Arg Ala Gln Ile Ala Glu Pro Ser Thr Ser Arg Tyr Phe Pro
        505                 510                 515

agc agc tgc ctg gat ctg aac agc cct aca agc ccc aca cct acc agg      2300
Ser Ser Cys Leu Asp Leu Asn Ser Pro Thr Ser Pro Thr Pro Thr Arg
    520                 525                 530

cac agc gat acc aga aca ctg ctg tcc cca agc ggc cgg aac aac aga      2348
His Ser Asp Thr Arg Thr Leu Leu Ser Pro Ser Gly Arg Asn Asn Arg
535                 540                 545                 550

aat gag ggc acc ctg gac agc aga cgg acc acc aca aga cac agc aag      2396
Asn Glu Gly Thr Leu Asp Ser Arg Arg Thr Thr Thr Arg His Ser Lys
                555                 560                 565

acc atg gaa gaa ctg aag ctg ccc gag cac atg gac tct agc cac tct      2444
Thr Met Glu Glu Leu Lys Leu Pro Glu His Met Asp Ser Ser His Ser
```

```
            570                 575                 580

cat tct ctg agc gcc cct cac gag tcc ttt agc tac ggc ctg ggc tac      2492
His Ser Leu Ser Ala Pro His Glu Ser Phe Ser Tyr Gly Leu Gly Tyr
        585                 590                 595

aca agc cca ttt tcc agt cag cag cgg ccc cac aga cac tct atg tac      2540
Thr Ser Pro Phe Ser Ser Gln Gln Arg Pro His Arg His Ser Met Tyr
    600                 605                 610

gtg acc aga gac aaa gtc cgc gcc aaa ggc ctg gat ggc tct ctg tct      2588
Val Thr Arg Asp Lys Val Arg Ala Lys Gly Leu Asp Gly Ser Leu Ser
615                 620                 625                 630

att gga caa ggc atg gcc gcc aga gcc aat agc ctg caa ctt ctg tct      2636
Ile Gly Gln Gly Met Ala Ala Arg Ala Asn Ser Leu Gln Leu Leu Ser
            635                 640                 645

cct cag cct ggc gaa cag ctg cct cct gaa atg aca gtg gcc cgg tcc      2684
Pro Gln Pro Gly Glu Gln Leu Pro Pro Glu Met Thr Val Ala Arg Ser
            650                 655                 660

agc gtg aaa gaa acc agc aga gag ggc acc tcc agc ttc cac acc aga      2732
Ser Val Lys Glu Thr Ser Arg Glu Gly Thr Ser Ser Phe His Thr Arg
        665                 670                 675

cag aaa agc gaa ggc ggc gtg tac cac gat cct cac tct gat gat ggc      2780
Gln Lys Ser Glu Gly Gly Val Tyr His Asp Pro His Ser Asp Asp Gly
    680                 685                 690

aca gcc cct aaa gag aac aga cac ctg tac aac gac ccc gtg cct aga      2828
Thr Ala Pro Lys Glu Asn Arg His Leu Tyr Asn Asp Pro Val Pro Arg
695                 700                 705                 710

aga gtg ggc tcc ttc tac aga gtg cct tct cct aga cct gac aac tcc      2876
Arg Val Gly Ser Phe Tyr Arg Val Pro Ser Pro Arg Pro Asp Asn Ser
                715                 720                 725

ttc cac gag aac aac gtg tca acc cgg gtg tcc agc ctg cct tct gag      2924
Phe His Glu Asn Asn Val Ser Thr Arg Val Ser Ser Leu Pro Ser Glu
            730                 735                 740

agc agc tct ggc aca aac cac tcc aag agg cag ccc gcc ttc gat cct      2972
Ser Ser Ser Gly Thr Asn His Ser Lys Arg Gln Pro Ala Phe Asp Pro
        745                 750                 755

tgg aag tcc cct gag aat atc agc cac tcc gag cag ctg aaa gag aaa      3020
Trp Lys Ser Pro Glu Asn Ile Ser His Ser Glu Gln Leu Lys Glu Lys
    760                 765                 770

gag aag cag ggc ttt ttc cgg tcc atg aag aag aag aaa aag aag tcc      3068
Glu Lys Gln Gly Phe Phe Arg Ser Met Lys Lys Lys Lys Lys Lys Ser
775                 780                 785                 790

cag aca gtc ccc aac agc gac agc cct gat ctc ctg aca ctg cag aag      3116
Gln Thr Val Pro Asn Ser Asp Ser Pro Asp Leu Leu Thr Leu Gln Lys
            795                 800                 805

tcc atc cac agc gcc agc aca cct agc agc aga cct aaa gag tgg cgg      3164
Ser Ile His Ser Ala Ser Thr Pro Ser Ser Arg Pro Lys Glu Trp Arg
            810                 815                 820

cca gag aag atc agc gac ctg caa aca cag agc cag cct ctg aag tcc      3212
Pro Glu Lys Ile Ser Asp Leu Gln Thr Gln Ser Gln Pro Leu Lys Ser
        825                 830                 835

ctg agg aag ctg ctg cat ctg tcc tcc gcc tct aat cac cct gcc agc      3260
Leu Arg Lys Leu Leu His Leu Ser Ser Ala Ser Asn His Pro Ala Ser
    840                 845                 850

agc gat ccc aga ttt cag cca ctg aca gcc cag cag acc aag aac tcc      3308
Ser Asp Pro Arg Phe Gln Pro Leu Thr Ala Gln Gln Thr Lys Asn Ser
855                 860                 865                 870

ttc agc gag atc cgg att cac cca ctg tct cag gcc agc ggc ggc agc      3356
Phe Ser Glu Ile Arg Ile His Pro Leu Ser Gln Ala Ser Gly Gly Ser
            875                 880                 885

tct aat atc aga caa gag ccc gct cct aag ggc aga cct gct ctc caa      3404
```

-continued

```
Ser Asn Ile Arg Gln Glu Pro Ala Pro Lys Gly Arg Pro Ala Leu Gln
            890                 895                 900

ctg cct gga cag atg gat cct ggc tgg cac gtg tcc tct gtg aca aga     3452
Leu Pro Gly Gln Met Asp Pro Gly Trp His Val Ser Ser Val Thr Arg
        905                 910                 915

tct gcc acc gag gga cct agc tat tct gag cag ctg ggc gcc aag tct     3500
Ser Ala Thr Glu Gly Pro Ser Tyr Ser Glu Gln Leu Gly Ala Lys Ser
    920                 925                 930

ggc ccc aat gga cac ccc tac aac cgg acc aat cgg agc aga atg ccc     3548
Gly Pro Asn Gly His Pro Tyr Asn Arg Thr Asn Arg Ser Arg Met Pro
935                 940                 945                 950

aac ctg aac gac ctc aaa gaa aca gcc ctc tga gagcttatac cggtagtgaa   3601
Asn Leu Asn Asp Leu Lys Glu Thr Ala Leu
                955                 960

ttctaccagt gccataggat agtgaattct accagtgcca tacacgtgag tgaattctac   3661

cagtgccata gcatgcagtg aattctacca gtgccatagg tacccgataa tcaacctctg   3721

gattacaaaa tttgtgaaag attgactggt attcttaact atgttgctcc ttttacgcta   3781

tgtggatacg ctgctttaat gcctttgtat catgctattg cttcccgtat ggctttcatt   3841

ttctcctcct tgtataaatc ctggttgctg tctctttatg aggagttgtg gcccgttgtc   3901

aggcaacgtg gcgtggtgtg cactgtgttt gctgacgcaa cccccactgg ttggggcatt   3961

gccaccacct gtcagctcct ttccgggact ttcgctttcc ccctccctat tgccacggcg   4021

gaactcatcg ccgcctgcct tgcccgctgc tggacagggg ctcggctgtt gggcactgac   4081

aattccgtgg tgttgtcggg gaaatcatcg tcctttcctt ggctgctcgc ctgtgttgcc   4141

acctggattc tgcgcgggac gtccttctgc tacgtccctt cggccctcaa tccagcggac   4201

cttccttccc gcggcctgct gccggctctg cggcctcttc cgcgtcttcg ccttcgccct   4261

cagacgagtc ggatctccct ttgggccgcc tccccgcatc gataccgtcg atcgaggccg   4321

cttcgagcag acatgataag atacattgat gagtttggac aaaccacaac tagaatgcag   4381

tgaaaaaaat gctttatttg tgaaatttgt gatgctattg ctttatttgt aaccattata   4441

agctgcaata aacaagttaa caacaacaat tgcattcatt ttatgtttca ggttcagggg   4501

gagatgtggg aggtttttta aagcaagtaa aacctctaca aatgtggtaa aatcgataag   4561

gatcttccta gagcatggct acgtagataa gtagcatggc gggttaatca ttaactacaa   4621

ggaaccccta gtgatggagt tggccactcc ctctctgcgc gctcgctcgc tcactgaggc   4681

cgggcgacca aaggtcgccc gacgcccggg ctttgcccgg gcggcctcag tgagcgagcg   4741

agcgcgcag                                                           4750


<210> SEQ ID NO 4
<211> LENGTH: 960
<212> TYPE: PRT
<213> ORGANISM: Artificial Sequence
<220> FEATURE:
<223> OTHER INFORMATION: Synthetic Construct

<400> SEQUENCE: 4

Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
```

```
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480
```

```
Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750

Gln Pro Ala Phe Asp Pro Trp Lys Ser Pro Glu Asn Ile Ser His Ser
        755                 760                 765

Glu Gln Leu Lys Glu Lys Glu Lys Gln Gly Phe Phe Arg Ser Met Lys
    770                 775                 780

Lys Lys Lys Lys Lys Ser Gln Thr Val Pro Asn Ser Asp Ser Pro Asp
785                 790                 795                 800

Leu Leu Thr Leu Gln Lys Ser Ile His Ser Ala Ser Thr Pro Ser Ser
                805                 810                 815

Arg Pro Lys Glu Trp Arg Pro Glu Lys Ile Ser Asp Leu Gln Thr Gln
            820                 825                 830

Ser Gln Pro Leu Lys Ser Leu Arg Lys Leu Leu His Leu Ser Ser Ala
        835                 840                 845

Ser Asn His Pro Ala Ser Ser Asp Pro Arg Phe Gln Pro Leu Thr Ala
    850                 855                 860

Gln Gln Thr Lys Asn Ser Phe Ser Glu Ile Arg Ile His Pro Leu Ser
865                 870                 875                 880

Gln Ala Ser Gly Gly Ser Ser Asn Ile Arg Gln Glu Pro Ala Pro Lys
                885                 890                 895
```

```
Gly Arg Pro Ala Leu Gln Leu Pro Gly Gln Met Asp Pro Gly Trp His
            900                 905                 910

Val Ser Ser Val Thr Arg Ser Ala Thr Glu Gly Pro Ser Tyr Ser Glu
        915                 920                 925

Gln Leu Gly Ala Lys Ser Gly Pro Asn Gly His Pro Tyr Asn Arg Thr
    930                 935                 940

Asn Arg Ser Arg Met Pro Asn Leu Asn Asp Leu Lys Glu Thr Ala Leu
945                 950                 955                 960


<210> SEQ ID NO 5
<211> LENGTH: 4757
<212> TYPE: DNA
<213> ORGANISM: Artificial Sequence
<220> FEATURE:
<223> OTHER INFORMATION: Expression Cassette
<220> FEATURE:
<221> NAME/KEY: repeat_region
<222> LOCATION: (1)..(130)
<223> OTHER INFORMATION: 5'ITR
<220> FEATURE:
<221> NAME/KEY: misc_feature
<222> LOCATION: (130)..(168)
<223> OTHER INFORMATION: AAV2 seq usptream of 3'ITR
<220> FEATURE:
<221> NAME/KEY: promoter
<222> LOCATION: (213)..(678)
<223> OTHER INFORMATION: hSynapsin
<220> FEATURE:
<221> NAME/KEY: misc_feature
<222> LOCATION: (690)..(695)
<223> OTHER INFORMATION: Kozak
<220> FEATURE:
<221> NAME/KEY: CDS
<222> LOCATION: (696)..(3704)
<223> OTHER INFORMATION: hCDKL5-2GS
<220> FEATURE:
<221> NAME/KEY: misc_feature
<222> LOCATION: (3719)..(4306)
<223> OTHER INFORMATION: WRPE
<220> FEATURE:
<221> NAME/KEY: polyA_signal
<222> LOCATION: (4324)..(4562)
<223> OTHER INFORMATION: SV40 polyA
<220> FEATURE:
<221> NAME/KEY: misc_feature
<222> LOCATION: (4590)..(4628)
<223> OTHER INFORMATION: AAV2 seq usptream of 3'ITR
<220> FEATURE:
<221> NAME/KEY: repeat_region
<222> LOCATION: (4628)..(4757)
<223> OTHER INFORMATION: 3'ITR

<400> SEQUENCE: 5

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatcc tctagaacta tagctagcat gcctgcagag ggccctgcgt atgagtgcaa    240

gtgggtttta ggaccaggat gaggcggggt gggggtgcct acctgacgac cgaccccgac    300

ccactggaca agcacccaac ccccattccc caaattgcgc atcccctatc agagaggggg    360

aggggaaaca ggatgcggcg aggcgcgtgc gcactgccag cttcagcacc gcggacagtg    420

ccttcgcccc cgcctggcgg cgcgcgccac cgccgcctca gcactgaagg cgcgctgacg    480

tcactcgccg gtcccccgca aactcccctt cccggccacc ttggtcgcgt ccgcgccgcc    540

gccggcccag ccggaccgca ccacgcgagg cgcgagatag ggggcacggg cgcgaccat     600

ctgcgctgcg gcgccggcga ctcagcgctg cctcagtctg cggtgggcag cggaggagtc    660
```

```
gtgtcgtgcc tgagagcgca gtcgaattcg ccacc atg aag atc ccc aat atc       713
                                       Met Lys Ile Pro Asn Ile
                                       1               5

ggc aac gtg atg aat aag ttc gag atc ctg gga gtg gtg gga gag gga      761
Gly Asn Val Met Asn Lys Phe Glu Ile Leu Gly Val Val Gly Glu Gly
            10                  15                  20

gca tac ggc gtg gtg ctg aag tgc aga cac aag gag aca cac gag atc      809
Ala Tyr Gly Val Val Leu Lys Cys Arg His Lys Glu Thr His Glu Ile
        25                  30                  35

gtg gcc atc aag aag ttt aag gat agc gag gag aat gag gag gtg aag      857
Val Ala Ile Lys Lys Phe Lys Asp Ser Glu Glu Asn Glu Glu Val Lys
    40                  45                  50

gag aca acc ctg cgc gag ctg aag atg ctg cgg aca ctg aag cag gag      905
Glu Thr Thr Leu Arg Glu Leu Lys Met Leu Arg Thr Leu Lys Gln Glu
55                  60                  65                  70

aac atc gtg gag ctg aag gag gcc ttc cgg aga agg ggc aag ctg tac      953
Asn Ile Val Glu Leu Lys Glu Ala Phe Arg Arg Arg Gly Lys Leu Tyr
                75                  80                  85

ctg gtg ttt gag tac gtg gag aag aac atg ctg gag ctg ctg gag gag     1001
Leu Val Phe Glu Tyr Val Glu Lys Asn Met Leu Glu Leu Leu Glu Glu
            90                  95                  100

atg cct aat ggc gtg ccc cct gag aag gtg aag agc tac atc tat cag     1049
Met Pro Asn Gly Val Pro Pro Glu Lys Val Lys Ser Tyr Ile Tyr Gln
        105                 110                 115

ctg atc aag gcc atc cac tgg tgc cac aag aac gac atc gtg cac cgc     1097
Leu Ile Lys Ala Ile His Trp Cys His Lys Asn Asp Ile Val His Arg
    120                 125                 130

gat atc aag cca gag aac ctg ctg atc agc cac aat gac gtg ctg aag     1145
Asp Ile Lys Pro Glu Asn Leu Leu Ile Ser His Asn Asp Val Leu Lys
135                 140                 145                 150

ctg tgc gat ttc ggc ttt gcc cgg aac ctg tcc gag ggc aac aac gcc     1193
Leu Cys Asp Phe Gly Phe Ala Arg Asn Leu Ser Glu Gly Asn Asn Ala
                155                 160                 165

aat tac aca gag tac gtg gca acc agg tgg tac cgg tcc cct gag ctg     1241
Asn Tyr Thr Glu Tyr Val Ala Thr Arg Trp Tyr Arg Ser Pro Glu Leu
            170                 175                 180

ctg ctg gga gca cca tac ggc aag tct gtg gac atg tgg agc gtg ggc     1289
Leu Leu Gly Ala Pro Tyr Gly Lys Ser Val Asp Met Trp Ser Val Gly
        185                 190                 195

tgc atc ctg gga gag ctg tcc gac gga cag cca ctg ttc cct ggc gag     1337
Cys Ile Leu Gly Glu Leu Ser Asp Gly Gln Pro Leu Phe Pro Gly Glu
    200                 205                 210

tct gag atc gat cag ctg ttt acc atc cag aag gtg ctg ggc ccc ctg     1385
Ser Glu Ile Asp Gln Leu Phe Thr Ile Gln Lys Val Leu Gly Pro Leu
215                 220                 225                 230

cct tcc gag cag atg aag ctg ttc tac tct aac cca agg ttc cac ggc     1433
Pro Ser Glu Gln Met Lys Leu Phe Tyr Ser Asn Pro Arg Phe His Gly
                235                 240                 245

ctg agg ttt cca gcc gtg aat cac ccc cag tct ctg gag cgc cgg tat     1481
Leu Arg Phe Pro Ala Val Asn His Pro Gln Ser Leu Glu Arg Arg Tyr
            250                 255                 260

ctg ggc atc ctg aac agc gtg ctg ctg gat ctg atg aag aat ctg ctg     1529
Leu Gly Ile Leu Asn Ser Val Leu Leu Asp Leu Met Lys Asn Leu Leu
        265                 270                 275

aag ctg gac cct gcc gat cgc tac ctg acc gag cag tgt ctg aat cac     1577
Lys Leu Asp Pro Ala Asp Arg Tyr Leu Thr Glu Gln Cys Leu Asn His
    280                 285                 290

cca aca ttt cag acc cag aga ctg ctg gac agg agc ccc tcc cgc tct     1625
Pro Thr Phe Gln Thr Gln Arg Leu Leu Asp Arg Ser Pro Ser Arg Ser
```

```
295                 300                 305                 310

gcc aag agg aag cct tat cac gtg gag agc tcc acc ctg agc aat cgc      1673
Ala Lys Arg Lys Pro Tyr His Val Glu Ser Ser Thr Leu Ser Asn Arg
                315                 320                 325

aac cag gcc ggc aag tcc aca gcc ctg cag tct cac cac cgg agc aac      1721
Asn Gln Ala Gly Lys Ser Thr Ala Leu Gln Ser His His Arg Ser Asn
            330                 335                 340

tcc aag gac atc cag aat ctg agc gtg ggc ctg cca agg gca gac gag      1769
Ser Lys Asp Ile Gln Asn Leu Ser Val Gly Leu Pro Arg Ala Asp Glu
        345                 350                 355

ggc ctg cct gcc aac gag tcc ttc ctg aat gga aac ctg gca gga gcc      1817
Gly Leu Pro Ala Asn Glu Ser Phe Leu Asn Gly Asn Leu Ala Gly Ala
    360                 365                 370

tct ctg agc cca ctg cac aca aag acc tac cag gcc tct agc cag cct      1865
Ser Leu Ser Pro Leu His Thr Lys Thr Tyr Gln Ala Ser Ser Gln Pro
375                 380                 385                 390

ggc tcc aca tct aag gac ctg acc aac aat aac atc cct cac ctg ctg      1913
Gly Ser Thr Ser Lys Asp Leu Thr Asn Asn Asn Ile Pro His Leu Leu
                395                 400                 405

agc cca aag gag gcc aag tcc aag acc gag ttc gac ttt aat atc gat      1961
Ser Pro Lys Glu Ala Lys Ser Lys Thr Glu Phe Asp Phe Asn Ile Asp
            410                 415                 420

cca aag ccc agc gag ggc cca ggc aca aag tat ctg aag agc aac tcc      2009
Pro Lys Pro Ser Glu Gly Pro Gly Thr Lys Tyr Leu Lys Ser Asn Ser
        425                 430                 435

aga tct cag cag aat agg cac tct ttc atg gag tcc tct cag agc aag      2057
Arg Ser Gln Gln Asn Arg His Ser Phe Met Glu Ser Ser Gln Ser Lys
    440                 445                 450

gcc ggc acc ctg cag ccc aac gag aag cag agc agg cac tcc tac atc      2105
Ala Gly Thr Leu Gln Pro Asn Glu Lys Gln Ser Arg His Ser Tyr Ile
455                 460                 465                 470

gat acc atc cca cag agc tcc cgc agc ccc tcc tat cgg aca aag gcc      2153
Asp Thr Ile Pro Gln Ser Ser Arg Ser Pro Ser Tyr Arg Thr Lys Ala
                475                 480                 485

aag agc cac ggc gcc ctg tct gac agc aag tcc gtg tct aat ctg tcc      2201
Lys Ser His Gly Ala Leu Ser Asp Ser Lys Ser Val Ser Asn Leu Ser
            490                 495                 500

gag gca aga gca cag atc gca gag cca agc acc tcc agg tac ttt ccc      2249
Glu Ala Arg Ala Gln Ile Ala Glu Pro Ser Thr Ser Arg Tyr Phe Pro
        505                 510                 515

tct tcc tgt ctg gac ctg aac tct cca aca agc cct aca cca acc aga      2297
Ser Ser Cys Leu Asp Leu Asn Ser Pro Thr Ser Pro Thr Pro Thr Arg
    520                 525                 530

cac agc gat aca agg acc ctg ctg tct ccc agc ggc aga aat aac agg      2345
His Ser Asp Thr Arg Thr Leu Leu Ser Pro Ser Gly Arg Asn Asn Arg
535                 540                 545                 550

aac gag ggc acc ctg gat agc aga agg acc aca acc aga cac tcc aag      2393
Asn Glu Gly Thr Leu Asp Ser Arg Arg Thr Thr Thr Arg His Ser Lys
                555                 560                 565

aca atg gag gag ctg aag ctg ccc gag cac atg gac tcc tct cac tcc      2441
Thr Met Glu Glu Leu Lys Leu Pro Glu His Met Asp Ser Ser His Ser
            570                 575                 580

cac tct ctg agc gcc cct cac gag tcc ttc tct tac ggc ctg ggc tat      2489
His Ser Leu Ser Ala Pro His Glu Ser Phe Ser Tyr Gly Leu Gly Tyr
        585                 590                 595

acc agc cct ttt agc tcc cag cag cgc cca cac agg cac tcc atg tac      2537
Thr Ser Pro Phe Ser Ser Gln Gln Arg Pro His Arg His Ser Met Tyr
    600                 605                 610

gtg aca aga gac aag gtg agg gcc aag ggc ctg gac ggc agc ctg tcc      2585
```

```
Val Thr Arg Asp Lys Val Arg Ala Lys Gly Leu Asp Gly Ser Leu Ser
615                 620                 625                 630

atc gga cag gga atg gca gca agg gca aat agc ctg cag ctg ctg tcc      2633
Ile Gly Gln Gly Met Ala Ala Arg Ala Asn Ser Leu Gln Leu Leu Ser
                635                 640                 645

cca cag cct gga gag cag ctg cca cca gag atg acc gtg gcc aga tct      2681
Pro Gln Pro Gly Glu Gln Leu Pro Pro Glu Met Thr Val Ala Arg Ser
            650                 655                 660

agc gtg aag gag aca agc agg gag ggc acc tcc tct ttc cac aca aga      2729
Ser Val Lys Glu Thr Ser Arg Glu Gly Thr Ser Ser Phe His Thr Arg
        665                 670                 675

cag aag agc gag ggc ggc gtg tat cac gac cca cac tcc gac gac gga      2777
Gln Lys Ser Glu Gly Gly Val Tyr His Asp Pro His Ser Asp Asp Gly
    680                 685                 690

acc gca ccc aag gag aac agg cac ctg tac aac gat cca gtg ccc cgc      2825
Thr Ala Pro Lys Glu Asn Arg His Leu Tyr Asn Asp Pro Val Pro Arg
695                 700                 705                 710

cgg gtg ggc tct ttc tat cgg gtg cct agc cca cgg ccc gac aac tcc      2873
Arg Val Gly Ser Phe Tyr Arg Val Pro Ser Pro Arg Pro Asp Asn Ser
                715                 720                 725

ttt cac gag aat aac gtg tct acc aga gtg agc tcc ctg cct agc gag      2921
Phe His Glu Asn Asn Val Ser Thr Arg Val Ser Ser Leu Pro Ser Glu
            730                 735                 740

tct agc tcc ggc aca aac cac tcc aag agg cag cca gcc ttt gat ccc      2969
Ser Ser Ser Gly Thr Asn His Ser Lys Arg Gln Pro Ala Phe Asp Pro
        745                 750                 755

tgg aag tct cct gag aat atc tct cac agc gag cag ctg aag gag aag      3017
Trp Lys Ser Pro Glu Asn Ile Ser His Ser Glu Gln Leu Lys Glu Lys
    760                 765                 770

gag aag cag ggc ttc ttt cgc agc atg aag aag aag aag aag aag agc      3065
Glu Lys Gln Gly Phe Phe Arg Ser Met Lys Lys Lys Lys Lys Lys Ser
775                 780                 785                 790

cag aca acc gac agc acc aac ggc gag aat cct agc atc aag aag tcc      3113
Gln Thr Thr Asp Ser Thr Asn Gly Glu Asn Pro Ser Ile Lys Lys Ser
                795                 800                 805

ctg ttc cca ctg ttt aac tcc aag aat cac ctg aag cac tct agc tcc      3161
Leu Phe Pro Leu Phe Asn Ser Lys Asn His Leu Lys His Ser Ser Ser
            810                 815                 820

ctg aag aag ctg ccc gtg gtg aca cct cca atg gtg ccc aat tcc gac      3209
Leu Lys Lys Leu Pro Val Val Thr Pro Pro Met Val Pro Asn Ser Asp
        825                 830                 835

tct cct gat ctg ctg acc ctg cag aag agc atc cac agc gcc tcc aca      3257
Ser Pro Asp Leu Leu Thr Leu Gln Lys Ser Ile His Ser Ala Ser Thr
    840                 845                 850

cca tct agc aga ccc aag gag tgg agg cca gag aag atc tcc gat ctg      3305
Pro Ser Ser Arg Pro Lys Glu Trp Arg Pro Glu Lys Ile Ser Asp Leu
855                 860                 865                 870

cag acc cag tcc cag ccc ctg aag tct ctg cgg aag ctg ctg cac ctg      3353
Gln Thr Gln Ser Gln Pro Leu Lys Ser Leu Arg Lys Leu Leu His Leu
                875                 880                 885

tcc tct gcc agc aac cac cct gca agc tcc gac cct agg ttc cag cca      3401
Ser Ser Ala Ser Asn His Pro Ala Ser Ser Asp Pro Arg Phe Gln Pro
            890                 895                 900

ctg aca gcc cag cag acc aag aac tct ttt agc gag atc aga atc cac      3449
Leu Thr Ala Gln Gln Thr Lys Asn Ser Phe Ser Glu Ile Arg Ile His
        905                 910                 915

cca ctg tcc cag gcc tct gga ggc tct agc aac atc cgc cag gag cct      3497
Pro Leu Ser Gln Ala Ser Gly Gly Ser Ser Asn Ile Arg Gln Glu Pro
    920                 925                 930
```

```
gcc cca aag ggc cgg cca gcc ctg cag ctg cca gga cag atg gac ccc     3545
Ala Pro Lys Gly Arg Pro Ala Leu Gln Leu Pro Gly Gln Met Asp Pro
935                 940                 945                 950

ggc tgg cac gtg tcc tct gtg aca aga tcc gcc acc gag gga cca tcc     3593
Gly Trp His Val Ser Ser Val Thr Arg Ser Ala Thr Glu Gly Pro Ser
                955                 960                 965

tac tct gag cag ctg gga gca aag tct gga cca aac gga cac cct tat     3641
Tyr Ser Glu Gln Leu Gly Ala Lys Ser Gly Pro Asn Gly His Pro Tyr
            970                 975                 980

aac agg acc aat aga tcc agg atg cct aat ctg aac gac ctg aag gag     3689
Asn Arg Thr Asn Arg Ser Arg Met Pro Asn Leu Asn Asp Leu Lys Glu
        985                 990                 995

aca gcc  ctg tga tag aagcttatcg ataatcaacc tctggattac aaaatttgtg    3744
Thr Ala  Leu
    1000

aaagattgac tggtattctt aactatgttg ctccttttac gctatgtgga tacgctgctt   3804

taatgccttt gtatcatgct attgcttccc gtatggcttt cattttctcc tccttgtata   3864

aatcctggtt gctgtctctt tatgaggagt tgtggcccgt tgtcaggcaa cgtggcgtgg   3924

tgtgcactgt gtttgctgac gcaaccccca ctggttgggg cattgccacc acctgtcagc   3984

tcctttccgg gactttcgct ttccccctcc ctattgccac ggcggaactc atcgccgcct   4044

gccttgcccg ctgctggaca ggggctcggc tgttgggcac tgacaattcc gtggtgttgt   4104

cggggaaatc atcgtccttt ccttggctgc tcgcctgtgt tgccacctgg attctgcgcg   4164

ggacgtcctt ctgctacgtc ccttcggccc tcaatccagc ggaccttcct tcccgcggcc   4224

tgctgccggc tctgcggcct cttccgcgtc ttcgccttcg ccctcagacg agtcggatct   4284

ccctttgggc cgcctccccg catcgatacc gtcgatcgag gccgcttcga gcagacatga   4344

taagatacat tgatgagttt ggacaaacca caactagaat gcagtgaaaa aaatgcttta   4404

tttgtgaaat ttgtgatgct attgctttat ttgtaaccat tataagctgc aataaacaag   4464

ttaacaacaa caattgcatt cattttatgt ttcaggttca gggggagatg tgggaggttt   4524

tttaaagcaa gtaaaacctc tacaaatgtg gtaaaatcga taaggatctt cctagagcat   4584

ggctacgtag ataagtagca tggcgggtta atcattaact acaaggaacc cctagtgatg   4644

gagttggcca ctccctctct gcgcgctcgc tcgctcactg aggccgggcg accaaaggtc   4704

gcccgacgcc cgggctttgc ccgggcggcc tcagtgagcg agcgagcgcg cag          4757
```

<210> SEQ ID NO 6
<211> LENGTH: 1001
<212> TYPE: PRT
<213> ORGANISM: Artificial Sequence
<220> FEATURE:
<223> OTHER INFORMATION: Synthetic Construct

<400> SEQUENCE: 6

```
Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80
```

```
Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
```

-continued

```
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750

Gln Pro Ala Phe Asp Pro Trp Lys Ser Pro Glu Asn Ile Ser His Ser
        755                 760                 765

Glu Gln Leu Lys Glu Lys Glu Lys Gln Gly Phe Phe Arg Ser Met Lys
    770                 775                 780

Lys Lys Lys Lys Lys Ser Gln Thr Thr Asp Ser Thr Asn Gly Glu Asn
785                 790                 795                 800

Pro Ser Ile Lys Lys Ser Leu Phe Pro Leu Phe Asn Ser Lys Asn His
                805                 810                 815

Leu Lys His Ser Ser Ser Leu Lys Lys Leu Pro Val Val Thr Pro Pro
            820                 825                 830

Met Val Pro Asn Ser Asp Ser Pro Asp Leu Leu Thr Leu Gln Lys Ser
        835                 840                 845

Ile His Ser Ala Ser Thr Pro Ser Ser Arg Pro Lys Glu Trp Arg Pro
    850                 855                 860

Glu Lys Ile Ser Asp Leu Gln Thr Gln Ser Gln Pro Leu Lys Ser Leu
865                 870                 875                 880

Arg Lys Leu Leu His Leu Ser Ser Ala Ser Asn His Pro Ala Ser Ser
                885                 890                 895

Asp Pro Arg Phe Gln Pro Leu Thr Ala Gln Gln Thr Lys Asn Ser Phe
            900                 905                 910

Ser Glu Ile Arg Ile His Pro Leu Ser Gln Ala Ser Gly Gly Ser Ser
        915                 920                 925
```

```
Asn Ile Arg Gln Glu Pro Ala Pro Lys Gly Arg Pro Ala Leu Gln Leu
    930                 935                 940

Pro Gly Gln Met Asp Pro Gly Trp His Val Ser Ser Val Thr Arg Ser
945                 950                 955                 960

Ala Thr Glu Gly Pro Ser Tyr Ser Glu Gln Leu Gly Ala Lys Ser Gly
                965                 970                 975

Pro Asn Gly His Pro Tyr Asn Arg Thr Asn Arg Ser Arg Met Pro Asn
            980                 985                 990

Leu Asn Asp Leu Lys Glu Thr Ala  Leu
        995                 1000


<210> SEQ ID NO 7
<211> LENGTH: 4583
<212> TYPE: DNA
<213> ORGANISM: Artificial Sequence
<220> FEATURE:
<223> OTHER INFORMATION: Expression Cassette
<220> FEATURE:
<221> NAME/KEY: repeat_region
<222> LOCATION: (1)..(130)
<223> OTHER INFORMATION: 5'ITR
<220> FEATURE:
<221> NAME/KEY: misc_feature
<222> LOCATION: (130)..(168)
<223> OTHER INFORMATION: AAV2 seq upstream of 3'ITR
<220> FEATURE:
<221> NAME/KEY: promoter
<222> LOCATION: (213)..(678)
<223> OTHER INFORMATION: hSynapsin
<220> FEATURE:
<221> NAME/KEY: misc_feature
<222> LOCATION: (690)..(695)
<223> OTHER INFORMATION: Kozak
<220> FEATURE:
<221> NAME/KEY: CDS
<222> LOCATION: (696)..(3530)
<223> OTHER INFORMATION: hCDKL5-3GS
<220> FEATURE:
<221> NAME/KEY: misc_feature
<222> LOCATION: (3545)..(4132)
<223> OTHER INFORMATION: WRPE
<220> FEATURE:
<221> NAME/KEY: polyA_signal
<222> LOCATION: (4150)..(4388)
<223> OTHER INFORMATION: SV40 polyA
<220> FEATURE:
<221> NAME/KEY: misc_feature
<222> LOCATION: (4416)..(4454)
<223> OTHER INFORMATION: AAV2 seq upstream of 3'ITR
<220> FEATURE:
<221> NAME/KEY: repeat_region
<222> LOCATION: (4454)..(4583)
<223> OTHER INFORMATION: 3'ITR

<400> SEQUENCE: 7

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctacgta gccatgctct     180

aggaagatcc tctagaacta tagctagcat gcctgcagag ggccctgcgt atgagtgcaa     240

gtgggtttta ggaccaggat gaggcggggt gggggtgcct acctgacgac cgaccccgac     300

ccactggaca agcacccaac ccccattccc caaattgcgc atcccctatc agagaggggg     360

aggggaaaca ggatgcggcg aggcgcgtgc gcactgccag cttcagcacc gcggacagtg     420

ccttcgcccc cgcctggcgg cgcgcgccac cgccgcctca gcactgaagg cgcgctgacg     480

tcactcgccg gtcccccgca aactcccctt cccggccacc ttggtcgcgt ccgcgccgcc     540
```

```
gccggcccag ccggaccgca ccacgcgagg cgcgagatag gggggcacgg gcgcgaccat    600

ctgcgctgcg gcgccggcga ctcagcgctg cctcagtctg cggtgggcag cggaggagtc    660

gtgtcgtgcc tgagagcgca gtcgaattcg ccacc atg aag atc ccc aat atc       713
                                       Met Lys Ile Pro Asn Ile
                                       1               5

ggc aac gtg atg aat aag ttc gag atc ctg gga gtg gtg gga gag gga      761
Gly Asn Val Met Asn Lys Phe Glu Ile Leu Gly Val Val Gly Glu Gly
            10                  15                  20

gca tac gga gtg gtg ctg aag tgc cgg cac aag gag aca cac gag atc      809
Ala Tyr Gly Val Val Leu Lys Cys Arg His Lys Glu Thr His Glu Ile
        25                  30                  35

gtg gcc atc aag aag ttt aag gat agc gag gag aat gag gag gtg aag      857
Val Ala Ile Lys Lys Phe Lys Asp Ser Glu Glu Asn Glu Glu Val Lys
    40                  45                  50

gag aca acc ctg agg gag ctg aag atg ctg cgc aca ctg aag cag gag      905
Glu Thr Thr Leu Arg Glu Leu Lys Met Leu Arg Thr Leu Lys Gln Glu
55                  60                  65                  70

aac atc gtg gag ctg aag gag gcc ttc cgg aga agg ggc aag ctg tac      953
Asn Ile Val Glu Leu Lys Glu Ala Phe Arg Arg Arg Gly Lys Leu Tyr
                75                  80                  85

ctg gtg ttt gag tac gtg gag aag aac atg ctg gag ctg ctg gag gag     1001
Leu Val Phe Glu Tyr Val Glu Lys Asn Met Leu Glu Leu Leu Glu Glu
            90                  95                  100

atg cct aat ggc gtg ccc cct gag aag gtg aag agc tac atc tat cag     1049
Met Pro Asn Gly Val Pro Pro Glu Lys Val Lys Ser Tyr Ile Tyr Gln
        105                 110                 115

ctg atc aag gcc atc cac tgg tgc cac aag aac gac atc gtg cac agg     1097
Leu Ile Lys Ala Ile His Trp Cys His Lys Asn Asp Ile Val His Arg
    120                 125                 130

gat atc aag cca gag aac ctg ctg atc agc cac aat gac gtg ctg aag     1145
Asp Ile Lys Pro Glu Asn Leu Leu Ile Ser His Asn Asp Val Leu Lys
135                 140                 145                 150

ctg tgc gat ttc ggc ttt gcc cgc aac ctg tcc gag ggc aac aac gcc     1193
Leu Cys Asp Phe Gly Phe Ala Arg Asn Leu Ser Glu Gly Asn Asn Ala
                155                 160                 165

aat tac aca gag tac gtg gca acc agg tgg tac cgg tcc cca gag ctg     1241
Asn Tyr Thr Glu Tyr Val Ala Thr Arg Trp Tyr Arg Ser Pro Glu Leu
            170                 175                 180

ctg ctg gga gca cca tac ggc aag agc gtg gac atg tgg tcc gtg ggc     1289
Leu Leu Gly Ala Pro Tyr Gly Lys Ser Val Asp Met Trp Ser Val Gly
        185                 190                 195

tgc atc ctg ggc gag ctg tct gac ggc cag cct ctg ttc cca ggc gag     1337
Cys Ile Leu Gly Glu Leu Ser Asp Gly Gln Pro Leu Phe Pro Gly Glu
    200                 205                 210

agc gag atc gat cag ctg ttt acc atc cag aag gtg ctg ggc cct ctg     1385
Ser Glu Ile Asp Gln Leu Phe Thr Ile Gln Lys Val Leu Gly Pro Leu
215                 220                 225                 230

cca agc gag cag atg aag ctg ttc tac tcc aac cct agg ttc cac ggc     1433
Pro Ser Glu Gln Met Lys Leu Phe Tyr Ser Asn Pro Arg Phe His Gly
                235                 240                 245

ctg cgc ttt ccc gcc gtg aat cac cct cag agc ctg gag cgc cgg tat     1481
Leu Arg Phe Pro Ala Val Asn His Pro Gln Ser Leu Glu Arg Arg Tyr
            250                 255                 260

ctg ggc atc ctg aac tcc gtg ctg ctg gat ctg atg aag aat ctg ctg     1529
Leu Gly Ile Leu Asn Ser Val Leu Leu Asp Leu Met Lys Asn Leu Leu
        265                 270                 275

aag ctg gac ccc gcc gat agg tac ctg acc gag cag tgt ctg aac cac     1577
Lys Leu Asp Pro Ala Asp Arg Tyr Leu Thr Glu Gln Cys Leu Asn His
```

```
    280                 285                 290

ccc aca ttc cag acc cag aga ctg ctg gac agg tcc cct tct cgc aat      1625
Pro Thr Phe Gln Thr Gln Arg Leu Leu Asp Arg Ser Pro Ser Arg Asn
295                 300                 305                 310

cag gcc ggc aag tct aca gcc ctg cag agc cac cac agg agc aac tcc      1673
Gln Ala Gly Lys Ser Thr Ala Leu Gln Ser His His Arg Ser Asn Ser
                315                 320                 325

aag gac atc cag aat ctg agc gtg ggc ctg cct agg gca gac gag ggc      1721
Lys Asp Ile Gln Asn Leu Ser Val Gly Leu Pro Arg Ala Asp Glu Gly
            330                 335                 340

ctg cca gca aac gag tcc ttt ctg aat gga aac ctg gca gga gcc tct      1769
Leu Pro Ala Asn Glu Ser Phe Leu Asn Gly Asn Leu Ala Gly Ala Ser
        345                 350                 355

ctg agc cca ctg cac aca aag acc tac cag gcc agc tcc cag cca ggc      1817
Leu Ser Pro Leu His Thr Lys Thr Tyr Gln Ala Ser Ser Gln Pro Gly
    360                 365                 370

tcc aca tct aag gat ctg acc aac aat aac atc cca cac ctg ctg tct      1865
Ser Thr Ser Lys Asp Leu Thr Asn Asn Asn Ile Pro His Leu Leu Ser
375                 380                 385                 390

ccc aag gag gcc aag agc aag acc gag ttc gac ttt aat atc gat ccc      1913
Pro Lys Glu Ala Lys Ser Lys Thr Glu Phe Asp Phe Asn Ile Asp Pro
                395                 400                 405

aag cct agc gag ggc cca ggc aca aag tat ctg aag agc aac tcc cgg      1961
Lys Pro Ser Glu Gly Pro Gly Thr Lys Tyr Leu Lys Ser Asn Ser Arg
            410                 415                 420

agc cag cag aat aga cac tcc ttc atg gag tct agc cag tct aag gcc      2009
Ser Gln Gln Asn Arg His Ser Phe Met Glu Ser Ser Gln Ser Lys Ala
        425                 430                 435

ggc acc ctg cag ccc aac gag aag cag agc cgc cac tcc tac atc gat      2057
Gly Thr Leu Gln Pro Asn Glu Lys Gln Ser Arg His Ser Tyr Ile Asp
    440                 445                 450

acc atc ccc cag tcc tct agg agc cct tcc tat cgc aca aag gcc aag      2105
Thr Ile Pro Gln Ser Ser Arg Ser Pro Ser Tyr Arg Thr Lys Ala Lys
455                 460                 465                 470

agc cac ggc gcc ctg tct gac agc aag tcc gtg tct aat ctg tcc gag      2153
Ser His Gly Ala Leu Ser Asp Ser Lys Ser Val Ser Asn Leu Ser Glu
                475                 480                 485

gca agg gca cag atc gca gag ccc agc acc tcc aga tac ttt cct agc      2201
Ala Arg Ala Gln Ile Ala Glu Pro Ser Thr Ser Arg Tyr Phe Pro Ser
            490                 495                 500

tcc tgt ctg gac ctg aac tct cca aca agc cca aca ccc acc cgg cac      2249
Ser Cys Leu Asp Leu Asn Ser Pro Thr Ser Pro Thr Pro Thr Arg His
        505                 510                 515

agc gat aca aga acc ctg ctg tct ccc agc ggc aga aat aac agg aac      2297
Ser Asp Thr Arg Thr Leu Leu Ser Pro Ser Gly Arg Asn Asn Arg Asn
    520                 525                 530

gag ggc acc ctg gat tct aga agg acc aca acc cgg cac agc aag aca      2345
Glu Gly Thr Leu Asp Ser Arg Arg Thr Thr Thr Arg His Ser Lys Thr
535                 540                 545                 550

atg gag gag ctg aag ctg ccc gag cac atg gac tct agc cac tcc cac      2393
Met Glu Glu Leu Lys Leu Pro Glu His Met Asp Ser Ser His Ser His
                555                 560                 565

tct ctg agc gcc cct cac gag tcc ttc tct tac ggc ctg ggc tat acc      2441
Ser Leu Ser Ala Pro His Glu Ser Phe Ser Tyr Gly Leu Gly Tyr Thr
            570                 575                 580

tcc cca ttt tcc tct caa cag cgc ccc cac cgg cac tct atg tac gtg      2489
Ser Pro Phe Ser Ser Gln Gln Arg Pro His Arg His Ser Met Tyr Val
        585                 590                 595

aca cgg gac aag gtg aga gcc aag ggc ctg gac ggc agc ctg tcc atc      2537
```

-continued

```
Thr Arg Asp Lys Val Arg Ala Lys Gly Leu Asp Gly Ser Leu Ser Ile
    600                 605                 610

gga cag gga atg gca gca aga gca aac tcc ctg cag ctg ctg tct cct     2585
Gly Gln Gly Met Ala Ala Arg Ala Asn Ser Leu Gln Leu Leu Ser Pro
615                 620                 625                 630

cag cca gga gag cag ctg cca cca gag atg acc gtg gca cgg agc tcc     2633
Gln Pro Gly Glu Gln Leu Pro Pro Glu Met Thr Val Ala Arg Ser Ser
                635                 640                 645

gtg aag gag aca agc aga gag ggc acc tct agc ttc cac aca cgg cag     2681
Val Lys Glu Thr Ser Arg Glu Gly Thr Ser Ser Phe His Thr Arg Gln
            650                 655                 660

aag tcc gag ggc ggc gtg tat cac gac cct cac tct gac gac ggc acc     2729
Lys Ser Glu Gly Gly Val Tyr His Asp Pro His Ser Asp Asp Gly Thr
        665                 670                 675

gcc cca aag gag aac aga cac ctg tac aac gat cca gtg cct agg agg     2777
Ala Pro Lys Glu Asn Arg His Leu Tyr Asn Asp Pro Val Pro Arg Arg
    680                 685                 690

gtg ggc tcc ttc tat cgg gtg cca tct ccc cgc cct gac aat agc ttt     2825
Val Gly Ser Phe Tyr Arg Val Pro Ser Pro Arg Pro Asp Asn Ser Phe
695                 700                 705                 710

cac gag aat aac gtg tcc acc cgg gtg tcc tct ctg ccc tct gag agc     2873
His Glu Asn Asn Val Ser Thr Arg Val Ser Ser Leu Pro Ser Glu Ser
                715                 720                 725

tcc tct ggc aca aac cac tct aag aga cag ccc gcc ttt gac cct tgg     2921
Ser Ser Gly Thr Asn His Ser Lys Arg Gln Pro Ala Phe Asp Pro Trp
            730                 735                 740

aag agc cca gag aat atc tct cac agc gag cag ctg aag gag aag gag     2969
Lys Ser Pro Glu Asn Ile Ser His Ser Glu Gln Leu Lys Glu Lys Glu
        745                 750                 755

aag cag ggc ttc ttt agg agc atg aag aag aag aag aag aag agc cag     3017
Lys Gln Gly Phe Phe Arg Ser Met Lys Lys Lys Lys Lys Lys Ser Gln
    760                 765                 770

acc gtg cct aac tcc gac tct ccc gat ctg ctg acc ctg cag aag agc     3065
Thr Val Pro Asn Ser Asp Ser Pro Asp Leu Leu Thr Leu Gln Lys Ser
775                 780                 785                 790

atc cac agc gcc tcc aca cca agc tcc cgg cct aag gag tgg cgg ccc     3113
Ile His Ser Ala Ser Thr Pro Ser Ser Arg Pro Lys Glu Trp Arg Pro
                795                 800                 805

gag aag atc tcc gat ctg cag acc cag agc cag cca ctg aag tcc ctg     3161
Glu Lys Ile Ser Asp Leu Gln Thr Gln Ser Gln Pro Leu Lys Ser Leu
            810                 815                 820

cgc aag ctg ctg cac ctg tct agc gcc agc aac cac cct gcc tcc tct     3209
Arg Lys Leu Leu His Leu Ser Ser Ala Ser Asn His Pro Ala Ser Ser
        825                 830                 835

gac cca agg ttc cag ccc ctg aca gcc cag cag acc aag aac tct ttt     3257
Asp Pro Arg Phe Gln Pro Leu Thr Ala Gln Gln Thr Lys Asn Ser Phe
    840                 845                 850

agc gag atc cgc atc cac cca ctg tcc caa gcc tct gga ggc agc tcc     3305
Ser Glu Ile Arg Ile His Pro Leu Ser Gln Ala Ser Gly Gly Ser Ser
855                 860                 865                 870

aac atc agg cag gag cca gca cca aag ggc cgc ccc gcc ctg cag ctg     3353
Asn Ile Arg Gln Glu Pro Ala Pro Lys Gly Arg Pro Ala Leu Gln Leu
                875                 880                 885

cct gga cag atg gac ccc gga tgg cac gtg tct agc gtg aca cgg tcc     3401
Pro Gly Gln Met Asp Pro Gly Trp His Val Ser Ser Val Thr Arg Ser
            890                 895                 900

gcc acc gag gga cca tcc tac tct gag cag ctg gga gca aag agc gga     3449
Ala Thr Glu Gly Pro Ser Tyr Ser Glu Gln Leu Gly Ala Lys Ser Gly
        905                 910                 915
```

```
cct aac gga cac cca tat aac aga acc aat aga tcc agg atg cct aat     3497
Pro Asn Gly His Pro Tyr Asn Arg Thr Asn Arg Ser Arg Met Pro Asn
    920                 925                 930

ctg aac gac ctg aag gag aca gcc ctg tga tag aagcttatcg ataatcaacc   3550
Leu Asn Asp Leu Lys Glu Thr Ala Leu
935                 940

tctggattac aaaatttgtg aaagattgac tggtattctt aactatgttg ctccttttac   3610

gctatgtgga tacgctgctt taatgccttt gtatcatgct attgcttccc gtatggcttt   3670

cattttctcc tccttgtata aatcctggtt gctgtctctt tatgaggagt tgtggcccgt   3730

tgtcaggcaa cgtggcgtgg tgtgcactgt gtttgctgac gcaaccccca ctggttgggg   3790

cattgccacc acctgtcagc tcctttccgg gactttcgct ttccccctcc ctattgccac   3850

ggcggaactc atcgccgcct gccttgcccg ctgctggaca ggggctcggc tgttgggcac   3910

tgacaattcc gtggtgttgt cggggaaatc atcgtccttt ccttggctgc tcgcctgtgt   3970

tgccacctgg attctgcgcg ggacgtcctt ctgctacgtc ccttcggccc tcaatccagc   4030

ggaccttcct tcccgcggcc tgctgccggc tctgcggcct cttccgcgtc ttcgccttcg   4090

ccctcagacg agtcggatct ccctttgggc cgcctccccg catcgatacc gtcgatcgag   4150

gccgcttcga gcagacatga taagatacat tgatgagttt ggacaaacca caactagaat   4210

gcagtgaaaa aaatgcttta tttgtgaaat ttgtgatgct attgctttat ttgtaaccat   4270

tataagctgc aataaacaag ttaacaacaa caattgcatt cattttatgt ttcaggttca   4330

ggggggagatg tgggaggttt tttaaagcaa gtaaaacctc tacaaatgtg gtaaaatcga   4390

taaggatctt cctagagcat ggctacgtag ataagtagca tggcgggtta atcattaact   4450

acaaggaacc cctagtgatg gagttggcca ctccctctct gcgcgctcgc tcgctcactg   4510

aggccgggcg accaaaggtc gcccgacgcc cgggctttgc ccgggcggcc tcagtgagcg   4570

agcgagcgcg cag                                                      4583
```

```
<210> SEQ ID NO 8
<211> LENGTH: 943
<212> TYPE: PRT
<213> ORGANISM: Artificial Sequence
<220> FEATURE:
<223> OTHER INFORMATION: Synthetic Construct

<400> SEQUENCE: 8

Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
```

-continued

```
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Asn Gln Ala Gly Lys Ser Thr Ala Leu Gln Ser
305                 310                 315                 320

His His Arg Ser Asn Ser Lys Asp Ile Gln Asn Leu Ser Val Gly Leu
                325                 330                 335

Pro Arg Ala Asp Glu Gly Leu Pro Ala Asn Glu Ser Phe Leu Asn Gly
            340                 345                 350

Asn Leu Ala Gly Ala Ser Leu Ser Pro Leu His Thr Lys Thr Tyr Gln
        355                 360                 365

Ala Ser Ser Gln Pro Gly Ser Thr Ser Lys Asp Leu Thr Asn Asn Asn
    370                 375                 380

Ile Pro His Leu Leu Ser Pro Lys Glu Ala Lys Ser Lys Thr Glu Phe
385                 390                 395                 400

Asp Phe Asn Ile Asp Pro Lys Pro Ser Glu Gly Pro Gly Thr Lys Tyr
                405                 410                 415

Leu Lys Ser Asn Ser Arg Ser Gln Gln Asn Arg His Ser Phe Met Glu
            420                 425                 430

Ser Ser Gln Ser Lys Ala Gly Thr Leu Gln Pro Asn Glu Lys Gln Ser
        435                 440                 445

Arg His Ser Tyr Ile Asp Thr Ile Pro Gln Ser Ser Arg Ser Pro Ser
    450                 455                 460

Tyr Arg Thr Lys Ala Lys Ser His Gly Ala Leu Ser Asp Ser Lys Ser
465                 470                 475                 480

Val Ser Asn Leu Ser Glu Ala Arg Ala Gln Ile Ala Glu Pro Ser Thr
                485                 490                 495

Ser Arg Tyr Phe Pro Ser Ser Cys Leu Asp Leu Asn Ser Pro Thr Ser
            500                 505                 510

Pro Thr Pro Thr Arg His Ser Asp Thr Arg Thr Leu Leu Ser Pro Ser
        515                 520                 525

Gly Arg Asn Asn Arg Asn Glu Gly Thr Leu Asp Ser Arg Arg Thr Thr
    530                 535                 540

Thr Arg His Ser Lys Thr Met Glu Glu Leu Lys Leu Pro Glu His Met
545                 550                 555                 560
```

```
Asp Ser Ser His Ser His Ser Leu Ser Ala Pro His Glu Ser Phe Ser
                565                 570                 575

Tyr Gly Leu Gly Tyr Thr Ser Pro Phe Ser Ser Gln Gln Arg Pro His
            580                 585                 590

Arg His Ser Met Tyr Val Thr Arg Asp Lys Val Arg Ala Lys Gly Leu
        595                 600                 605

Asp Gly Ser Leu Ser Ile Gly Gln Gly Met Ala Ala Arg Ala Asn Ser
    610                 615                 620

Leu Gln Leu Leu Ser Pro Gln Pro Gly Glu Gln Leu Pro Pro Glu Met
625                 630                 635                 640

Thr Val Ala Arg Ser Ser Val Lys Glu Thr Ser Arg Glu Gly Thr Ser
                645                 650                 655

Ser Phe His Thr Arg Gln Lys Ser Glu Gly Gly Val Tyr His Asp Pro
            660                 665                 670

His Ser Asp Asp Gly Thr Ala Pro Lys Glu Asn Arg His Leu Tyr Asn
        675                 680                 685

Asp Pro Val Pro Arg Arg Val Gly Ser Phe Tyr Arg Val Pro Ser Pro
    690                 695                 700

Arg Pro Asp Asn Ser Phe His Glu Asn Asn Val Ser Thr Arg Val Ser
705                 710                 715                 720

Ser Leu Pro Ser Glu Ser Ser Ser Gly Thr Asn His Ser Lys Arg Gln
                725                 730                 735

Pro Ala Phe Asp Pro Trp Lys Ser Pro Glu Asn Ile Ser His Ser Glu
            740                 745                 750

Gln Leu Lys Glu Lys Glu Lys Gln Gly Phe Phe Arg Ser Met Lys Lys
        755                 760                 765

Lys Lys Lys Lys Ser Gln Thr Val Pro Asn Ser Asp Ser Pro Asp Leu
    770                 775                 780

Leu Thr Leu Gln Lys Ser Ile His Ser Ala Ser Thr Pro Ser Ser Arg
785                 790                 795                 800

Pro Lys Glu Trp Arg Pro Glu Lys Ile Ser Asp Leu Gln Thr Gln Ser
                805                 810                 815

Gln Pro Leu Lys Ser Leu Arg Lys Leu Leu His Leu Ser Ser Ala Ser
            820                 825                 830

Asn His Pro Ala Ser Ser Asp Pro Arg Phe Gln Pro Leu Thr Ala Gln
        835                 840                 845

Gln Thr Lys Asn Ser Phe Ser Glu Ile Arg Ile His Pro Leu Ser Gln
    850                 855                 860

Ala Ser Gly Gly Ser Ser Asn Ile Arg Gln Glu Pro Ala Pro Lys Gly
865                 870                 875                 880

Arg Pro Ala Leu Gln Leu Pro Gly Gln Met Asp Pro Gly Trp His Val
                885                 890                 895

Ser Ser Val Thr Arg Ser Ala Thr Glu Gly Pro Ser Tyr Ser Glu Gln
            900                 905                 910

Leu Gly Ala Lys Ser Gly Pro Asn Gly His Pro Tyr Asn Arg Thr Asn
        915                 920                 925

Arg Ser Arg Met Pro Asn Leu Asn Asp Leu Lys Glu Thr Ala Leu
    930                 935                 940
```

<210> SEQ ID NO 9
<211> LENGTH: 4706
<212> TYPE: DNA
<213> ORGANISM: Artificial Sequence
<220> FEATURE:

<223> OTHER INFORMATION: Expression Cassette
<220> FEATURE:
<221> NAME/KEY: repeat_region
<222> LOCATION: (1)..(130)
<223> OTHER INFORMATION: 5'ITR
<220> FEATURE:
<221> NAME/KEY: misc_feature
<222> LOCATION: (130)..(168)
<223> OTHER INFORMATION: AAV2 seq upstream of 3'ITR
<220> FEATURE:
<221> NAME/KEY: promoter
<222> LOCATION: (213)..(678)
<223> OTHER INFORMATION: hSynapsin
<220> FEATURE:
<221> NAME/KEY: misc_feature
<222> LOCATION: (690)..(695)
<223> OTHER INFORMATION: Kozak
<220> FEATURE:
<221> NAME/KEY: CDS
<222> LOCATION: (696)..(3653)
<223> OTHER INFORMATION: hCDKL5-4GS
<220> FEATURE:
<221> NAME/KEY: misc_feature
<222> LOCATION: (3668)..(4255)
<223> OTHER INFORMATION: WRPE
<220> FEATURE:
<221> NAME/KEY: polyA_signal
<222> LOCATION: (4273)..(4511)
<223> OTHER INFORMATION: SV40 PolyA
<220> FEATURE:
<221> NAME/KEY: misc_feature
<222> LOCATION: (4539)..(4577)
<223> OTHER INFORMATION: AAV2 seq upstream of 3'ITR
<220> FEATURE:
<221> NAME/KEY: repeat_region
<222> LOCATION: (4577)..(4706)
<223> OTHER INFORMATION: 3'ITR

<400> SEQUENCE: 9
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcc tctagaacta tagctagcat gcctgcagag ggccctgcgt atgagtgcaa 240
gtgggtttta ggaccaggat gaggcggggt gggggtgcct acctgacgac cgaccccgac 300
ccactggaca agcacccaac ccccattccc caaattgcgc atcccctatc agagaggggg 360
aggggaaaca ggatgcggcg aggcgcgtgc gcactgccag cttcagcacc gcggacagtg 420
ccttcgcccc cgcctggcgg cgcgcgccac cgccgcctca gcactgaagg cgcgctgacg 480
tcactcgccg gtcccccgca aactcccctt cccggccacc ttggtcgcgt ccgcgccgcc 540
gccggcccag ccggaccgca ccacgcgagg cgcgagatag gggggcacgg gcgcgaccat 600
ctgcgctgcg gcgccggcga ctcagcgctg cctcagtctg cggtgggcag cggaggagtc 660
gtgtcgtgcc tgagagcgca gtcgaattcg ccacc atg aag atc ccc aat atc 713
Met Lys Ile Pro Asn Ile
1 5 ggc aac gtg atg aat aag ttc gag atc ctg gga gtg gtg gga gag gga 761
Gly Asn Val Met Asn Lys Phe Glu Ile Leu Gly Val Val Gly Glu Gly
10 15 20 gca tac gga gtg gtg ctg aag tgc cgg cac aag gag aca cac gag atc 809
Ala Tyr Gly Val Val Leu Lys Cys Arg His Lys Glu Thr His Glu Ile
25 30 35 gtg gcc atc aag aag ttt aag gat agc gag gag aat gag gag gtg aag 857
Val Ala Ile Lys Lys Phe Lys Asp Ser Glu Glu Asn Glu Glu Val Lys
40 45 50 gag aca acc ctg agg gag ctg aag atg ctg cgc aca ctg aag cag gag 905

```
Glu Thr Thr Leu Arg Glu Leu Lys Met Leu Arg Thr Leu Lys Gln Glu
55                  60                  65                  70

aac atc gtg gag ctg aag gag gcc ttc cgg aga agg ggc aag ctg tac      953
Asn Ile Val Glu Leu Lys Glu Ala Phe Arg Arg Arg Gly Lys Leu Tyr
                75                  80                  85

ctg gtg ttt gag tac gtg gag aag aac atg ctg gag ctg ctg gag gag     1001
Leu Val Phe Glu Tyr Val Glu Lys Asn Met Leu Glu Leu Leu Glu Glu
            90                  95                  100

atg cca aat ggc gtg ccc cct gag aag gtg aag tcc tac atc tat cag     1049
Met Pro Asn Gly Val Pro Pro Glu Lys Val Lys Ser Tyr Ile Tyr Gln
        105                 110                 115

ctg atc aag gcc atc cac tgg tgc cac aag aac gac atc gtg cac agg     1097
Leu Ile Lys Ala Ile His Trp Cys His Lys Asn Asp Ile Val His Arg
    120                 125                 130

gat atc aag ccc gag aac ctg ctg atc tcc cac aat gac gtg ctg aag     1145
Asp Ile Lys Pro Glu Asn Leu Leu Ile Ser His Asn Asp Val Leu Lys
135                 140                 145                 150

ctg tgc gat ttc ggc ttt gcc cgc aac ctg agc gag ggc aac aac gcc     1193
Leu Cys Asp Phe Gly Phe Ala Arg Asn Leu Ser Glu Gly Asn Asn Ala
                155                 160                 165

aat tac aca gag tac gtg gca acc agg tgg tac cgg agc cct gag ctg     1241
Asn Tyr Thr Glu Tyr Val Ala Thr Arg Trp Tyr Arg Ser Pro Glu Leu
            170                 175                 180

ctg ctg gga gca cca tac ggc aag tct gtg gac atg tgg agc gtg ggc     1289
Leu Leu Gly Ala Pro Tyr Gly Lys Ser Val Asp Met Trp Ser Val Gly
        185                 190                 195

tgc atc ctg gga gag ctg tcc gac gga cag cca ctg ttc cct ggc gag     1337
Cys Ile Leu Gly Glu Leu Ser Asp Gly Gln Pro Leu Phe Pro Gly Glu
    200                 205                 210

tct gag atc gat cag ctg ttt acc atc cag aag gtg ctg ggc ccc ctg     1385
Ser Glu Ile Asp Gln Leu Phe Thr Ile Gln Lys Val Leu Gly Pro Leu
215                 220                 225                 230

cct tcc gag cag atg aag ctg ttc tac tct aac cct agg ttc cac ggc     1433
Pro Ser Glu Gln Met Lys Leu Phe Tyr Ser Asn Pro Arg Phe His Gly
                235                 240                 245

ctg cgc ttt cca gcc gtg aat cac ccc cag tct ctg gag cgc cgg tat     1481
Leu Arg Phe Pro Ala Val Asn His Pro Gln Ser Leu Glu Arg Arg Tyr
            250                 255                 260

ctg ggc atc ctg aac agc gtg ctg ctg gat ctg atg aag aat ctg ctg     1529
Leu Gly Ile Leu Asn Ser Val Leu Leu Asp Leu Met Lys Asn Leu Leu
        265                 270                 275

aag ctg gac ccc gcc gat agg tac ctg acc gag cag tgt ctg aac cac     1577
Lys Leu Asp Pro Ala Asp Arg Tyr Leu Thr Glu Gln Cys Leu Asn His
    280                 285                 290

cct aca ttc cag acc cag aga ctg ctg gac agg tcc cca tct cgc aat     1625
Pro Thr Phe Gln Thr Gln Arg Leu Leu Asp Arg Ser Pro Ser Arg Asn
295                 300                 305                 310

cag gcc ggc aag tcc aca gcc ctg cag tct cac cac agg agc aac tcc     1673
Gln Ala Gly Lys Ser Thr Ala Leu Gln Ser His His Arg Ser Asn Ser
                315                 320                 325

aag gac atc cag aat ctg tcc gtg ggc ctg cca agg gca gac gag ggc     1721
Lys Asp Ile Gln Asn Leu Ser Val Gly Leu Pro Arg Ala Asp Glu Gly
            330                 335                 340

ctg cct gcc aac gag agc ttt ctg aat gga aac ctg gca gga gcc tct     1769
Leu Pro Ala Asn Glu Ser Phe Leu Asn Gly Asn Leu Ala Gly Ala Ser
        345                 350                 355

ctg agc cca ctg cac aca aag acc tac cag gcc agc tcc cag cct ggc     1817
Leu Ser Pro Leu His Thr Lys Thr Tyr Gln Ala Ser Ser Gln Pro Gly
    360                 365                 370
```

```
tcc aca tct aag gac ctg acc aac aat aac atc cct cac ctg ctg agc      1865
Ser Thr Ser Lys Asp Leu Thr Asn Asn Asn Ile Pro His Leu Leu Ser
375                 380                 385                 390

cca aag gag gcc aag tcc aag acc gag ttc gac ttt aat atc gat cca      1913
Pro Lys Glu Ala Lys Ser Lys Thr Glu Phe Asp Phe Asn Ile Asp Pro
                395                 400                 405

aag cca tcc gag gga cca gga aca aag tat ctg aag agc aac tcc cgg      1961
Lys Pro Ser Glu Gly Pro Gly Thr Lys Tyr Leu Lys Ser Asn Ser Arg
            410                 415                 420

agc cag cag aat aga cac tct ttc atg gag tct agc cag agc aag gcc      2009
Ser Gln Gln Asn Arg His Ser Phe Met Glu Ser Ser Gln Ser Lys Ala
        425                 430                 435

ggc acc ctg cag cct aac gag aag cag agc cgc cac tcc tac atc gat      2057
Gly Thr Leu Gln Pro Asn Glu Lys Gln Ser Arg His Ser Tyr Ile Asp
    440                 445                 450

acc atc cca cag tcc tct agg agc ccc tcc tat cgc aca aag gcc aag      2105
Thr Ile Pro Gln Ser Ser Arg Ser Pro Ser Tyr Arg Thr Lys Ala Lys
455                 460                 465                 470

tcc cac ggc gcc ctg tct gac agc aag tcc gtg tct aat ctg agc gag      2153
Ser His Gly Ala Leu Ser Asp Ser Lys Ser Val Ser Asn Leu Ser Glu
                475                 480                 485

gca agg gca cag atc gca gag cca agc acc tcc aga tac ttt ccc agc      2201
Ala Arg Ala Gln Ile Ala Glu Pro Ser Thr Ser Arg Tyr Phe Pro Ser
            490                 495                 500

tcc tgt ctg gac ctg aac tct ccc aca agc cct aca cca acc cgg cac      2249
Ser Cys Leu Asp Leu Asn Ser Pro Thr Ser Pro Thr Pro Thr Arg His
        505                 510                 515

agc gat aca aga acc ctg ctg tct cct agc ggc aga aat aac agg aac      2297
Ser Asp Thr Arg Thr Leu Leu Ser Pro Ser Gly Arg Asn Asn Arg Asn
    520                 525                 530

gag ggc acc ctg gat agc aga agg acc aca acc agg cac tcc aag aca      2345
Glu Gly Thr Leu Asp Ser Arg Arg Thr Thr Thr Arg His Ser Lys Thr
535                 540                 545                 550

atg gag gag ctg aag ctg cct gag cac atg gac tct agc cac tcc cac      2393
Met Glu Glu Leu Lys Leu Pro Glu His Met Asp Ser Ser His Ser His
                555                 560                 565

tct ctg agc gcc cca cac gag tcc ttc tct tac ggc ctg ggc tat acc      2441
Ser Leu Ser Ala Pro His Glu Ser Phe Ser Tyr Gly Leu Gly Tyr Thr
            570                 575                 580

agc cct ttt tcc tct caa caa cgc cca cac cgg cac tcc atg tac gtg      2489
Ser Pro Phe Ser Ser Gln Gln Arg Pro His Arg His Ser Met Tyr Val
        585                 590                 595

aca cgg gac aag gtg aga gcc aag ggc ctg gac ggc agc ctg tcc atc      2537
Thr Arg Asp Lys Val Arg Ala Lys Gly Leu Asp Gly Ser Leu Ser Ile
    600                 605                 610

gga cag gga atg gca gca agg gca aat agc ctg cag ctg ctg tcc cca      2585
Gly Gln Gly Met Ala Ala Arg Ala Asn Ser Leu Gln Leu Leu Ser Pro
615                 620                 625                 630

cag cct gga gag cag ctg cca cca gag atg acc gtg gca cgg agc tcc      2633
Gln Pro Gly Glu Gln Leu Pro Pro Glu Met Thr Val Ala Arg Ser Ser
                635                 640                 645

gtg aag gag aca agc aga gag ggc acc tct agc ttc cac aca cgg cag      2681
Val Lys Glu Thr Ser Arg Glu Gly Thr Ser Ser Phe His Thr Arg Gln
            650                 655                 660

aag agc gag ggc ggc gtg tat cac gac cca cac tcc gac gac gga acc      2729
Lys Ser Glu Gly Gly Val Tyr His Asp Pro His Ser Asp Asp Gly Thr
        665                 670                 675

gca cct aag gag aac aga cac ctg tac aac gat cca gtg ccc cgc cgg      2777
Ala Pro Lys Glu Asn Arg His Leu Tyr Asn Asp Pro Val Pro Arg Arg
    680                 685                 690
```

```
gtg ggc tct ttc tat cgg gtg cct agc cca cgc ccc gac aac tcc ttt     2825
Val Gly Ser Phe Tyr Arg Val Pro Ser Pro Arg Pro Asp Asn Ser Phe
695                 700                 705                 710

cac gag aat aac gtg tct acc cgg gtg tcc tct ctg ccc agc gag agc     2873
His Glu Asn Asn Val Ser Thr Arg Val Ser Ser Leu Pro Ser Glu Ser
                715                 720                 725

tcc tct ggc aca aac cac tcc aag aga cag cca gcc ttt gat ccc tgg     2921
Ser Ser Gly Thr Asn His Ser Lys Arg Gln Pro Ala Phe Asp Pro Trp
            730                 735                 740

aag tct cct gag aat atc tct cac agc gag cag ctg aag gag aag gag     2969
Lys Ser Pro Glu Asn Ile Ser His Ser Glu Gln Leu Lys Glu Lys Glu
        745                 750                 755

aag cag ggc ttc ttt cgg tcc atg aag aag aag aag aag aag agc cag     3017
Lys Gln Gly Phe Phe Arg Ser Met Lys Lys Lys Lys Lys Lys Ser Gln
    760                 765                 770

aca acc gac agc acc aac ggc gag aat cca agc atc aag aag tcc ctg     3065
Thr Thr Asp Ser Thr Asn Gly Glu Asn Pro Ser Ile Lys Lys Ser Leu
775                 780                 785                 790

ttc ccc ctg ttt aac agc aag aat cac ctg aag cac agc tcc tct ctg     3113
Phe Pro Leu Phe Asn Ser Lys Asn His Leu Lys His Ser Ser Ser Leu
                795                 800                 805

aag aag ctg ccc gtg gtg aca cct cca atg gtg ccc aat tcc gac tct     3161
Lys Lys Leu Pro Val Val Thr Pro Pro Met Val Pro Asn Ser Asp Ser
            810                 815                 820

cct gat ctg ctg acc ctg cag aag tcc atc cac agc gcc tcc aca cca     3209
Pro Asp Leu Leu Thr Leu Gln Lys Ser Ile His Ser Ala Ser Thr Pro
        825                 830                 835

agc tcc cgg ccc aag gag tgg cgg ccc gag aag atc agc gat ctg cag     3257
Ser Ser Arg Pro Lys Glu Trp Arg Pro Glu Lys Ile Ser Asp Leu Gln
    840                 845                 850

acc cag tcc cag ccc ctg aag tct ctg aga aag ctg ctg cac ctg tct     3305
Thr Gln Ser Gln Pro Leu Lys Ser Leu Arg Lys Leu Leu His Leu Ser
855                 860                 865                 870

agc gcc tcc aac cac cca gcc tcc tct gac cct cgg ttc cag cca ctg     3353
Ser Ala Ser Asn His Pro Ala Ser Ser Asp Pro Arg Phe Gln Pro Leu
                875                 880                 885

aca gcc cag cag acc aag aac tct ttt agc gag atc cgc atc cac cca     3401
Thr Ala Gln Gln Thr Lys Asn Ser Phe Ser Glu Ile Arg Ile His Pro
            890                 895                 900

ctg tcc caa gcc tct gga ggc agc tcc aac atc agg cag gag cct gcc     3449
Leu Ser Gln Ala Ser Gly Gly Ser Ser Asn Ile Arg Gln Glu Pro Ala
        905                 910                 915

cca aag ggc cgc cca gcc ctg cag ctg cca gga cag atg gac ccc ggc     3497
Pro Lys Gly Arg Pro Ala Leu Gln Leu Pro Gly Gln Met Asp Pro Gly
    920                 925                 930

tgg cac gtg tct agc gtg aca cgg agc gcc acc gag gga cct tcc tac     3545
Trp His Val Ser Ser Val Thr Arg Ser Ala Thr Glu Gly Pro Ser Tyr
935                 940                 945                 950

tct gag cag ctg gga gca aag tct gga cca aac gga cac cct tat aac     3593
Ser Glu Gln Leu Gly Ala Lys Ser Gly Pro Asn Gly His Pro Tyr Asn
                955                 960                 965

aga acc aat aga agc agg atg cca aat ctg aac gac ctg aag gag aca     3641
Arg Thr Asn Arg Ser Arg Met Pro Asn Leu Asn Asp Leu Lys Glu Thr
            970                 975                 980

gcc ctg tga tag aagcttatcg ataatcaacc tctggattac aaaatttgtg         3693
Ala Leu

aaagattgac tggtattctt aactatgttg ctccttttac gctatgtgga tacgctgctt   3753

taatgccttt gtatcatgct attgcttccc gtatggcttt cattttctcc tccttgtata   3813
```

aatcctggtt gctgtctctt tatgaggagt tgtggcccgt tgtcaggcaa cgtggcgtgg 3873 tgtgcactgt gtttgctgac gcaaccccca ctggttgggg cattgccacc acctgtcagc 3933 tcctttccgg gactttcgct ttccccctcc ctattgccac ggcggaactc atcgccgcct 3993 gccttgcccg ctgctggaca ggggctcggc tgttgggcac tgacaattcc gtggtgttgt 4053 cggggaaatc atcgtccttt ccttggctgc tcgcctgtgt tgccacctgg attctgcgcg 4113 ggacgtcctt ctgctacgtc ccttcggccc tcaatccagc ggaccttcct tcccgcggcc 4173 tgctgccggc tctgcggcct cttccgcgtc ttcgccttcg ccctcagacg agtcggatct 4233 ccctttgggc cgcctccccg catcgatacc gtcgatcgag gccgcttcga gcagacatga 4293 taagatacat tgatgagttt ggacaaacca caactagaat gcagtgaaaa aaatgcttta 4353 tttgtgaaat ttgtgatgct attgctttat ttgtaaccat tataagctgc aataaacaag 4413 ttaacaacaa caattgcatt cattttatgt ttcaggttca gggggagatg tgggaggttt 4473 tttaaagcaa gtaaaacctc tacaaatgtg gtaaaatcga taaggatctt cctagagcat 4533 ggctacgtag ataagtagca tggcgggtta atcattaact acaaggaacc cctagtgatg 4593 gagttggcca ctccctctct gcgcgctcgc tcgctcactg aggccgggcg accaaaggtc 4653 gcccgacgcc cgggctttgc ccgggcggcc tcagtgagcg agcgagcgcg cag 4706

<210> SEQ ID NO 10
<211> LENGTH: 984
<212> TYPE: PRT
<213> ORGANISM: Artificial Sequence
<220> FEATURE:
<223> OTHER INFORMATION: Synthetic Construct

<400> SEQUENCE: 10

Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

```
Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Asn Gln Ala Gly Lys Ser Thr Ala Leu Gln Ser
305                 310                 315                 320

His His Arg Ser Asn Ser Lys Asp Ile Gln Asn Leu Ser Val Gly Leu
                325                 330                 335

Pro Arg Ala Asp Glu Gly Leu Pro Ala Asn Glu Ser Phe Leu Asn Gly
            340                 345                 350

Asn Leu Ala Gly Ala Ser Leu Ser Pro Leu His Thr Lys Thr Tyr Gln
        355                 360                 365

Ala Ser Ser Gln Pro Gly Ser Thr Ser Lys Asp Leu Thr Asn Asn Asn
    370                 375                 380

Ile Pro His Leu Leu Ser Pro Lys Glu Ala Lys Ser Lys Thr Glu Phe
385                 390                 395                 400

Asp Phe Asn Ile Asp Pro Lys Pro Ser Glu Gly Pro Gly Thr Lys Tyr
                405                 410                 415

Leu Lys Ser Asn Ser Arg Ser Gln Gln Asn Arg His Ser Phe Met Glu
            420                 425                 430

Ser Ser Gln Ser Lys Ala Gly Thr Leu Gln Pro Asn Glu Lys Gln Ser
        435                 440                 445

Arg His Ser Tyr Ile Asp Thr Ile Pro Gln Ser Ser Arg Ser Pro Ser
    450                 455                 460

Tyr Arg Thr Lys Ala Lys Ser His Gly Ala Leu Ser Asp Ser Lys Ser
465                 470                 475                 480

Val Ser Asn Leu Ser Glu Ala Arg Ala Gln Ile Ala Glu Pro Ser Thr
                485                 490                 495

Ser Arg Tyr Phe Pro Ser Ser Cys Leu Asp Leu Asn Ser Pro Thr Ser
            500                 505                 510

Pro Thr Pro Thr Arg His Ser Asp Thr Arg Thr Leu Leu Ser Pro Ser
        515                 520                 525

Gly Arg Asn Asn Arg Asn Glu Gly Thr Leu Asp Ser Arg Arg Thr Thr
    530                 535                 540

Thr Arg His Ser Lys Thr Met Glu Glu Leu Lys Leu Pro Glu His Met
545                 550                 555                 560

Asp Ser Ser His Ser His Ser Leu Ser Ala Pro His Glu Ser Phe Ser
                565                 570                 575

Tyr Gly Leu Gly Tyr Thr Ser Pro Phe Ser Ser Gln Gln Arg Pro His
            580                 585                 590

Arg His Ser Met Tyr Val Thr Arg Asp Lys Val Arg Ala Lys Gly Leu
        595                 600                 605

Asp Gly Ser Leu Ser Ile Gly Gln Gly Met Ala Ala Arg Ala Asn Ser
    610                 615                 620
```

```
Leu Gln Leu Leu Ser Pro Gln Pro Gly Glu Gln Leu Pro Pro Glu Met
625                 630                 635                 640

Thr Val Ala Arg Ser Ser Val Lys Glu Thr Ser Arg Glu Gly Thr Ser
                645                 650                 655

Ser Phe His Thr Arg Gln Lys Ser Glu Gly Gly Val Tyr His Asp Pro
            660                 665                 670

His Ser Asp Asp Gly Thr Ala Pro Lys Glu Asn Arg His Leu Tyr Asn
        675                 680                 685

Asp Pro Val Pro Arg Arg Val Gly Ser Phe Tyr Arg Val Pro Ser Pro
    690                 695                 700

Arg Pro Asp Asn Ser Phe His Glu Asn Asn Val Ser Thr Arg Val Ser
705                 710                 715                 720

Ser Leu Pro Ser Glu Ser Ser Ser Gly Thr Asn His Ser Lys Arg Gln
                725                 730                 735

Pro Ala Phe Asp Pro Trp Lys Ser Pro Glu Asn Ile Ser His Ser Glu
            740                 745                 750

Gln Leu Lys Glu Lys Glu Lys Gln Gly Phe Phe Arg Ser Met Lys Lys
        755                 760                 765

Lys Lys Lys Lys Ser Gln Thr Thr Asp Ser Thr Asn Gly Glu Asn Pro
    770                 775                 780

Ser Ile Lys Lys Ser Leu Phe Pro Leu Phe Asn Ser Lys Asn His Leu
785                 790                 795                 800

Lys His Ser Ser Ser Leu Lys Lys Leu Pro Val Val Thr Pro Pro Met
                805                 810                 815

Val Pro Asn Ser Asp Ser Pro Asp Leu Leu Thr Leu Gln Lys Ser Ile
            820                 825                 830

His Ser Ala Ser Thr Pro Ser Ser Arg Pro Lys Glu Trp Arg Pro Glu
        835                 840                 845

Lys Ile Ser Asp Leu Gln Thr Gln Ser Gln Pro Leu Lys Ser Leu Arg
    850                 855                 860

Lys Leu Leu His Leu Ser Ser Ala Ser Asn His Pro Ala Ser Ser Asp
865                 870                 875                 880

Pro Arg Phe Gln Pro Leu Thr Ala Gln Gln Thr Lys Asn Ser Phe Ser
                885                 890                 895

Glu Ile Arg Ile His Pro Leu Ser Gln Ala Ser Gly Gly Ser Ser Asn
            900                 905                 910

Ile Arg Gln Glu Pro Ala Pro Lys Gly Arg Pro Ala Leu Gln Leu Pro
        915                 920                 925

Gly Gln Met Asp Pro Gly Trp His Val Ser Ser Val Thr Arg Ser Ala
    930                 935                 940

Thr Glu Gly Pro Ser Tyr Ser Glu Gln Leu Gly Ala Lys Ser Gly Pro
945                 950                 955                 960

Asn Gly His Pro Tyr Asn Arg Thr Asn Arg Ser Arg Met Pro Asn Leu
                965                 970                 975

Asn Asp Leu Lys Glu Thr Ala Leu
            980
```

<210> SEQ ID NO 11
<211> LENGTH: 22
<212> TYPE: DNA
<213> ORGANISM: Artificial Sequence
<220> FEATURE:
<223> OTHER INFORMATION: targeting site

<400> SEQUENCE: 11
agtgaattct accagtgcca ta 22

<210> SEQ ID NO 12
<211> LENGTH: 23
<212> TYPE: DNA
<213> ORGANISM: Artificial Sequence
<220> FEATURE:
<223> OTHER INFORMATION: targeting site

<400> SEQUENCE: 12
agcaaaaatg tgctagtgcc aaa 23

<210> SEQ ID NO 13
<211> LENGTH: 24
<212> TYPE: DNA
<213> ORGANISM: Artificial Sequence
<220> FEATURE:
<223> OTHER INFORMATION: targeting sequence

<400> SEQUENCE: 13
agtgtgagtt ctaccattgc caaa 24

<210> SEQ ID NO 14
<211> LENGTH: 23
<212> TYPE: DNA
<213> ORGANISM: Artificial Sequence
<220> FEATURE:
<223> OTHER INFORMATION: targeting sequence

<400> SEQUENCE: 14
agggattcct gggaaaactg gac 23

<210> SEQ ID NO 15
<211> LENGTH: 16
<212> TYPE: DNA
<213> ORGANISM: Artificial Sequence
<220> FEATURE:
<223> OTHER INFORMATION: spacer

<400> SEQUENCE: 15
atgacttaaa ccaggt 16

<210> SEQ ID NO 16
<211> LENGTH: 3430
<212> TYPE: DNA
<213> ORGANISM: Artificial Sequence
<220> FEATURE:
<223> OTHER INFORMATION: transcript variant

<400> SEQUENCE: 16
gggggagttg gaggaggaag accctacagg aagttgagct gtactctcca acaggcgagc 60
acatggtcgt ctcctctctc ccttcaggga gtcatttaat acttcatgat tagaacaaat 120
atgtgaaagt tcccaccaac cagtgagaat ttcttccttc agacggtttt ggatcttact 180
gcacagcttt ctgagaagtt cttttggtgc catgttttgt ggcttgcatc aaaagaggag 240
tttgtcttca tgaagattcc taacattggt aatgtgatga ataaatttga gatccttggg 300
gttgtaggtg aaggagccta tggagttgta cttaaatgca gacacaagga aacacatgaa 360
attgtggcga tcaagaaatt caaggacagt gaagaaaatg aagaagtcaa agaaacgact 420
ttacgagagc ttaaaatgct tcggactctc aagcaggaaa acattgtgga gttgaaggaa 480
gcatttcgtc ggaggggaaa gttgtacttg gtgtttgagt atgttgaaaa aaatatgctc 540
gaattgctgg aagaaatgcc aaatggagtt ccacctgaga aagtaaaaag ctacatctat 600
cagctaatca aggctattca ctggtgccat aagaatgata ttgtccatcg agatataaaa 660
ccagaaaatc tcttaatcag ccacaatgat gtcctaaaac tgtgtgactt tggttttgct 720
cgtaatctgt cagaaggcaa taatgctaat tacacagagt acgttgccac cagatggtat 780
cggtccccag aactcttact tggcgctccc tatggaaagt ccgtggacat gtggtcggtg 840
ggctgtattc ttggggagct tagcgatgga cagcctttat ttcctggaga aagtgaaatt 900
gaccaacttt ttactattca gaaggtgcta ggaccacttc catctgagca gatgaagctt 960
ttctacagta atcctcgctt ccatgggctc cggtttccag ctgttaacca tcctcagtcc 1020
ttggaaagaa gataccttgg aattttgaat agtgttctac ttgacctaat gaagaattta 1080
ctgaagttgg acccagctga cagatacttg acagaacagt gtttgaatca ccctacattt 1140
caaacccaga gacttctgga tcgttctcct tcaaggtcag caaaaagaaa accttaccat 1200
gtggaaagca gcacattgtc taatagaaac caagccggca aaagtactgc tttgcagtct 1260
caccacagat ctaacagcaa ggacatccag aacctgagtg taggcctgcc ccgggctgac 1320
gaaggtctcc ctgccaatga aagcttccta aatggaaacc ttgctggagc tagtcttagt 1380
ccactgcaca ccaaaaccta ccaagcaagc agccagcctg ggtctaccag caaagatctc 1440
accaacaaca acataccaca ccttcttagc ccaaaagaag ccaagtcaaa aacagagttt 1500
gattttaata ttgacccaaa gccttcagaa ggcccaggga caaagtacct caagtcaaac 1560
agcagatctc agcagaaccg ccactcattc atggaaagct ctcaaagcaa agctgggaca 1620
ctgcagccca atgaaaagca gagtcggcat agctatattg acacaattcc ccagtcctct 1680
aggagtccct cctacaggac caaggccaaa agccatgggg cactgagtga ctccaagtct 1740
gtgagcaacc tttctgaagc cagggcccaa attgcggagc ccagtaccag taggtacttc 1800
ccatctagct gcttagactt gaattctccc accagcccaa cccccaccag acacagtgac 1860
acgagaactt tgctcagccc ttctggaaga aataaccgaa atgagggaac gctggactca 1920
cgtcgaacca caaccagaca ttctaagacg atggaggaat tgaagctgcc ggagcacatg 1980
gacagtagcc attcccattc actgtctgca cctcacgaat ctttttctta tggactgggc 2040
tacaccagcc ccttttcttc ccagcaacgt cctcataggc attctatgta tgtgacccgt 2100
gacaaagtga gagccaaggg cttggatgga agcttgagca tagggcaagg gatggcagct 2160
agagccaaca gcctgcaact cttgtcaccc cagcctggag aacagctccc tccagagatg 2220
actgtggcaa gatcttcggt caaagagacc tccagagaag gcacctcttc cttccataca 2280
cgccagaagt ctgagggtgg agtgtatcat gacccacact ctgatgatgg cacagccccc 2340
aaagaaaata gacacctata caatgatcct gtgccaagga gagttggtag cttttacaga 2400
gtgccatctc cacgtccaga caattctttc catgaaaata atgtgtcaac tagagtttct 2460
tctctaccat cagagagcag ttctggaacc aaccactcaa aaagacaacc agcattcgat 2520
ccatggaaaa gtcctgaaaa tattagtcat tcagagcaac tcaaggaaaa agagaagcaa 2580
ggatttttca ggtcaatgaa aaagaaaaag aagaaatctc aaacagtacc caattccgac 2640
agccctgatc ttctgacgtt gcagaaatcc attcattctg ctagcactcc aagcagcaga 2700
ccaaaggagt ggcgccccga gaagatctca gatctgcaga cccaaagcca gccattaaaa 2760
tcactgcgca agttgttaca tctctcttcg gcctcaaatc acccggcttc ctcagatccc 2820
cgcttccagc ccttaacagc tcaacaaacc aaaaattcct tctcagaaat tcggattcac 2880
cccctgagcc aggcctctgg cgggagcagc aacatccggc aggaacccgc accgaagggc 2940

```
aggccagccc tccagctgcc agacggtgga tgtgatggca gaagacagag acaccattct   3000

ggaccccaag atagacgctt catgttaagg acgacagaac aacaaggaga atacttctgc   3060

tgtggtgacc caaagaagcc tcacactccg tgcgtcccaa accgagccct tcatcgtcca   3120

atctccagtc ctgctcccta tccagtactc caggtccgag gcacttccat gtgcccgaca   3180

ctccaggtcc gaggcactga tgctttcagc tgcccaaccc agcaatccgg gttctctttc   3240

ttcgtgagac acgttatgag ggaagccctg attcacaggg cccaggtaaa ccaagctgcg   3300

ctcctgacat accatgagaa tgcggcactg acgggcaagt gacttctgca agcctgcggc   3360

tggtcccaat gccctgaatc acctctctca tggaagaacc aattaacacc aatgaatcaa   3420

ccattaaaaa                                                          3430
```

<210> SEQ ID NO 17
<211> LENGTH: 14572
<212> TYPE: DNA
<213> ORGANISM: Artificial Sequence
<220> FEATURE:
<223> OTHER INFORMATION: transcript variant

<400> SEQUENCE: 17

```
agttgtctct gccgctgggg aaggtaaagc ggcgacggcg tcctcaggag ctgtggggtc     60

ccctgctaga agtgggggac tcggcggggg agtcatttaa tacttcatga ttagaacaaa    120

tatgtgaaag ttcccaccaa ccagtgagaa tttcttcctt cagacggttt tggatcttac    180

tgcacagctt tctgagaagt tcttttggtg ccatgttttg tggcttgcat caaaagagga    240

gtttgtcttc atgaagattc ctaacattgg taatgtgatg aataaatttg agatccttgg    300

ggttgtaggt gaaggagcct atggagttgt acttaaatgc agacacaagg aaacacatga    360

aattgtggcg atcaagaaat tcaaggacag tgaagaaaat gaagaagtca aagaaacgac    420

tttacgagag cttaaaatgc ttcggactct caagcaggaa aacattgtgg agttgaagga    480

agcatttcgt cggaggggaa agttgtactt ggtgtttgag tatgttgaaa aaaatatgct    540

cgaattgctg gaagaaatgc caaatggagt tccacctgag aaagtaaaaa gctacatcta    600

tcagctaatc aaggctattc actggtgcca taagaatgat attgtccatc gagatataaa    660

accagaaaat ctcttaatca gccacaatga tgtcctaaaa ctgtgtgact ttggttttgc    720

tcgtaatctg tcagaaggca ataatgctaa ttacacagag tacgttgcca ccagatggta    780

tcggtcccca gaactcttac ttggcgctcc ctatggaaag tccgtggaca tgtggtcggt    840

gggctgtatt cttggggagc ttagcgatgg acagccttta tttcctggag aaagtgaaat    900

tgaccaactt tttactattc agaaggtgct aggaccactt ccatctgagc agatgaagct    960

tttctacagt aatcctcgct tccatgggct ccggtttcca gctgttaacc atcctcagtc   1020

cttggaaaga agataccttg gaattttgaa tagtgttcta cttgacctaa tgaagaattt   1080

actgaagttg gacccagctg acagatactt gacagaacag tgtttgaatc accctacatt   1140

tcaaacccag agacttctgg atcgttctcc ttcaaggtca gcaaaaagaa aaccttacca   1200

tgtggaaagc agcacattgt ctaatagaaa ccaagccggc aaaagtactg ctttgcagtc   1260

tcaccacaga tctaacagca aggacatcca gaacctgagt gtaggcctgc cccgggctga   1320

cgaaggtctc cctgccaatg aaagcttcct aaatggaaac cttgctggag ctagtcttag   1380

tccactgcac accaaaacct accaagcaag cagccagcct gggtctacca gcaaagatct   1440

caccaacaac aacataccac accttcttag cccaaaagaa gccaagtcaa aaacagagtt   1500

tgattttaat attgacccaa agccttcaga aggcccaggg acaaagtacc tcaagtcaaa   1560
```

```
cagcagatct cagcagaacc gccactcatt catggaaagc tctcaaagca aagctgggac   1620
actgcagccc aatgaaaagc agagtcggca tagctatatt gacacaattc cccagtcctc   1680
taggagtccc tcctacagga ccaaggccaa aagccatggg gcactgagtg actccaagtc   1740
tgtgagcaac ctttctgaag ccagggccca aattgcggag cccagtacca gtaggtactt   1800
cccatctagc tgcttagact tgaattctcc caccagccca acccccacca gacacagtga   1860
cacgagaact ttgctcagcc cttctggaag aaataaccga aatgagggaa cgctggactc   1920
acgtcgaacc acaaccagac attctaagac gatggaggaa ttgaagctgc cggagcacat   1980
ggacagtagc cattcccatt cactgtctgc acctcacgaa tctttttctt atggactggg   2040
ctacaccagc cccttttctt cccagcaacg tcctcatagg cattctatgt atgtgacccg   2100
tgacaaagtg agagccaagg gcttggatgg aagcttgagc atagggcaag ggatggcagc   2160
tagagccaac agcctgcaac tcttgtcacc ccagcctgga gaacagctcc ctccagagat   2220
gactgtggca agatcttcgg tcaaagagac ctccagagaa ggcacctctt ccttccatac   2280
acgccagaag tctgagggtg gagtgtatca tgacccacac tctgatgatg gcacagcccc   2340
caaagaaaat agacacctat acaatgatcc tgtgccaagg agagttggta gcttttacag   2400
agtgccatct ccacgtccag acaattcttt ccatgaaaat aatgtgtcaa ctagagtttc   2460
ttctctacca tcagagagca gttctggaac caaccactca aaaagacaac cagcattcga   2520
tccatggaaa agtcctgaaa atattagtca ttcagagcaa ctcaaggaaa aagagaagca   2580
aggatttttc aggtcaatga aaaagaaaaa gaagaaatct caaacagtac ccaattccga   2640
cagccctgat cttctgacgt tgcagaaatc cattcattct gctagcactc caagcagcag   2700
accaaaggag tggcgccccg agaagatctc agatctgcag acccaaagcc agccattaaa   2760
atcactgcgc aagttgttac atctctcttc ggcctcaaat cacccggctt cctcagatcc   2820
ccgcttccag cccttaacag ctcaacaaac caaaaattcc ttctcagaaa ttcggattca   2880
ccccctgagc caggcctctg gcgggagcag caacatccgg caggaacccg caccgaaggg   2940
caggccagcc ctccagctgc caggtcagat ggatcctggt tggcatgtgt cctctgtgac   3000
caggagtgcc acagagggcc cttcctactc tgaacagctg ggtgccaaaa gtgggccaaa   3060
tgggcacccc tataacagaa caaatcgctc acgaatgcca aatctgaatg atttaaaaga   3120
gacagccttg taatttgtgc tggtaggggg gaggggtgga cagacaagcc agtggggagg   3180
ggtgggaaag ggtgggctgg gcttggggca tgggccgggc caagtggtga gccaatattt   3240
tcagctttat gaaggtgtgt gcaatattgc atgtgttggg gccgttgagc tcctcgcggc   3300
cacaaatgct agtcagggat cttagagcca caggagttcc ttagggatcg ccactcccca   3360
caggtcttgt gtgagaatag atagagtgtg ccattgagga agaagaaatt cttgccagtt   3420
tctccccttt acattccagc tttagtgcaa tctctgttga acttgggaat gccaggatgt   3480
gtcctggcac tgcaagggat aggaaagtcg tgttgaccga tgcccttact acatattttt   3540
ttctgcctag agtaaatgtg gggtttattg taatccaaga gtatcccttt gaagggttag   3600
cagatgaact gtatgtctta aattgttttc taaacttcca tatttgatag gatttgtaac   3660
atttatttat aattaatatt gtactgttaa aatcatatct tttatgttat aatgtaaagt   3720
tattttgagc tgtttgaaac attgtgaagc agtgggacag ctacagtagt ttctataaaa   3780
actaaacagt aacatttata tattgcatca ggagtatttt attctatata taatatatat   3840
atatggtaaa tatctgtttt ataaatatat tcatttaaag aaagtatcgt tatgacacta   3900
```

tctgccatat ttttatacat ttgtgatatg aagtgagtat tatacttcta ctaaagggag 3960
ttgaattgtg gctacacgtg actgtaacag tatgaacctt gctcaacttt gaggccccag 4020
cagtagcctc tagacatgat ccttggtagc agacgagatg cagcatctct ttccaaacct 4080
gcaggggaag aaagtcagat aggccagtga gaattccagc aggcctggtt tccgtcctca 4140
cacacttggc tcctgtttgt gtccagggac gttacttgca cacaggggag aatagattga 4200
ggcgttactc gtgggtcttt gtagagagaa tgtgctcttc cacttagcat tagtgtagag 4260
cgtagaccaa agatttgcca gtgaacattc cttgttgtga gatcataaga ggtacctgtc 4320
tgcagatctt gcaaaccatc tctatgctcc tgaatattgt ccactgtccc ggagactctt 4380
ggctgatggg gtgtgagata tatgtgtggc atttctattt ctgaatgcct tttttgctat 4440
tgctctctcc aataccatat ttaaaaggct cctggagcaa ttccagatag ataaaaaatt 4500
actctatcca tttttttctt cctggggctg tccacttatg acaagatttt catgcacacc 4560
tgttacgcac acaaccccca tcagaacagg acctatcttc ccctcatctg atctctttca 4620
gctcccaagt tactcccaag tatcatcaaa ccctttggcc atcaagtgtt atcctcccat 4680
gcctctgggt catccttgag ggaagtcacc tcagcaccat catctatcag tagtagtaga 4740
tttttggaat tagtctctga gcaataatac ttttaaaggt ccctcccacc cctcaaagag 4800
ataacttctc agtatttatt acttgtcctc aaattctgag tgtcagcccc tgcatcaagt 4860
cagctatgat caaaatgtgc tgttactgtt aaccctcccc cgagattttg agaatcatag 4920
ctctgatgat tatgaagatt ataaagacta aggtcctagt ttccctgaag cttaaattgt 4980
gcacatattg catttttata taaatactat aatgtgtatt gattatatag ataggtcatt 5040
ttaaggtgct ttttatttaa ttttaatgag tgtaataggc actaaaatga aactcgactg 5100
ggtactatta ctgaaaaaat ttgactcaaa ccaatagttt tgcatgctct ttagttcttt 5160
ttctgtctta cttctttcac cagttcagta ctgtttgggt agctctgaat tctggctttt 5220
ccaggcagct gcttgatgat acaaatgagg tggaccatca gcagttttgc ctggacacta 5280
atgactctaa aagggtgtgt atttaactct tctttttcat actagatctc taccttgtat 5340
tccccccttg caaaccagaa actacacttt ttttctctgg aaagacttct cactgtgcta 5400
tgcgcttagg aactgcacgg tcccgttgcc atgctgtggc attcgaggct cgtcacctag 5460
gggctggttt cccatgttgt catccttgct aacactggga tctcagatgt ttgcagaaca 5520
tttctattca tgacggttct tcaaagaagg gctagaatat ttgccttcta cctagagcaa 5580
agtaaaccta attgttgaag agtcaatacg tactttttgt actttcccag atttgagcca 5640
gaaaatacct acagatatct acaaatgttt tcaaccagtg ttttcgaggt agctctttaa 5700
tcctcttctc agcttttgtc tgttctgact tttcatccaa taagctgtaa gtgaactaca 5760
atctgcattt ccagcatgca attctcttcc tgctcacgga gggggatgca aaagttttct 5820
ctcacaccta atgggccctc tcttagcttt taactgttgt tttcccctgt tgatgaaaaa 5880
ttactgacat cacaaagatt gccatccatg gtagaaagga cttgatttaa agtcagaaaa 5940
atttgccttt tctttaggaa ggggaattca tgacatccat gtcctattat cggccgtaac 6000
ttcctaaaga agaaaaaggg tgaatgaaag cttatgttac ttttatgaaa gtatcactga 6060
tctcctttgg aaaagaaact ctgcttcact gtttttctac ctttatttct ctgccatcct 6120
cgtttttcct ctctgaagtt ctaaataccc tttaactgaa ccttgttggt cttgctctaa 6180
aatttagcct ctttctagag cccaagacca aaagggagtg cttcatgctg aggggctcaa 6240
gtgagctgac tctacaactg tggttctcaa ctaggggcag atttaccccc aagggtacat 6300

```
ttggcaatgt ctggggacat ttggttgtca tagctggggg ggaggtgatg gtatgctact   6360
ggcatcaagt ggttagaggc cacagatgct actaaacacc ctgccatgca caggacagcc   6420
ccccaaacaa acagtggtcc agccccaagc actactagtg ctgaggttga gaaaccctgc   6480
cctacaccat cccaagccca ccagtctgca gagcttggct ctggccttgt tctgtccagg   6540
ctacagtact gcaggtgtga tttcttcaac atcacattct cttaagagtc ttcaaccact   6600
atgcctgaat ccttggaatc ctattgttcg tttccattgt cttgggcctg ctaaaaggtg   6660
catactttgg aaggagacca gagttacttt ataggtgttg gagaacttaa attctaggtt   6720
agcatcctta gaaaatcttt catagagcca tgaggcttat atttagaagc aagcaacagc   6780
ctggcagatt ggcatgattt ttaccaactg ctcaaaggca tccgtggctt tcagctgtgt   6840
ctcccgaaag aaaatgtctt tgttttttat tcaagtcatt taatagctct ttacaaatat   6900
tagcatatgg cagaccaatt agaagcaaaa aagtccgtat tggtggttgt gatgtggctg   6960
ttatagaagt atttgtgctg tatgctttgg ttaaatctgt tttaaaacat gctttaagat   7020
tcaccttacg cagttgtact ttaattctaa gctcagagct atgctgtcag tctctagtca   7080
cgccatgtat tataaagtat gttgtggttg tagagttagc cagtttagca tgttcctaat   7140
ctgagaatta gtggactata ctaggaaatg ctatcccatt ttccctttcc agcccctctt   7200
agttaagatc atagtatcct cacttcttaa actagtcttt agagtaaata aggaaaaaag   7260
ccatttattt tcttctagcc atgtattatt gagaatgact catagtacaa cttttttca   7320
aaggccagag gattactttg caagtgtgta gaaagatctg tctatttctg ttcacctggg   7380
acctggtggt gactgaactc tttcagcaag ggcaatggct caatgtgatt cggtgctgga   7440
gctcagctgg gactcagtaa atctgcacgt tctctgctgg tcagaacatg tttcctggag   7500
agcattgctt ttctatctag aagttcgtta cctcctgcat gatagtggga tattgagatg   7560
tgggttctaa gatccacaga ctcatacttt tgtgaacttt ggaatgtggt agggtacact   7620
gaaccaagtc agaaaatagt gaaatatttc cttgcctcct tcagttcatc actaagaaag   7680
tgtgtaggca gagaaaactt acttatggtt tgaagaacca caattgtttt tgaaagggga   7740
catagaaaag acagtacaaa ggttgtaagt gtcctgtcgc taattcccag ggccagaatc   7800
tcacaagaag atcctctcaa agacttaaaa gcctggctta caaaaataac cagaaaccaa   7860
acttgtaagc agttacaatt tcttcctttt gcttcttgac cagctgagat acagaatatc   7920
ttgaggtctg gttcagctga tgaaaaattc tgtctcagaa acgatgagta agaaaccata   7980
caagaaaaag aagtccctca tctatctgca tacacgcaat gtgggagaag tggggtggct   8040
aggaaactct gggcctgctg ccccccttcga ttcttttttt ttttctttgt gaattgaatg   8100
tacgatacaa atggtaggcc ttcatgtgag ccagttacta catgaatctt catttcccac   8160
agtggtttgt tcattcatca gcgttaggct tggtcctggc tccacctttc tcctctccgg   8220
gcactgaccc cacctttccg tgtatttact gtaggctatt aaatatgatc atgacccgcc   8280
ttgcattttc attcatcacc tgtttatgcc caaatttaaa ggaagtttgt ctcattttgc   8340
cagaaaaaaa ttgtaatagt cggcacgctg gatttgtagg gccagcaaaa ttgcggcagt   8400
gaaactagtt tcacttctaa agcccttcat ttcccacaag gttaagctct cgaaacccca   8460
tttgatcctt ggttcctatt tcgatcctcc tttggaatct gaaaatcggt ctccatgttg   8520
tatgcagatt agaagttgcc ttgtttgtta ctcttccaac acagggtatc agggagaaag   8580
aggccttatc tgttcctcca tccccccctgt tttgacagac tgctaagaat tcctcaggac   8640
```

ttcctttggt tggggatttt actttcccaa aagtctgatc tgatttcttt caggggtaga 8700
caagcttgtc ctagtgctct gcttcaggtc ttatcagaag aaacccagga atagaaaagg 8760
tagatgcctt gacttttgtc cctgttgtgg ggactaaagt gttttttgcc agaattgtca 8820
aaagctccgg ttcaaactct gtagagtttc atggaaaaac aaaacaaaac aaaaaagatg 8880
cttatcgtcc cggagaatgt gtaagtaagt tctccagcac ggcttaggtt ttccaaaatg 8940
gaaagcaaag cttgcagaca acctgttttc tctagagaca cacaatgatt ctggccctca 9000
gtctgtttcc ctccccttgt ttactctttg gtcaccgatc gagtcaggct agaggggtaa 9060
tacggtgatt aaaagaagta aattctcact gtaaacttgg attgattaac agaaacaatt 9120
aaaccaaaca aaatcattgc cccaaatttc tatctccaag aattgctttg tgccattttg 9180
aattcaggta gttattctgt atatacttag ctaactattc agagcttctt caatctctag 9240
taagcttgaa ggtggtgtct gggaagacac agggcagggt gacatttaga ctctgttcat 9300
tcttaaaaat agggataagc cagaatgatg tgacatctag tatgtggtag atgaagaatc 9360
agtggaaatt cttaattgca cagactttat aatccattat ataaagtgta attccatact 9420
ttttactgtg gcaagggtgt gatgtgattg ttaatctttt taatttttga atccaaactg 9480
aatttaaagt gttgaatact taaatcctca caagtgaatt atgaaccatt tgtaaagtgt 9540
ttctataact ctttgtatca tgtgttggta catcttatca agttttttct ggcatgtaat 9600
tccattctaa acttatgtaa aatttctatt gttgctgtaa atattacaca aatatctatt 9660
ccgtgataac cttcattatc agcatgaaat ggttaatttt tactgagcac aatgtatttt 9720
tgaatggatc ttcccaaatg tctttaataa aatgcagatt ttgcactgac tgatgtgact 9780
gccaggccgt cccaatcttg agcactgtgg tccttcgtgt ttgaactgcg aacagctcca 9840
ttttagttcc ttcttgggaa gaaagaatgc attcgaattc aaatgaggga tgatgggcct 9900
ttgaggttgt aatcagtttg agacagaaat taatgtaaaa ctaggcaaat cctgtaactt 9960
aatgatgttg atctttgttt tcctatttat aaagcttttt tccccttacg gcattttgaa 10020
aactttggtt tgttttatac ttgagtgttg tcacctttgc acgtcgctag acactcacgt 10080
ggtagtttga ggaggatggg aagagaggcc aatcttgtgc taagtgctat ggagaaagca 10140
aagatgcaca gcttaataag ggtttttga ttctagagga gaggtgggca agcttttcct 10200
gtaaagggcc agatggtaaa tattgggggc tctgtggccc atcagttccc tgtcaacatt 10260
actcagctct gcctttgtat tgcagaggct gcatggataa tatgtaaatc agtaagtgtg 10320
gctgtggtcc cgtaaaactt tacttataga aacaggccat agtttactaa cccgttttag 10380
gccctcagtt tcatcattta gggtaacacc aaccgagtac atgttcaatc aggagggaaa 10440
gaacttagct tttgtgataa cttatagatg aaatattccc cagttttctt tctctttcta 10500
aacaaagggt aggagctgaa agtcagtgct ctccattctt aaaagtcctc tgtcaaccac 10560
ctcttcactc tatctcctta agtgacatgg aaacttgtgg cctgtgcttt caactataat 10620
cttaccaaga ctgaatgaaa gtatttggtg cttatacttt ttaatgttca tagcacttac 10680
tatggccagg cacaatgccc aagtgttttg ctttattatt attattatta ttattattat 10740
tattattatt attattattt tcacaacaac ccagcgaaac aggtactatt attatcccct 10800
ttttgtaaat gaggaaacag atttccatac ttgacattaa cctgcccaag gtcacccagt 10860
ttggaagtgg cagggccagg atttgaagcc gaatatgttc attgtaaagc ccatataccc 10920
ttaaaagtca ctgcacgtcc acgtatggta atgtggtcac aatcagtatt gtttctcttt 10980
agtaattcag atttattcaa gtaactccaa ggttcaaatt ttcaaaaaca gtttccaaca 11040

```
caggttatat taaaaacttt gcctgaagtt tactctaggt gcagaaataa agacaactta  11100
gtcaagtgaa ggaaagggta acagacttag aaatggctat ctacactgat ggaataagta  11160
tactaattag agcaggtaac aagtccccac gatgtataac atattcttct ctaaaagctc  11220
acaacaattt atgtgccacc ttccatcccc tttcccagca gatggtaatt gatgcaattt  11280
gagaatagaa cacttcattg aaacaagtca ctggaggtcc tctggggatg cagcttaaaa  11340
gcccaggatc aggccaggtg tggtggctca cgcctgtaat cccagcactg tgggagactg  11400
agacgggcag atcacctgaa gtcaggagtt cgagaccagc ctggccaata tagagaaacc  11460
ccgtctgtac taaaaataca aaaattaggt ctgggcggtg gctcacgccc gtaatcctag  11520
cactttggga ggccaaggtg ggtggatcac gaggtcagga gttcgagacc agcctggcca  11580
acatggtgaa accccgtctc tactaaaaat acaaaaattg ggtgtggtgg tacatgcctg  11640
taatcccagc tgcttaggag gctgaggcag gagaatcact tgaacccaaa aggcagaggt  11700
tgcagtgagc cgagatcacg ccactgcact ccagcctggc aacagagcga gactctgtct  11760
caaaaaaaaa aaaaaaaaaa tacaaaaatt agccgggaat ggtggtgaat gtctataatc  11820
ccagccactc gggaggctga ggcaggagaa tcacttgaac ccaaaaggca gaggttgcag  11880
tgagccaaga tcgcaccact gcactcccac ctggacgaca gagcgagacg ccatctcaaa  11940
aataaataaa taaataaatc cctaggatat agagtccgct tgcctgggtg gagtcttggc  12000
tccatctcct acatctcatg tgacttgaag caaggcactt cactatgcct cagtttcctt  12060
atctttaaat ggaggtaatc acagtaccta cctcagtgtt gttgtgaaga tttaatgaga  12120
taataacctg cagagcactt gagagtctca agaaatatga gctcttataa cattattgct  12180
attgtaaaac attgctatta cttctgtccc aatttggcag tttcaggaaa ttgagaagga  12240
atgtcactga atctttaatg ccagttacac agagctcagt aggtgtccgc acagcccttt  12300
agatgcacgt agcctatttg atcttcgtat cagccctgta aggttgggct taagaatgac  12360
ccagcatgga agtactcttg ggaccacagg ggaagcaaca gtccttgtaa gctgtttgtc  12420
agtgggcctt agcaaccaag ccccaagtgg acagaaagat ggggttctgt gagcatccat  12480
tccaagggtc actttagggg tgcaatcttc tgggctctga gaatggattc acagcagcat  12540
ctctatctgg aaataccttt gctttgtcca agtaacctcc tcccacacag agtacccgaa  12600
tcagctcaga tttttttcc ttaatattgg caacacttaa tgctacttct ttgttcgtaa  12660
catttcattt aattatttaa aaatctgcaa atgttgtgta tattttaccg caatttttaa  12720
acaaactcca gtgtagaccg tgctctagca tttctaaaaa taaaagtaaa tatgttaaaa  12780
taaggtaaga gtgagttttt cctacactat gtataatttt taattgaaag tttcccccac  12840
aaaagaaatg atacttggaa gcatagtttg tgtgtttgac agcaagattc tattaggctt  12900
cagatttccc tcaataaaag ttttagtttt tatacattct gtcatgaatt gaatgaagta  12960
aataatatgc tgttgtaagc aaattatctg cagataaatg tcttatgaat cgtatatctt  13020
actgtttatt aaattctgaa gtattgagca gtttccaatg tgaaatccca gctggcttct  13080
ttgcaatgat ggacaagtta gttataattc atatggaaat tcaaggaacc cagaatagcc  13140
aaaacaatcc cgaagagcaa agttggagga ctcacatgcc ccaatttcaa aacttactac  13200
aaagctacaa taatgaagaa agtgaggtaa tagaatttgg agtccagaaa taaaccctct  13260
cacatttatg gtcaattgtt ttttgacaag ggtgccaaga tcattcaatg ggggaaagaa  13320
tagtcttttc agcaaatagt ggtgggacaa ctggatatcc acatgcaaaa gaatgacgtt  13380
```

```
ggactcctat ttcacaccat atacaaaaat taactcaaaa tggaacaaag atctaactgt  13440
aagaggtaga actataaaac tcatagaaga aaacataggg gtaaatcttc atgaccttgg  13500
atttggcagt ggtttctcag atatgacacc aaaggcacaa gcaaagagaa aaataaattg  13560
gacttcatca aatatttaaa attttgtgct taagaggact ctatcgagag ggttaaaaag  13620
atccacagaa tgggagaaaa tatttgcaaa tcatatccaa taagggaatt agaatataca  13680
aagaattctt aaactcagta agttgtaagc cgatttaaaa tgggcagagg atctgaaaaa  13740
cctttatcca aagatgtaca aatggccagt aaacacatga aaagatgctc aacatcatta  13800
gtcactaggg aaatgcaaat caaaaccaca gttgagatgc aacttcacac attatgggta  13860
tagtcaaaga tggacagtaa caagtgttgc tgaggatgtg gagaaagtgg aagcctccta  13920
cattgctggt ggaaatgtaa aatgatgcag ccacttggga taatagttcc tccaaagatt  13980
aaacaagagt gactgtgtgt cccagcagtt ttactcctaa gtatataccc aagataaatg  14040
aaaacacaca tccgcacaaa aacttataca caaatgttca tagcagcatt attcataata  14100
gctaaagagt ggaaacccaa atatccatca atggatgaat ggataaataa caatgtgctc  14160
ttgacatgat actgaacaat gatgttcagc aataaaaagg agtgacaagt gacatagtga  14220
tacacatgtt ataacgtgga tgaactttaa aacactatgc taagtgaaag aagccagtca  14280
cgaaatacca catactatat gatttcattt atgtagaacg tccagaaggc caatctacag  14340
agacagtcga ttcgtggttg cagagggctt ggggtggccg atgggttggg gagtgttggc  14400
tgatgggtgc aggatttctc tttggggtga taaactttct aaaattgatc tagtgataat  14460
ggttgcacaa ctctgaatat accaaaagtc atcaaattgt acactttaaa tggatacaaa  14520
ttgtatgtga acttaatctc aataaagccg tgacaaaagt ttccaacatg aa          14572
```

<210> SEQ ID NO 18
<211> LENGTH: 3434
<212> TYPE: DNA
<213> ORGANISM: Artificial Sequence
<220> FEATURE:
<223> OTHER INFORMATION: transcript variant

<400> SEQUENCE: 18

```
attagttgtc tctgccgctg gggaaggtaa agcggcgacg gcgtcctcag gagctgtggg    60
gtcccctgct agaagtgggg gactcggcgg gggagtcatt taatacttca tgattagaac   120
aaatatgtga aagttcccac caaccagtga gaatttcttc cttcagacgg ttttggatct   180
tactgcacag ctttctgaga agttcttttg gtgccatgtt ttgtggcttg catcaaaaga   240
ggagtttgtc ttcatgaaga ttcctaacat tggtaatgtg atgaataaat ttgagatcct   300
tggggttgta ggtgaaggag cctatggagt tgtacttaaa tgcagacaca aggaaacaca   360
tgaaattgtg gcgatcaaga aattcaagga cagtgaagaa aatgaagaag tcaaagaaac   420
gactttacga gagcttaaaa tgcttcggac tctcaagcag gaaaacattg tggagttgaa   480
ggaagcattt cgtcggaggg gaaagttgta cttggtgttt gagtatgttg aaaaaaatat   540
gctcgaattg ctggaagaaa tgccaaatgg agttccacct gagaaagtaa aaagctacat   600
ctatcagcta atcaaggcta ttcactggtg ccataagaat gatattgtcc atcgagatat   660
aaaaccagaa aatctcttaa tcagccacaa tgatgtccta aaactgtgtg actttggttt   720
tgctcgtaat ctgtcagaag gcaataatgc taattacaca gagtacgttg ccaccagatg   780
gtatcggtcc ccagaactct tacttggcgc tccctatgga aagtccgtgg acatgtggtc   840
ggtgggctgt attcttgggg agcttagcga tggacagcct ttatttcctg gagaaagtga   900
```

```
aattgaccaa ctttttacta ttcagaaggt gctaggacca cttccatctg agcagatgaa    960
gcttttctac agtaatcctc gcttccatgg gctccggttt ccagctgtta accatcctca   1020
gtccttggaa agaagatacc ttggaatttt gaatagtgtt ctacttgacc taatgaagaa   1080
tttactgaag ttggacccag ctgacagata cttgacagaa cagtgtttga atcaccctac   1140
atttcaaacc cagagacttc tggatcgttc tccttcaagg tcagcaaaaa gaaaacctta   1200
ccatgtggaa agcagcacat tgtctaatag aaaccaagcc ggcaaaagta ctgctttgca   1260
gtctcaccac agatctaaca gcaaggacat ccagaacctg agtgtaggcc tgccccgggc   1320
tgacgaaggt ctccctgcca atgaaagctt cctaaatgga aaccttgctg gagctagtct   1380
tagtccactg cacaccaaaa cctaccaagc aagcagccag cctgggtcta ccagcaaaga   1440
tctcaccaac aacaacatac cacaccttct tagcccaaaa gaagccaagt caaaaacaga   1500
gtttgatttt aatattgacc caaagccttc agaaggccca gggacaaagt acctcaagtc   1560
aaacagcaga tctcagcaga accgccactc attcatggaa agctctcaaa gcaaagctgg   1620
gacactgcag cccaatgaaa agcagagtcg gcatagctat attgacacaa ttccccagtc   1680
ctctaggagt ccctcctaca ggaccaaggc caaaagccat ggggcactga gtgactccaa   1740
gtctgtgagc aacctttctg aagccagggc ccaaattgcg gagcccagta ccagtaggta   1800
cttcccatct agctgcttag acttgaattc tcccaccagc ccaaccccca ccagacacag   1860
tgacacgaga actttgctca gcccttctgg aagaaataac cgaaatgagg gaacgctgga   1920
ctcacgtcga accacaacca gacattctaa gacgatggag gaattgaagc tgccggagca   1980
catggacagt agccattccc attcactgtc tgcacctcac gaatcttttt cttatggact   2040
gggctacacc agcccctttt cttcccagca acgtcctcat aggcattcta tgtatgtgac   2100
ccgtgacaaa gtgagagcca agggcttgga tggaagcttg agcatagggc aagggatggc   2160
agctagagcc aacagcctgc aactcttgtc accccagcct ggagaacagc tccctccaga   2220
gatgactgtg gcaagatctt cggtcaaaga gacctccaga gaaggcacct cttccttcca   2280
tacacgccag aagtctgagg gtggagtgta tcatgaccca cactctgatg atggcacagc   2340
ccccaaagaa aatagacacc tatacaatga tcctgtgcca aggagagttg gtagctttta   2400
cagagtgcca tctccacgtc cagacaattc tttccatgaa aataatgtgt caactagagt   2460
ttcttctcta ccatcagaga gcagttctgg aaccaaccac tcaaaaagac aaccagcatt   2520
cgatccatgg aaaagtcctg aaaatattag tcattcagag caactcaagg aaaaagagaa   2580
gcaaggattt ttcaggtcaa tgaaaaagaa aaagaagaaa tctcaaacag tacccaattc   2640
cgacagccct gatcttctga cgttgcagaa atccattcat tctgctagca ctccaagcag   2700
cagaccaaag gagtggcgcc ccgagaagat ctcagatctg cagacccaaa gccagccatt   2760
aaaatcactg cgcaagttgt tacatctctc ttcggcctca aatcacccgg cttcctcaga   2820
tccccgcttc cagcccttaa cagctcaaca aaccaaaaat tccttctcag aaattcggat   2880
tcaccccctg agccaggcct ctggcgggag cagcaacatc cggcaggaac ccgcaccgaa   2940
gggcaggcca gccctccagc tgccagacgg tggatgtgat ggcagaagac agagacacca   3000
ttctggaccc caagatagac gcttcatgtt aaggacgaca gaacaacaag gagaatactt   3060
ctgctgtggt gacccaaaga agcctcacac tccgtgcgtc ccaaaccgag cccttcatcg   3120
tccaatctcc agtcctgctc cctatccagt actccaggtc cgaggcactt ccatgtgccc   3180
gacactccag gtccgaggca ctgatgcttt cagctgccca acccagcaat ccgggttctc   3240
```

```
tttcttcgtg agacacgtta tgagggaagc cctgattcac agggcccagg taaaccaagc   3300

tgcgctcctg acataccatg agaatgcggc actgacgggc aagtgacttc tgcaagcctg   3360

cggctggtcc caatgccctg aatcacctct ctcatggaag aaccaattaa caccaatgaa   3420

tcaaccatta aaaa                                                     3434


<210> SEQ ID NO 19
<211> LENGTH: 1030
<212> TYPE: PRT
<213> ORGANISM: Artificial Sequence
<220> FEATURE:
<223> OTHER INFORMATION: amino acid sequence

<400> SEQUENCE: 19

Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
```

```
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750
```

Gln Pro Ala Phe Asp Pro Trp Lys Ser Pro Glu Asn Ile Ser His Ser
755 760 765

Glu Gln Leu Lys Glu Lys Glu Lys Gln Gly Phe Phe Arg Ser Met Lys
770 775 780

Lys Lys Lys Lys Lys Ser Gln Thr Val Pro Asn Ser Asp Ser Pro Asp
785 790 795 800

Leu Leu Thr Leu Gln Lys Ser Ile His Ser Ala Ser Thr Pro Ser Ser
805 810 815

Arg Pro Lys Glu Trp Arg Pro Glu Lys Ile Ser Asp Leu Gln Thr Gln
820 825 830

Ser Gln Pro Leu Lys Ser Leu Arg Lys Leu Leu His Leu Ser Ser Ala
835 840 845

Ser Asn His Pro Ala Ser Ser Asp Pro Arg Phe Gln Pro Leu Thr Ala
850 855 860

Gln Gln Thr Lys Asn Ser Phe Ser Glu Ile Arg Ile His Pro Leu Ser
865 870 875 880

Gln Ala Ser Gly Gly Ser Ser Asn Ile Arg Gln Glu Pro Ala Pro Lys
885 890 895

Gly Arg Pro Ala Leu Gln Leu Pro Asp Gly Gly Cys Asp Gly Arg Arg
900 905 910

Gln Arg His His Ser Gly Pro Gln Asp Arg Arg Phe Met Leu Arg Thr
915 920 925

Thr Glu Gln Gln Gly Glu Tyr Phe Cys Cys Gly Asp Pro Lys Lys Pro
930 935 940

His Thr Pro Cys Val Pro Asn Arg Ala Leu His Arg Pro Ile Ser Ser
945 950 955 960

Pro Ala Pro Tyr Pro Val Leu Gln Val Arg Gly Thr Ser Met Cys Pro
965 970 975

Thr Leu Gln Val Arg Gly Thr Asp Ala Phe Ser Cys Pro Thr Gln Gln
980 985 990

Ser Gly Phe Ser Phe Phe Val Arg His Val Met Arg Glu Ala Leu Ile
995 1000 1005

His Arg Ala Gln Val Asn Gln Ala Ala Leu Leu Thr Tyr His Glu
1010 1015 1020

Asn Ala Ala Leu Thr Gly Lys
1025 1030

<210> SEQ ID NO 20
<211> LENGTH: 960
<212> TYPE: PRT
<213> ORGANISM: Artificial Sequence
<220> FEATURE:
<223> OTHER INFORMATION: amino acid sequence

<400> SEQUENCE: 20

Met Lys Ile Pro Asn Ile Gly Asn Val Met Asn Lys Phe Glu Ile Leu
1 5 10 15

Gly Val Val Gly Glu Gly Ala Tyr Gly Val Val Leu Lys Cys Arg His
20 25 30

Lys Glu Thr His Glu Ile Val Ala Ile Lys Lys Phe Lys Asp Ser Glu
35 40 45

Glu Asn Glu Glu Val Lys Glu Thr Thr Leu Arg Glu Leu Lys Met Leu
50 55 60

Arg Thr Leu Lys Gln Glu Asn Ile Val Glu Leu Lys Glu Ala Phe Arg
65 70 75 80

-continued

```
Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495
```

```
Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750

Gln Pro Ala Phe Asp Pro Trp Lys Ser Pro Glu Asn Ile Ser His Ser
        755                 760                 765

Glu Gln Leu Lys Glu Lys Glu Lys Gln Gly Phe Phe Arg Ser Met Lys
    770                 775                 780

Lys Lys Lys Lys Lys Ser Gln Thr Val Pro Asn Ser Asp Ser Pro Asp
785                 790                 795                 800

Leu Leu Thr Leu Gln Lys Ser Ile His Ser Ala Ser Thr Pro Ser Ser
                805                 810                 815

Arg Pro Lys Glu Trp Arg Pro Glu Lys Ile Ser Asp Leu Gln Thr Gln
            820                 825                 830

Ser Gln Pro Leu Lys Ser Leu Arg Lys Leu Leu His Leu Ser Ser Ala
        835                 840                 845

Ser Asn His Pro Ala Ser Ser Asp Pro Arg Phe Gln Pro Leu Thr Ala
    850                 855                 860

Gln Gln Thr Lys Asn Ser Phe Ser Glu Ile Arg Ile His Pro Leu Ser
865                 870                 875                 880

Gln Ala Ser Gly Gly Ser Ser Asn Ile Arg Gln Glu Pro Ala Pro Lys
                885                 890                 895

Gly Arg Pro Ala Leu Gln Leu Pro Gly Gln Met Asp Pro Gly Trp His
            900                 905                 910

Val Ser Ser Val Thr Arg Ser Ala Thr Glu Gly Pro Ser Tyr Ser Glu
```

915 920 925

Gln Leu Gly Ala Lys Ser Gly Pro Asn Gly His Pro Tyr Asn Arg Thr
930 935 940

Asn Arg Ser Arg Met Pro Asn Leu Asn Asp Leu Lys Glu Thr Ala Leu
945 950 955 960

<210> SEQ ID NO 21
<211> LENGTH: 1030
<212> TYPE: PRT
<213> ORGANISM: Artificial Sequence
<220> FEATURE:
<223> OTHER INFORMATION: amino acid sequence

<400> SEQUENCE: 21

Met Lys Ile Pro Asn Ile Gly Asn Val Met Asn Lys Phe Glu Ile Leu
1 5 10 15

Gly Val Val Gly Glu Gly Ala Tyr Gly Val Val Leu Lys Cys Arg His
20 25 30

Lys Glu Thr His Glu Ile Val Ala Ile Lys Lys Phe Lys Asp Ser Glu
35 40 45

Glu Asn Glu Glu Val Lys Glu Thr Thr Leu Arg Glu Leu Lys Met Leu
50 55 60

Arg Thr Leu Lys Gln Glu Asn Ile Val Glu Leu Lys Glu Ala Phe Arg
65 70 75 80

Arg Arg Gly Lys Leu Tyr Leu Val Phe Glu Tyr Val Glu Lys Asn Met
85 90 95

Leu Glu Leu Leu Glu Glu Met Pro Asn Gly Val Pro Pro Glu Lys Val
100 105 110

Lys Ser Tyr Ile Tyr Gln Leu Ile Lys Ala Ile His Trp Cys His Lys
115 120 125

Asn Asp Ile Val His Arg Asp Ile Lys Pro Glu Asn Leu Leu Ile Ser
130 135 140

His Asn Asp Val Leu Lys Leu Cys Asp Phe Gly Phe Ala Arg Asn Leu
145 150 155 160

Ser Glu Gly Asn Asn Ala Asn Tyr Thr Glu Tyr Val Ala Thr Arg Trp
165 170 175

Tyr Arg Ser Pro Glu Leu Leu Leu Gly Ala Pro Tyr Gly Lys Ser Val
180 185 190

Asp Met Trp Ser Val Gly Cys Ile Leu Gly Glu Leu Ser Asp Gly Gln
195 200 205

Pro Leu Phe Pro Gly Glu Ser Glu Ile Asp Gln Leu Phe Thr Ile Gln
210 215 220

Lys Val Leu Gly Pro Leu Pro Ser Glu Gln Met Lys Leu Phe Tyr Ser
225 230 235 240

Asn Pro Arg Phe His Gly Leu Arg Phe Pro Ala Val Asn His Pro Gln
245 250 255

Ser Leu Glu Arg Arg Tyr Leu Gly Ile Leu Asn Ser Val Leu Leu Asp
260 265 270

Leu Met Lys Asn Leu Leu Lys Leu Asp Pro Ala Asp Arg Tyr Leu Thr
275 280 285

Glu Gln Cys Leu Asn His Pro Thr Phe Gln Thr Gln Arg Leu Leu Asp
290 295 300

Arg Ser Pro Ser Arg Ser Ala Lys Arg Lys Pro Tyr His Val Glu Ser
305 310 315 320

Ser Thr Leu Ser Asn Arg Asn Gln Ala Gly Lys Ser Thr Ala Leu Gln

```
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750
```

```
Gln Pro Ala Phe Asp Pro Trp Lys Ser Pro Glu Asn Ile Ser His Ser
        755                 760                 765

Glu Gln Leu Lys Glu Lys Glu Lys Gln Gly Phe Phe Arg Ser Met Lys
    770                 775                 780

Lys Lys Lys Lys Lys Ser Gln Thr Val Pro Asn Ser Asp Ser Pro Asp
785                 790                 795                 800

Leu Leu Thr Leu Gln Lys Ser Ile His Ser Ala Ser Thr Pro Ser Ser
                805                 810                 815

Arg Pro Lys Glu Trp Arg Pro Glu Lys Ile Ser Asp Leu Gln Thr Gln
            820                 825                 830

Ser Gln Pro Leu Lys Ser Leu Arg Lys Leu Leu His Leu Ser Ser Ala
        835                 840                 845

Ser Asn His Pro Ala Ser Ser Asp Pro Arg Phe Gln Pro Leu Thr Ala
    850                 855                 860

Gln Gln Thr Lys Asn Ser Phe Ser Glu Ile Arg Ile His Pro Leu Ser
865                 870                 875                 880

Gln Ala Ser Gly Gly Ser Ser Asn Ile Arg Gln Glu Pro Ala Pro Lys
                885                 890                 895

Gly Arg Pro Ala Leu Gln Leu Pro Asp Gly Gly Cys Asp Gly Arg Arg
            900                 905                 910

Gln Arg His His Ser Gly Pro Gln Asp Arg Arg Phe Met Leu Arg Thr
        915                 920                 925

Thr Glu Gln Gln Gly Glu Tyr Phe Cys Cys Gly Asp Pro Lys Lys Pro
    930                 935                 940

His Thr Pro Cys Val Pro Asn Arg Ala Leu His Arg Pro Ile Ser Ser
945                 950                 955                 960

Pro Ala Pro Tyr Pro Val Leu Gln Val Arg Gly Thr Ser Met Cys Pro
                965                 970                 975

Thr Leu Gln Val Arg Gly Thr Asp Ala Phe Ser Cys Pro Thr Gln Gln
            980                 985                 990

Ser Gly Phe Ser Phe Phe Val Arg  His Val Met Arg Glu  Ala Leu Ile
        995                 1000                 1005

His Arg  Ala Gln Val Asn Gln  Ala Ala Leu Leu Thr  Tyr His Glu
    1010                 1015                 1020

Asn Ala  Ala Leu Thr Gly Lys
    1025                 1030
```

<210> SEQ ID NO 22
<211> LENGTH: 2883
<212> TYPE: DNA
<213> ORGANISM: Artificial Sequence
<220> FEATURE:
<223> OTHER INFORMATION: nucleic acid sequence

<400> SEQUENCE: 22

```
atgaagatcc ccaacatcgg caacgtgatg aacaagttcg agatcctggg cgttgtcgga      60

gaaggcgctt atggcgtggt gctgaagtgc agacacaaag aaacccacga gatcgtggcc     120

atcaagaagt tcaaggacag cgaagagaac gaggaagtga aagagacaac cctgcgcgag     180

ctgaagatgc tgagaaccct gaagcaagag aacatcgtgg aactgaaaga ggccttccgg     240

cggagaggca agctgtacct ggtgttcgag tacgtggaaa agaacatgct cgagctgctg     300

gaagagatgc ccaatggcgt gccacctgag aaagtgaagt cctacatcta ccagctgatc     360

aaggccatcc actggtgcca caagaacgac atcgtgcaca gagacatcaa gcccgagaac     420
```

```
ctgctgatct cccacaacga cgtgctgaag ctgtgcgact tcggcttcgc cagaaatctg    480
agcgagggca acaacgccaa ctacaccgag tatgtggcca ccagatggta cagaagccct    540
gaactgctgc tgggagcccc ttacggcaag tctgtggata tgtggtccgt gggctgtatc    600
ctgggagagc tgtctgatgg ccaacctctg tttcctggcg agtccgagat cgaccagctg    660
ttcacaatcc agaaggtgct gggccctctg cctagcgagc agatgaagct gttctacagc    720
aaccccagat tccacggcct gagattccct gccgtgaatc accctcagag cctggaaaga    780
agatacctgg gcatcctgaa cagcgtgctg ctggacctga tgaagaatct gctgaaactg    840
gaccccgccg acagatacct gaccgagcag tgtctgaacc atcctacctt tcagacccag    900
agactgctgg atagaagccc cagcagaagc gccaagagaa agccctacca cgtggaaagc    960
agcaccctga gcaatagaaa ccaggccgga aagagcactg ccctgcagag ccaccacaga   1020
agcaacagca aggacatcca gaacctgagc gtgggcctgc ctagagctga tgaaggactg   1080
cctgccaacg agagcttcct gaatggaaat ctggctggcg cctctctgag ccctctgcac   1140
acaaagacat accaggccag cagccagcct ggcagcacaa gcaaggacct gaccaacaac   1200
aacatccctc atctgctgag ccccaaagag gccaagagca agaccgagtt cgacttcaac   1260
atcgacccca agcctagcga aggccctggc accaagtacc tgaagtccaa ctccagaagc   1320
cagcagaacc ggcactcctt catggaaagc tctcagagca aggccggcac actgcagcct   1380
aacgagaagc agagcagaca cagctacatc gacacaatcc ctcagtcctc tcggagcccc   1440
agctacagaa caaaggccaa atctcacggc gccctgagcg atagcaagag cgtgtccaat   1500
ctgtccgagg ctagagccca gatcgccgag cctagcacca gcagatactt ccctagcagc   1560
tgcctggatc tgaacagccc tacaagcccc acacctacca ggcacagcga taccagaaca   1620
ctgctgtccc caagcggccg gaacaacaga aatgagggca ccctggacag cagacggacc   1680
accacaagac acagcaagac catggaagaa ctgaagctgc ccgagcacat ggactctagc   1740
cactctcatt ctctgagcgc ccctcacgag tcctttagct acggcctggg ctacacaagc   1800
ccattttcca gtcagcagcg gccccacaga cactctatgt acgtgaccag agacaaagtc   1860
cgcgccaaag gcctggatgg ctctctgtct attggacaag gcatggccgc cagagccaat   1920
agcctgcaac ttctgtctcc tcagcctggc gaacagctgc ctcctgaaat gacagtggcc   1980
cggtccagcg tgaaagaaac cagcagagag ggcacctcca gcttccacac cagacagaaa   2040
agcgaaggcg gcgtgtacca cgatcctcac tctgatgatg gcacagcccc taaagagaac   2100
agacacctgt acaacgaccc cgtgcctaga agagtgggct ccttctacag agtgccttct   2160
cctagacctg acaactcctt ccacgagaac aacgtgtcaa cccgggtgtc cagcctgcct   2220
tctgagagca gctctggcac aaaccactcc aagaggcagc ccgccttcga tccttggaag   2280
tcccctgaga atatcagcca ctccgagcag ctgaaagaga aagagaagca gggctttttc   2340
cggtccatga agaagaagaa aaagaagtcc cagacagtcc ccaacagcga cagccctgat   2400
ctcctgacac tgcagaagtc catccacagc gccagcacac ctagcagcag acctaaagag   2460
tggcggccag agaagatcag cgacctgcaa acacagagcc agcctctgaa gtccctgagg   2520
aagctgctgc atctgtcctc cgcctctaat caccctgcca gcagcgatcc cagatttcag   2580
ccactgacag cccagcagac caagaactcc ttcagcgaga tccggattca cccactgtct   2640
caggccagcg gcggcagctc taatatcaga caagagcccg ctcctaaggg cagacctgct   2700
ctccaactgc ctggacagat ggatcctggc tggcacgtgt cctctgtgac aagatctgcc   2760
accgagggac ctagctattc tgagcagctg ggcgccaagt ctggccccaa tggacacccc   2820
```

tacaaccgga ccaatcggag cagaatgccc aacctgaacg acctcaaaga aacagccctc 2880
tga 2883

<210> SEQ ID NO 23
<211> LENGTH: 466
<212> TYPE: DNA
<213> ORGANISM: Artificial Sequence
<220> FEATURE:
<223> OTHER INFORMATION: promoter

<400> SEQUENCE: 23
ctgcagaggg ccctgcgtat gagtgcaagt gggttttagg accaggatga ggcggggtgg 60
gggtgcctac ctgacgaccg accccgaccc actggacaag cacccaaccc ccattcccca 120
aattgcgcat cccctatcag agagggggag gggaaacagg atgcggcgag gcgcgtgcgc 180
actgccagct tcagcaccgc ggacagtgcc ttcgcccccg cctggcggcg cgcgccaccg 240
ccgcctcagc actgaaggcg cgctgacgtc actcgccggt cccccgcaaa ctccccttcc 300
cggccacctt ggtcgcgtcc gcgccgccgc cggcccagcc ggaccgcacc acgcgaggcg 360
cgagataggg gggcacgggc gcgaccatct gcgctgcggc gccggcgact cagcgctgcc 420
tcagtctgcg gtgggcagcg gaggagtcgt gtcgtgcctg agagcg 466

<210> SEQ ID NO 24
<211> LENGTH: 3009
<212> TYPE: DNA
<213> ORGANISM: Artificial Sequence
<220> FEATURE:
<223> OTHER INFORMATION: nucleic acid sequence

<400> SEQUENCE: 24
atgaagatcc ccaatatcgg caacgtgatg aataagttcg agatcctggg agtggtggga 60
gagggagcat acggcgtggt gctgaagtgc agacacaagg agacacacga gatcgtggcc 120
atcaagaagt ttaaggatag cgaggagaat gaggaggtga aggagacaac cctgcgcgag 180
ctgaagatgc tgcggacact gaagcaggag aacatcgtgg agctgaagga ggccttccgg 240
agaaggggca agctgtacct ggtgtttgag tacgtggaga agaacatgct ggagctgctg 300
gaggagatgc ctaatggcgt gccccctgag aaggtgaaga gctacatcta tcagctgatc 360
aaggccatcc actggtgcca caagaacgac atcgtgcacc gcgatatcaa gccagagaac 420
ctgctgatca gccacaatga cgtgctgaag ctgtgcgatt tcggctttgc ccggaacctg 480
tccgagggca acaacgccaa ttacacagag tacgtggcaa ccaggtggta ccggtcccct 540
gagctgctgc tgggagcacc atacggcaag tctgtggaca tgtggagcgt gggctgcatc 600
ctgggagagc tgtccgacgg acagccactg ttccctggcg agtctgagat cgatcagctg 660
tttaccatcc agaaggtgct gggcccccctg ccttccgagc agatgaagct gttctactct 720
aacccaaggt tccacggcct gaggtttcca gccgtgaatc acccccagtc tctggagcgc 780
cggtatctgg gcatcctgaa cagcgtgctg ctggatctga tgaagaatct gctgaagctg 840
gaccctgccg atcgctacct gaccgagcag tgtctgaatc acccaacatt tcagacccag 900
agactgctgg acaggagccc ctcccgctct gccaagagga agccttatca cgtggagagc 960
tccaccctga gcaatcgcaa ccaggccggc aagtccacag ccctgcagtc tcaccaccgg 1020
agcaactcca aggacatcca gaatctgagc gtgggcctgc caagggcaga cgagggcctg 1080
cctgccaacg agtccttcct gaatggaaac ctggcaggag cctctctgag cccactgcac 1140

-continued

```
acaaagacct accaggcctc tagccagcct ggctccacat ctaaggacct gaccaacaat   1200

aacatccctc acctgctgag cccaaaggag gccaagtcca agaccgagtt cgactttaat   1260

atcgatccaa agcccagcga gggcccaggc acaaagtatc tgaagagcaa ctccagatct   1320

cagcagaata ggcactcttt catggagtcc tctcagagca aggccggcac cctgcagccc   1380

aacgagaagc agagcaggca ctcctacatc gataccatcc cacagagctc ccgcagcccc   1440

tcctatcgga caaaggccaa gagccacggc gccctgtctg acagcaagtc cgtgtctaat   1500

ctgtccgagg caagagcaca gatcgcagag ccaagcacct ccaggtactt tccctcttcc   1560

tgtctggacc tgaactctcc aacaagccct acaccaacca gacacagcga tacaaggacc   1620

ctgctgtctc ccagcggcag aaataacagg aacgagggca ccctggatag cagaaggacc   1680

acaaccagac actccaagac aatggaggag ctgaagctgc ccgagcacat ggactcctct   1740

cactcccact ctctgagcgc ccctcacgag tccttctctt acggcctggg ctataccagc   1800

ccttttagct cccagcagcg cccacacagg cactccatgt acgtgacaag agacaaggtg   1860

agggccaagg gcctggacgg cagcctgtcc atcggacagg gaatggcagc aagggcaaat   1920

agcctgcagc tgctgtcccc acagcctgga gagcagctgc caccagagat gaccgtggcc   1980

agatctagcg tgaaggagac aagcagggag ggcacctcct ctttccacac aagacagaag   2040

agcgagggcg gcgtgtatca cgacccacac tccgacgacg gaaccgcacc caaggagaac   2100

aggcacctgt acaacgatcc agtgccccgc cgggtgggct ctttctatcg ggtgcctagc   2160

ccacggcccg acaactcctt tcacgagaat aacgtgtcta ccagagtgag ctccctgcct   2220

agcgagtcta gctccggcac aaaccactcc aagaggcagc cagcctttga tccctggaag   2280

tctcctgaga atatctctca cagcgagcag ctgaaggaga aggagaagca gggcttcttt   2340

cgcagcatga agaagaagaa gaagaagagc cagacaaccg acagcaccaa cggcgagaat   2400

cctagcatca agaagtccct gttcccactg tttaactcca agaatcacct gaagcactct   2460

agctccctga agaagctgcc cgtggtgaca cctccaatgg tgcccaattc cgactctcct   2520

gatctgctga ccctgcagaa gagcatccac agcgcctcca caccatctag cagacccaag   2580

gagtggaggc cagagaagat ctccgatctg cagacccagt cccagcccct gaagtctctg   2640

cggaagctgc tgcacctgtc ctctgccagc aaccaccctg caagctccga ccctaggttc   2700

cagccactga cagcccagca gaccaagaac tcttttagcg agatcagaat ccacccactg   2760

tcccaggcct ctggaggctc tagcaacatc cgccaggagc ctgccccaaa gggccggcca   2820

gccctgcagc tgccaggaca gatggacccc ggctggcacg tgtcctctgt gacaagatcc   2880

gccaccgagg gaccatccta ctctgagcag ctgggagcaa agtctggacc aaacggacac   2940

ccttataaca ggaccaatag atccaggatg cctaatctga acgacctgaa ggagacagcc   3000

ctgtgatag                                                           3009
```

<210> SEQ ID NO 25
<211> LENGTH: 2835
<212> TYPE: DNA
<213> ORGANISM: Artificial Sequence
<220> FEATURE:
<223> OTHER INFORMATION: nucleic acid sequence

<400> SEQUENCE: 25

```
atgaagatcc ccaatatcgg caacgtgatg aataagttcg agatcctggg agtggtggga     60

gagggagcat acggagtggt gctgaagtgc cggcacaagg agacacacga gatcgtggcc    120

atcaagaagt ttaaggatag cgaggagaat gaggaggtga aggagacaac cctgagggag    180
```

```
ctgaagatgc tgcgcacact gaagcaggag aacatcgtgg agctgaagga ggccttccgg    240
agaaggggca agctgtacct ggtgtttgag tacgtggaga agaacatgct ggagctgctg    300
gaggagatgc ctaatggcgt gccccctgag aaggtgaaga gctacatcta tcagctgatc    360
aaggccatcc actggtgcca caagaacgac atcgtgcaca gggatatcaa gccagagaac    420
ctgctgatca gccacaatga cgtgctgaag ctgtgcgatt tcggctttgc ccgcaacctg    480
tccgagggca acaacgccaa ttacacagag tacgtggcaa ccaggtggta ccggtcccca    540
gagctgctgc tgggagcacc atacggcaag agcgtggaca tgtggtccgt gggctgcatc    600
ctgggcgagc tgtctgacgg ccagcctctg ttcccaggcg agagcgagat cgatcagctg    660
tttaccatcc agaaggtgct gggccctctg ccaagcgagc agatgaagct gttctactcc    720
aaccctaggt tccacggcct gcgctttccc gccgtgaatc accctcagag cctggagcgc    780
cggtatctgg gcatcctgaa ctccgtgctg ctggatctga tgaagaatct gctgaagctg    840
gaccccgccg ataggtacct gaccgagcag tgtctgaacc accccacatt ccagacccag    900
agactgctgg acaggtcccc ttctcgcaat caggccggca agtctacagc cctgcagagc    960
caccacagga gcaactccaa ggacatccag aatctgagcg tgggcctgcc tagggcagac   1020
gagggcctgc cagcaaacga gtcctttctg aatggaaacc tggcaggagc ctctctgagc   1080
ccactgcaca caaagaccta ccaggccagc tcccagccag gctccacatc taaggatctg   1140
accaacaata acatcccaca cctgctgtct cccaaggagg ccaagagcaa gaccgagttc   1200
gactttaata tcgatcccaa gcctagcgag ggcccaggca caaagtatct gaagagcaac   1260
tcccggagcc agcagaatag acactccttc atggagtcta gccagtctaa ggccggcacc   1320
ctgcagccca acgagaagca gagccgccac tcctacatcg ataccatccc ccagtcctct   1380
aggagccctt cctatcgcac aaaggccaag agccacggcg ccctgtctga cagcaagtcc   1440
gtgtctaatc tgtccgaggc aagggcacag atcgcagagc ccagcacctc cagatacttt   1500
cctagctcct gtctggacct gaactctcca acaagcccaa cacccacccg gcacagcgat   1560
acaagaaccc tgctgtctcc cagcggcaga aataacagga acgagggcac cctggattct   1620
agaaggacca caacccggca cagcaagaca atggaggagc tgaagctgcc cgagcacatg   1680
gactctagcc actcccactc tctgagcgcc cctcacgagt ccttctctta cggcctgggc   1740
tatacctccc cattttcctc tcaacagcgc ccccaccggc actctatgta cgtgacacgg   1800
gacaaggtga gagccaaggg cctggacggc agcctgtcca tcggacaggg aatggcagca   1860
agagcaaact ccctgcagct gctgtctcct cagccaggag agcagctgcc accagagatg   1920
accgtggcac ggagctccgt gaaggagaca agcagagagg gcacctctag cttccacaca   1980
cggcagaagt ccgagggcgg cgtgtatcac gaccctcact ctgacgacgg caccgcccca   2040
aaggagaaca gacacctgta caacgatcca gtgcctagga gggtgggctc cttctatcgg   2100
gtgccatctc cccgccctga caatagcttt cacgagaata acgtgtccac ccgggtgtcc   2160
tctctgccct ctgagagctc ctctggcaca aaccactcta agagacagcc cgcctttgac   2220
ccttggaaga gcccagagaa tatctctcac agcgagcagc tgaaggagaa ggagaagcag   2280
ggcttcttta ggagcatgaa gaagaagaag aagaagagcc agaccgtgcc taactccgac   2340
tctcccgatc tgctgaccct gcagaagagc atccacagcg cctccacacc aagctcccgg   2400
cctaaggagt ggcggcccga gaagatctcc gatctgcaga cccagagcca gccactgaag   2460
tccctgcgca agctgctgca cctgtctagc gccagcaacc accctgcctc ctctgaccca   2520
```

```
aggttccagc ccctgacagc ccagcagacc aagaactctt ttagcgagat ccgcatccac   2580

ccactgtccc aagcctctgg aggcagctcc aacatcaggc aggagccagc accaaagggc   2640

cgcccccgccc tgcagctgcc tggacagatg gaccccggat ggcacgtgtc tagcgtgaca   2700

cggtccgcca ccgagggacc atcctactct gagcagctgg gagcaaagag cggacctaac   2760

ggacacccat ataacagaac caatagatcc aggatgccta atctgaacga cctgaaggag   2820

acagccctgt gatag                                                     2835
```

<210> SEQ ID NO 26
<211> LENGTH: 2958
<212> TYPE: DNA
<213> ORGANISM: Artificial Sequence
<220> FEATURE:
<223> OTHER INFORMATION: nucleic acid sequence

<400> SEQUENCE: 26

```
atgaagatcc ccaatatcgg caacgtgatg aataagttcg agatcctggg agtggtggga     60

gagggagcat acggagtggt gctgaagtgc cggcacaagg agacacacga gatcgtggcc    120

atcaagaagt ttaaggatag cgaggagaat gaggaggtga aggagacaac cctgagggag    180

ctgaagatgc tgcgcacact gaagcaggag aacatcgtgg agctgaagga ggccttccgg    240

agaaggggca agctgtacct ggtgtttgag tacgtggaga agaacatgct ggagctgctg    300

gaggagatgc caaatggcgt gccccctgag aaggtgaagt cctacatcta tcagctgatc    360

aaggccatcc actggtgcca caagaacgac atcgtgcaca gggatatcaa gcccgagaac    420

ctgctgatct cccacaatga cgtgctgaag ctgtgcgatt tcggctttgc ccgcaacctg    480

agcgagggca acaacgccaa ttacacagag tacgtggcaa ccaggtggta ccggagccct    540

gagctgctgc tgggagcacc atacggcaag tctgtggaca tgtggagcgt gggctgcatc    600

ctgggagagc tgtccgacgg acagccactg ttccctggcg agtctgagat cgatcagctg    660

tttaccatcc agaaggtgct gggcccccctg ccttccgagc agatgaagct gttctactct    720

aaccctaggt tccacggcct gcgctttcca gccgtgaatc acccccagtc tctggagcgc    780

cggtatctgg gcatcctgaa cagcgtgctg ctggatctga tgaagaatct gctgaagctg    840

gaccccgccg ataggtacct gaccgagcag tgtctgaacc accctacatt ccagacccag    900

agactgctgg acaggtcccc atctcgcaat caggccggca agtccacagc cctgcagtct    960

caccacagga gcaactccaa ggacatccag aatctgtccg tgggcctgcc aagggcagac   1020

gagggcctgc ctgccaacga gagctttctg aatggaaacc tggcaggagc ctctctgagc   1080

ccactgcaca caaagaccta ccaggccagc tcccagcctg gctccacatc taaggacctg   1140

accaacaata acatccctca cctgctgagc ccaaaggagg ccaagtccaa gaccgagttc   1200

gactttaata tcgatccaaa gccatccgag ggaccaggaa caaagtatct gaagagcaac   1260

tcccggagcc agcagaatag acactctttc atggagtcta gccagagcaa ggccggcacc   1320

ctgcagccta acgagaagca gagccgccac tcctacatcg ataccatccc acagtcctct   1380

aggagcccct cctatcgcac aaaggccaag tcccacggcg ccctgtctga cagcaagtcc   1440

gtgtctaatc tgagcgaggc aagggcacag atcgcagagc caagcacctc cagatacttt   1500

cccagctcct gtctggacct gaactctccc acaagcccta caccaacccg gcacagcgat   1560

acaagaaccc tgctgtctcc tagcggcaga aataacagga acgagggcac cctggatagc   1620

agaaggacca caaccaggca ctccaagaca atggaggagc tgaagctgcc tgagcacatg   1680

gactctagcc actcccactc tctgagcgcc ccacacgagt ccttctctta cggcctgggc   1740
```

```
tataccagcc ctttttcctc tcaacaacgc ccacaccggc actccatgta cgtgacacgg   1800

gacaaggtga gagccaaggg cctggacggc agcctgtcca tcggacaggg aatggcagca   1860

agggcaaata gcctgcagct gctgtcccca cagcctggag agcagctgcc accagagatg   1920

accgtggcac ggagctccgt gaaggagaca agcagagagg gcacctctag cttccacaca   1980

cggcagaaga gcgagggcgg cgtgtatcac gacccacact ccgacgacgg aaccgcacct   2040

aaggagaaca gacacctgta caacgatcca gtgccccgcc gggtgggctc tttctatcgg   2100

gtgcctagcc cacgccccga caactccttt cacgagaata acgtgtctac ccgggtgtcc   2160

tctctgccca gcgagagctc ctctggcaca aaccactcca agagacagcc agcctttgat   2220

ccctggaagt ctcctgagaa tatctctcac agcgagcagc tgaaggagaa ggagaagcag   2280

ggcttctttc ggtccatgaa gaagaagaag aagaagagcc agacaaccga cagcaccaac   2340

ggcgagaatc caagcatcaa gaagtccctg ttcccccctgt ttaacagcaa gaatcacctg   2400

aagcacagct cctctctgaa gaagctgccc gtggtgacac ctccaatggt gcccaattcc   2460

gactctcctg atctgctgac cctgcagaag tccatccaca gcgcctccac accaagctcc   2520

cggcccaagg agtggcggcc cgagaagatc agcgatctgc agacccagtc ccagcccctg   2580

aagtctctga gaaagctgct gcacctgtct agcgcctcca accacccagc ctcctctgac   2640

cctcggttcc agccactgac agcccagcag accaagaact cttttagcga gatccgcatc   2700

cacccactgt cccaagcctc tggaggcagc tccaacatca ggcaggagcc tgccccaaag   2760

ggccgcccag ccctgcagct gccaggacag atggaccccg gctggcacgt gtctagcgtg   2820

acacggagcg ccaccgaggg accttcctac tctgagcagc tgggagcaaa gtctggacca   2880

aacggacacc cttataacag aaccaataga agcaggatgc caaatctgaa cgacctgaag   2940

gagacagccc tgtgatag                                                 2958
```

<210> SEQ ID NO 27
<211> LENGTH: 588
<212> TYPE: DNA
<213> ORGANISM: Artificial Sequence
<220> FEATURE:
<223> OTHER INFORMATION: nucleic acid sequence

<400> SEQUENCE: 27

```
tcaacctctg gattacaaaa tttgtgaaag attgactggt attcttaact atgttgctcc     60

ttttacgcta tgtggatacg ctgctttaat gcctttgtat catgctattg cttcccgtat    120

ggctttcatt ttctcctcct tgtataaatc ctggttgctg tctctttatg aggagttgtg    180

gcccgttgtc aggcaacgtg gcgtggtgtg cactgtgttt gctgacgcaa cccccactgg    240

ttggggcatt gccaccacct gtcagctcct ttccgggact ttcgctttcc ccctccctat    300

tgccacggcg gaactcatcg ccgcctgcct tgcccgctgc tggacagggg ctcggctgtt    360

gggcactgac aattccgtgg tgttgtcggg gaaatcatcg tcctttcctt ggctgctcgc    420

ctgtgttgcc acctggattc tgcgcgggac gtccttctgc tacgtccctt cggccctcaa    480

tccagcggac cttccttccc gcggcctgct gccggctctg cggcctcttc cgcgtcttcg    540

ccttcgccct cagacgagtc ggatctccct ttgggccgcc tccccgca                 588
```

<210> SEQ ID NO 28
<211> LENGTH: 239
<212> TYPE: DNA
<213> ORGANISM: Artificial Sequence
<220> FEATURE:

<223> OTHER INFORMATION: nucleic acid sequence

<400> SEQUENCE: 28
ggccgcttcg agcagacatg ataagataca ttgatgagtt tggacaaacc acaactagaa 60
tgcagtgaaa aaaatgcttt atttgtgaaa tttgtgatgc tattgcttta tttgtaacca 120
ttataagctg caataaacaa gttaacaaca acaattgcat tcattttatg tttcaggttc 180
agggggagat gtgggaggtt ttttaaagca agtaaaacct ctacaaatgt ggtaaaatc 239

<210> SEQ ID NO 29
<211> LENGTH: 7627
<212> TYPE: DNA
<213> ORGANISM: Artificial Sequence
<220> FEATURE:
<223> OTHER INFORMATION: Expression cassette
<220> FEATURE:
<221> NAME/KEY: repeat_region
<222> LOCATION: (1)..(130)
<223> OTHER INFORMATION: 5' ITR
<220> FEATURE:
<221> NAME/KEY: misc_feature
<222> LOCATION: (130)..(168)
<223> OTHER INFORMATION: AAV2 seq upstream of 3'ITR
<220> FEATURE:
<221> NAME/KEY: promoter
<222> LOCATION: (226)..(1454)
<223> OTHER INFORMATION: UbC promoter
<220> FEATURE:
<221> NAME/KEY: misc_feature
<222> LOCATION: (308)..(308)
<223> OTHER INFORMATION: Insertion (C)
<220> FEATURE:
<221> NAME/KEY: misc_feature
<222> LOCATION: (1009)..(1009)
<223> OTHER INFORMATION: Insertion (G)
<220> FEATURE:
<221> NAME/KEY: CDS
<222> LOCATION: (1470)..(4352)
<223> OTHER INFORMATION: hCDKL5_1
<220> FEATURE:
<221> NAME/KEY: misc_feature
<222> LOCATION: (4353)..(4353)
<223> OTHER INFORMATION: Deletion (G)
<220> FEATURE:
<221> NAME/KEY: misc_feature
<222> LOCATION: (4370)..(4391)
<223> OTHER INFORMATION: miRNA183
<220> FEATURE:
<221> NAME/KEY: misc_feature
<222> LOCATION: (4396)..(4417)
<223> OTHER INFORMATION: miRNA183
<220> FEATURE:
<221> NAME/KEY: misc_feature
<222> LOCATION: (4424)..(4445)
<223> OTHER INFORMATION: miRNA183
<220> FEATURE:
<221> NAME/KEY: misc_feature
<222> LOCATION: (4452)..(4473)
<223> OTHER INFORMATION: miRNA183
<220> FEATURE:
<221> NAME/KEY: polyA_signal
<222> LOCATION: (4482)..(4608)
<223> OTHER INFORMATION: Rabbit Globin polyA
<220> FEATURE:
<221> NAME/KEY: misc_feature
<222> LOCATION: (4639)..(4677)
<223> OTHER INFORMATION: AAV2 seq upstream of 3'ITR
<220> FEATURE:
<221> NAME/KEY: repeat_region
<222> LOCATION: (4677)..(4806)
<223> OTHER INFORMATION: 3'ITR

<400> SEQUENCE: 29
ctgcgcgctc gctcgctcac tgaggccgcc cgggcaaagc ccgggcgtcg ggcgaccttt 60

```
ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatcc tctagaacta tagctagcat gctctaggaa gatctggcct ccgcgccggg    240

ttttggcgcc tcccgcgggc gcccccctcc tcacggcgag cgctgccacg tcagacgaag    300

ggcgcagcga gcgtcctgat ccttccgccc ggacgctcag gacagcggcc cgctgctcat    360

aagactcggc cttagaaccc cagtatcagc agaaggacat tttaggacgg gacttgggtg    420

actctagggc actggttttc tttccagaga gcggaacagg cgaggaaaag tagtcccttc    480

tcggcgattc tgcggaggga tctccgtggg gcggtgaacg ccgatgatta tataaggacg    540

cgccgggtgt ggcacagcta gttccgtcgc agccgggatt tgggtcgcgg ttcttgtttg    600

tggatcgctg tgatcgtcac ttggtgagta gcgggctgct gggctggccg ggctttcgt     660

ggccgccggg ccgctcggtg ggacggaagc gtgtggagag accgccaagg gctgtagtct    720

gggtccgcga gcaaggttgc cctgaactgg gggttggggg gagcgcagca aaatggcggc    780

tgttcccgag tcttgaatgg aagacgcttg tgaggcgggc tgtgaggtcg ttgaaacaag    840

gtggggggca tggtgggcgg caagaaccca aggtcttgag gccttcgcta atgcgggaaa    900

gctcttattc gggtgagatg ggctggggca ccatctgggg accctgacgt gaagtttgtc    960

actgactgga gaactcggtt tgtcgtctgt tgcggggggcg gcagttatgg cggtgccgtt   1020

gggcagtgca cccgtacctt tgggagcgcg cgccctcgtc gtgtcgtgac gtcacccgtt   1080

ctgttggctt ataatgcagg gtggggccac ctgccggtag gtgtgcggta ggcttttctc   1140

cgtcgcagga cgcagggttc gggcctaggg taggctctcc tgaatcgaca ggcgccggac   1200

ctctggtgag gggagggata agtgaggcgt cagtttcttt ggtcggtttt atgtacctat   1260

cttcttaagt agctgaagct ccggttttga actatgcgct cggggttggc gagtgtgttt   1320

tgtgaagttt tttaggcacc ttttgaaatg taatcatttg ggtcaatatg taattttcag   1380

tgttagacta gtaaattgtc cgctaaattc tggccgtttt tggctttttt gttagacgaa   1440

gctttattgc ggtagaattc gccgccacc atg aag atc ccc aac atc ggc aac     1493
                                Met Lys Ile Pro Asn Ile Gly Asn
                                1               5

gtg atg aac aag ttc gag atc ctg ggc gtt gtc gga gaa ggc gct tat     1541
Val Met Asn Lys Phe Glu Ile Leu Gly Val Val Gly Glu Gly Ala Tyr
    10                  15                  20

ggc gtg gtg ctg aag tgc aga cac aaa gaa acc cac gag atc gtg gcc     1589
Gly Val Val Leu Lys Cys Arg His Lys Glu Thr His Glu Ile Val Ala
25                  30                  35                  40

atc aag aag ttc aag gac agc gaa gag aac gag gaa gtg aaa gag aca     1637
Ile Lys Lys Phe Lys Asp Ser Glu Glu Asn Glu Glu Val Lys Glu Thr
                45                  50                  55

acc ctg cgc gag ctg aag atg ctg aga acc ctg aag caa gag aac atc     1685
Thr Leu Arg Glu Leu Lys Met Leu Arg Thr Leu Lys Gln Glu Asn Ile
            60                  65                  70

gtg gaa ctg aaa gag gcc ttc cgg cgg aga ggc aag ctg tac ctg gtg     1733
Val Glu Leu Lys Glu Ala Phe Arg Arg Arg Gly Lys Leu Tyr Leu Val
        75                  80                  85

ttc gag tac gtg gaa aag aac atg ctc gag ctg ctg gaa gag atg ccc     1781
Phe Glu Tyr Val Glu Lys Asn Met Leu Glu Leu Leu Glu Glu Met Pro
    90                  95                  100

aat ggc gtg cca cct gag aaa gtg aag tcc tac atc tac cag ctg atc     1829
Asn Gly Val Pro Pro Glu Lys Val Lys Ser Tyr Ile Tyr Gln Leu Ile
105                 110                 115                 120
```

-continued

```
aag gcc atc cac tgg tgc cac aag aac gac atc gtg cac aga gac atc      1877
Lys Ala Ile His Trp Cys His Lys Asn Asp Ile Val His Arg Asp Ile
                125                 130                 135

aag ccc gag aac ctg ctg atc tcc cac aac gac gtg ctg aag ctg tgc      1925
Lys Pro Glu Asn Leu Leu Ile Ser His Asn Asp Val Leu Lys Leu Cys
            140                 145                 150

gac ttc ggc ttc gcc aga aat ctg agc gag ggc aac aac gcc aac tac      1973
Asp Phe Gly Phe Ala Arg Asn Leu Ser Glu Gly Asn Asn Ala Asn Tyr
        155                 160                 165

acc gag tat gtg gcc acc aga tgg tac aga agc cct gaa ctg ctg ctg      2021
Thr Glu Tyr Val Ala Thr Arg Trp Tyr Arg Ser Pro Glu Leu Leu Leu
    170                 175                 180

gga gcc cct tac ggc aag tct gtg gat atg tgg tcc gtg ggc tgt atc      2069
Gly Ala Pro Tyr Gly Lys Ser Val Asp Met Trp Ser Val Gly Cys Ile
185                 190                 195                 200

ctg gga gag ctg tct gat ggc caa cct ctg ttt cct ggc gag tcc gag      2117
Leu Gly Glu Leu Ser Asp Gly Gln Pro Leu Phe Pro Gly Glu Ser Glu
                205                 210                 215

atc gac cag ctg ttc aca atc cag aag gtg ctg ggc cct ctg cct agc      2165
Ile Asp Gln Leu Phe Thr Ile Gln Lys Val Leu Gly Pro Leu Pro Ser
            220                 225                 230

gag cag atg aag ctg ttc tac agc aac ccc aga ttc cac ggc ctg aga      2213
Glu Gln Met Lys Leu Phe Tyr Ser Asn Pro Arg Phe His Gly Leu Arg
        235                 240                 245

ttc cct gcc gtg aat cac cct cag agc ctg gaa aga aga tac ctg ggc      2261
Phe Pro Ala Val Asn His Pro Gln Ser Leu Glu Arg Arg Tyr Leu Gly
    250                 255                 260

atc ctg aac agc gtg ctg ctg gac ctg atg aag aat ctg ctg aaa ctg      2309
Ile Leu Asn Ser Val Leu Leu Asp Leu Met Lys Asn Leu Leu Lys Leu
265                 270                 275                 280

gac ccc gcc gac aga tac ctg acc gag cag tgt ctg aac cat cct acc      2357
Asp Pro Ala Asp Arg Tyr Leu Thr Glu Gln Cys Leu Asn His Pro Thr
                285                 290                 295

ttt cag acc cag aga ctg ctg gat aga agc ccc agc aga agc gcc aag      2405
Phe Gln Thr Gln Arg Leu Leu Asp Arg Ser Pro Ser Arg Ser Ala Lys
            300                 305                 310

aga aag ccc tac cac gtg gaa agc agc acc ctg agc aat aga aac cag      2453
Arg Lys Pro Tyr His Val Glu Ser Ser Thr Leu Ser Asn Arg Asn Gln
        315                 320                 325

gcc gga aag agc act gcc ctg cag agc cac cac aga agc aac agc aag      2501
Ala Gly Lys Ser Thr Ala Leu Gln Ser His His Arg Ser Asn Ser Lys
    330                 335                 340

gac atc cag aac ctg agc gtg ggc ctg cct aga gct gat gaa gga ctg      2549
Asp Ile Gln Asn Leu Ser Val Gly Leu Pro Arg Ala Asp Glu Gly Leu
345                 350                 355                 360

cct gcc aac gag agc ttc ctg aat gga aat ctg gct ggc gcc tct ctg      2597
Pro Ala Asn Glu Ser Phe Leu Asn Gly Asn Leu Ala Gly Ala Ser Leu
                365                 370                 375

agc cct ctg cac aca aag aca tac cag gcc agc agc cag cct ggc agc      2645
Ser Pro Leu His Thr Lys Thr Tyr Gln Ala Ser Ser Gln Pro Gly Ser
            380                 385                 390

aca agc aag gac ctg acc aac aac aac atc cct cat ctg ctg agc ccc      2693
Thr Ser Lys Asp Leu Thr Asn Asn Asn Ile Pro His Leu Leu Ser Pro
        395                 400                 405

aaa gag gcc aag agc aag acc gag ttc gac ttc aac atc gac ccc aag      2741
Lys Glu Ala Lys Ser Lys Thr Glu Phe Asp Phe Asn Ile Asp Pro Lys
    410                 415                 420

cct agc gaa ggc cct ggc acc aag tac ctg aag tcc aac tcc aga agc      2789
Pro Ser Glu Gly Pro Gly Thr Lys Tyr Leu Lys Ser Asn Ser Arg Ser
425                 430                 435                 440
```

```
cag cag aac cgg cac tcc ttc atg gaa agc tct cag agc aag gcc ggc     2837
Gln Gln Asn Arg His Ser Phe Met Glu Ser Ser Gln Ser Lys Ala Gly
                445                 450                 455

aca ctg cag cct aac gag aag cag agc aga cac agc tac atc gac aca     2885
Thr Leu Gln Pro Asn Glu Lys Gln Ser Arg His Ser Tyr Ile Asp Thr
            460                 465                 470

atc cct cag tcc tct cgg agc ccc agc tac aga aca aag gcc aaa tct     2933
Ile Pro Gln Ser Ser Arg Ser Pro Ser Tyr Arg Thr Lys Ala Lys Ser
        475                 480                 485

cac ggc gcc ctg agc gat agc aag agc gtg tcc aat ctg tcc gag gct     2981
His Gly Ala Leu Ser Asp Ser Lys Ser Val Ser Asn Leu Ser Glu Ala
    490                 495                 500

aga gcc cag atc gcc gag cct agc acc agc aga tac ttc cct agc agc     3029
Arg Ala Gln Ile Ala Glu Pro Ser Thr Ser Arg Tyr Phe Pro Ser Ser
505                 510                 515                 520

tgc ctg gat ctg aac agc cct aca agc ccc aca cct acc agg cac agc     3077
Cys Leu Asp Leu Asn Ser Pro Thr Ser Pro Thr Pro Thr Arg His Ser
                525                 530                 535

gat acc aga aca ctg ctg tcc cca agc ggc cgg aac aac aga aat gag     3125
Asp Thr Arg Thr Leu Leu Ser Pro Ser Gly Arg Asn Asn Arg Asn Glu
            540                 545                 550

ggc acc ctg gac agc aga cgg acc acc aca aga cac agc aag acc atg     3173
Gly Thr Leu Asp Ser Arg Arg Thr Thr Thr Arg His Ser Lys Thr Met
        555                 560                 565

gaa gaa ctg aag ctg ccc gag cac atg gac tct agc cac tct cat tct     3221
Glu Glu Leu Lys Leu Pro Glu His Met Asp Ser Ser His Ser His Ser
    570                 575                 580

ctg agc gcc cct cac gag tcc ttt agc tac ggc ctg ggc tac aca agc     3269
Leu Ser Ala Pro His Glu Ser Phe Ser Tyr Gly Leu Gly Tyr Thr Ser
585                 590                 595                 600

cca ttt tcc agt cag cag cgg ccc cac aga cac tct atg tac gtg acc     3317
Pro Phe Ser Ser Gln Gln Arg Pro His Arg His Ser Met Tyr Val Thr
                605                 610                 615

aga gac aaa gtc cgc gcc aaa ggc ctg gat ggc tct ctg tct att gga     3365
Arg Asp Lys Val Arg Ala Lys Gly Leu Asp Gly Ser Leu Ser Ile Gly
            620                 625                 630

caa ggc atg gcc gcc aga gcc aat agc ctg caa ctt ctg tct cct cag     3413
Gln Gly Met Ala Ala Arg Ala Asn Ser Leu Gln Leu Leu Ser Pro Gln
        635                 640                 645

cct ggc gaa cag ctg cct cct gaa atg aca gtg gcc cgg tcc agc gtg     3461
Pro Gly Glu Gln Leu Pro Pro Glu Met Thr Val Ala Arg Ser Ser Val
    650                 655                 660

aaa gaa acc agc aga gag ggc acc tcc agc ttc cac acc aga cag aaa     3509
Lys Glu Thr Ser Arg Glu Gly Thr Ser Ser Phe His Thr Arg Gln Lys
665                 670                 675                 680

agc gaa ggc ggc gtg tac cac gat cct cac tct gat gat ggc aca gcc     3557
Ser Glu Gly Gly Val Tyr His Asp Pro His Ser Asp Asp Gly Thr Ala
                685                 690                 695

cct aaa gag aac aga cac ctg tac aac gac ccc gtg cct aga aga gtg     3605
Pro Lys Glu Asn Arg His Leu Tyr Asn Asp Pro Val Pro Arg Arg Val
            700                 705                 710

ggc tcc ttc tac aga gtg cct tct cct aga cct gac aac tcc ttc cac     3653
Gly Ser Phe Tyr Arg Val Pro Ser Pro Arg Pro Asp Asn Ser Phe His
        715                 720                 725

gag aac aac gtg tca acc cgg gtg tcc agc ctg cct tct gag agc agc     3701
Glu Asn Asn Val Ser Thr Arg Val Ser Ser Leu Pro Ser Glu Ser Ser
    730                 735                 740

tct ggc aca aac cac tcc aag agg cag ccc gcc ttc gat cct tgg aag     3749
Ser Gly Thr Asn His Ser Lys Arg Gln Pro Ala Phe Asp Pro Trp Lys
```

```
745                 750                 755                 760

tcc cct gag aat atc agc cac tcc gag cag ctg aaa gag aaa gag aag     3797
Ser Pro Glu Asn Ile Ser His Ser Glu Gln Leu Lys Glu Lys Glu Lys
                765                 770                 775

cag ggc ttt ttc cgg tcc atg aag aag aag aaa aag aag tcc cag aca     3845
Gln Gly Phe Phe Arg Ser Met Lys Lys Lys Lys Lys Lys Ser Gln Thr
            780                 785                 790

gtc ccc aac agc gac agc cct gat ctc ctg aca ctg cag aag tcc atc     3893
Val Pro Asn Ser Asp Ser Pro Asp Leu Leu Thr Leu Gln Lys Ser Ile
        795                 800                 805

cac agc gcc agc aca cct agc agc aga cct aaa gag tgg cgg cca gag     3941
His Ser Ala Ser Thr Pro Ser Ser Arg Pro Lys Glu Trp Arg Pro Glu
    810                 815                 820

aag atc agc gac ctg caa aca cag agc cag cct ctg aag tcc ctg agg     3989
Lys Ile Ser Asp Leu Gln Thr Gln Ser Gln Pro Leu Lys Ser Leu Arg
825                 830                 835                 840

aag ctg ctg cat ctg tcc tcc gcc tct aat cac cct gcc agc agc gat     4037
Lys Leu Leu His Leu Ser Ser Ala Ser Asn His Pro Ala Ser Ser Asp
                845                 850                 855

ccc aga ttt cag cca ctg aca gcc cag cag acc aag aac tcc ttc agc     4085
Pro Arg Phe Gln Pro Leu Thr Ala Gln Gln Thr Lys Asn Ser Phe Ser
            860                 865                 870

gag atc cgg att cac cca ctg tct cag gcc agc ggc ggc agc tct aat     4133
Glu Ile Arg Ile His Pro Leu Ser Gln Ala Ser Gly Gly Ser Ser Asn
        875                 880                 885

atc aga caa gag ccc gct cct aag ggc aga cct gct ctc caa ctg cct     4181
Ile Arg Gln Glu Pro Ala Pro Lys Gly Arg Pro Ala Leu Gln Leu Pro
    890                 895                 900

gga cag atg gat cct ggc tgg cac gtg tcc tct gtg aca aga tct gcc     4229
Gly Gln Met Asp Pro Gly Trp His Val Ser Ser Val Thr Arg Ser Ala
905                 910                 915                 920

acc gag gga cct agc tat tct gag cag ctg ggc gcc aag tct ggc ccc     4277
Thr Glu Gly Pro Ser Tyr Ser Glu Gln Leu Gly Ala Lys Ser Gly Pro
                925                 930                 935

aat gga cac ccc tac aac cgg acc aat cgg agc aga atg ccc aac ctg     4325
Asn Gly His Pro Tyr Asn Arg Thr Asn Arg Ser Arg Met Pro Asn Leu
            940                 945                 950

aac gac ctc aaa gaa aca gcc ctc tga agcttatcga taccggtagt           4372
Asn Asp Leu Lys Glu Thr Ala Leu
        955                 960

gaattctacc agtgccatag gatagtgaat tctaccagtg ccatacacgt gagtgaattc   4432

taccagtgcc atagcatgca gtgaattcta ccagtgccat agcggccgcg atctttttcc   4492

ctctgccaaa aattatgggg acatcatgaa gccccttgag catctgactt ctggctaata   4552

aaggaaattt attttcattg caatagtgtg ttggaatttt ttgtgtctct cactcgatcg   4612

ataaggatct tcctagagca tggctacgta gataagtagc atggcgggtt aatcattaac   4672

tacaaggaac ccctagtgat ggagttggcc actccctctc tgcgcgctcg ctcgctcact   4732

gaggccgggc gaccaaaggt cgcccgacgc ccgggctttg cccgggcggc ctcagtgagc   4792

gagcgagcgc gcagccttaa ttaacctaat tcactggccg tcgttttaca acgtcgtgac   4852

tgggaaaacc ctggcgttac ccaacttaat cgccttgcag cacatccccc tttcgccagc   4912

tggcgtaata gcgaagaggc ccgcaccgat cgcccttccc aacagttgcg cagcctgaat   4972

ggcgaatggg acgcgccctg tagcggcgca ttaagcgcgg cgggtgtggt ggttacgcgc   5032

agcgtgaccg ctacacttgc cagcgcccta gcgcccgctc ctttcgcttt cttcccttcc   5092

tttctcgcca cgttcgccgg ctttccccgt caagctctaa atcgggggct ccctttaggg   5152
```

```
ttccgattta gtgctttacg gcacctcgac cccaaaaaac ttgattaggg tgatggttca   5212
cgtagtgggc catcgccctg atagacggtt tttcgccctt tgacgttgga gtccacgttc   5272
tttaatagtg gactcttgtt ccaaactgga acaacactca accctatctc ggtctattct   5332
tttgatttat aagggatttt gccgatttcg gcctattggt taaaaaatga gctgatttaa   5392
caaaaattta acgcgaattt taacaaaata ttaacgctta caatttaggt ggcacttttc   5452
ggggaaatgt gcgcggaacc cctatttgtt tatttttcta aatacattca aatatgtatc   5512
cgctcatgag acaataaccc tgataaatgc ttcaataata ttgaaaaagg aagagtatga   5572
gtattcaaca tttccgtgtc gcccttattc ccttttttgc ggcattttgc cttcctgttt   5632
ttgctcaccc agaaacgctg gtgaaagtaa aagatgctga agatcagttg ggtgcacgag   5692
tgggttacat cgaactggat ctcaacagcg gtaagatcct tgagagtttt cgccccgaag   5752
aacgttttcc aatgatgagc acttttaaag ttctgctatg tggcgcggta ttatcccgta   5812
ttgacgccgg gcaagagcaa ctcggtcgcc gcatacacta ttctcagaat gacttggttg   5872
agtactcacc agtcacagaa aagcatctta cggatggcat gacagtaaga gaattatgca   5932
gtgctgccat aaccatgagt gataacactg cggccaactt acttctgaca acgatcggag   5992
gaccgaagga gctaaccgct tttttgcaca acatggggga tcatgtaact cgccttgatc   6052
gttgggaacc ggagctgaat gaagccatac caaacgacga gcgtgacacc acgatgcctg   6112
tagcaatggc aacaacgttg cgcaaactat taactggcga actacttact ctagcttccc   6172
ggcaacaatt aatagactgg atggaggcgg ataaagttgc aggaccactt ctgcgctcgg   6232
cccttccggc tggctggttt attgctgata aatctggagc cggtgagcgt gggtctcgcg   6292
gtatcattgc agcactgggg ccagatggta agccctcccg tatcgtagtt atctacacga   6352
cggggagtca ggcaactatg gatgaacgaa atagacagat cgctgagata ggtgcctcac   6412
tgattaagca ttggtaactg tcagaccaag tttactcata tatactttag attgatttaa   6472
aacttcattt ttaatttaaa aggatctagg tgaagatcct ttttgataat ctcatgacca   6532
aaatccctta acgtgagttt tcgttccact gagcgtcaga ccccgtagaa aagatcaaag   6592
gatcttcttg agatcctttt tttctgcgcg taatctgctg cttgcaaaca aaaaaaccac   6652
cgctaccagc ggtggtttgt ttgccggatc aagagctacc aactcttttt ccgaaggtaa   6712
ctggcttcag cagagcgcag ataccaaata ctgttcttct agtgtagccg tagttaggcc   6772
accacttcaa gaactctgta gcaccgccta catacctcgc tctgctaatc ctgttaccag   6832
tggctgctgc cagtggcgat aagtcgtgtc ttaccgggtt ggactcaaga cgatagttac   6892
cggataaggc gcagcggtcg ggctgaacgg ggggttcgtg cacacagccc agcttggagc   6952
gaacgaccta caccgaactg agatacctac agcgtgagct atgagaaagc gccacgcttc   7012
ccgaagggag aaaggcggac aggtatccgg taagcggcag ggtcggaaca ggagagcgca   7072
cgagggagct tccaggggga aacgcctggt atctttatag tcctgtcggg tttcgccacc   7132
tctgacttga gcgtcgattt ttgtgatgct cgtcaggggg gcggagccta tggaaaaacg   7192
ccagcaacgc ggccttttta cggttcctgg ccttttgctg gccttttgct cacatgttct   7252
ttcctgcgtt atcccctgat tctgtggata accgtattac cgcctttgag tgagctgata   7312
ccgctcgccg cagccgaacg accgagcgca gcgagtcagt gagcgaggaa gcggaagagc   7372
gcccaatacg caaaccgcct ctccccgcgc gttggccgat tcattaatgc agctggcacg   7432
acaggtttcc cgactggaaa gcgggcagtg agcgcaacgc aattaatgtg agttagctca   7492
```

```
ctcattaggc accccaggct ttacacttta tgcttccggc tcgtatgttg tgtggaattg   7552

tgagcggata acaatttcac acaggaaaca gctatgacca tgattacgcc agatttaatt   7612

aaggccttaa ttagg                                                    7627


<210> SEQ ID NO 30
<211> LENGTH: 960
<212> TYPE: PRT
<213> ORGANISM: Artificial Sequence
<220> FEATURE:
<223> OTHER INFORMATION: Synthetic Construct

<400> SEQUENCE: 30

Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335
```

```
Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750

Gln Pro Ala Phe Asp Pro Trp Lys Ser Pro Glu Asn Ile Ser His Ser
```

```
        755                 760                 765

Glu Gln Leu Lys Glu Lys Glu Lys Gln Gly Phe Phe Arg Ser Met Lys
    770                 775                 780

Lys Lys Lys Lys Lys Ser Gln Thr Val Pro Asn Ser Asp Ser Pro Asp
785                 790                 795                 800

Leu Leu Thr Leu Gln Lys Ser Ile His Ser Ala Ser Thr Pro Ser Ser
                805                 810                 815

Arg Pro Lys Glu Trp Arg Pro Glu Lys Ile Ser Asp Leu Gln Thr Gln
            820                 825                 830

Ser Gln Pro Leu Lys Ser Leu Arg Lys Leu Leu His Leu Ser Ser Ala
        835                 840                 845

Ser Asn His Pro Ala Ser Ser Asp Pro Arg Phe Gln Pro Leu Thr Ala
    850                 855                 860

Gln Gln Thr Lys Asn Ser Phe Ser Glu Ile Arg Ile His Pro Leu Ser
865                 870                 875                 880

Gln Ala Ser Gly Gly Ser Ser Asn Ile Arg Gln Glu Pro Ala Pro Lys
                885                 890                 895

Gly Arg Pro Ala Leu Gln Leu Pro Gly Gln Met Asp Pro Gly Trp His
            900                 905                 910

Val Ser Ser Val Thr Arg Ser Ala Thr Glu Gly Pro Ser Tyr Ser Glu
        915                 920                 925

Gln Leu Gly Ala Lys Ser Gly Pro Asn Gly His Pro Tyr Asn Arg Thr
    930                 935                 940

Asn Arg Ser Arg Met Pro Asn Leu Asn Asp Leu Lys Glu Thr Ala Leu
945                 950                 955                 960
```

```
<210> SEQ ID NO 31
<211> LENGTH: 7210
<212> TYPE: DNA
<213> ORGANISM: Artificial Sequence
<220> FEATURE:
<223> OTHER INFORMATION: Expression cassette
<220> FEATURE:
<221> NAME/KEY: repeat_region
<222> LOCATION: (1)..(130)
<223> OTHER INFORMATION: 5' ITR
<220> FEATURE:
<221> NAME/KEY: misc_feature
<222> LOCATION: (130)..(168)
<223> OTHER INFORMATION: AAV2 seq upstream of 3' ITR
<220> FEATURE:
<221> NAME/KEY: promoter
<222> LOCATION: (224)..(1021)
<223> OTHER INFORMATION: CBh
<220> FEATURE:
<221> NAME/KEY: misc_feature
<222> LOCATION: (801)..(801)
<223> OTHER INFORMATION: A deletion
<220> FEATURE:
<221> NAME/KEY: CDS
<222> LOCATION: (1053)..(3935)
<223> OTHER INFORMATION: hCDKL5-1
<220> FEATURE:
<221> NAME/KEY: misc_feature
<222> LOCATION: (3936)..(3936)
<223> OTHER INFORMATION: Deletion (G)
<220> FEATURE:
<221> NAME/KEY: misc_feature
<222> LOCATION: (3953)..(3974)
<223> OTHER INFORMATION: miRNA183
<220> FEATURE:
<221> NAME/KEY: misc_feature
<222> LOCATION: (3979)..(4000)
<223> OTHER INFORMATION: miRNA183
<220> FEATURE:
<221> NAME/KEY: misc_feature
```

```
<222> LOCATION: (4007)..(4028)
<223> OTHER INFORMATION: miRNA183
<220> FEATURE:
<221> NAME/KEY: misc_feature
<222> LOCATION: (4035)..(4056)
<223> OTHER INFORMATION: miRNA183
<220> FEATURE:
<221> NAME/KEY: polyA_signal
<222> LOCATION: (4065)..(4191)
<223> OTHER INFORMATION: Rabbit Globin PolyA
<220> FEATURE:
<221> NAME/KEY: misc_feature
<222> LOCATION: (4222)..(4260)
<223> OTHER INFORMATION: AAV2 seq upstream of 3' ITR
<220> FEATURE:
<221> NAME/KEY: repeat_region
<222> LOCATION: (4260)..(4389)
<223> OTHER INFORMATION: 3' ITR

<400> SEQUENCE: 31

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatcc tctagaacta tagctagcgc ccttaagggt acccgttaca taacttacgg    240

taaatggccc gcctggctga ccgcccaacg acccccgccc attgacgtca atagtaacgc    300

caatagggac tttccattga cgtcaatggg tggagtattt acggtaaact gcccacttgg    360

cagtacatca agtgtatcat atgccaagta cgccccctat tgacgtcaat gacggtaaat    420

ggcccgcctg gcattgtgcc cagtacatga ccttatggga ctttcctact tggcagtaca    480

tctacgtatt agtcatcgct attaccatgg tcgaggtgag ccccacgttc tgcttcactc    540

tccccatctc ccccccctcc ccacccccaa ttttgtattt atttattttt taattatttt    600

gtgcagcgat gggggcgggg gggggggggg ggcgcgcgcc aggcggggcg gggcggggcg    660

aggggcgggg cggggcgagg cggagaggtg cggcggcagc caatcagagc ggcgcgctcc    720

gaaagtttcc ttttatggcg aggcggcggc ggcggcggcc ctataaaaag cgaagcgcgc    780

ggcgggcggg agtcgctgcg cgctgccttc gccccgtgcc ccgctccgcc gccgcctcgc    840

gccgcccgcc ccggctctga ctgaccgcgt tactcccaca ggtgagcggg cgggacggcc    900

cttctcctcc gggctgtaat tagctgagca agaggtaagg gtttaaggga tggttggttg    960

gtggggtatt aatgtttaat tacctggagc acctgcctga aatcactttt tttcaggttg   1020

gcttaagctg cagaccggaa ttcgccgcca cc atg aag atc ccc aac atc ggc     1073
                                    Met Lys Ile Pro Asn Ile Gly
                                    1               5

aac gtg atg aac aag ttc gag atc ctg ggc gtt gtc gga gaa ggc gct     1121
Asn Val Met Asn Lys Phe Glu Ile Leu Gly Val Val Gly Glu Gly Ala
        10                  15                  20

tat ggc gtg gtg ctg aag tgc aga cac aaa gaa acc cac gag atc gtg     1169
Tyr Gly Val Val Leu Lys Cys Arg His Lys Glu Thr His Glu Ile Val
    25                  30                  35

gcc atc aag aag ttc aag gac agc gaa gag aac gag gaa gtg aaa gag     1217
Ala Ile Lys Lys Phe Lys Asp Ser Glu Glu Asn Glu Glu Val Lys Glu
40                  45                  50                  55

aca acc ctg cgc gag ctg aag atg ctg aga acc ctg aag caa gag aac     1265
Thr Thr Leu Arg Glu Leu Lys Met Leu Arg Thr Leu Lys Gln Glu Asn
                60                  65                  70

atc gtg gaa ctg aaa gag gcc ttc cgg cgg aga ggc aag ctg tac ctg     1313
Ile Val Glu Leu Lys Glu Ala Phe Arg Arg Arg Gly Lys Leu Tyr Leu
            75                  80                  85
```

-continued

```
gtg ttc gag tac gtg gaa aag aac atg ctc gag ctg ctg gaa gag atg     1361
Val Phe Glu Tyr Val Glu Lys Asn Met Leu Glu Leu Leu Glu Glu Met
        90                  95                  100

ccc aat ggc gtg cca cct gag aaa gtg aag tcc tac atc tac cag ctg     1409
Pro Asn Gly Val Pro Pro Glu Lys Val Lys Ser Tyr Ile Tyr Gln Leu
    105                 110                 115

atc aag gcc atc cac tgg tgc cac aag aac gac atc gtg cac aga gac     1457
Ile Lys Ala Ile His Trp Cys His Lys Asn Asp Ile Val His Arg Asp
120                 125                 130                 135

atc aag ccc gag aac ctg ctg atc tcc cac aac gac gtg ctg aag ctg     1505
Ile Lys Pro Glu Asn Leu Leu Ile Ser His Asn Asp Val Leu Lys Leu
                140                 145                 150

tgc gac ttc ggc ttc gcc aga aat ctg agc gag ggc aac aac gcc aac     1553
Cys Asp Phe Gly Phe Ala Arg Asn Leu Ser Glu Gly Asn Asn Ala Asn
            155                 160                 165

tac acc gag tat gtg gcc acc aga tgg tac aga agc cct gaa ctg ctg     1601
Tyr Thr Glu Tyr Val Ala Thr Arg Trp Tyr Arg Ser Pro Glu Leu Leu
        170                 175                 180

ctg gga gcc cct tac ggc aag tct gtg gat atg tgg tcc gtg ggc tgt     1649
Leu Gly Ala Pro Tyr Gly Lys Ser Val Asp Met Trp Ser Val Gly Cys
    185                 190                 195

atc ctg gga gag ctg tct gat ggc caa cct ctg ttt cct ggc gag tcc     1697
Ile Leu Gly Glu Leu Ser Asp Gly Gln Pro Leu Phe Pro Gly Glu Ser
200                 205                 210                 215

gag atc gac cag ctg ttc aca atc cag aag gtg ctg ggc cct ctg cct     1745
Glu Ile Asp Gln Leu Phe Thr Ile Gln Lys Val Leu Gly Pro Leu Pro
                220                 225                 230

agc gag cag atg aag ctg ttc tac agc aac ccc aga ttc cac ggc ctg     1793
Ser Glu Gln Met Lys Leu Phe Tyr Ser Asn Pro Arg Phe His Gly Leu
            235                 240                 245

aga ttc cct gcc gtg aat cac cct cag agc ctg gaa aga aga tac ctg     1841
Arg Phe Pro Ala Val Asn His Pro Gln Ser Leu Glu Arg Arg Tyr Leu
        250                 255                 260

ggc atc ctg aac agc gtg ctg ctg gac ctg atg aag aat ctg ctg aaa     1889
Gly Ile Leu Asn Ser Val Leu Leu Asp Leu Met Lys Asn Leu Leu Lys
    265                 270                 275

ctg gac ccc gcc gac aga tac ctg acc gag cag tgt ctg aac cat cct     1937
Leu Asp Pro Ala Asp Arg Tyr Leu Thr Glu Gln Cys Leu Asn His Pro
280                 285                 290                 295

acc ttt cag acc cag aga ctg ctg gat aga agc ccc agc aga agc gcc     1985
Thr Phe Gln Thr Gln Arg Leu Leu Asp Arg Ser Pro Ser Arg Ser Ala
                300                 305                 310

aag aga aag ccc tac cac gtg gaa agc agc acc ctg agc aat aga aac     2033
Lys Arg Lys Pro Tyr His Val Glu Ser Ser Thr Leu Ser Asn Arg Asn
            315                 320                 325

cag gcc gga aag agc act gcc ctg cag agc cac cac aga agc aac agc     2081
Gln Ala Gly Lys Ser Thr Ala Leu Gln Ser His His Arg Ser Asn Ser
        330                 335                 340

aag gac atc cag aac ctg agc gtg ggc ctg cct aga gct gat gaa gga     2129
Lys Asp Ile Gln Asn Leu Ser Val Gly Leu Pro Arg Ala Asp Glu Gly
    345                 350                 355

ctg cct gcc aac gag agc ttc ctg aat gga aat ctg gct ggc gcc tct     2177
Leu Pro Ala Asn Glu Ser Phe Leu Asn Gly Asn Leu Ala Gly Ala Ser
360                 365                 370                 375

ctg agc cct ctg cac aca aag aca tac cag gcc agc agc cag cct ggc     2225
Leu Ser Pro Leu His Thr Lys Thr Tyr Gln Ala Ser Ser Gln Pro Gly
                380                 385                 390

agc aca agc aag gac ctg acc aac aac aac atc cct cat ctg ctg agc     2273
Ser Thr Ser Lys Asp Leu Thr Asn Asn Asn Ile Pro His Leu Leu Ser
            395                 400                 405
```

```
ccc aaa gag gcc aag agc aag acc gag ttc gac ttc aac atc gac ccc     2321
Pro Lys Glu Ala Lys Ser Lys Thr Glu Phe Asp Phe Asn Ile Asp Pro
        410                 415                 420

aag cct agc gaa ggc cct ggc acc aag tac ctg aag tcc aac tcc aga     2369
Lys Pro Ser Glu Gly Pro Gly Thr Lys Tyr Leu Lys Ser Asn Ser Arg
    425                 430                 435

agc cag cag aac cgg cac tcc ttc atg gaa agc tct cag agc aag gcc     2417
Ser Gln Gln Asn Arg His Ser Phe Met Glu Ser Ser Gln Ser Lys Ala
440                 445                 450                 455

ggc aca ctg cag cct aac gag aag cag agc aga cac agc tac atc gac     2465
Gly Thr Leu Gln Pro Asn Glu Lys Gln Ser Arg His Ser Tyr Ile Asp
                460                 465                 470

aca atc cct cag tcc tct cgg agc ccc agc tac aga aca aag gcc aaa     2513
Thr Ile Pro Gln Ser Ser Arg Ser Pro Ser Tyr Arg Thr Lys Ala Lys
            475                 480                 485

tct cac ggc gcc ctg agc gat agc aag agc gtg tcc aat ctg tcc gag     2561
Ser His Gly Ala Leu Ser Asp Ser Lys Ser Val Ser Asn Leu Ser Glu
        490                 495                 500

gct aga gcc cag atc gcc gag cct agc acc agc aga tac ttc cct agc     2609
Ala Arg Ala Gln Ile Ala Glu Pro Ser Thr Ser Arg Tyr Phe Pro Ser
    505                 510                 515

agc tgc ctg gat ctg aac agc cct aca agc ccc aca cct acc agg cac     2657
Ser Cys Leu Asp Leu Asn Ser Pro Thr Ser Pro Thr Pro Thr Arg His
520                 525                 530                 535

agc gat acc aga aca ctg ctg tcc cca agc ggc cgg aac aac aga aat     2705
Ser Asp Thr Arg Thr Leu Leu Ser Pro Ser Gly Arg Asn Asn Arg Asn
                540                 545                 550

gag ggc acc ctg gac agc aga cgg acc acc aca aga cac agc aag acc     2753
Glu Gly Thr Leu Asp Ser Arg Arg Thr Thr Thr Arg His Ser Lys Thr
            555                 560                 565

atg gaa gaa ctg aag ctg ccc gag cac atg gac tct agc cac tct cat     2801
Met Glu Glu Leu Lys Leu Pro Glu His Met Asp Ser Ser His Ser His
        570                 575                 580

tct ctg agc gcc cct cac gag tcc ttt agc tac ggc ctg ggc tac aca     2849
Ser Leu Ser Ala Pro His Glu Ser Phe Ser Tyr Gly Leu Gly Tyr Thr
    585                 590                 595

agc cca ttt tcc agt cag cag cgg ccc cac aga cac tct atg tac gtg     2897
Ser Pro Phe Ser Ser Gln Gln Arg Pro His Arg His Ser Met Tyr Val
600                 605                 610                 615

acc aga gac aaa gtc cgc gcc aaa ggc ctg gat ggc tct ctg tct att     2945
Thr Arg Asp Lys Val Arg Ala Lys Gly Leu Asp Gly Ser Leu Ser Ile
                620                 625                 630

gga caa ggc atg gcc gcc aga gcc aat agc ctg caa ctt ctg tct cct     2993
Gly Gln Gly Met Ala Ala Arg Ala Asn Ser Leu Gln Leu Leu Ser Pro
            635                 640                 645

cag cct ggc gaa cag ctg cct cct gaa atg aca gtg gcc cgg tcc agc     3041
Gln Pro Gly Glu Gln Leu Pro Pro Glu Met Thr Val Ala Arg Ser Ser
        650                 655                 660

gtg aaa gaa acc agc aga gag ggc acc tcc agc ttc cac acc aga cag     3089
Val Lys Glu Thr Ser Arg Glu Gly Thr Ser Ser Phe His Thr Arg Gln
    665                 670                 675

aaa agc gaa ggc ggc gtg tac cac gat cct cac tct gat gat ggc aca     3137
Lys Ser Glu Gly Gly Val Tyr His Asp Pro His Ser Asp Asp Gly Thr
680                 685                 690                 695

gcc cct aaa gag aac aga cac ctg tac aac gac ccc gtg cct aga aga     3185
Ala Pro Lys Glu Asn Arg His Leu Tyr Asn Asp Pro Val Pro Arg Arg
                700                 705                 710

gtg ggc tcc ttc tac aga gtg cct tct cct aga cct gac aac tcc ttc     3233
Val Gly Ser Phe Tyr Arg Val Pro Ser Pro Arg Pro Asp Asn Ser Phe
```

```
            715                 720                 725

cac gag aac aac gtg tca acc cgg gtg tcc agc ctg cct tct gag agc     3281
His Glu Asn Asn Val Ser Thr Arg Val Ser Ser Leu Pro Ser Glu Ser
        730                 735                 740

agc tct ggc aca aac cac tcc aag agg cag ccc gcc ttc gat cct tgg     3329
Ser Ser Gly Thr Asn His Ser Lys Arg Gln Pro Ala Phe Asp Pro Trp
    745                 750                 755

aag tcc cct gag aat atc agc cac tcc gag cag ctg aaa gag aaa gag     3377
Lys Ser Pro Glu Asn Ile Ser His Ser Glu Gln Leu Lys Glu Lys Glu
760                 765                 770                 775

aag cag ggc ttt ttc cgg tcc atg aag aag aag aaa aag aag tcc cag     3425
Lys Gln Gly Phe Phe Arg Ser Met Lys Lys Lys Lys Lys Lys Ser Gln
                780                 785                 790

aca gtc ccc aac agc gac agc cct gat ctc ctg aca ctg cag aag tcc     3473
Thr Val Pro Asn Ser Asp Ser Pro Asp Leu Leu Thr Leu Gln Lys Ser
            795                 800                 805

atc cac agc gcc agc aca cct agc agc aga cct aaa gag tgg cgg cca     3521
Ile His Ser Ala Ser Thr Pro Ser Ser Arg Pro Lys Glu Trp Arg Pro
        810                 815                 820

gag aag atc agc gac ctg caa aca cag agc cag cct ctg aag tcc ctg     3569
Glu Lys Ile Ser Asp Leu Gln Thr Gln Ser Gln Pro Leu Lys Ser Leu
    825                 830                 835

agg aag ctg ctg cat ctg tcc tcc gcc tct aat cac cct gcc agc agc     3617
Arg Lys Leu Leu His Leu Ser Ser Ala Ser Asn His Pro Ala Ser Ser
840                 845                 850                 855

gat ccc aga ttt cag cca ctg aca gcc cag cag acc aag aac tcc ttc     3665
Asp Pro Arg Phe Gln Pro Leu Thr Ala Gln Gln Thr Lys Asn Ser Phe
                860                 865                 870

agc gag atc cgg att cac cca ctg tct cag gcc agc ggc ggc agc tct     3713
Ser Glu Ile Arg Ile His Pro Leu Ser Gln Ala Ser Gly Gly Ser Ser
            875                 880                 885

aat atc aga caa gag ccc gct cct aag ggc aga cct gct ctc caa ctg     3761
Asn Ile Arg Gln Glu Pro Ala Pro Lys Gly Arg Pro Ala Leu Gln Leu
        890                 895                 900

cct gga cag atg gat cct ggc tgg cac gtg tcc tct gtg aca aga tct     3809
Pro Gly Gln Met Asp Pro Gly Trp His Val Ser Ser Val Thr Arg Ser
    905                 910                 915

gcc acc gag gga cct agc tat tct gag cag ctg ggc gcc aag tct ggc     3857
Ala Thr Glu Gly Pro Ser Tyr Ser Glu Gln Leu Gly Ala Lys Ser Gly
920                 925                 930                 935

ccc aat gga cac ccc tac aac cgg acc aat cgg agc aga atg ccc aac     3905
Pro Asn Gly His Pro Tyr Asn Arg Thr Asn Arg Ser Arg Met Pro Asn
                940                 945                 950

ctg aac gac ctc aaa gaa aca gcc ctc tga agcttatcga taccggtagt       3955
Leu Asn Asp Leu Lys Glu Thr Ala Leu
            955                 960

gaattctacc agtgccatag gatagtgaat tctaccagtg ccatacacgt gagtgaattc   4015

taccagtgcc atagcatgca gtgaattcta ccagtgccat agcggccgcg atctttttcc   4075

ctctgccaaa aattatgggg acatcatgaa gccccttgag catctgactt ctggctaata   4135

aaggaaattt attttcattg caatagtgtg ttggaatttt ttgtgtctct cactcgatcg   4195

ataaggatct tcctagagca tggctacgta gataagtagc atggcgggtt aatcattaac   4255

tacaaggaac ccctagtgat ggagttggcc actccctctc tgcgcgctcg ctcgctcact   4315

gaggccgggc gaccaaaggt cgcccgacgc ccgggctttg cccgggcggc ctcagtgagc   4375

gagcgagcgc gcagccttaa ttaacctaat tcactggccg tcgttttaca acgtcgtgac   4435

tgggaaaacc ctggcgttac ccaacttaat cgccttgcag cacatccccc tttcgccagc   4495
```

```
tggcgtaata gcgaagaggc ccgcaccgat cgcccttccc aacagttgcg cagcctgaat   4555
ggcgaatggg acgcgccctg tagcggcgca ttaagcgcgg cgggtgtggt ggttacgcgc   4615
agcgtgaccg ctacacttgc cagcgcccta gcgcccgctc ctttcgcttt cttcccttcc   4675
tttctcgcca cgttcgccgg ctttccccgt caagctctaa atcgggggct ccctttaggg   4735
ttccgattta gtgctttacg gcacctcgac cccaaaaaac ttgattaggg tgatggttca   4795
cgtagtgggc catcgccctg atagacggtt tttcgccctt tgacgttgga gtccacgttc   4855
tttaatagtg gactcttgtt ccaaactgga acaacactca accctatctc ggtctattct   4915
tttgatttat aagggatttt gccgatttcg gcctattggt taaaaaatga gctgatttaa   4975
caaaaattta acgcgaattt taacaaaata ttaacgctta caatttaggt ggcacttttc   5035
ggggaaatgt gcgcggaacc cctatttgtt tatttttcta aatacattca aatatgtatc   5095
cgctcatgag acaataaccc tgataaatgc ttcaataata ttgaaaaagg aagagtatga   5155
gtattcaaca tttccgtgtc gcccttattc cctttttgc ggcattttgc cttcctgttt   5215
ttgctcaccc agaaacgctg gtgaaagtaa aagatgctga agatcagttg ggtgcacgag   5275
tgggttacat cgaactggat ctcaacagcg gtaagatcct tgagagtttt cgccccgaag   5335
aacgttttcc aatgatgagc acttttaaag ttctgctatg tggcgcggta ttatcccgta   5395
ttgacgccgg gcaagagcaa ctcggtcgcc gcatacacta ttctcagaat gacttggttg   5455
agtactcacc agtcacagaa aagcatctta cggatggcat gacagtaaga gaattatgca   5515
gtgctgccat aaccatgagt gataacactg cggccaactt acttctgaca acgatcggag   5575
gaccgaagga gctaaccgct tttttgcaca acatggggga tcatgtaact cgccttgatc   5635
gttgggaacc ggagctgaat gaagccatac caaacgacga gcgtgacacc acgatgcctg   5695
tagcaatggc aacaacgttg cgcaaactat taactggcga actacttact ctagcttccc   5755
ggcaacaatt aatagactgg atggaggcgg ataaagttgc aggaccactt ctgcgctcgg   5815
cccttccggc tggctggttt attgctgata aatctggagc cggtgagcgt gggtctcgcg   5875
gtatcattgc agcactgggg ccagatggta agccctcccg tatcgtagtt atctacacga   5935
cggggagtca ggcaactatg gatgaacgaa atagacagat cgctgagata ggtgcctcac   5995
tgattaagca ttggtaactg tcagaccaag tttactcata tatactttag attgatttaa   6055
aacttcattt ttaatttaaa aggatctagg tgaagatcct ttttgataat ctcatgacca   6115
aaatccctta acgtgagttt tcgttccact gagcgtcaga ccccgtagaa aagatcaaag   6175
gatcttcttg agatcctttt tttctgcgcg taatctgctg cttgcaaaca aaaaaaccac   6235
cgctaccagc ggtggtttgt ttgccggatc aagagctacc aactcttttt ccgaaggtaa   6295
ctggcttcag cagagcgcag ataccaaata ctgttcttct agtgtagccg tagttaggcc   6355
accacttcaa gaactctgta gcaccgccta catacctcgc tctgctaatc ctgttaccag   6415
tggctgctgc cagtggcgat aagtcgtgtc ttaccgggtt ggactcaaga cgatagttac   6475
cggataaggc gcagcggtcg ggctgaacgg ggggttcgtg cacacagccc agcttggagc   6535
gaacgaccta caccgaactg agatacctac agcgtgagct atgagaaagc gccacgcttc   6595
ccgaagggag aaaggcggac aggtatccgg taagcggcag ggtcggaaca ggagagcgca   6655
cgagggagct tccaggggga aacgcctggt atctttatag tcctgtcggg tttcgccacc   6715
tctgacttga gcgtcgattt ttgtgatgct cgtcaggggg gcggagccta tggaaaaacg   6775
ccagcaacgc ggccttttta cggttcctgg ccttttgctg gccttttgct cacatgttct   6835
```

```
ttcctgcgtt atcccctgat tctgtggata accgtattac cgcctttgag tgagctgata   6895

ccgctcgccg cagccgaacg accgagcgca gcgagtcagt gagcgaggaa gcggaagagc   6955

gcccaatacg caaaccgcct ctccccgcgc gttggccgat tcattaatgc agctggcacg   7015

acaggtttcc cgactggaaa gcgggcagtg agcgcaacgc aattaatgtg agttagctca   7075

ctcattaggc accccaggct ttacacttta tgcttccggc tcgtatgttg tgtggaattg   7135

tgagcggata acaatttcac acaggaaaca gctatgacca tgattacgcc agatttaatt   7195

aaggccttaa ttagg                                                    7210


<210> SEQ ID NO 32
<211> LENGTH: 960
<212> TYPE: PRT
<213> ORGANISM: Artificial Sequence
<220> FEATURE:
<223> OTHER INFORMATION: Synthetic Construct

<400> SEQUENCE: 32

Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
```

```
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720
```

Pro Arg Pro Asp Asn Ser Phe His Glu Asn Asn Val Ser Thr Arg Val
725 730 735

Ser Ser Leu Pro Ser Glu Ser Ser Ser Gly Thr Asn His Ser Lys Arg
740 745 750

Gln Pro Ala Phe Asp Pro Trp Lys Ser Pro Glu Asn Ile Ser His Ser
755 760 765

Glu Gln Leu Lys Glu Lys Glu Lys Gln Gly Phe Phe Arg Ser Met Lys
770 775 780

Lys Lys Lys Lys Lys Ser Gln Thr Val Pro Asn Ser Asp Ser Pro Asp
785 790 795 800

Leu Leu Thr Leu Gln Lys Ser Ile His Ser Ala Ser Thr Pro Ser Ser
805 810 815

Arg Pro Lys Glu Trp Arg Pro Glu Lys Ile Ser Asp Leu Gln Thr Gln
820 825 830

Ser Gln Pro Leu Lys Ser Leu Arg Lys Leu Leu His Leu Ser Ser Ala
835 840 845

Ser Asn His Pro Ala Ser Ser Asp Pro Arg Phe Gln Pro Leu Thr Ala
850 855 860

Gln Gln Thr Lys Asn Ser Phe Ser Glu Ile Arg Ile His Pro Leu Ser
865 870 875 880

Gln Ala Ser Gly Gly Ser Ser Asn Ile Arg Gln Glu Pro Ala Pro Lys
885 890 895

Gly Arg Pro Ala Leu Gln Leu Pro Gly Gln Met Asp Pro Gly Trp His
900 905 910

Val Ser Ser Val Thr Arg Ser Ala Thr Glu Gly Pro Ser Tyr Ser Glu
915 920 925

Gln Leu Gly Ala Lys Ser Gly Pro Asn Gly His Pro Tyr Asn Arg Thr
930 935 940

Asn Arg Ser Arg Met Pro Asn Leu Asn Asp Leu Lys Glu Thr Ala Leu
945 950 955 960

<210> SEQ ID NO 33
<211> LENGTH: 2211
<212> TYPE: DNA
<213> ORGANISM: adeno-associated virus rh91
<220> FEATURE:
<221> NAME/KEY: CDS
<222> LOCATION: (1)..(2211)
<223> OTHER INFORMATION: AAVrh.91

<400> SEQUENCE: 33 atg gct gcc gat ggt tat ctt cca gat tgg ctc gag gac aac ctc tct 48
Met Ala Ala Asp Gly Tyr Leu Pro Asp Trp Leu Glu Asp Asn Leu Ser
1 5 10 15 gag ggc att cgc gag tgg tgg gcg ctg aaa cct gga gcc ccg aaa ccc 96
Glu Gly Ile Arg Glu Trp Trp Ala Leu Lys Pro Gly Ala Pro Lys Pro
20 25 30 aaa gcc aac cag caa aag cag gac gac ggc cgg ggt ctg gtg ctt cct 144
Lys Ala Asn Gln Gln Lys Gln Asp Asp Gly Arg Gly Leu Val Leu Pro
35 40 45 ggc tac aag tac ctc gga ccc ttc aac gga ctc gac aag ggg gag ccc 192
Gly Tyr Lys Tyr Leu Gly Pro Phe Asn Gly Leu Asp Lys Gly Glu Pro
50 55 60 gtc aac gcg gcg gac gca gcg gcc ctc gag cac gac aag gcc tac gac 240
Val Asn Ala Ala Asp Ala Ala Ala Leu Glu His Asp Lys Ala Tyr Asp
65 70 75 80 cag cag ctc aaa gcg ggt gac aat ccg tac ctg cgg tat aac cac gcc 288

```
Gln Gln Leu Lys Ala Gly Asp Asn Pro Tyr Leu Arg Tyr Asn His Ala
                85                  90                  95

gac gcc gag ttt cag gag cgt ctg caa gaa gat acg tct ttt ggg ggc      336
Asp Ala Glu Phe Gln Glu Arg Leu Gln Glu Asp Thr Ser Phe Gly Gly
            100                 105                 110

aac ctc ggg cga gca gtc ttc cag gcc aag aag cgg gtt ctc gaa cct      384
Asn Leu Gly Arg Ala Val Phe Gln Ala Lys Lys Arg Val Leu Glu Pro
        115                 120                 125

ttt ggt ctg gtt gag gaa gca gct aag acg gct cct gga aag aaa cgt      432
Phe Gly Leu Val Glu Glu Ala Ala Lys Thr Ala Pro Gly Lys Lys Arg
    130                 135                 140

ccg gta gag cag tcg ccc caa gaa cca gac tcc tcc tcg ggc att ggc      480
Pro Val Glu Gln Ser Pro Gln Glu Pro Asp Ser Ser Ser Gly Ile Gly
145                 150                 155                 160

aaa tca ggc cag cag ccc gcc aaa aag aga ctc aat ttc ggt cag act      528
Lys Ser Gly Gln Gln Pro Ala Lys Lys Arg Leu Asn Phe Gly Gln Thr
                165                 170                 175

ggc gac tca gag tca gtc ccc gac cct caa cct ctc gga gaa cct cca      576
Gly Asp Ser Glu Ser Val Pro Asp Pro Gln Pro Leu Gly Glu Pro Pro
            180                 185                 190

gaa acc ccc gct gct gtg gga cct act aca atg gct tca ggc ggt ggc      624
Glu Thr Pro Ala Ala Val Gly Pro Thr Thr Met Ala Ser Gly Gly Gly
        195                 200                 205

gca cca atg gca gac aat aac gaa ggc gcc gac gga gtg ggt aat gcc      672
Ala Pro Met Ala Asp Asn Asn Glu Gly Ala Asp Gly Val Gly Asn Ala
    210                 215                 220

tca gga aat tgg cat tgc gat tcc aca tgg ctg ggc gac aga gtc atc      720
Ser Gly Asn Trp His Cys Asp Ser Thr Trp Leu Gly Asp Arg Val Ile
225                 230                 235                 240

acc acc agc acc cga acc tgg gcc ctt cct acc tac aac aac cac ctc      768
Thr Thr Ser Thr Arg Thr Trp Ala Leu Pro Thr Tyr Asn Asn His Leu
                245                 250                 255

tac aag caa atc tcc agc gct tca acg ggg gcc agt aac gac aac cac      816
Tyr Lys Gln Ile Ser Ser Ala Ser Thr Gly Ala Ser Asn Asp Asn His
            260                 265                 270

tac ttt ggc tac agc acc ccc tgg ggg tat ttt gat ttc aac aga ttc      864
Tyr Phe Gly Tyr Ser Thr Pro Trp Gly Tyr Phe Asp Phe Asn Arg Phe
        275                 280                 285

cac tgc cac ttc tca cca cgt gac tgg cag cga ctc att aac aac aac      912
His Cys His Phe Ser Pro Arg Asp Trp Gln Arg Leu Ile Asn Asn Asn
    290                 295                 300

tgg gga ttc cgg ccc aag aga ctc aac ttc aag ctc ttc aac atc cag      960
Trp Gly Phe Arg Pro Lys Arg Leu Asn Phe Lys Leu Phe Asn Ile Gln
305                 310                 315                 320

gtc aag gag gtc acg acg aat gat ggc gtc aca acc atc gct aat aac     1008
Val Lys Glu Val Thr Thr Asn Asp Gly Val Thr Thr Ile Ala Asn Asn
                325                 330                 335

ctt acc agc acg gtt caa gtg ttc tcg gac tcg gag tac cag ctg ccg     1056
Leu Thr Ser Thr Val Gln Val Phe Ser Asp Ser Glu Tyr Gln Leu Pro
            340                 345                 350

tac gtc ctc ggt tct gcg cac cag ggc tgc ctc cct ccg ttc ccg gcg     1104
Tyr Val Leu Gly Ser Ala His Gln Gly Cys Leu Pro Pro Phe Pro Ala
        355                 360                 365

gac gta ttc atg att cct cag tac ggc tac cta acg ctc aac aat ggc     1152
Asp Val Phe Met Ile Pro Gln Tyr Gly Tyr Leu Thr Leu Asn Asn Gly
    370                 375                 380

agc cag gcc gta gga cgt tca tcc ttt tat tgc ctg gaa tat ttc cca     1200
Ser Gln Ala Val Gly Arg Ser Ser Phe Tyr Cys Leu Glu Tyr Phe Pro
385                 390                 395                 400
```

```
tct caa atg ctg aga acg ggc aac aac ttt acc ttc agc tac acc ttt      1248
Ser Gln Met Leu Arg Thr Gly Asn Asn Phe Thr Phe Ser Tyr Thr Phe
                405                 410                 415

gaa gat gtg cct ttc cac agc agt tac gcg cac agc cag agc ctg gac      1296
Glu Asp Val Pro Phe His Ser Ser Tyr Ala His Ser Gln Ser Leu Asp
            420                 425                 430

agg cta atg aat cct cta atc gac cag tac ctg tat tac cta aac aga      1344
Arg Leu Met Asn Pro Leu Ile Asp Gln Tyr Leu Tyr Tyr Leu Asn Arg
        435                 440                 445

act cag aat caa tcc gga agt gca caa aac aag gac ttg ctg ttt agc      1392
Thr Gln Asn Gln Ser Gly Ser Ala Gln Asn Lys Asp Leu Leu Phe Ser
    450                 455                 460

cgg ggg tct cca gct ggc atg tct gtt cag ccc aaa aac tgg cta ccc      1440
Arg Gly Ser Pro Ala Gly Met Ser Val Gln Pro Lys Asn Trp Leu Pro
465                 470                 475                 480

ggg ccc tgt tac cga cag cag cgt gtt tct aaa aca aaa aca gac aac      1488
Gly Pro Cys Tyr Arg Gln Gln Arg Val Ser Lys Thr Lys Thr Asp Asn
                485                 490                 495

aac aac agc aac ttt acc tgg act ggt gcc tcc aaa tac aat ctg aac      1536
Asn Asn Ser Asn Phe Thr Trp Thr Gly Ala Ser Lys Tyr Asn Leu Asn
            500                 505                 510

gga cgt gaa tcc atc att aac cct ggc acc gct atg gca tcc cac aag      1584
Gly Arg Glu Ser Ile Ile Asn Pro Gly Thr Ala Met Ala Ser His Lys
        515                 520                 525

gac gac gaa gac aaa ttt ttt ccc atg agc ggt gtt atg att ttt ggc      1632
Asp Asp Glu Asp Lys Phe Phe Pro Met Ser Gly Val Met Ile Phe Gly
    530                 535                 540

aaa gaa aat gca gga gca tca aac act gca tta gac aat gtt atg att      1680
Lys Glu Asn Ala Gly Ala Ser Asn Thr Ala Leu Asp Asn Val Met Ile
545                 550                 555                 560

aca gat gaa gag gaa att aaa gct acc aac ccc gtg gcc acc gag aga      1728
Thr Asp Glu Glu Glu Ile Lys Ala Thr Asn Pro Val Ala Thr Glu Arg
                565                 570                 575

ttt gga act gtg gca gtc aat ctc caa agc agc aat aca gac cct gca      1776
Phe Gly Thr Val Ala Val Asn Leu Gln Ser Ser Asn Thr Asp Pro Ala
            580                 585                 590

aca gga gac gtg cat gtc atg ggg gct tta cct ggc atg gtg tgg caa      1824
Thr Gly Asp Val His Val Met Gly Ala Leu Pro Gly Met Val Trp Gln
        595                 600                 605

gac aga gac gtg tac ctg cag ggt ccc att tgg gcc aag att cct cac      1872
Asp Arg Asp Val Tyr Leu Gln Gly Pro Ile Trp Ala Lys Ile Pro His
    610                 615                 620

acg gat gga cac ttt cac ccg tct cct ctt atg ggc ggc ttt gga ctt      1920
Thr Asp Gly His Phe His Pro Ser Pro Leu Met Gly Gly Phe Gly Leu
625                 630                 635                 640

aag cac ccg cct cct cag atc ctc atc aaa aac acg cct gtt cct gcg      1968
Lys His Pro Pro Pro Gln Ile Leu Ile Lys Asn Thr Pro Val Pro Ala
                645                 650                 655

aat cct ccg gca gag ttt tcg gct aca aag ttt gct tca ttc atc acc      2016
Asn Pro Pro Ala Glu Phe Ser Ala Thr Lys Phe Ala Ser Phe Ile Thr
            660                 665                 670

cag tac tcc aca gga caa gtg agc gtg gaa att gaa tgg gag ctg cag      2064
Gln Tyr Ser Thr Gly Gln Val Ser Val Glu Ile Glu Trp Glu Leu Gln
        675                 680                 685

aaa gaa aac agt aag cgc tgg aat cct gaa gtg cag tac acc tcc aac      2112
Lys Glu Asn Ser Lys Arg Trp Asn Pro Glu Val Gln Tyr Thr Ser Asn
    690                 695                 700

tac gcg aaa tct gcc aac gtt gat ttc act gtg gac aac aat gga ctt      2160
Tyr Ala Lys Ser Ala Asn Val Asp Phe Thr Val Asp Asn Asn Gly Leu
705                 710                 715                 720
```

tat act gag cct cgc ccc att ggc acc cgt tac ctt acc cgt ccc ctt 2208
Tyr Thr Glu Pro Arg Pro Ile Gly Thr Arg Tyr Leu Thr Arg Pro Leu
725 730 735 taa 2211

<210> SEQ ID NO 34
<211> LENGTH: 736
<212> TYPE: PRT
<213> ORGANISM: adeno-associated virus rh91

<400> SEQUENCE: 34

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Phe Gly Leu Val Glu Glu Ala Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Ser Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Glu Thr Pro Ala Ala Val Gly Pro Thr Thr Met Ala Ser Gly Gly Gly
195 200 205

Ala Pro Met Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Ala Ser Thr Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Arg Leu Asn Phe Lys Leu Phe Asn Ile Gln
305 310 315 320

Val Lys Glu Val Thr Thr Asn Asp Gly Val Thr Thr Ile Ala Asn Asn
325 330 335

Leu Thr Ser Thr Val Gln Val Phe Ser Asp Ser Glu Tyr Gln Leu Pro

```
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Asn Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Asn Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 35
<211> LENGTH: 2211
<212> TYPE: DNA
<213> ORGANISM: adeno-associated virus rh91

```
<220> FEATURE:
<221> NAME/KEY: CDS
<222> LOCATION: (1)..(2211)
<223> OTHER INFORMATION: AAVrh.91

<400> SEQUENCE: 35

atg gct gct gac ggt tat ctt cca gat tgg ctc gag gac aac ctt tct       48
Met Ala Ala Asp Gly Tyr Leu Pro Asp Trp Leu Glu Asp Asn Leu Ser
1               5                   10                  15

gaa ggc att cgt gag tgg tgg gct ctg aaa cct gga gcc cct aaa ccc       96
Glu Gly Ile Arg Glu Trp Trp Ala Leu Lys Pro Gly Ala Pro Lys Pro
            20                  25                  30

aaa gcg aac caa caa aag cag gac gac ggc cgg ggt ctt gtg ctt ccg      144
Lys Ala Asn Gln Gln Lys Gln Asp Asp Gly Arg Gly Leu Val Leu Pro
        35                  40                  45

ggt tac aaa tac ctc gga ccc ttc aac gga ctc gac aaa gga gag ccg      192
Gly Tyr Lys Tyr Leu Gly Pro Phe Asn Gly Leu Asp Lys Gly Glu Pro
    50                  55                  60

gtc aac gcg gcg gac gcg gca gcc ctc gaa cac gac aaa gct tac gac      240
Val Asn Ala Ala Asp Ala Ala Ala Leu Glu His Asp Lys Ala Tyr Asp
65                  70                  75                  80

cag cag ctc aag gcc ggt gac aac ccg tac ctc cgg tac aac cac gcc      288
Gln Gln Leu Lys Ala Gly Asp Asn Pro Tyr Leu Arg Tyr Asn His Ala
                85                  90                  95

gac gcc gag ttt cag gag cgt ctt caa gaa gat acg tct ttt ggg ggc      336
Asp Ala Glu Phe Gln Glu Arg Leu Gln Glu Asp Thr Ser Phe Gly Gly
            100                 105                 110

aac ctt ggc aga gca gtc ttc cag gcc aaa aag agg gtt ctt gag cct      384
Asn Leu Gly Arg Ala Val Phe Gln Ala Lys Lys Arg Val Leu Glu Pro
        115                 120                 125

ttt ggt ctg gtt gag gaa gca gct aaa acg gct cct gga aag aag agg      432
Phe Gly Leu Val Glu Glu Ala Ala Lys Thr Ala Pro Gly Lys Lys Arg
    130                 135                 140

cct gta gag cag tct cct cag gaa ccg gac tca tca tct ggt att ggc      480
Pro Val Glu Gln Ser Pro Gln Glu Pro Asp Ser Ser Ser Gly Ile Gly
145                 150                 155                 160

aaa tcg ggc cag cag cct gcc aaa aaa aga cta aat ttc ggt cag act      528
Lys Ser Gly Gln Gln Pro Ala Lys Lys Arg Leu Asn Phe Gly Gln Thr
                165                 170                 175

ggc gac tca gag tca gtc ccc gac cct caa cct ctc gga gaa cct cca      576
Gly Asp Ser Glu Ser Val Pro Asp Pro Gln Pro Leu Gly Glu Pro Pro
            180                 185                 190

gaa acc ccc gct gct gtg gga cct act aca atg gct tca ggc ggt ggc      624
Glu Thr Pro Ala Ala Val Gly Pro Thr Thr Met Ala Ser Gly Gly Gly
        195                 200                 205

gca cca atg gca gac aat aac gaa ggc gcc gac gga gtg ggt aat gcc      672
Ala Pro Met Ala Asp Asn Asn Glu Gly Ala Asp Gly Val Gly Asn Ala
    210                 215                 220

tca gga aat tgg cat tgc gat tcc aca tgg ctg ggc gac aga gtc atc      720
Ser Gly Asn Trp His Cys Asp Ser Thr Trp Leu Gly Asp Arg Val Ile
225                 230                 235                 240

acc acc agc acc cga acc tgg gcc ctt cct acc tac aac aac cac ctc      768
Thr Thr Ser Thr Arg Thr Trp Ala Leu Pro Thr Tyr Asn Asn His Leu
                245                 250                 255

tac aag caa atc tcc agc gct tca acg ggg gcc agt aac gac aac cac      816
Tyr Lys Gln Ile Ser Ser Ala Ser Thr Gly Ala Ser Asn Asp Asn His
            260                 265                 270

tac ttt ggc tac agc acc ccc tgg ggg tat ttt gat ttc aac aga ttc      864
Tyr Phe Gly Tyr Ser Thr Pro Trp Gly Tyr Phe Asp Phe Asn Arg Phe
        275                 280                 285
```

```
cac tgc cac ttc tca cca cgt gac tgg cag cga ctc att aac aac aac      912
His Cys His Phe Ser Pro Arg Asp Trp Gln Arg Leu Ile Asn Asn Asn
    290                 295                 300

tgg gga ttc cgg ccc aag aga ctc aac ttc aag ctc ttc aac atc cag      960
Trp Gly Phe Arg Pro Lys Arg Leu Asn Phe Lys Leu Phe Asn Ile Gln
305                 310                 315                 320

gtc aag gag gtc acg acg aat gat ggc gtc aca acc atc gct aat aac     1008
Val Lys Glu Val Thr Thr Asn Asp Gly Val Thr Thr Ile Ala Asn Asn
                325                 330                 335

ctt acc agc acg gtt caa gtg ttc tcg gac tcg gag tac cag ctg ccg     1056
Leu Thr Ser Thr Val Gln Val Phe Ser Asp Ser Glu Tyr Gln Leu Pro
            340                 345                 350

tac gtc ctc ggt tct gcg cac cag ggc tgc ctc cct ccg ttc ccg gcg     1104
Tyr Val Leu Gly Ser Ala His Gln Gly Cys Leu Pro Pro Phe Pro Ala
        355                 360                 365

gac gta ttc atg att cct cag tat gga tac ctc acc ctg aac aac gga     1152
Asp Val Phe Met Ile Pro Gln Tyr Gly Tyr Leu Thr Leu Asn Asn Gly
    370                 375                 380

agt caa gcg gtg gga cgc tca tcc ttt tac tgc ctg gag tac ttc cct     1200
Ser Gln Ala Val Gly Arg Ser Ser Phe Tyr Cys Leu Glu Tyr Phe Pro
385                 390                 395                 400

tcg cag atg cta agg act gga aat aac ttc acc ttc agc tat acc ttc     1248
Ser Gln Met Leu Arg Thr Gly Asn Asn Phe Thr Phe Ser Tyr Thr Phe
                405                 410                 415

gag gat gta cct ttt cac agc agc tac gct cac agc cag agt ttg gat     1296
Glu Asp Val Pro Phe His Ser Ser Tyr Ala His Ser Gln Ser Leu Asp
            420                 425                 430

cgc ttg atg aat cct ctt att gat cag tat ctg tac tac ctg aac aga     1344
Arg Leu Met Asn Pro Leu Ile Asp Gln Tyr Leu Tyr Tyr Leu Asn Arg
        435                 440                 445

acg caa aat caa tct gga agt gca caa aac aag gac ctg ctt ttt agc     1392
Thr Gln Asn Gln Ser Gly Ser Ala Gln Asn Lys Asp Leu Leu Phe Ser
    450                 455                 460

cgg ggg tct cct gct ggc atg tct gtt cag ccc aaa aat tgg cta cct     1440
Arg Gly Ser Pro Ala Gly Met Ser Val Gln Pro Lys Asn Trp Leu Pro
465                 470                 475                 480

ggg ccc tgc tac cgg caa cag aga gtt tca aag act aaa aca gac aac     1488
Gly Pro Cys Tyr Arg Gln Gln Arg Val Ser Lys Thr Lys Thr Asp Asn
                485                 490                 495

aac aac agt aac ttt acc tgg aca ggt gcc agc aaa tat aat ctc aat     1536
Asn Asn Ser Asn Phe Thr Trp Thr Gly Ala Ser Lys Tyr Asn Leu Asn
            500                 505                 510

ggc cgc gaa tcg atc att aat cca gga acc gct atg gcc agt cac aag     1584
Gly Arg Glu Ser Ile Ile Asn Pro Gly Thr Ala Met Ala Ser His Lys
        515                 520                 525

gac gat gaa gac aaa ttt ttc cct atg agc ggc gtt atg ata ttt ggc     1632
Asp Asp Glu Asp Lys Phe Phe Pro Met Ser Gly Val Met Ile Phe Gly
    530                 535                 540

aaa gaa aat gca gga gca agt aac act gca tta gat aat gta atg att     1680
Lys Glu Asn Ala Gly Ala Ser Asn Thr Ala Leu Asp Asn Val Met Ile
545                 550                 555                 560

acg gat gaa gaa gag att aaa gct acc aat cct gtg gca aca gag aga     1728
Thr Asp Glu Glu Glu Ile Lys Ala Thr Asn Pro Val Ala Thr Glu Arg
                565                 570                 575

ttt gga act gtg gca gtc aac ttg cag agc tca aat aca gac ccc gca     1776
Phe Gly Thr Val Ala Val Asn Leu Gln Ser Ser Asn Thr Asp Pro Ala
            580                 585                 590

act gga gac gtc cat gtc atg ggg gcc tta cct ggc atg gtg tgg caa     1824
Thr Gly Asp Val His Val Met Gly Ala Leu Pro Gly Met Val Trp Gln
        595                 600                 605
```

```
gat cgt gac gtg tac ctt caa gga cct atc tgg gca aag att cct cac      1872
Asp Arg Asp Val Tyr Leu Gln Gly Pro Ile Trp Ala Lys Ile Pro His
    610                 615                 620

acg gat gga cac ttt cat cct tct cct ctg atg gga ggc ttt gga ctg      1920
Thr Asp Gly His Phe His Pro Ser Pro Leu Met Gly Gly Phe Gly Leu
625                 630                 635                 640

aaa cat ccg cct cct caa atc ctc atc aaa aat act ccg gta ccg gca      1968
Lys His Pro Pro Pro Gln Ile Leu Ile Lys Asn Thr Pro Val Pro Ala
                645                 650                 655

aat cct ccg gca gag ttc agc gct aca aag ttt gct tca ttt atc act      2016
Asn Pro Pro Ala Glu Phe Ser Ala Thr Lys Phe Ala Ser Phe Ile Thr
            660                 665                 670

cag tac tcc act gga cag gtc agc gtg gaa att gag tgg gag cta cag      2064
Gln Tyr Ser Thr Gly Gln Val Ser Val Glu Ile Glu Trp Glu Leu Gln
        675                 680                 685

aaa gaa aac agc aaa cgt tgg aat cca gag gtg cag tac act tcc aac      2112
Lys Glu Asn Ser Lys Arg Trp Asn Pro Glu Val Gln Tyr Thr Ser Asn
    690                 695                 700

tac gcg aag tct gcc aat gtg gac ttt act gta gac aac aat ggt ctt      2160
Tyr Ala Lys Ser Ala Asn Val Asp Phe Thr Val Asp Asn Asn Gly Leu
705                 710                 715                 720

tat act gaa cct cgc cct att gga acc cgg tat ctc aca cga ccc ttg      2208
Tyr Thr Glu Pro Arg Pro Ile Gly Thr Arg Tyr Leu Thr Arg Pro Leu
                725                 730                 735

taa                                                                  2211


<210> SEQ ID NO 36
<211> LENGTH: 736
<212> TYPE: PRT
<213> ORGANISM: adeno-associated virus rh91

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190
```

```
Glu Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Asn Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Asn Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
```

```
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 37
<211> LENGTH: 2883
<212> TYPE: DNA
<213> ORGANISM: Artificial Sequence
<220> FEATURE:
<223> OTHER INFORMATION: engineered nucleic acid sequence CDKL5co-A

<400> SEQUENCE: 37

atgaagatcc ccaacatcgg caacgtgatg aacaagttcg agatcctggg cgtggtgggc      60

gagggcgcct acggcgtggt gctgaagtgc aggcacaagg agacccacga gatcgtggcc     120

atcaagaagt tcaaggacag cgaggagaac gaggaggtga aggagaccac cctgagggag     180

ctgaagatgc tgaggaccct gaagcaggag aacatcgtgg agctgaagga ggccttcagg     240

aggaggggca agctgtacct ggtgttcgag tacgtggaga agaacatgct ggagctgctg     300

gaggagatgc ccaacggcgt gcccccccgag aaggtgaaga gctacatcta ccagctgatc     360

aaggccatcc actggtgcca caagaacgac atcgtgcaca gggacatcaa gcccgagaac     420

ctgctgatca gccacaacga cgtgctgaag ctgtgcgact tcggcttcgc caggaacctg     480

agcgagggca acaacgccaa ctacaccgag tacgtggcca ccaggtggta caggagcccc     540

gagctgctgc tgggcgcccc ctacggcaag agcgtggaca tgtggagcgt gggctgcatc     600

ctgggcgagc tgagcgacgg ccagcccctg ttccccggcg agagcgagat cgaccagctg     660

ttcaccatcc agaaggtgct gggcccccctg cccagcgagc agatgaagct gttctacagc     720

aaccccaggt tccacggcct gaggttcccc gccgtgaacc acccccagag cctggagagg     780

aggtacttgg gcatcctgaa cagcgtgctg ctggacctga tgaagaacct gctgaagctg     840

gaccccgccg acaggtactt gaccgagcag tgcctgaacc accccacctt ccagacccag     900

aggctgctgg acaggagccc cagcaggagc gccaagagga agccctacca cgtggagagc     960

agcaccctga gcaacaggaa ccaggccggc aagagcaccg ccctgcagag ccaccacagg    1020

agcaacagca aggacatcca gaacctgagc gtgggcctgc ccagggccga cgagggcctg    1080

cccgccaacg agagcttcct gaacggcaac ctggccggcg ccagcctgag cccccctgcac    1140

accaagacct accaggccag cagccagccc ggcagcacca gcaaggacct gaccaacaac    1200

aacatccccc acctgctgag ccccaaggag gccaagagca agaccgagtt cgacttcaac    1260

atcgacccca agcccagcga gggccccggc accaagtacc tgaagagcaa cagcaggagc    1320

cagcagaaca ggcacagctt catggagagc agccagagca aggccggcac cctgcagccc    1380
```

aacgagaagc agagcaggca cagctacatc gacaccatcc cccagagcag caggagcccc 1440
agctacagga ccaaggccaa gagccacggc gccctgagcg acagcaagag cgtgagcaac 1500
ctgagcgagg ccagggccca gatcgccgag cccagcacca gcaggtactt ccccagcagc 1560
tgcctggacc tgaacagccc caccagcccc acccccacca ggcacagcga caccaggacc 1620
ctgctgagcc ccagcggcag gaacaacagg aacgagggca ccctggacag caggaggacc 1680
accaccaggc acagcaagac catggaggag ctgaagctgc ccgagcacat ggacagcagc 1740
cacagccaca gcctgagcgc cccccacgag agcttcagct acggcctggg ctacaccagc 1800
cccttcagca gccagcagag gccccacagg cacagcatgt acgtgaccag ggacaaggtg 1860
agggccaagg gcctggacgg cagcctgagc atcggccagg gcatggccgc cagggccaac 1920
agcctgcagc tgctgagccc ccagcccggc gagcagctgc cccccgagat gaccgtggcc 1980
aggagcagcg tgaaggagac cagcagggag ggcaccagca gcttccacac caggcagaag 2040
agcgagggcg gcgtgtacca cgacccccac agcgacgacg gcaccgcccc caaggagaac 2100
aggcacctgt acaacgaccc cgtgcccagg agggtgggca gcttctacag ggtgcccagc 2160
cccaggcccg acaacagctt ccacgagaac aacgtgagca ccagggtgag cagcctgccc 2220
agcgagagca gcagcggcac caaccacagc aagaggcagc ccgccttcga cccctggaag 2280
agccccgaga acatcagcca cagcgagcag ctgaaggaga aggagaagca gggcttcttc 2340
aggagcatga agaagaagaa gaagaagagc cagaccgtgc ccaacagcga cagccccgac 2400
ctgctgaccc tgcagaagag catccacagc gccagcaccc ccagcagcag gcccaaggag 2460
tggaggcccg agaagatcag cgacctgcag acccagagcc agcccctgaa gagcctgagg 2520
aagctgctgc acctgagcag cgccagcaac caccccgcca gcagcgaccc caggttccag 2580
cccctgaccg cccagcagac caagaacagc ttcagcgaga tcaggatcca ccccctgagc 2640
caggccagcg gcggcagcag caacatcagg caggagcccg cccccaaggg caggcccgcc 2700
ctgcagctgc ccggccagat ggacccccggc tggcacgtga gcagcgtgac caggagcgcc 2760
accgagggcc ccagctacag cgagcagctg ggcgccaaga gcggccccaa cggccacccc 2820
tacaacagga ccaacaggag caggatgccc aacctgaacg acctgaagga gaccgccctg 2880
tga 2883

<210> SEQ ID NO 38
<211> LENGTH: 2883
<212> TYPE: DNA
<213> ORGANISM: Artificial Sequence
<220> FEATURE:
<223> OTHER INFORMATION: engineered nucleic acid sequence CDKL5co-B

<400> SEQUENCE: 38
atgaaaattc ccaatatcgg taacgtgatg aataaattcg aaatacttgg agtggtaggt 60
gagggcgcct atggtgttgt acttaaatgt agacacaaag aaacacacga aatcgtggcg 120
atcaagaaat ttaaggattc cgaggagaat gaggaagtca aagagaccac actacgcgag 180
ttgaaaatgt tacgaactct aaaacaggaa aacattgtag agttaaagga ggcttttcgc 240
cgtcgcggta aactatacct ggtctttgag tatgttgaga aaaacatgct agaactgctc 300
gaggaaatgc ctaatggcgt cccgccagaa aaagtcaaat cgtatattta ccagcttata 360
aaggccatcc attggtgtca taaaaacgat atcgttcatc gcgacattaa gccagaaaat 420
ctattgatat cccacaacga cgtgctaaaa ctttgcgact tcggcttcgc taggaaccta 480
tccgaaggga ataacgcgaa ttataccgaa tatgttgcga cacgatggta ccgtagtcct 540

```
gaacttctat taggggcgcc ctacggtaaa tctgtagata tgtggtcagt cgggtgtata    600
ttaggagaac tttcagacgg tcaacctctg ttcccaggcg agtccgagat cgatcagctt    660
tttacaatac agaaggtatt aggtcccctc ccaagtgagc aaatgaagct attctattca    720
aatccccggt ttcatggcct tagatttccg gcggtgaacc accctcagag tctggagagg    780
cgttatctcg ggatacttaa ttcagtctta ctcgatctga tgaagaattt gctaaaactg    840
gaccctgctg atcggtacct tacagagcaa tgccttaatc acccgacttt tcaaactcaa    900
cgactgttgg accggagtcc gtcacgctca gctaaaagga aaccatacca cgtagaatca    960
tcgacattat cgaatcgaaa ccaagcgggt aagagtaccg ctttgcaaag ccatcatcga   1020
tccaatagta aagacattca gaatctgtca gtgggattgc ctagagctga cgaaggatta   1080
ccggcgaacg agagttttct gaacggcaac ctcgcaggcg catctctgtc tccgcttcat   1140
acgaaaactt accaagcgtc atcacagcca ggcagtacga gtaaagacct gactaacaat   1200
aatattccac atctgttatc accgaaggaa gctaagagca agaccgagtt cgacttcaac   1260
atagacccca aaccctccga gggtcctggc accaagtatc tcaaatcaaa ctctagatct   1320
cagcagaaca ggcacagctt catggagtcc tcacaaagta aagctgggac actgcagccc   1380
aacgaaaagc aaagccgaca ttcttatatt gacacgatcc ctcagagttc acgcagccct   1440
agctatcgga caaaagctaa gtcccacggt gccctttctg attcgaagag tgttagtaac   1500
ctttccgaag ctagagccca aattgcggag cctagtacat cgagatactt cccctccagc   1560
tgcctggacc ttaactctcc aaccagcccc actccaacgc gccactcaga taccaggaca   1620
ctgctctcac catccggaag aaataataga aatgaaggaa cgcttgactc tcggcgcact   1680
acgacaaggc acagcaagac gatggaagaa cttaagctac ctgagcacat ggacagttcg   1740
cattcccact cactctcggc gccacatgag tcgttttcct atggactggg ttacacaagt   1800
ccctttagct ctcagcagcg tcctcaccgc cactctatgt acgttacaag ggataaagtt   1860
cgcgctaagg ggttggatgg gagtctttcc attggccaag gcatggccgc gcgggcaaat   1920
tctctacaac ttctttcgcc acagccaggt gagcaactcc caccagaaat gaccgtcgcc   1980
agaagcagtg ttaaagaaac ttcgagggag gggacatcat cgtttcatac ccgccagaaa   2040
tctgagggcg gtgtatatca tgatcctcat tccgacgacg gaacggcccc caaagagaac   2100
cgacacctat acaatgaccc tgtcccaagg agagtgggat ctttctatcg agttccttca   2160
ccaagacctg ataacagttt ccatgagaac aacgtttcca cgagggtgtc aagtctacct   2220
tcggaatcat cttccggaac caatcactca aaacgccagc cagctttcga tccatggaaa   2280
tcaccggaaa acatcagtca tagcgagcaa ttgaaagaga aagaaaagca aggttttttc   2340
agaagtatga agaagaagaa aaagaagtca cagaccgtac ctaattcaga tagtccagac   2400
ttgttaacgc tccagaaatc aattcatagc gcatcgactc catcgtcccg accaaaggaa   2460
tggcgccctg agaagatctc cgatctgcag acccaatccc aacccctgaa gtctctcagg   2520
aaattactcc acctctcgtc tgctagtaac cacccccgcat cgtctgaccc tcgcttccag   2580
ccgctgacag cccagcaaac aaagaacagt ttctcagaaa tccggattca tcctttaagc   2640
caagctagcg gcggtagttc taacataaga caagagcccg ctccaaaggg cagacccgct   2700
ctgcagttgc ctgggcagat ggatcccggg tggcacgtct catcagtaac ccgaagtgcc   2760
accgagggcc cgtcatattc agagcagctc ggagcgaaaa gtggtcctaa cgggcaccca   2820
tataatcgaa caaaccgttc aaggatgcca aatctcaacg atctaaagga aacggccctt   2880
```

taa 2883

<210> SEQ ID NO 39
<211> LENGTH: 2883
<212> TYPE: DNA
<213> ORGANISM: Artificial Sequence
<220> FEATURE:
<223> OTHER INFORMATION: engineered nucleic acid sequence CDKL5co-C

<400> SEQUENCE: 39
atgaagatcc ccaatatcgg aaacgtgatg aacaaattcg agattctcgg agtggtgggc 60
gagggcgcct atggagtggt tttaaaatgc agacacaagg agacccacga gatcgtcgct 120
atcaaaaagt tcaaagactc cgaggaaaac gaagaggtca aggagaccac cttacgtgag 180
ctcaaaatgc tcagaacact gaagcaagag aatatcgtcg agctcaagga ggccttcaga 240
aggaggggca aactgtattt agtgttcgag tacgtggaga agaacatgct ggagctgctg 300
gaggaaatgc ccaacggcgt cccccccgaa aaggtgaaat cctacattta ccaactgatc 360
aaggccattc actggtgcca caaaaatgat atcgtccatc gtgacatcaa gcccgagaat 420
ctgctgatca gccataacga cgtgctgaaa ctgtgcgact tcggattcgc cagaaattta 480
agcgagggca acaacgccaa ttacaccgag tacgtcgcca caaggtggta taggagcccc 540
gagctgctgc tcggagcccc ttatggcaag agcgtggaca tgtggagcgt gggctgcatt 600
ctgggagaac tgtccgacgg ccagcctctg ttccccggcg agtccgagat tgaccagctg 660
ttcacaatcc agaaagtcct cggccctctg cccagcgaac aaatgaagct cttctacagc 720
aaccctcgtt tccacggttt aaggttcccc gccgtgaatc acccccagag cctcgagaga 780
aggtatctgg gcattctgaa cagcgtgctg ctcgatttaa tgaagaattt attaaagctg 840
gaccccgctg ataggtacct cacagagcag tgtttaaatc accccacctt ccagacccag 900
agactgctcg atcgtagccc tagcagatcc gccaaaagga agccttacca cgtcgagagc 960
tccactttaa gcaatcgtaa ccaagctgga aaatccaccg ctttacagtc ccaccatagg 1020
tccaacagca aagacattca gaatttaagc gtgggactgc ctagggctga cgagggcctc 1080
cccgccaacg aatccttttt aaatggcaat ctcgccggag ccagcctcag ccctttacat 1140
acaaaaacct accaagctag ctcccagccc ggtagcacct ccaaggacct caccaacaac 1200
aacatccccc atttactgtc ccccaaggag gccaagagca agaccgagtt tgactttaat 1260
atcgacccta agcccagcga gggacccggc acaaagtatc tgaagtccaa ttctcgtagc 1320
cagcagaatc gtcacagctt catggagagc tcccaaagca aggccggcac actgcagccc 1380
aatgagaagc aatctcgtca ttcctacatc gacaccatcc cccagagctc tcgtagcccc 1440
tcctatagga caaaggccaa gtcccacggc gctctgtccg attccaagtc cgtctccaat 1500
ttatccgagg ctcgtgccca gatcgccgaa cctagcacct ctcgttattt cccctcctct 1560
tgtctggacc tcaattcccc cacaagccct acacctactc gtcacagcga caccagaact 1620
ttactgagcc ccagcggaag gaataatcgt aacgagggca ctttagactc tcgtagaacc 1680
accacaaggc acagcaagac catggaggag ctgaagctgc ccgaacatat ggactcctcc 1740
cattcccatt ctttatccgc cccccacgag agcttcagct atggtttagg ctatacatcc 1800
cccttcagct cccagcagag accccacaga cactccatgt acgtgactcg tgataaggtg 1860
agggccaaag gactggatgg aagcctctcc atcggccaag gcatggccgc tcgtgccaat 1920
agcctccagt tattatcccc ccaacccgga gaacagctgc ctcccgaaat gacagtggcc 1980
agaagcagcg tcaaggaaac atctcgtgag ggaacctcca gctttcacac aaggcagaag 2040
agcgagggcg gagtctatca tgacccccac tccgatgacg gcacagcccc caaagagaat 2100
cgtcatctct acaacgaccc cgtgcctcgt agagtcggct ccttctacag agtccccagc 2160
cccagacccg acaacagctt tcacgagaac aacgtgagca ctcgtgtctc ctctttacct 2220
agcgagagct cctccggaac caaccacagc aaaaggcagc ccgccttcga cccttggaag 2280
tcccccgaaa acatcagcca cagcgagcag ctgaaggaga aagagaagca aggtttcttc 2340
agaagcatga aaaagaagaa gaaaaaatcc caaaccgtgc ccaactccga ctcccccgat 2400
ttactgaccc tccagaagtc catccactcc gcttccaccc ctagctccag acccaaggag 2460
tggaggcccg agaagatttc cgatttacag acacagagcc agcctctcaa gtctttaaga 2520
aagctgctgc atttatccag cgccagcaat caccccgctt ccagcgaccc taggttccag 2580
cctttaaccg cccagcagac caagaatagc ttttccgaga tccgtattca tcctctgagc 2640
caagctagcg gaggcagctc caacatcaga caagaacccg ctcctaaggg cagacccgct 2700
ttacaactcc ccggtcagat ggatcccggt tggcacgtga gcagcgtcac aaggagcgcc 2760
acagagggcc ccagctatag cgaacagctg ggcgccaaaa gcggacccaa cggccatccc 2820
tacaatagaa ccaatcgttc cagaatgccc aatctcaacg acctcaagga aacagcttta 2880
tga 2883

<210> SEQ ID NO 40
<211> LENGTH: 2883
<212> TYPE: DNA
<213> ORGANISM: Artificial Sequence
<220> FEATURE:
<223> OTHER INFORMATION: engineered nucleic acid sequence CDKL5co-D

<400> SEQUENCE: 40
atgaagatcc ccaacatcgg caacgtgatg aacaagttcg agatcctggg cgtcgtcggc 60
gaaggcgctt atggcgttgt gctgaagtgc agacacaaag aaacccacga gatcgtggcc 120
atcaagaagt tcaaggacag cgaagagaac gaggaagtga aagagacaac cctgcgcgag 180
ctgaagatgc tgcggaccct gaagcaagag aacatcgtgg aactgaaaga ggccttccgg 240
cggagaggca agctgtacct ggtgttcgag tacgtggaaa agaacatgct cgagctgctg 300
gaagagatgc ccaacggcgt gccacctgag aaagtgaagt cctacatcta ccagctgatc 360
aaggccatcc actggtgcca caagaacgac atcgtgcacc gggacatcaa gcccgagaac 420
ctgctgatct cccacaacga cgtgctgaag ctgtgcgact tcggcttcgc cagaaatctg 480
agcgagggca acaacgccaa ctacaccgaa tacgtggcca ccagatggta cagaagccct 540
gagctgctgc tgggagcccc ttatggcaag tccgtggata tgtggagcgt gggctgtatc 600
ctgggagagc tgtctgatgg ccagcctctg tttcctggcg agtccgagat cgaccagctg 660
ttcaccatcc agaaggtgct gggccctctg cctagcgagc agatgaagct gttctacagc 720
aaccccagat tccacggcct gagattcccc gccgtgaatc accctcagag cctggaaaga 780
agatacctgg gcatcctgaa cagcgtgctg ctggacctga tgaagaatct gctgaaactg 840
gaccccgccg acagatacct gaccgagcag tgcctgaacc atcctacctt tcagacccag 900
agactgctgg atcggagccc tagcagaagc gccaagagaa agccctacca cgtggaaagc 960
agcaccctga gcaacagaaa ccaggccggc aagtctacag ccctgcagag ccaccacaga 1020
agcaacagca aggacatcca gaacctgtcc gtgggcctgc ctagagccga tgaaggactg 1080
cctgccaacg agagcttcct gaacggaaat ctggctggcg cctctctgag ccctctgcac 1140

```
acaaagacat accaggccag cagccagcct ggcagcacaa gcaaggatct gaccaacaac   1200

aacatccctc atctgctgag ccccaaagag gccaagagca agaccgagtt cgacttcaac   1260

atcgacccca agcctagcga aggccctggc accaagtacc tgaagtccaa cagcagaagc   1320

cagcagaacc ggcactcctt catggaaagc tcccagagca aggccggcac actgcagcct   1380

aatgagaagc agagcagaca cagctacatc gacacaatcc cacagagcag caggtcccca   1440

agctacagga ccaaggccaa atctcacggc gccctgagcg atagcaagag cgtgtccaat   1500

ctgtccgagg ctagagccca gatcgccgag cctagcacca gcagatactt ccctagctcc   1560

tgcctggatc tgaacagccc aacaagcccc acacctacca ggcacagcga caccagaaca   1620

ctgctgtccc catccggcag aaacaaccgg aatgagggca ccctggacag cagacggacc   1680

accacaagac acagcaagac catggaagaa ctgaagctgc ccgagcacat ggactccagc   1740

cactctcatt ctctgagcgc ccctcacgag tccttctctt acggcctggg ctacacaagc   1800

cccttcagct ctcagcagag gccccacaga cactctatgt acgtgacccg ggacaaagtg   1860

cgcgccaaag gcctggatgg ctctctgtct atcggccaag gcatggccgc cagagccaat   1920

tctctgcagc tgctgtctcc tcagcctggg gaacaactgc ctcctgagat gaccgtggcc   1980

agatccagcg tgaaagaaac cagcagagag ggcacctcca gcttccacac cagacagaaa   2040

agcgaaggcg gagtgtacca cgatcctcac agcgacgacg gcacagcccc taaagagaac   2100

agacacctgt acaacgaccc cgtgcctaga agagtgggct ccttctacag agtgccttct   2160

cctagacctg acaactcctt ccacgagaac aatgtgtcca ccagagtgtc cagcctgcct   2220

tccgaaagca gctccggcac caaccactcc aagagacagc ctgctttcga cccctggaag   2280

tcccctgaga acatcagcca ctccgagcag ctgaaagaga aagagaagca gggctttttc   2340

cggtccatga agaagaagaa aaagaagtcc cagacggtcc ccaacagcga ctccccagat   2400

ctgctgaccc tgcagaagtc catccactcc gccagcacac ctagcagcag acccaaagag   2460

tggcggccag agaagatcag cgatctgcag acccagtctc agcctctgaa gtccctgagg   2520

aagctgctgc atctgagcag cgcctctaat caccctgcca gcagcgaccc tagatttcag   2580

ccactgacag cccagcagac caagaactcc ttcagcgaga tccggattca cccactgtct   2640

caggccagcg gcggcagcag caatatcaga caagagcccg ctcctaaggg cagacctgct   2700

ctgcaactgc ctggccagat ggatccagga tggcacgtgt cctctgtgac cagatccgcc   2760

acagagggac ctagctacag cgaacagctc ggcgccaagt ctggccctaa tggacacccc   2820

tacaaccgga ccaaccggtc cagaatgccc aacctgaacg acctcaaaga aacagccctg   2880

tga                                                                 2883
```

<210> SEQ ID NO 41
<211> LENGTH: 2883
<212> TYPE: DNA
<213> ORGANISM: Artificial Sequence
<220> FEATURE:
<223> OTHER INFORMATION: engineered nucleic acid sequence CDKL5coA1

<400> SEQUENCE: 41

```
atgaagatcc ccaacatcgg caacgtgatg aacaagttcg agatcctggg cgtcgtcggc     60

gaaggcgctt atggcgttgt gctgaagtgc agacacaaag aaacccacga gatcgtggcc    120

atcaagaagt tcaaggacag cgaagagaac gaggaagtga aagagacaac cctgcgcgag    180

ctgaagatgc tgcggaccct gaagcaagag aacatcgtgg aactgaaaga ggccttccgg    240

cggagaggca agctgtacct ggtgttcgag tacgtggaaa agaacatgct cgagctgctg    300
```

```
gaagagatgc ccaacggcgt gccacctgag aaagtgaagt cctacatcta ccagctgatc    360
aaggccatcc actggtgcca caagaacgac atcgtgcacc gggacatcaa gcccgagaac    420
ctgctgatct cccacaacga cgtgctgaag ctgtgcgact tcggcttcgc cagaaatctg    480
agcgagggca acaacgccaa ctacaccgaa tacgtggcca ccagatggta cagaagccct    540
gagctgctgc tgggagcccc ttacggcaag tccgtggata tgtggagcgt gggctgtatc    600
ctgggagagc tgtctgacgg ccagcctctg tttcctggcg agtccgagat cgaccagctg    660
ttcaccatcc agaaggtgct gggccctctg cctagcgagc agatgaagct gttctacagc    720
aaccccagat tccacggcct gagattcccc gccgtgaatc accctcagag cctggaaaga    780
agatacctgg gcatcctgaa cagcgtgctg ctggacctga tgaagaatct gctgaaactg    840
gaccccgccg acagatacct gaccgagcag tgcctgaacc atcctacctt tcaaacccag    900
agactgctgg atcggagccc tagcagaagc gccaagagaa agccctacca cgtggaaagc    960
agcaccctga gcaacagaaa ccaggccggc aagtctacag ccctgcagag ccaccacaga   1020
agcaacagca aggacatcca gaacctgtcc gtgggcctgc ctagagccga cgaaggactg   1080
cctgccaacg agagcttcct gaacggaaat ctggctggcg cctctctgag ccctctgcac   1140
acaaagacat accaggccag cagccagcct ggcagcacaa gcaaggatct gaccaacaac   1200
aacatccctc atctgctgag ccccaaagag gccaagagca agaccgagtt cgacttcaac   1260
atcgacccca agcctagcga aggccctggc accaagtacc tgaagtccaa cagcagaagc   1320
cagcagaacc ggcactcctt catggaaagc tcccagagca aggccggcac actgcagcct   1380
aacgagaagc agagcagaca cagctacatc gacacaatcc cacagagcag caggtcccca   1440
agctacagga ccaaggccaa atctcacggc gccctgagcg atagcaagag cgtgtccaat   1500
ctgtccgagg ctagagccca gatcgccgag cctagcacca gcagatactt ccctagctcc   1560
tgcctggatc tgaacagccc aacaagcccc acacctacca ggcacagcga caccagaaca   1620
ctgctgtccc catccggcag aaacaaccgg aacgagggca ccctggacag cagacggacc   1680
accacaagac acagcaagac catggaagaa ctgaagctgc ccgagcacat ggactccagc   1740
cactctcatt ctctgagcgc ccctcacgag tccttctctt acggcctggg ctacacaagc   1800
cccttcagct ctcagcagag gccccacaga cacagcatgt atgtgacccg ggacaaagtg   1860
cgcgccaaag gcctggacgg ctctctgtct atcggccaag gcatggccgc cagagccaat   1920
tctctgcagc tgctgtctcc tcagcctggg gaacaactgc ctcctgagat gaccgtggcc   1980
agatccagcg tgaaagaaac cagcagagag ggcacctcca gcttccacac cagacagaaa   2040
agcgaaggcg gagtgtacca cgatcctcac agcgacgacg gcacagcccc taaagagaac   2100
agacacctgt acaacgaccc cgtgcctaga agagtgggct ccttctacag agtgccttct   2160
cctagacctg acaactcctt ccacgagaac aacgtgtcca ccagagtgtc cagcctgcct   2220
tccgaaagca gctccggcac caaccactcc aagagacagc ctgctttcga cccctggaag   2280
tcccctgaga acatcagcca ctccgagcag ctgaaagaga aagagaagca gggctttttc   2340
cggtccatga agaagaagaa aaagaagtcc cagacggtcc ccaacagcga ctccccagat   2400
ctgctgaccc tgcagaagtc catccactcc gccagcacac ctagcagcag acccaaagag   2460
tggcggccag agaagatcag cgatctgcag acccagtctc agcctctgaa gtccctgagg   2520
aagctgctgc atctgagcag cgcctctaat caccctgcca gcagcgaccc tagatttcag   2580
ccactgacag cccagcagac caagaactcc ttcagcgaga tccggattca cccactgtct   2640
```

caggccagcg gcggcagcag caatatcaga caagagcccg ctcctaaggg cagacctgct 2700
ctgcaactgc ctggccagat ggatccaggc tggcacgtgt cctctgtgac cagatccgcc 2760
acagagggac ctagctacag cgaacagctc ggcgccaagt ctggccctaa cggacacccc 2820
tacaaccgga ccaaccggtc cagaatgccc aacctgaacg acctcaaaga gactgccctt 2880
tga 2883

<210> SEQ ID NO 42
<211> LENGTH: 2883
<212> TYPE: DNA
<213> ORGANISM: Artificial Sequence
<220> FEATURE:
<223> OTHER INFORMATION: engineered nucleic acid sequence CDKL5coB1

<400> SEQUENCE: 42
atgaagatcc ctaatatcgg caacgtgatg aataagttcg agatcctggg agtggtggga 60
gagggagcat acggagtggt gctgaagtgc cgccacaagg agacccacga gatcgtggcc 120
atcaagaagt ttaaggatag cgaggagaat gaggaggtga aggagaccac actgagagag 180
ctgaagatgc tgaggacact gaagcaggag aacatcgtgg agctgaagga ggccttccgg 240
agaaggggca agctgtacct ggtgtttgag tacgtggaga agaacatgct ggagctgctg 300
gaggagatgc ccaatggcgt gccccctgag aaggtgaagt cctacatcta tcagctgatc 360
aaggccatcc actggtgcca caagaacgac atcgtgcaca gagatatcaa gcctgagaac 420
ctgctgatct cccacaatga cgtgctgaag ctgtgcgatt tcggctttgc caggaacctg 480
agcgagggca acaacgccaa ttacacagag tacgtggcca cccgctggta cagaagccca 540
gagctgctgc tgggagcacc atacggcaag agcgtggaca tgtggtccgt gggctgcatc 600
ctgggcgagc tgtctgacgg ccagcctctg ttcccaggcg agagcgagat cgatcagctg 660
tttaccatcc agaaggtgct gggccctctg ccaagcgagc agatgaagct gttctactcc 720
aaccccagat tccacggcct gaggtttccc gccgtgaatc accctcagag cctggagcgc 780
cggtatctgg gcatcctgaa ctccgtgctg ctggatctga tgaagaatct gctgaagctg 840
gaccccgccg atcgctacct gaccgagcag tgtctgaatc accctacatt tcagacccag 900
cgcctgctgg accggagccc ttccagatct gccaagagga agccatatca cgtggagagc 960
tccaccctgt ccaatagaaa ccaggccggc aagtctacag ccctgcagag ccaccacagg 1020
agcaactcca aggacatcca gaatctgtcc gtgggactgc ctagggcaga cgagggactg 1080
ccagcaaacg agagcttcct gaacggaaac ctggcaggag catctctgag cccactgcac 1140
acaaagacct accaggcctc tagccagccc ggctccacat ctaaggacct gaccaacaat 1200
aacatcccac acctgctgtc tcccaaggag gccaagagca agaccgagtt cgactttaat 1260
atcgatccca agcctagcga gggccctggc acaaagtatc tgaagagcaa ctcccgctct 1320
cagcagaatc ggcactcctt catggagtcc tctcagtcta aggccggcac cctgcagcca 1380
aacgagaagc agagcaggca ctcctacatc gataccatcc cccagagctc cagaagccct 1440
tcctatagaa caaaggccaa gtctcacggc gccctgtctg acagcaagtc cgtgtctaat 1500
ctgagcgagg caagggcaca gatcgcagag cccagcacct cccggtactt tccttcttcc 1560
tgtctggacc tgaactctcc tacaagccca acacccaccc gccactccga tacacggacc 1620
ctgctgtctc caagcggcag aaataacagg aacgagggca ccctggattc tagaaggacc 1680
acaaccagac acagcaagac aatggaggag ctgaagctgc cagagcacat ggactcctct 1740
cactcccact ctctgagcgc ccctcacgag tccttctctt acggcctggg ctatacctcc 1800

```
ccc ttctcct cccaacaaag gccacaccgg cacagcatgt atgtgacaag ggacaaggtc   1860
```

cccttctcct cccaacaaag gccacaccgg cacagcatgt atgtgacaag ggacaaggtc 1860
cgggcaaagg gactggacgg aagcctgtcc atcggacagg gaatggcagc aagggccaac 1920
tccctgcagc tgctgtctcc tcagccagga gagcagctgc caccagagat gaccgtggca 1980
cgctctagcg tgaaggagac aagccgggag ggcacctcct ctttccacac acgccagaag 2040
tccgagggcg gcgtgtatca cgacccccac tctgacgacg gcacagcccc taaggagaac 2100
cggcacctgt acaacgatcc cgtgcctagg agggtgggat ccttctatag agtgccatct 2160
cccaggcctg acaatagctt tcacgagaat aacgtgtcca cccgcgtgag ctccctgcca 2220
tctgagtcta gctccggcac aaaccactct aagcggcagc ccgcctttga tccttggaag 2280
agcccagaga atatctctca cagcgagcag ctgaaggaga aggagaagca gggcttcttt 2340
agaagcatga agaagaagaa gaagaagagc cagaccgtgc ctaactccga ctctccagac 2400
ctgctgaccc tgcagaagtc catccacagc gcctccacac catctagcag gcctaaggag 2460
tggcggcctg agaagatcag cgatctgcag acccagagcc agccactgaa gtccctgagg 2520
aagctgctgc acctgtcctc tgccagcaac cacccagcca gctccgaccc aagattccag 2580
cccctgacag cccagcagac caagaacagc ttcagcgaga tcaggatcca cccactgtcc 2640
caggcatctg gaggatctag caacatcaga caggagccag caccaaaggg caggcccgcc 2700
ctgcagctgc ctggccagat ggacccaggc tggcacgtgt cctctgtgac acgctccgcc 2760
accgagggac catcctactc tgagcagctg ggagcaaaga gcggacctaa cggacaccca 2820
tataaccgga ccaatagatc caggatgccc aatctgaacg acctgaagga gacagccctg 2880
tga 2883

<210> SEQ ID NO 43
<211> LENGTH: 2883
<212> TYPE: DNA
<213> ORGANISM: Artificial Sequence
<220> FEATURE:
<223> OTHER INFORMATION: engineered nucleic acid sequence CDKL5coC1

<400> SEQUENCE: 43
atgaagatcc ccaacatcgg caacgtgatg aacaagttcg agatcctggg cgtggtgggc 60
gagggcgcct acggcgtggt gctgaagtgc aggcacaagg agacccacga gatcgtggcc 120
atcaagaagt tcaaggacag cgaggagaac gaggaggtga aggagaccac cctgagggag 180
ctgaagatgc tgaggaccct gaagcaggag aacatcgtgg agctgaagga ggccttcagg 240
aggaggggca agctgtacct ggtgttcgag tacgtggaga agaacatgct ggagctgctg 300
gaggagatgc ccaacggcgt gccccccgag aaggtgaaga gctacatcta ccagctgatc 360
aaggccatcc actggtgcca caagaacgac atcgtgcaca gggacatcaa gcccgagaac 420
ctgctgatca gccacaacga cgtgctgaag ctgtgcgact tcggcttcgc caggaacctg 480
agcgagggca acaacgccaa ctacaccgag tacgtggcca ccaggtggta caggagcccc 540
gagctgctgc tgggcgcccc ctacggcaag agcgtggaca tgtggagcgt gggctgcatc 600
ctgggcgagc tgagcgacgg ccagcccctg ttccccggcg agagcgagat cgaccagctg 660
ttcaccatcc agaaggtgct gggcccccctg cccagcgagc agatgaagct gttctacagc 720
aaccccaggt tccacggcct gaggttcccc gccgtgaacc acccccagag cctggagagg 780
aggtatctgg gcatcctgaa cagcgtgctg ctggacctga tgaagaacct gctgaagctg 840
gaccccgccg acaggtatct gaccgagcag tgcctgaacc accccacctt ccagacccag 900
aggctgctgg acaggagccc cagcaggagc gccaagagga agccctacca cgtggagagc 960
agcaccctga gcaacaggaa ccaggccggc aagagcaccg ccctgcagag ccaccacagg 1020
agcaacagca aggacatcca gaacctgagc gtgggcctgc ccagggccga cgagggcctg 1080
cccgccaacg agagcttcct gaacggcaac ctggccggcg ccagcctgag ccccctgcac 1140
accaagacct accaggccag cagccagccc ggcagcacca gcaaggacct gaccaacaac 1200
aacatccccc acctgctgag ccccaaggag gccaagagca agaccgagtt cgacttcaac 1260
atcgacccca agcccagcga gggccccggc accaagtacc tgaagagcaa cagcaggagc 1320
cagcagaaca ggcacagctt catggagagc agccagagca aggccggcac cctgcagccc 1380
aacgagaagc agagcaggca cagctacatc gacaccatcc cccagagcag caggagcccc 1440
agctacagga ccaaggccaa gagccacggc gccctgagcg acagcaagag cgtgagcaac 1500
ctgagcgagg ccagggccca gatcgccgag cccagcacca gcagatactt ccccagcagc 1560
tgcctggacc tgaacagccc caccagcccc acccccaccc gccacagcga caccaggacc 1620
ctgctgagcc ccagcggcag gaacaacagg aacgagggca ccctggacag caggaggacc 1680
accaccaggc acagcaagac catggaggag ctgaagctgc ccgagcacat ggacagcagc 1740
cacagccaca gcctgagcgc cccccacgag agcttcagct acggcctggg ctacaccagc 1800
cccttcagca gccagcagag gccccacagg cacagcatgt acgtgaccag ggacaaagtg 1860
agggccaagg gcctggacgg cagcctgagc atcggccagg gcatggccgc cagggccaac 1920
agcctgcagc tgctgagccc ccagcccggc gagcagctgc cccccgagat gaccgtggcc 1980
aggagcagcg tgaaggagac cagcagggag ggcaccagca gcttccacac caggcagaag 2040
agcgagggcg gcgtgtacca cgacccccac agcgacgacg gcaccgcccc caaggagaac 2100
aggcacctgt acaacgaccc cgtgcccagg agggtgggca gcttctacag ggtgcccagc 2160
cccaggcccg acaacagctt ccacgagaac aatgtgagca ccagagtcag cagcctgccc 2220
agcgagagca gcagcggcac caaccacagc aagaggcagc ccgccttcga cccctggaag 2280
agccccgaga acatcagcca cagcgagcag ctgaaggaga aggagaagca gggcttcttc 2340
aggagcatga agaagaagaa gaagaagagc cagaccgtgc ccaacagcga cagccccgac 2400
ctgctgaccc tgcagaagag catccacagc gccagcaccc ccagcagcag gcccaaggag 2460
tggaggcccg agaagatcag cgacctgcag acccagagcc agcccctgaa gagcctgagg 2520
aagctgctgc acctgagcag cgccagcaac caccccgcca gcagcgaccc caggttccag 2580
cccctgaccg cccagcagac caagaacagc ttcagcgaga tcaggatcca ccccctgagc 2640
caggccagcg gcggcagcag caacatcagg caggagcccg cccccaaggg caggcccgcc 2700
ctgcagctgc ccggccagat ggacccccggc tggcacgtga gcagcgtgac caggagcgcc 2760
accgagggcc ccagctacag cgagcagctg ggcgccaaga gcggccccaa cggccacccc 2820
tacaacagga ccaacaggag caggatgccc aacctgaacg acctgaagga gaccgccctg 2880
tga 2883

<210> SEQ ID NO 44
<211> LENGTH: 2883
<212> TYPE: DNA
<213> ORGANISM: Artificial Sequence
<220> FEATURE:
<223> OTHER INFORMATION: engineered nucleic acid sequence CDKL5coD1

<400> SEQUENCE: 44
atgaagattc ccaacattgg gaatgtcatg aacaagtttg agattctggg cgtggtggga 60

```
gagggagcct acggcgttgt tctcaagtgc cgccacaagg aaactcacga gatcgtggct    120
atcaagaaat tcaaggatag tgaggaaaat gaagaagtca aggagacaac tcttcgagaa    180
ttaaagatgc tcagaacctt aaaacaagaa aatattgtgg aattgaaaga ggccttcaga    240
agacgaggaa aactctacct ggtgtttgaa tatgtggaga agaacatgct ggaactgttg    300
gaagagatgc ctaatggggt ccctcctgaa aaagtgaagt cctacatcta tcagctaatc    360
aaggccatcc actggtgcca caaaaatgat attgtccacc gggacatcaa accagagaat    420
ttgctcatca gccacaatga tgtgctcaaa ctttgtgatt ttggatttgc ccgaaacctc    480
tccgaaggca ataatgccaa ctacaccgag tacgtggcca cccgctggta tcgctctcca    540
gagcttctgc ttggggcccc ctatggcaag tctgtggaca tgtggagcgt tggctgcatc    600
ctgggcgagc tgtcagatgg gcagccactc ttcccagggg agtccgaaat cgaccagctg    660
ttcaccatcc agaaagtcct ggggccactt cccagcgagc aaatgaaact gttttacagc    720
aatccaagat ttcatggatt acgcttccct gctgtcaacc accctcaatc cctggagagg    780
agatacttgg gcatcctcaa cagtgtgctg ctggacctca tgaagaatct cctcaagttg    840
gaccctgccg acagatatct tactgagcag tgcctgaacc atcccacatt tcagacccag    900
agattgctag acaggagccc atcaaggagt gccaagagaa agccttatca tgtggagagc    960
agcacactat caaacagaaa ccaggctgga aagagtacag ctttacaatc tcaccaccgc   1020
tccaactcaa aggacattca gaacttgtca gttggactgc ccagagcaga tgagggactc   1080
cccgccaatg aaagcttcct gaatggaaac ctggcaggtg cctccctttc tcctctgcac   1140
acaaagacct accaggcgtc cagccaacct ggatccacat caaaagatct gaccaacaac   1200
aatatccccc accttttatc accaaaggaa gccaaaagta aaacagagtt cgacttcaac   1260
atcgacccca aaccttcaga agggcctggc accaaatatt taaaatcaaa ttcaagaagc   1320
cagcagaatc ggcactcatt catggaatcc tcacagagca aagctgggac actccagcca   1380
aatgagaagc agtccagaca tagttatatt gacaccattc ctcagtcatc cagatcccca   1440
agctaccgga caaaagccaa gagccatggc gcgctgtccg attccaagtc agtatcaaat   1500
ctttcagaag caagagctca gatcgcagag ccctccactt cccgctactt cccctcttca   1560
tgtttggatc tcaattcccc tacttcacct acacccaccc gtcatagtga cacacggacc   1620
ctgctcagtc caagcggcag gaataaccgg aacgagggca cactggacag ccgccgcacc   1680
accacaaggc attctaaaac catggaggag ctgaaattgc ccgagcacat ggactcttca   1740
cattctcatt cactatctgc acctcatgaa agttttagct atggattggg atataccagc   1800
cccttctcca gtcagcagag gcctcacaga cacagcatgt atgtcaccag ggacaaggtg   1860
cgggcaaagg gcctggatgg atctttaagt attggccagg gcatggctgc cagagcaaat   1920
tctcttcagc tgctttcacc ccagcctggg gaacaactgc caccagaaat gacagtggca   1980
aggagcagtg taaaagagac ctccagagaa ggaacatcca gcttccatac tcgccagaag   2040
tcggaaggtg gtgtgtacca cgacccacat tctgatgatg ggaccgctcc caaggaaaac   2100
aggcacctgt acaacgatcc tgtgccccgc cgcgtgggct ctttctacag agttccttct   2160
cctagaccag acaactcctt ccacgaaaac aatgtgtcca ccagagtgag cagtttaccc   2220
tctgagagtt ctagtggaac caatcattcc aaaagacagc ctgcatttga cccctggaag   2280
tccccggaga atatctccca ctccgagcag ctcaaagaaa aggagaaaca gggattcttc   2340
aggtccatga aaaagaagaa gaaaaaaagc cagacagtac caaacagcga ttctccagat   2400
```

```
cttctcactc tgcaaaaatc catccattct gccagtactc catcatctcg acccaaggag   2460

tggagacctg agaaaatttc agacctgcag actcagtctc agcccctgaa atctttgagg   2520

aagttattac acctctcatc agcttccaat cacccagcca gctcagatcc caggttccag   2580

ccgctcacag cccagcaaac aaaaaactct ttttcagaaa tacgtattca tcctttgtcc   2640

caggcatcag gaggcagcag caacatcagg caggagccag ctccaaaagg aaggcccgct   2700

ctgcagctgc caggacagat ggatccaggc tggcatgttt cctctgtcac tagatcagcc   2760

acagaaggac catcctattc tgaacagctg ggtgcaaaaa gtggccccaa tggccacccc   2820

tacaatagaa caaatcgcag cagaatgccc aacttaaatg acttgaaaga aacagcactg   2880

tga                                                                 2883
```

```
<210> SEQ ID NO 45
<211> LENGTH: 2883
<212> TYPE: DNA
<213> ORGANISM: Artificial Sequence
<220> FEATURE:
<223> OTHER INFORMATION: engineered nucleic acid sequence CDKL5coA2

<400> SEQUENCE: 45

atgaagatcc ccaacatcgg caacgtgatg aacaagttcg agatcctggg cgtcgtcggc     60

gaaggcgctt atggcgttgt gctgaagtgc agacacaaag aaacccacga gatcgtggcc    120

atcaagaagt tcaaggacag cgaagagaac gaggaagtga aagagacaac cctgcgcgag    180

ctgaagatgc tgcggaccct gaagcaagag aacatcgtgg aactgaaaga ggccttccgg    240

cggagaggca agctgtacct ggtgttcgag tacgtggaaa agaacatgct cgagctgctg    300

gaagagatgc ccaacggcgt gccacctgag aaagtgaagt cctacatcta ccagctgatc    360

aaggccatcc actggtgcca caagaacgac atcgtgcacc gggacatcaa gcccgagaac    420

ctgctgatct cccacaacga cgtgctgaag ctgtgcgact tcggcttcgc cagaaatctg    480

agcgagggca acaacgccaa ctacaccgaa tacgtggcca ccagatggta cagaagccct    540

gagctgctgc tgggagcccc ttacggcaag tccgtggata tgtggagcgt gggctgtatc    600

ctgggagagc tgtctgacgg ccagcctctg tttcctggcg agtccgagat cgaccagctg    660

ttcaccatcc agaaggtgct gggccctctg cctagcgagc agatgaagct gttctacagc    720

aaccccagat tccacggcct gagattcccc gccgtgaatc accctcagag cctggaaaga    780

agatacctgg gcatcctgaa cagcgtgctg ctggacctga tgaagaatct gctgaaactg    840

gaccccgccg acagatacct gaccgagcag tgcctgaacc atcctacctt tcaaacccag    900

agactgctgg atcggagccc tagcagaagc gccaagagaa agccctacca cgtggaaagc    960

agcaccctga gcaacagaaa ccaggccggc aagtctacag ccctgcagag ccaccacaga   1020

agcaacagca aggacatcca gaacctgtcc gtgggcctgc ctagagccga cgaaggactg   1080

cctgccaacg agagcttcct gaacggaaat ctggctggcg cctctctgag ccctctgcac   1140

acaaagacat accaggccag cagccagcct ggcagcacaa gcaaggatct gaccaacaac   1200

aacatccctc atctgctgag ccccaaagag gccaagagca agaccgagtt cgacttcaac   1260

atcgacccca agcctagcga aggccctggc accaagtacc tgaagtccaa cagcagaagc   1320

cagcagaacc ggcactcctt catggaaagc tcccagagca aggccggcac actgcagcct   1380

aacgagaagc agagcagaca cagctacatc gacacaatcc cacagagcag caggtcccca   1440

agctacagga ccaaggccaa atctcacggc gccctgagcg atagcaagag cgtgtccaat   1500

ctgtccgagg ctagagccca gatcgccgag cctagcacca gcagatactt ccctagctcc   1560
```

```
tgcctggatc tgaacagccc aacaagcccc acacctacca ggcacagcga caccagaaca   1620

ctgctgtccc catccggcag aaacaaccgg aacgagggca ccctggacag cagacggacc   1680

accacaagac acagcaagac catggaagaa ctgaagctgc ccgagcacat ggactccagc   1740

cactctcatt ctctgagcgc ccctcacgag tccttctctt acggcctggg ctacacaagc   1800

cccttcagct ctcagcagag gccccacaga cacagtatgt atgtgacccg ggacaaagtg   1860

cgcgccaaag gcctggacgg ctctctgtct atcggccaag gcatggccgc cagagccaat   1920

tctctgcagc tgctgtctcc tcagcctggg gaacaactgc ctcctgagat gaccgtggcc   1980

agatccagcg tgaaagaaac cagcagagag ggcacctcca gcttccacac cagacagaaa   2040

agcgaaggcg gagtgtacca cgatcctcac agcgacgacg gcacagcccc taaagagaac   2100

agacacctgt acaacgaccc cgtgcctaga agagtgggct ccttctacag agtgccttct   2160

cctagacctg acaactcctt ccacgagaac aacgtgtcca ccagagtgtc cagcctgcct   2220

tccgaaagca gctccggcac caaccactcc aagagacagc ctgctttcga cccctggaag   2280

tcccctgaga acatcagcca ctccgagcag ctgaaagaga aagagaagca gggctttttc   2340

cggtccatga agaagaagaa aaagaagtcc cagacggtcc ccaacagcga ctccccagat   2400

ctgctgaccc tgcagaagtc catccactcc gccagcacac ctagcagcag acccaaagag   2460

tggcggccag agaagatcag cgatctgcag acccagtctc agcctctgaa gtccctgagg   2520

aagctgctgc atctgagcag cgcctctaat caccctgcca gcagcgaccc tagatttcag   2580

ccactgacag cccagcagac caagaactcc ttcagcgaga tccggattca cccactgtct   2640

caggccagcg gcggcagcag caatatcaga caagagcccg ctcctaaggg cagacctgct   2700

ctgcaactgc ctggccagat ggatccaggc tggcacgtgt cctctgtgac cagatccgcc   2760

acagagggac ctagctacag cgaacagctc ggcgccaagt ctggccctaa cggacacccc   2820

tacaaccgga ccaaccggtc cagaatgccc aatctgaacg acctcaaaga aacggccctg   2880

tga                                                                 2883
```

<210> SEQ ID NO 46
<211> LENGTH: 2883
<212> TYPE: DNA
<213> ORGANISM: Artificial Sequence
<220> FEATURE:
<223> OTHER INFORMATION: engineered nucleic acid sequence CDKL5coB2

<400> SEQUENCE: 46

```
atgaagatcc caaatatcgg caacgtgatg aataagttcg agatcctggg agtggtggga     60

gagggagcat atggcgtggt gctgaagtgc aggcacaagg agacccacga gatcgtggcc    120

atcaagaagt ttaaggacag cgaggagaat gaggaggtga aggagaccac actgagagag    180

ctgaagatgc tgaggacact gaagcaggag aacatcgtgg agctgaagga ggccttccgg    240

agaaggggca agctgtacct ggtgtttgag tacgtggaga agaacatgct ggagctgctg    300

gaggagatgc caaatggcgt gccccctgag aaggtgaagt cctacatcta tcagctgatc    360

aaggccatcc actggtgcca caagaacgac atcgtgcaca gagatatcaa gcccgagaac    420

ctgctgatct cccacaatga cgtgctgaag ctgtgcgatt tcggctttgc caggaacctg    480

agcgagggca acaacgccaa ttacacagag tacgtggcca ccaggtggta caggagccca    540

gagctgctgc tgggagcacc atacggcaag agcgtggata tgtggtccgt gggctgcatc    600

ctgggcgagc tgtctgacgg ccagcctctg ttcccaggcg agagcgagat cgatcagctg    660
```

```
tttaccatcc agaaggtgct gggccctctg ccaagcgagc agatgaagct gttctactcc    720
aaccctagat tccacggcct gaggtttccc gccgtgaatc accctcagag cctggagcgc    780
cggtatctgg gcatcctgaa ctccgtgctg ctggatctga tgaagaatct gctgaagctg    840
gaccccgccg atagatacct gaccgagcag tgtctgaatc accctacatt tcagacccag    900
cgcctgctgg accggagccc ttccagatct gccaagagga agccatatca cgtggagagc    960
tccaccctgt ccaatagaaa ccaggccggc aagtctacag ccctgcagag ccaccacagg   1020
agcaactcca aggacatcca gaatctgtcc gtgggactgc ctagggcaga cgagggactg   1080
ccagccaacg agagcttcct gaacggaaac ctggcaggag catctctgag cccactgcac   1140
acaaagacct accaggcctc tagccagccc ggctccacat ctaaggacct gaccaacaat   1200
aacatcccac acctgctgtc tcccaaggag gccaagagca agaccgagtt cgactttaat   1260
atcgatccaa agcctagcga gggaccaggc acaaagtatc tgaagagcaa ctcccgctct   1320
cagcagaatc ggcactcctt catggagtcc tctcagtcta aggccggcac cctgcagcct   1380
aacgagaagc agagcagaca ctcctacatc gataccatcc cccagagctc cagaagccct   1440
tcctatagaa caaaggccaa gtctcacggc gccctgtctg acagcaagtc cgtgtctaat   1500
ctgagcgagg caagggcaca gatcgcagag cccagcacct cccggtactt tccttcttcc   1560
tgtctggacc tgaactctcc tacaagccca acacccaccc gccacagcga tacacggacc   1620
ctgctgtctc caagcggccg caataaccgg aacgagggca ccctggattc tagaaggacc   1680
acaacccgcc acagcaagac aatggaggag ctgaagctgc cagagcacat ggactcctct   1740
cactcccact ctctgagcgc ccctcacgag tccttctctt acggcctggg ctatacctcc   1800
cccttctcct cccaacaaag accccacagg cacagcatgt acgtgacaag ggacaaggtc   1860
cgggcaaagg gactggacgg aagcctgtcc atcggacagg gaatggcagc aagggccaac   1920
tccctgcagc tgctgtctcc tcagccagga gagcagctgc caccagagat gaccgtggca   1980
cgctctagcg tgaaggagac aagccgggag ggcacctcct ctttccacac acgccagaag   2040
tccgagggag gcgtgtacca cgacccacac tctgacgacg gcacagcccc taaggagaac   2100
cggcacctgt acaacgatcc cgtgcctagg agggtgggat ccttctatag agtgccatct   2160
cccaggcctg acaatagctt tcacgagaat aacgtgtcca cccgcgtgag ctccctgcca   2220
tctgagtcta gctccggcac aaaccactct aagcggcagc ccgcctttga cccttggaag   2280
agcccagaga atatctctca cagcgagcag ctgaaggaga aggagaagca gggcttcttt   2340
cgcagcatga agaagaagaa gaagaagagc cagaccgtgc ctaactccga ctctccagac   2400
ctgctgaccc tgcagaagtc catccacagc gcctccacac catctagcag gcctaaggag   2460
tggcggcctg agaagatcag cgatctgcag acccagagcc agccactgaa gtccctgcgg   2520
aagctgctgc acctgtcctc tgcctccaac cacccagcaa gctccgaccc aagattccag   2580
cccctgacag cccagcagac caagaacagc ttcagcgaga tcaggatcca ccctctgtcc   2640
caagcatctg gaggatctag caacatcaga caggagccag caccaaaggg caggcccgcc   2700
ctgcagctgc ctggccagat ggatccaggc tggcacgtgt cctctgtgac acgcagcgcc   2760
accgagggac catcctactc tgagcagctg ggagcaaaga gcggacctaa cggacaccca   2820
tataaccgga ccaatagatc caggatgccc aatctgaacg acctgaagga gacagccctg   2880
tga                                                                  2883
```

<210> SEQ ID NO 47
<211> LENGTH: 2883

<212> TYPE: DNA
<213> ORGANISM: Artificial Sequence
<220> FEATURE:
<223> OTHER INFORMATION: engineered nucleic acid sequence CDKL5coC2

<400> SEQUENCE: 47
atgaagatcc ccaacatcgg caacgtgatg aacaagttcg agatcctggg cgtggtgggc 60
gagggcgcct acggcgtggt gctgaagtgc aggcacaagg agacccacga gatcgtggcc 120
atcaagaagt tcaaggacag cgaggagaac gaggaggtga aggagaccac cctgagggag 180
ctgaagatgc tgaggaccct gaagcaggag aacatcgtgg agctgaagga ggccttcagg 240
aggaggggca agctgtacct ggtgttcgag tacgtggaga agaacatgct ggagctgctg 300
gaggagatgc ccaacggcgt gccccctgag aaggtgaaga gctacatcta ccagctgatc 360
aaggccatcc actggtgcca caagaacgac atcgtgcaca gggacatcaa gcccgagaac 420
ctgctgatca gccacaacga cgtgctgaag ctgtgcgact tcggcttcgc caggaacctg 480
agcgagggca acaacgccaa ctacaccgag tacgtggcca ccaggtggta caggagcccc 540
gagctgctgc tgggcgcccc ctacggcaag agcgtggaca tgtggagcgt gggctgcatc 600
ctgggcgagc tgagcgacgg ccagcccctg ttccccggcg agagcgagat cgaccagctg 660
ttcaccatcc agaaggtgct gggcccccctg cccagcgagc agatgaagct gttctacagc 720
aaccccaggt tccacggcct gaggttcccc gccgtgaacc acccccagag cctggagagg 780
agatacctgg gcatcctgaa cagcgtgctg ctggacctga tgaagaacct gctgaagctg 840
gaccccgccg acagatacct gaccgagcag tgcctgaacc accccacctt ccagacccag 900
aggctgctgg acaggagccc cagcaggagc gccaagagga agccctacca cgtggagagc 960
agcaccctga gcaacaggaa ccaggccggc aagagcaccg ccctgcagag ccaccacagg 1020
agcaacagca aggacatcca gaacctgagc gtgggcctgc ccagggccga cgagggcctg 1080
cccgccaacg agagcttcct gaacggcaac ctggccggcg ccagcctgag ccccctgcac 1140
accaagacct accaggccag cagccagccc ggcagcacca gcaaggacct gaccaacaac 1200
aacatccccc acctgctgag ccccaaggag gccaagagca agaccgagtt cgacttcaac 1260
atcgacccca agcccagcga gggccccggc accaagtacc tgaagagcaa cagcaggagc 1320
cagcagaaca ggcacagctt catggagagc agccagagca aggccggcac cctgcagccc 1380
aacgagaagc agagcaggca cagctacatc gacaccatcc cccagagcag caggagcccc 1440
agctacagga ccaaggccaa gagccacggc gccctgagcg acagcaagag cgtgagcaac 1500
ctgagcgagg ccagggccca gatcgccgag cccagcacca gcagatactt ccccagcagc 1560
tgcctggacc tgaacagccc caccagcccc acccccacca ggcacagcga caccaggacc 1620
ctgctgagcc ccagcggcag gaacaacagg aacgagggca ccctggacag caggaggacc 1680
accaccaggc acagcaagac catggaggag ctgaagctgc ccgagcacat ggacagcagc 1740
cacagccaca gcctgagcgc ccctcacgag agcttcagct acggcctggg ctacaccagc 1800
cccttcagca gccagcagag gccccacagg cacagcatgt acgtgaccag ggacaaagtg 1860
agggccaagg gcctggacgg cagcctgagc atcggccagg gcatggccgc cagggccaac 1920
agcctgcagc tgctgagccc ccagcccggc gagcagctgc ctcccgagat gaccgtggcc 1980
aggagcagcg tgaaggagac cagcagggag ggcaccagca gcttccacac caggcagaag 2040
agcgagggcg gcgtgtacca cgacccccac agcgacgacg gcaccgcccc caaggagaac 2100
aggcacctgt acaacgaccc cgtgcccagg agggtgggca gcttctacag ggtgcccagc 2160
cccaggcccg acaacagctt ccacgagaac aatgtgagca ccagagtgag cagcctgccc 2220
agcgagagca gcagcggcac caaccacagc aagaggcagc ccgccttcga cccctggaag 2280
agccccgaga acatcagcca cagcgagcag ctgaaggaga aggagaagca gggcttcttc 2340
aggagcatga agaagaagaa gaagaagagc cagaccgtgc ccaacagcga cagccccgac 2400
ctgctgaccc tgcagaagag catccacagc gccagcaccc ccagcagcag gcccaaggag 2460
tggaggcccg agaagatcag cgacctgcag acccagagcc agcccctgaa gagcctgagg 2520
aagctgctgc acctgagcag cgccagcaac caccccgcca gcagcgaccc caggttccag 2580
cccctgaccg cccagcagac caagaacagc ttcagcgaga tcaggatcca ccccctgagc 2640
caggccagcg gcggcagcag caacatcagg caggagcccg cccccaaggg caggcccgcc 2700
ctgcagctgc ccggccagat ggaccccggc tggcacgtga gcagcgtgac caggagcgcc 2760
accgagggcc ccagctacag cgagcagctg ggcgccaaga gcggccccaa cggccacccc 2820
tacaacagga ccaacaggag caggatgccc aacctgaacg acctgaagga gaccgccctg 2880
tga 2883

<210> SEQ ID NO 48
<211> LENGTH: 2883
<212> TYPE: DNA
<213> ORGANISM: Artificial Sequence
<220> FEATURE:
<223> OTHER INFORMATION: engineered nucleic acid sequence CDKL5coD2

<400> SEQUENCE: 48
atgaagatcc ctaacatcgg gaatgtcatg aacaagtttg aaatcctggg ggtggtgggg 60
gagggagctt atggagttgt tttgaaatgt cgtcataagg aaactcatga aatcgtggcc 120
attaagaagt tcaaggacag tgaggagaat gaagaggtga aggagaccac tctccgcgag 180
ctgaagatgc tgaggacact gaagcaggaa aacattgtgg agctgaagga ggccttccga 240
cgacggggta agttgtacct ggtgtttgag tacgtggaga aaaacatgtt agaacttctg 300
gaggaaatgc caaacggtgt acctccagaa aaagtcaagt catatatcta ccagttgatc 360
aaagccatcc actggtgtca taaaaatgac atcgtccaca gagatataaa accagagaat 420
cttctgatct ctcacaatga tgtattaaaa ctttgtgatt ttggttttgc ccgtaatctg 480
tctgaaggta ataatgctaa ctatactgag tatgtagcaa ctcgctggta cagatcgcct 540
gaactgctac tgggtgctcc ttacggaaaa agtgtggaca tgtggagcgt tggttgtatc 600
ctaggagagc tgagtgatgg gcagccattg ttcccggggg agagtgaaat tgaccaacta 660
ttcacaatcc agaaagtgct ggggccacta ccaagtgaac aaatgaaact tttttattca 720
aatcctagat ttcacggtct acgtttcccc gctgtgaacc atcctcagtc cttagaacgg 780
cgatatttag gcattctgaa ctctgttctg ttagatctga tgaagaattt actaaaatta 840
gacccggctg accgctattt gacagagcag tgtttaaatc atccaacctt ccagacacag 900
agactcctag accgttcacc atctagaagt gcgaaaagaa aaccctacca cgttgaatca 960
agtaccctct ccaatcgcaa ccaggctggg aagagtactg ccctacaatc gcaccacagg 1020
agtaatagta aagatattca gaatctatct gtagggcttc ctcgagcgga cgagggtcta 1080
cctgccaatg aaagtttcct caatggtaac ttagctgggg catcactgtc gccccttcat 1140
actaagacct accaagcctc atctcaaccg gggagtacta gtaaagacct caccaacaat 1200
aacatccccc atttattatc tcccaaggag gcgaaatcca agactgagtt cgatttcaac 1260
attgacccaa agccctctga agggcctggc accaaatacc tgaaatctaa tagcagaagt 1320

-continued

```
caacaaaata ggcacagctt catggagtcc tcgcagagca aagctggcac actgcaacct   1380

aatgaaaagc aaagccgaca ttcatatatt gataccatcc cccaatctag tagaagccct   1440

tcataccgca cgaaagcaaa gtctcatggc gcactgtcag attctaaatc cgtcagcaat   1500

ctcagtgaag ccagggctca gatcgccgag ccctctacat ctcgctactt tccctcatcc   1560

tgcctggacc taaactcccc gacctctccc acccccacgc gtcacagcga cacccgaaca   1620

ttactttcac cttcgggcag gaataatcga aatgagggca ccctagattc gcgccgtacg   1680

actacacggc attcaaaaac catggaagaa ttgaaattgc ctgagcacat ggattcgtca   1740

cactctcaca gtctatcggc ccctcacgag agtttcagtt acgggcttgg ctacaccagt   1800

cccttctcca gccagcaacg cccacaccgc cactccatgt atgtcacccg cgacaaggtc   1860

cgtgccaaag gactcgatgg cagcctaagc ataggacagg gcatggccgc cagggccaac   1920

agtctccagt tactaagtcc ccagcccgga gaacagctgc cacccgagat gactgtggct   1980

agatcgtccg tgaaagagac aagtagggaa gggacctcta gcttccacac cagacagaaa   2040

tccgaggggg gcgtgtatca tgaccctcat agtgatgatg gtacagcccc gaaggaaaat   2100

agacacttgt acaatgaccc tgtgccccga agagttggct ccttctaccg ggtgccctct   2160

ccacggccag acaacagctt ccatgagaac aatgtttcaa cccgggtaag ctccctgcct   2220

agtgaaagtt catccggaac aaatcactcg aagcgtcagc cagccttcga cccctggaag   2280

tctccggaga acataagtca cagcgagcag ctcaaagaaa aagaaaaaca aggcttcttc   2340

agaagcatga agaagaaaaa aaaaaagtct caaacagtgc caaattccga ttcccccgac   2400

ttattaacac tacaaaagag catccattca gcttctacgc caagcagtag gcccaaagag   2460

tggagacccg agaagatttc tgatctacag acccagtctc agcctttaaa atcgctcagg   2520

aagctgctgc acctgtcttc cgcttcaaac cacccggcct ccagtgaccc tcggtttcag   2580

ccactgactg cccagcagac taaaaatagt ttttcagaga tcaggattca tcccttatca   2640

caggcctctg gcggcagcag caatatccgg caggagcctg cccctaaagg ccggcccgcg   2700

ttgcagctgc ccggccagat ggacccaggc tggcatgtgt catcagttac acgcagtgcc   2760

acagaaggcc ccagctactc agaacaattg ggtgctaagt caggacccaa tggccaccca   2820

tacaaccgaa ccaacagatc aaggatgccc aacctcaacg acctcaaaga aacagctctc   2880

tga                                                                  2883
```

COMPOSITIONS USEFUL IN TREATMENT OF CDKL5 DEFICIENCY DISORDER (CDD)

CROSS-REFERENCE TO RELATED APPLICATIONS

This is a National Stage Entry under 35 U.S.C. 371 of International Patent Application No. PCT/US2021/029185, filed Apr. 26, 2021, which claims priority to U.S. Provisional Application No. 63/109,608, filed Nov. 4, 2020, U.S. Provisional Application No. 63/091,032, filed Oct. 13, 2020, and U.S. Provisional Application No. 63/016,036, filed Apr. 27, 2020. These applications are incorporated by reference herein.

REFERENCE TO AN ELECTRONIC SEQUENCE LISTING

The electronic sequence listing filed herewith named "20-9196PCT_SeqListing_ST25.txt" with size of 341,968 bytes, created on date of Apr. 22, 2021, and the contents of the electronic sequence listing (e.g., the sequences and text therein) are incorporated herein by reference in entirety.

BACKGROUND OF THE INVENTION

CDKL5 Deficiency Disorder (CDD) is a serious neurodevelopmental disorder affecting young children. The underlying cause is lack of CDKL5 protein expression due to mutations in the X-linked Cyclin-Dependent Kinase-Like 5 gene, CDKL5 (Mendelian Inheritance in Man, MIM: 300203; previously known as STK9), resulting in a range of phenotypes, including EIEE2 (MIM: 300672), a form of early infantile epileptic encephalopathy [Bahi-Buisson, N. et al. Key clinical features to identify girls with CDKL5 mutations. Brain 131, 2647-2661, doi: 10.1093/brain/awn197 (2008)], and infantile spasms [Fehr, S. et al. Eur J Hum Genet 21, 266-273, doi: 10.1038/ejhg.2012.156 (2013); Kalscheuer, V. M. et al., American Journal of Human Genetics, 72, 1401-1411, doi: 10.1086/375538 (2003); Tao, J. et al. American Journal of Human Genetics 75, 1149-1154, doi: 10.1086/426460 (2004). Weaving, L. S. et al. American Journal of Human Genetics 75, 1079-1093, doi: 10.1086/426462 (2004)]. In addition to the characteristic early-onset seizures, the phenotype may also include a number of other features, such as stereotypic hand movements, severe psychomotor retardation and general hypotonia. The early postnatal onset of symptoms indicates that CDKL5 plays a crucial role in brain development. CDKL5 is also expressed within the mature adult nervous system. CDKL5 is expressed throughout the cell, including the nucleus and the cytoplasm of the cell soma and dendrites.

CDKL5 gene mutations are the cause of most cases of CDD, a progressive neurologic developmental disorder and one of the most common causes of cognitive disability in females. Males who have the genetic mutation that causes CDD are affected in devastating ways. Most of them die before birth or in early infancy. See, e.g., ninds.nih.gov/Disorders/Patient-Caregiver-Education/Fact-Sheets/Rett-Syndrome-Fact-Sheet and omim.org/entry/312750.

Currently, there is no cure for CDD, and treatment focuses on alleviating disease symptoms. In many cases seizures are poorly controlled, thus there is an urgent medical need to find novel therapeutic approaches.

SUMMARY OF THE INVENTION

Provided herein is a recombinant adeno-associated virus (rAAV) which is useful for treating CDKL5 Deficiency Disorder (CDD) in a subject in need thereof. The rAAV carries a vector genome comprising inverted terminal repeats (ITR) and a novel nucleic acid sequence encoding a functional human CDKL5 protein under the control of regulatory sequences which direct the hCDKL5 expression in a target cell.

In certain embodiments, a recombinant adeno-associated virus (rAAV) useful for treating CDD is provided. The rAAV comprises: (a) an AAV capsid; and (b) a vector genome packaged in the AAV capsid of (a), wherein the vector genome comprises inverted terminal repeats (ITR) and a nucleic acid sequence encoding a functional human CDKL5 (hCDKLK5) under control of regulatory sequences which direct the hCDKL5 expression in central nervous system cells, and wherein the hCDKL5-coding sequence is nt 699 to 3581 of SEQ ID NO: 3 (or SEQ ID NO: 22) or a sequence at least about 95% identical to nt 699 to 3581 of SEQ ID NO: 3 (or SEQ ID NO: 22). In certain embodiments, the functional hCDKL5 has an amino acid sequence of SEQ ID NO: 2. In certain embodiments, the regulatory sequences comprise Ubiquitin C (UbC) promoter. In some embodiments, the regulatory sequences comprise WPRE element.

In certain embodiments, a recombinant adeno-associated virus (rAAV) useful for treating CDD is provided in which the functional human CDKL5 (hCDKLK5) is hCDKL5 isoform 2. In certain embodiments, a recombinant adeno-associated virus (rAAV) useful for treating CDD is provided in which the functional human CDKL5 (hCDKLK5) is hCDKL5 isoform 3. In certain embodiments, a recombinant adeno-associated virus (rAAV) useful for treating CDD is provided in which the functional human CDKL5 (hCDKLK5) is hCDKL5 isoform 4.

In certain embodiments, the rAAV useful for treating CDD comprises an AAV9 capsid. In some embodiments, the rAAV useful for treating CDD comprises an AAVhu68 capsid. In other embodiments, the rAAV useful for treating CDD comprises an AAVrh91 capsid.

In certain embodiments, the CDKL5-2GS coding sequence is SEQ ID NO: 24 or a sequence at least 95% identical thereto which encodes SEQ ID NO: 6. In certain embodiments, the CDKL5-3GS coding sequence is SEQ ID NO: 25 or a sequence at least 95% identical thereto which encodes SEQ ID NO: 8. In certain embodiments, the CDKL5-4GS coding sequence is SEQ ID NO: 26 or a sequence at least 95% identical thereto which encodes SEQ ID NO: 10.

In certain embodiments, the vector genome comprises: at least two tandem repeats of dorsal root ganglion (drg)-specific miRNA target sequences in the 3' untranslated region for the hCDKL5, wherein the at least two tandem repeats comprise at least a first miRNA target sequence and at least a second miRNA target sequence which may be the same or different, and target miR183 or miR182.

In certain embodiments, a vector other than rAAV is used for delivery of an expression cassette as described herein. The vector may be a recombinant parvovirus, a recombinant lentivirus, a recombinant retrovirus, or a recombinant adenovirus; or a non-viral vector selected from naked DNA, naked RNA, an inorganic particle, a lipid particle, a polymer-based vector, or a chitosan-based formulation.

In certain embodiment, a composition comprising a stock of rAAV or other viral vector as described herein and an aqueous suspension media is provided.

In certain embodiments, a method of treating CDD is provided which comprises administrating an effective amount of the rAAV or other vector described herein to a subject in need thereof.

In certain embodiments, an rAAV production system useful for producing a vector as described herein is provided.

In certain embodiments, a vector comprising an expression cassette is provided, wherein the expression cassette comprises a nucleic acid sequence encoding a functional human CDKL5-col (hCDKL5) under control of regulatory sequences which direct the hCDKL5 expression, and wherein the hCDKL5-coding sequence is SEQ ID NO: 22 or a sequence at least about 95% identical to SEQ ID NO: 22. In certain embodiments, a vector comprising an expression cassette is provided, wherein the expression cassette comprises a nucleic acid sequence encoding a functional human CDKL5-2GS (hCDKL5-2GS) under control of regulatory sequences which direct the hCDKL5-2GS expression, and wherein the hCDKL5-2GS-coding sequence is SEQ ID NO: 24 or a sequence at least about 95% identical to SEQ ID NO: 24. In certain embodiments, a vector comprising an expression cassette is provided, wherein the expression cassette comprises a nucleic acid sequence encoding a functional human CDKL5-3GS (hCDKL5-3GS) under control of regulatory sequences which direct the hCDKL5-3GS expression, and wherein the hCDKL5-3GS-coding sequence is SEQ ID NO: 25 or a sequence at least about 95% identical to SEQ ID NO: 25. In certain embodiments, a vector comprising an expression cassette, wherein the expression cassette comprises a nucleic acid sequence encoding a functional human CDKL5-4GS (hCDKL5-4GS) under control of regulatory sequences which direct the hCDKL5-4GS expression, and wherein the hCDKL5-4GS-coding sequence is SEQ ID NO: 26 or a sequence at least about 95% identical to SEQ ID NO: 26.

In certain embodiments, the vector genome further comprises at least two tandem repeats of dorsal root ganglion (drg)-specific miRNA target sequences. In certain embodiments, the rAAV or a composition comprising the rAAV is administrable to a subject in need thereof to ameliorate symptoms of CDD and/or to delay progression of CDD.

In a further aspect, provided herein is a composition comprising a rAAV or a vector as described herein and an aqueous suspension media.

In another aspect, a method of treating a subject having CDD, or ameliorating symptoms of CDD, or delaying progression of CDD is provided. The method comprises administrating an effective amount of a rAAV or a vector as described herein to a subject in need thereof. In certain embodiments, the vector or rAAV is administrable to a patient via an intra-cisterna *magna* injection (ICM).

These and other aspects of the invention are apparent from the following detailed description of the invention.

BRIEF DESCRIPTION OF THE DRAWINGS

FIG. 2A shows CDKL5 expression by Western blotting, charting CDKL5/tubulin levels in wild-type mice with a PBS injection, KO mice with PBS injection, and treated KO mouse. FIG. 2B shows CDKL5 activity as determined using the pS222EB2 (Baltussen et al, 2018) levels in wild-type mice with a PBS injection, KO mice with PBS injection, and treated KO mice.

FIG. 5A shows exploratory activity of mice in an Open Field Arena, plotted as beam breaks/bin versus time (min). The dotted line shows wt mice, which are curious but within 10 min have explored the arena and calm down. The line with long dashes shows that Cdk15-ko spend a longer time exploring but eventually calm down. The line with dashes and dots show that after AAV-CDKL5 treatment, activity of Cdk15-ko mice is reduced, and their overall activity levels resemble wt mice. FIG. 5B shows cumulative activity data of total beam breaks taken by mice, which confirms results in FIG. 5A.

FIG. 7A shows the percentage of spontaneous alterations for the test group and the two control groups. FIG. 7B shows the distance moved (m) for the test group and the two control groups. The wt mice show a strong tendency to explore the maze arm that they have not visited recently (spontaneous alteration behavior).

FIG. 8A shows quantified expression levels of CDKL5 isoforms 1, 2, 3, and 4 in knock-out mice injected with AAV vectors ($5\times10^{10}$ GC, neonatal ICV), as compared to a wild-type mouse injected with vehicle and a knock-out mouse injected with vehicle. FIG. 8B shows CDKL5 activity as determined from quantified signal of pS222EB2 from western blot analysis of tissue from treated a wild-type mouse (injected with vehicle (PBS)), a knock-out mouse (injected with vehicle, or the AAV.CDKL5-1co). FIG. 8C shows CDKL5 activity as determined from quantified signal of pS222EB2 from western blot analysis of tissue from treated a wild-type mouse (injected with vehicle (PBS)), a knock-out mouse (injected with vehicle, or the AAV.CDKL5-isoform 1, 2, 3 or 4 (from FIG. 8A)). FIG. 8D shows quantified CDKL5 expression levels of isoform 1 in KO mice (from FIG. 8B).

FIG. 9A show body weight gain (g) over a period of 10 weeks for mice treated with AAV.CDKL5 at a dose of $5\times10^{10}$ GC or PBS. FIG. 9B show body weight gain (g) over a period of 10 weeks for mice treated with AAV.CDKL5 at a dose of $2.5\times10^{10}$ GC or PBS. FIG. 9C shows a dose-dependent results of the hindlimb clasping test for AAV.CDKL5-treated group at a dose of $5\times10^{10}$ GC compared to untreated Cdk15-ko mice. FIG. 9D shows a dose-dependent results of the hindlimb clasping test for AAV.CDKL5-treated group at a dose of a dose of $2.5\times10^{10}$ GC compared to untreated Cdk15-ko mice. FIG. 9E shows a dose-dependent results of the hindlimb clasping test for AAV.CDKL5-treated group at a dose of $1\times10^{10}$ GC compared to untreated Cdk15-ko mice. FIG. 9F shows a dose-dependent results of the hindlimb clasping test for AAV.CDKL5-treated group at a dose of $6\times10^{9}$ GC compared to untreated Cdk15-ko mice. WT mice showed no clasping, while KO mice showed pronounced clasping. After treatment, KO mice displayed a significantly reduced among of clasping. Injected WT mice were not affected.

FIG. 10A shows results in nest building (nest quality/score) for the AAV.CDKL5-treated group at a dose of $5\times10^{10}$ GC, compared to untreated Cdk15-ko mice. FIG. 10B shows results from a marble burying tasks with a trend to normalization in the AAV.CDLK5-treated group at a dose of $5\times10^{10}$ GC, compared to WT and Cdk15-ko mice. FIG. 10C shows results in nest building (nest quality/score) for the AAV.CDKL5-treated group at a dose of $2.5\times10^{10}$ GC, compared to untreated Cdk15-ko mice. FIG. 10D shows results from a marble burying tasks with a trend to normalization in the AAV.CDLK5-treated group at a dose of $2.5\times10^{10}$ GC, compared to WT and Cdk15-ko mice. FIG. 10E shows results in nest building (nest quality/score) for the AAV.CDKL5-treated group at a dose of $1\times10^{10}$ GC compared to untreated Cdk15-ko mice.

FIG. 11A shows ambulatory activity/bin vs. time (5-minute intervals to 30 min) in AAV.CDKL5-treated ko mice at a dose of $5\times10^{10}$ GC. FIG. 11B shows total activity in AAV.CDKL5-treated ko mice at a dose of $5\times10^{10}$ GC. FIG. 11C shows ambulatory activity/bin vs. time (5-minute intervals to 30 min) in AAV.CDKL5-treated ko mice at a dose of $2.5\times10^{10}$ GC. FIG. 11D shows total activity in AAV.CDKL5-treated ko mice at a dose of $2.5\times10^{10}$ GC. FIG. 11E shows ambulatory activity/bin vs. time (5-minute intervals to 30 min) in AAV.CDKL5-treated ko mice at a dose of $6\times10^{9}$ GC. FIG. 11F shows total activity in AAV.CDKL5-treated ko mice at a dose of $6\times10^{9}$ GC. Normalization of increase risk-taking was observed in the elevated zero maze and normalization of hippocampal learning deficits are seen in the Y-maze in the AAV.CDKL5-treated ko mice.

FIG. 13A show activity in elevated in KO mice treated with AAV.CDKL5-isoform 1 at a dose of $5\times10^{10}$ GC. FIG. 13B show activity in elevated in KO mice treated with AAV.CDKL5-isoform 1 at a dose of $2.5\times10^{10}$ GC. FIG. 13C show activity in Y-Maze in KO mice treated with AAV.CDKL5-isoform 1 at a dose of $5\times10^{10}$ GC. FIG. 13D show activity in Y-Maze in KO mice treated with AAV.CDKL5-isoform 1 at a dose of $2.5\times10^{10}$ GC.

FIG. 14A shows hindlimb clasping following treating of male knock-out mice with the AAV.CDKL5-isoform 1. FIG. 14B shows hindlimb clasping following treating of female knock-out mice with the AAV.CDKL5-isoform 1. Both hemizygous males and heterozygous females displayed hindlimb clasping in Cdk15-ko mice, which was significantly reduced after treatment. None of the WT groups showed clasping. FIG. 14C shows an ambulatory activity at high dose ($5\times10^{10}$ GC, neonatal ICV) with significant improvement in female heterozygous mice.

FIG. 15A shows results in ambulatory activity in an open field assessment in males (KO) mouse treated with AAV.CDKL5-isoform 1, plotted as X, Y axis beam breaks over time. FIG. 15B shows results in ambulatory activity in an open field assessment in female (ht) mouse treated with AAV.CDKL5-isoform 1, plotted as X, Y axis beam breaks over time. Full correction to wild-type is observed for multiple timepoints in both males (KO) and females (ht) mice treated with AAV.CDKL5-isoform 1.

FIG. 16A shows results in open field-ambulatory activity in an in an elevated zero maze assessment in males (KO) mouse treated with AAV.CDKL5-isoform 1, plotted as time spent(s) in an open zone. FIG. 16B shows results in open field-ambulatory activity in an in an elevated zero maze assessment in females (ht) mouse treated with AAV.CDKL5-isoform 1, plotted as time spent(s) in an open zone. Risk-prone behavior is corrected, with a size effect being more pronounced in males.

FIG. 19A shows no significant hindlimb clasp severity score changes in WT mice injected at $7.5\times10^{10}$ GC and $1\times10^{11}$ GC of AAV, as compared with control mice treated with PBS. FIG. 19B shows no significant ambulatory activity changes in WT mice injected at $7.5\times10^{10}$ GC and $1\times10^{11}$ GC of AAV, as compared with control mice treated with PBS.

DETAILED DESCRIPTION OF THE INVENTION

Figure 1A:
FIG. 1A shows an AAV vector design for an AAV CDKL5 vector genome comprising a 5' AAV inverted terminal repeat (ITR), an expression cassette comprising: a neuronal promoter, an engineered human CDKL5 DNA coding sequence, an enhancer, and poly A, and an AAV 3' ITR.

Compositions and methods for treating CDD are provided herein. An effective amount of a recombinant adeno-associated virus (rAAV) having an AAV capsid (e.g., AAVhu68 or AAV-PHP.B) and packaged therein a vector genome encoding a functional human cyclin dependent kinase like 5 (hCDKL5) is delivered to a subject in need.

I. HUMAN CDKL5

Cyclin dependent kinase like 5 (CDKL5, also known as CFAP247, serine/threonine kinase 9, STK9; Uniprot #076039) gene is natively located on the short (p) arm of the X chromosome at position 22.13. The N-terminus of the CDLK5 protein acts as a kinase, which is an enzyme that changes the activity of other proteins. Several direct substrates for CDKL5 have been identified (Baltussen et al, 2018; Munoz et al, 2018). The CDKL5 C-terminus is of unknown function.

As used herein, a functional hCDKL5 protein refers to an isoform, a natural variant, a variant, a polymorph, or a truncation of a CKDL5 protein which is not associated with CDD and/or delivery or expression of which may ameliorate symptoms or delay progression of CDD in an animal model or a patient. See, OMIM #300203, each of the webpages is incorporated herein by reference in its entirety. In certain embodiments, the functional hCDKL5 has an amino acid sequence of SEQ ID NO: 2 (isoform 1) or an amino acid sequence at least about 90% (e.g., at least about 90%, 91%, 92%, 93%, 94%, 95%, 96%, 97%, 98%, 99%, or 99.9%) identical thereto. In certain embodiment, the functional hCDKL5 protein has an amino acid sequence of SEQ ID NO: 19 (isoform 2) or an amino acid sequence at least about 90% (e.g., at least about 90%, 91%, 92%, 93%, 94%, 95%, 96%, 97%, 98%, 99%, or 99.9%) identical thereto. In certain embodiment, the functional hCDKL5 protein has an amino acid sequence of SEQ ID NO: 20 (isoform 3) or an amino acid sequence at least about 90% (e.g., at least about 90%, 91%, 92%, 93%, 94%, 95%, 96%, 97%, 98%, 99%, or 99.9%) identical thereto. In certain embodiment, the functional hCDKL5 protein has an amino acid sequence of SEQ ID NO: 21 (isoform 4) or an amino acid sequence at least about 90% (e.g., at least about 90%, 91%, 92%, 93%, 94%, 95%, 96%, 97%, 98%, 99%, or 99.9%) identical thereto. In certain embodiment, the functional hCDKL5 is a truncated hCDKL5 which comprises a methyl-CpG binding domain (MBD) having the sequence and a NCoR/SMRT Interaction Domain (NID). See, WO2018172795A1, which is incorporated herein by reference in its entirety.

In certain embodiments, a functional hCDKL5 protein ameliorates symptoms or delays progression of CDD in an animal model. One exemplified animal model is a CDKL5-ko mouse. Other suitable models are described herein.

The CDD symptoms or progression may be evaluated using various assays/methods, including but not limited to, a survival plot (e.g., Kaplan-Meier survival plot), monitoring body weights, and observing behavior changes (for example, by hind limb clasping, Open Field Assay (motor function), Elevated Zone Maze (anxiety/risk vs. exploration), Y Maze (learning and memory/hippocampus), Marble Burying Assay (inborn behavior and locomotion), Nesting (inborn social behavior), and rotarod assay (motor function, coordination)). In certain embodiment, administration or expression of a functional hCDKL5 protein in an animal model leads to amelioration of CDD symptoms or delay in CDD progression shown by an assay result which is at least about 10%, 20%, 30%, 40%, 50%, 60%, 70%, 80%, 90%, 95%, 100%, or more than 100% of that obtained in a corresponding wildtype animal. In certain embodiment, administration or expression of a functional hCDKL5 protein in a CDD animal model leads to amelioration of CDD symptoms or delay in CDD progression shown by an improved assay result which is at least about 10%, 20%, 30%, 40%, 50%, 60%, 70%, 80%, 90%, 95%, 100%, or more than 100% of that obtained from a corresponding non-treated CDD animal.

Provided herein is a nucleic acid sequence encoding a functional hCDKL5 protein, termed as hCDKL5 coding sequence or CDKL5 coding sequence. In certain embodiments, the hCDKL5-coding sequence is SEQ ID NO: 3 or a sequence at least about 95% identical to SEQ ID NO: 3. In certain embodiments, the hCDKL5 coding sequence is selected from SEQ ID NO: 2 (referred to as CDKL5 or CDKL5co or CDKL5-1 or CDKL5-1co) or NCBI Reference Sequences NM_001037343.1 (referred to as CDKL5 or CDKL5e1; SEQ ID NO: 16) encoding amino acid sequence NP_001032420.1 (SEQ ID NO: 19), NM_001323289.2 (SEQ ID NO: 17) encoding amino acid sequence NP_001310218.1 (SEQ ID NO: 20), and NM_003159.2 (SEQ ID NO: 18) encoding amino acid sequence NP_003150.1 (SEQ ID NO: 21), or a nucleic acid sequence at least about 70% (e.g., at least about 75%, 80%, 85%, 90%, 91%, 92%, 93%, 94%, 95%, 96%, 97%, 98%, 99%, or 99.9%) identical thereto. Each of the NCBI Reference Sequences is incorporated herein by reference in its entirety. In certain embodiments, the hCDKL5 coding sequence is a modified or engineered (hCDKL5 or hCDKL5co or CDKL5-1 or CDKL5-1co). The modified or engineered shares less than about 70% (e.g., about 75%, 80%, 85%, 90%, 91%, 92%, 93%, 94%, 95%, 96%, 97%, 98%, 99%, or 99.9%) identity to the NCBI Reference Sequences.

In certain embodiments, the hCDKL5 coding sequence is SEQ ID NO: 22 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto. In certain embodiments, the hCDKL5 coding sequence is SEQ ID NO: 24 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto. In certain embodiments, the hCDKL5 coding sequence is SEQ ID NO: 25 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto. In certain embodiments, the hCDKL5 coding sequence is SEQ ID NO: 26 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto.

In certain embodiments, the hCDKL5-coding sequence is an engineered sequence of SEQ ID NO: 37 or a sequence at least about 95% identical to SEQ ID NO: 37. In certain embodiments, the hCDKL5-coding sequence is an engineered sequence of SEQ ID NO: 38 or a sequence at least about 95% identical to SEQ ID NO: 38. In certain embodiments, the hCDKL5-coding sequence is an engineered sequence of SEQ ID NO: 39 or a sequence at least about 95% identical to SEQ ID NO: 39. In certain embodiments, the hCDKL5-coding sequence is an engineered sequence of SEQ ID NO: 40 or a sequence at least about 95% identical to SEQ ID NO: 40. In certain embodiments, the hCDKL5-coding sequence is an engineered sequence of SEQ ID NO: 41 or a sequence at least about 95% identical to SEQ ID NO: 41. In certain embodiments, the hCDKL5-coding sequence is an engineered sequence of SEQ ID NO: 42 or a sequence at least about 95% identical to SEQ ID NO: 42. In certain embodiments, the hCDKL5-coding sequence is an engineered sequence of SEQ ID NO: 43 or a sequence at least about 95% identical to SEQ ID NO: 43. In certain embodiments, the hCDKL5-coding sequence is an engineered sequence of SEQ ID NO: 44 or a sequence at least about 95% identical to SEQ ID NO: 44. In certain embodiments, the hCDKL5-coding sequence is an engineered sequence of SEQ ID NO: 45 or a sequence at least about 95% identical to SEQ ID NO: 45. In certain embodiments, the hCDKL5-coding sequence is an engineered sequence of SEQ ID NO: 46 or a sequence at least about 95% identical to SEQ ID NO: 46. In certain embodiments, the hCDKL5-coding sequence is an engineered sequence of SEQ ID NO: 47 or a sequence at least about 95% identical to SEQ ID NO: 47. In certain embodiments, the hCDKL5-coding sequence is an engineered sequence of SEQ ID NO: 48 or a sequence at least about 95% identical to SEQ ID NO: 48.

A "nucleic acid", as described herein, can be RNA, DNA, or a modification thereof, and can be single or double stranded, and can be selected, for example, from a group including: nucleic acid encoding a protein of interest, oligonucleotides, nucleic acid analogues, for example peptide-nucleic acid (PNA), pseudocomplementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g., of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Alignments are performed using any of a variety of publicly or commercially available Multiple Sequence Alignment Programs. Sequence alignment programs are available for amino acid sequences, e.g., the "Clustal X", "Clustal Omega" "MAP" "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Multiple sequence alignment programs are also available for nucleic acid sequences. Examples of such programs include, "Clustal W", "Clustal Omega", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

II. EXPRESSION CASSETTE

Provided herein is a nucleic acid sequence comprising the hCDKL5 coding sequence under control of regulatory sequences which direct the hCDKL5 expression in a target cell, also termed as an expression cassette. As used herein, an "expression cassette" refers to a nucleic acid molecule which comprises a coding sequence (e.g., a CDKL5 coding sequence), and regulatory sequences operably linked thereto. In certain embodiments, a vector genome contains two or more expression cassettes. The term "transgene" refers to a DNA sequence from an exogenous source which is inserted into a target cell; typically, the transgene encodes a product (e.g., CDKL5). Typically, such an expression cassette to be packed into a viral vector contains the coding sequence for the gene product described herein flanked by packaging signals of the viral genome and other expression control sequences such as those described herein. The regulatory sequences necessary are operably linked to the hCDKL5 coding sequence in a manner which permits its transcription, translation and/or expression in target cell. As used herein, "operably linked" sequences include sequences which modulate transcription, translation, and/or expression that are contiguous with the hCDKL5 coding sequence and regulatory sequences that act in trans or at a distance to control the hCDKL5 coding sequence. The expression cassette may contain regulatory sequences upstream (5' to) of the gene sequence, e.g., one or more of a promoter, an enhancer, an intron, etc., and one or more of an enhancer, or regulatory sequences downstream (3' to) a gene sequence, e.g., 3' untranslated region (3' UTR) comprising a polyadenylation site, among other elements. Such regulatory sequences typically include, e.g., one or more of a promoter, an enhancer, an intron, a Kozak sequence, a polyadenylation sequence, and a TATA signal. In certain embodiment, the promoter is a tissue-specific promoter, e.g., a CNS-specific or neuron-specific promoter. In certain embodiments, the promote is a human synapsin promoter (SEQ ID NO: 23). In certain embodiments, an additional or alternative neuron-specific promoter sequence may be selected from neuron-specific enolase (NSE) promoter (Andersen et al., (1993) Cell. Mol. Neurobiol., 13:503 15), neurofilament light chain gene promoter (Piccioli et al., (1991) Proc. Natl. Acad. Sci. USA, 88:5611 5), neuron-specific vgf gene promoter (Piccioli et al., (1995) Neuron, 15:373 84), and/or others.

In certain embodiments, the human synapsin promoter has a sequence (e.g., nt 213 to nt 678 of SEQ ID NOs: 1, 3, 5, 7, 9 or SEQ ID NO: 23, also termed as hSyn or Syn herein.

In other embodiments, the promoter is a constitutive promoter, e.g., a chicken beta actin promoter with a cytomegalovirus enhancer (CB7) promoter, a human elongation initiation factor 1 alpha promoter (EFla) promoter, a human ubiquitin C (UbC) promoter. In certain embodiments, the regulatory sequences direct hCDKL5 expression in central nervous system (CNS) cells.

In certain embodiment, the target cell may be a central nervous system cell. In certain embodiments, the target cell is one or more of an excitatory neuron, an inhibitory neuron, a glial cell, a cortex cell, a frontal cortex cell, a cerebral cortex cell, a spinal cord cell. In certain embodiments, the target cell is a peripheral nervous system (PNS) cell, for example a retina cell. Other cells other than those from nervous system may also be chosen as a target cell, such as a monocyte, a B lymphocyte, a T lymphocyte, a NK cell, a lymph node cell, a tonsil cell, a bone marrow mesenchymal cell, a stem cell, a bone marrow stem cell, a heart cell, an epithelium cell, a esophagus cell, a stomach cell, a fetal cut cell, a colon cell, a rectum cell, a liver cell, a kidney cell, a lung cell, a salivary gland cell, a thyroid cell, an adrenal cell, a breast cell, a pancreas cell, an islet of Langerhans cell, a gallbladder cell, a prostate cell, a urinary bladder cell, a skin cell, a uterus cell, a cervix cell, a testis cell, or any other cell which expresses a functional CDKL5 protein in a subject without CDD.

In certain embodiments, an additional or alternative promoter sequence may be included as part of the expression control sequences (regulatory sequences), e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter.

In addition to a promoter, a vector may contain one or more other appropriate transcription initiation sequences, transcription termination sequences, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the regulatory sequences comprise one or more expression enhancers. In one embodiment, the regulatory sequences contain two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. In certain embodiments, the intron is a chimeric intron (CI)—a hybrid intron consisting of a human beta-globin splice donor and immunoglobulin G (IgG) splice acceptor elements. Other suitable introns include those known in the art, e.g., such as are described in WO 2011/126808. Examples of suitable polyA sequences include, e.g., Rabbit globin poly A, SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the poly A sequence and downstream of the coding sequence (see, e.g., MA Zanta-Boussif, et al, Gene Therapy (2009) 16:605-619). In certain embodiments, no WPRE sequence is present.

In certain embodiments, an expression cassette refers to nucleic acid molecule with sequence of nt 213-4439 of SEQ ID NO: 1, encoding for amino acid sequence of hCDKL5 (isoform 1; SEQ ID NO: 2). In certain embodiments, an expression cassette refers to nucleic acid molecule with sequence of nt 213-4562 of SEQ ID NO: 5 encoding for amino acid sequence of hCDKL5 (isoform 2 or 2GS SEQ ID NO: 6). In certain embodiments, an expression cassette refers to nucleic acid molecule with sequence of nt 213-4388 of SEQ ID NO: 7 encoding for amino acid sequence of hCDKL5 (isoform 3 or 3GS; SEQ ID NO: 8). In certain embodiments, an expression cassette refers to nucleic acid molecule with sequence of nt 213-4511 of SEQ ID NO: 9 encoding for amino acid sequence of hCDKL5 (isoform 4 or 4GS; SEQ ID NO: 10). In certain embodiments, an expression cassette comprises an engineered nucleic acid sequence selected from SEQ ID NOs: 37, 38, 39, 40, 41, 42, 43, 44, 45, 46, 47, or 48 and encoding for an amino acid sequence of hCDKL5 (isoform 1; SEQ ID NO: 2). In certain embodiments, an expression cassette refers to nucleic acid molecule with sequence of nt 213-4555 of SEQ ID NO: 3, encoding for amino acid sequence of hCDKL5 (isoform 1; SEQ ID NO: 4) and comprising of miRNA 183 (SEQ ID NO: 11). In certain embodiments, these expression cassettes further comprise one, two, three, four or more drg-detargetting sequences (i.e., miRNA). See, e.g., PCT/US19/67872, filed Dec. 20, 2019 and now published as WO 2020/132455, III. rAAV Provided herein is a recombinant adeno-associated virus (rAAV) useful for treating CDD. The rAAV comprises (a) an AAV capsid; and (b) a vector genome packaged in the AAV capsid of (a). Suitably, the AAV capsid selected targets the cells to be treated. In certain embodiments, the capsid is from Clade F. However, in certain embodiments, another AAV capsid source may be selected. The vector genome comprises inverted terminal repeats (ITR) and a nucleic acid sequence encoding a functional human cyclin dependent kinase like 5 (hCDKL5) under control of regulatory sequences which direct the hCDKL5 expression. In certain embodiments CDKL5 may be referring to CDKL5 or hCDKL5, CDKL5-2GS or hCDKL5-2GS, CDKL5-3GS or hCDKL5-3GS, and CDKL5-4GS or hCDKL5-4GS. In certain embodiments, the hCDKL5-coding sequence is at least about 95% identical to SEQ ID NO: 22 (encoding amino acid sequence of CDKL5-1 or hCDKL5-1; SEQ ID NO: 2). In certain embodiments, the hCDKL5-coding sequence is at least about 95% identical to SEQ ID NO: 24 (encoding amino acid sequence of CDKL5-2GS or hCDKL5-2GS; SEQ ID NO: 6). In certain embodiments, the hCDKL5-coding sequence is at least about 95% identical to SEQ ID NO: 25 (encoding amino acid sequence of CDKL5-3GS or hCDKL5-3GS; SEQ ID NO: 8). In certain embodiments, the hCDKL5-coding sequence is at least about 95% identical to SEQ ID NO: 26 (encoding amino acid sequence of CDKL5-4GS or hCDKL5-4GS; SEQ ID NO: 10). In certain embodiments, the hCDKL5-coding sequence is less than 80% identical to any one of hCDKL5 transcript variants 1 to 3 (NM 001037343.1 with SEQ ID NO: 16 and encoding amino acid sequence NP_001032420.1 with SEQ ID NO: 19; NM_001323289.2 with SEQ ID NO: 17 and encoding amino acid sequence NP_001310218.1 with SEQ ID NO: 20; NM_003159.2 with SEQ ID NO: 18 encoding amino acid sequence NP_003150.1 with SEQ ID NO: 21). In certain embodiments, the hCDKL5-coding sequence is SEQ ID NOs: 37, 38, 39, 40, 41, 42, 43, 44, 45, 46 and 47 or at least about 95% identical thereto (encoding amino acid sequence of CDKL5-1 or hCDKL5-1; SEQ ID NO: 2). In certain embodiments, the functional hCDKL5 has an amino acid sequence of SEQ ID NO: 2 (CDKL5-1 or hCDKL5-1). In certain embodiments, the functional hCDKL5 has an amino acid sequence of SEQ ID NO: 6 (CDKL5-2GS or hCDKL5-2GS). In certain embodiments, the functional hCDKL5 has an amino acid sequence of SEQ ID NO: 8 (CDKL5-3GS or hCDKL5-3GS). In certain embodiments, the functional hCDKL5 has an amino acid sequence of SEQ ID NO: 10 (CDKL5-4GS or hCDKL5-4GS). In certain embodiments, the regulatory sequences direct hCDKL5 expression in central nervous system cells. In certain embodiments, the regulatory sequences comprise a human Synaspin promoter (hSyn) or a CB7 promoter. In certain embodiments, the regulatory elements comprise one or more of a Kozak sequence, a polyadenylation sequence, an intron, an enhancer, and a TATA signal. In certain embodiments, the vector genome further comprises at least two tandem repeats of dorsal root ganglion (drg)-specific miRNA target sequences, wherein the at least two tandem repeats comprise at least a first miRNA target sequence and at least a second miRNA target sequence which may be the same or different. In certain embodiments, the vector genome is nt 1 to nt 4634 of SEQ ID NO: 1, or nt 1 to nt 4750 of SEQ ID NO: 3, or nt 1 to nt 4757 of SEQ ID NO: 5, or nt 1 to nt 4583 of SEQ ID NO: 7, or nt 1 to nt 4706 of SEQ ID NO: 9 or a nucleic acid sequence at least about 70% (e.g., at least about 75%, 80%, 85%, 90%, 91%, 92%, 93%, 94%, 95%, 96%, 97%, 98%, 99%, or 99.9%) identical thereto.

In certain embodiments, a vector genome refers to nucleic acid molecule comprising SEQ ID NO: 1, encoding for amino acid sequence of hCDKL5 (isoform 1; SEQ ID NO: 2). In certain embodiments, a vector genome refers to nucleic acid molecule comprising SEQ ID NO: 5 encoding for amino acid sequence of hCDKL5 (isoform 2 or 2GS SEQ ID NO: 6). In certain embodiments, a vector genome refers to nucleic acid molecule comprising SEQ ID NO: 7 encoding for amino acid sequence of hCDKL5 (isoform 3 or 3GS; SEQ ID NO: 8). In certain embodiments, a vector genome refers to nucleic acid molecule comprising SEQ ID NO: 9 encoding for amino acid sequence of hCDKL5 (isoform 4 or 4GS; SEQ ID NO: 10). In certain embodiments, a vector genome refers to nucleic acid molecule comprising SEQ ID NO: 3, encoding for amino acid sequence of hCDKL5 (isoform 1; SEQ ID NO: 4) and comprising of miRNA 183 (SEQ ID NO: 11).

In certain embodiments, in addition to the hCDKL5 coding sequence, another non-AAV coding sequence may be included, e.g., a peptide, polypeptide, protein, functional RNA molecule (e.g., miRNA, miRNA inhibitor) or other gene product, of interest. Useful gene products may include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

As used herein, an "miRNA target sequence" is a sequence located on the DNA positive strand (5' to 3') and is at least partially complementary to a miRNA sequence, including the miRNA seed sequence. The miRNA target sequence is exogenous to the untranslated region of the encoded transgene product and is designed to be specifically targeted by miRNA in cells in which repression of transgene expression is desired. The term "miR183 cluster target sequence" refers to a target sequence that responds to one or members of the miR183 cluster (alternatively termed family), including miRs-183, -96 and -182 (as described by Dambal, S. et al. Nucleic Acids Res 43:7173-7188, 2015, which is incorporated herein by reference).

Typically, the miRNA target sequence is at least 7 nucleotides to about 28 nucleotides in length, at least 8 nucleotides to about 28 nucleotides in length, 7 nucleotides to 28 nucleotides, 8 nucleotides to 18 nucleotides, 12 nucleotides to 28 nucleotides in length, about 20 to about 26 nucleotides, about 22 nucleotides, about 24 nucleotides, or about 26 nucleotides, and contains at least one consecutive region (e.g., 7 or 8 nucleotides) which is complementary to the miRNA seed sequence. In certain embodiments, the target sequence comprises a sequence with exact complementarity (100%) or partial complementarity to the miRNA seed sequence with some mismatches. In certain embodiments, the target sequence comprises at least 7 to 8 nucleotides which are 100% complementary to the miRNA seed sequence. In certain embodiments, the target sequence consists of a sequence which is 100% complementary to the miRNA seed sequence. In certain embodiments, the target sequence contains multiple copies (e.g., two or three copies) of the sequence which is 100% complementary to the seed sequence. In certain embodiments, the region of 100% complementarity comprises at least 30% of the length of the target sequence. In certain embodiments, the remainder of the target sequence has at least about 80% to about 99% complementarity to the miRNA. In certain embodiments, in an expression cassette containing a DNA positive strand, the miRNA target sequence is the reverse complement of the miRNA.

As used herein, an "miRNA target sequence" is a sequence located on the DNA positive strand (5' to 3') and is at least partially complementary to a miRNA sequence, including the miRNA seed sequence. The miRNA target sequence is exogenous to the untranslated region of the encoded transgene product and is designed to be specifically targeted by miRNA in cells in which repression of transgene expression is desired. The term "miR183 cluster target sequence" refers to a target sequence that responds to one or members of the miR183 cluster (alternatively termed family), including miRs-183,-96 and 182 (as described by Dambal, S. et al. Nucleic Acids Res 43:7173-7188, 2015, which is incorporated herein by reference). Without wishing to be bound by theory, the messenger RNA (mRNA) for the transgene (encoding the gene product) is present in a cell type to which the expression cassette containing the miRNA is delivered, such that specific binding of the miRNA to the 3' UTR miRNA target sequences results in mRNA silencing and cleavage, thereby reducing or eliminating transgene expression only in the cells that express the miRNA.

Typically, the miRNA target sequence is at least 7 nucleotides to about 28 nucleotides in length, at least 8 nucleotides to about 28 nucleotides in length, 7 nucleotides to 28 nucleotides, 8 nucleotides to 18 nucleotides, 12 nucleotides to 28 nucleotides in length, about 20 to about 26 nucleotides, about 22 nucleotides, about 24 nucleotides, or about 26 nucleotides, and contains at least one consecutive region (e.g., 7 or 8 nucleotides) which is complementary to the miRNA seed sequence. In certain embodiments, the target sequence comprises a sequence with exact complementarity (100%) or partial complementarity to the miRNA seed sequence with some mismatches. In certain embodiments, the target sequence comprises at least 7 to 8 nucleotides which are 100% complementary to the miRNA seed sequence. In certain embodiments, the target sequence consists of a sequence which is 100% complementary to the miRNA seed sequence. In certain embodiments, the target sequence contains multiple copies (e.g., two or three copies) of the sequence which is 100% complementary to the seed sequence. In certain embodiments, the region of 100% complementarity comprises at least 30% of the length of the target sequence. In certain embodiments, the remainder of the target sequence has at least about 80% to about 99% complementarity to the miRNA. In certain embodiments, in an expression cassette containing a DNA positive strand, the miRNA target sequence is the reverse complement of the miRNA.

In certain embodiments, the miRNA target sequence for the at least first and/or at least second miRNA target sequence for the expression cassette mRNA or DNA positive strand is selected from (i) AGTGAATTCTACCAGTGCCATA (miR183, SEQ ID NO: 11); (ii) AGCAAAAATGTGCTAGTGCCAAA (miR-96, SEQ ID NO: 12), (iii) AGTGTGAGTTCTACCATTGCCAAA (miR182, SEQ ID NO: 13). In other embodiments, AGGGATTCCTGGGAAAACTGGAC (SEQ ID NO: 14) is selected.

In certain embodiments, the vector genome or expression cassette contains at least one miRNA target sequence that is a miR-183 target sequence. In certain embodiments, the vector genome or expression cassette contains an miR-183 target sequence that includes AGTGAATTCTACCAGTGCCATA (SEQ ID NO:11), where the sequence complementary to the miR-183 seed sequence is GTGCCAT. In certain embodiments, the vector genome or expression cassette contains more than one copy (e.g., two or three copies) of a sequence that is 100% complementary to the miR-183 seed sequence. In certain embodiments, a miR-183 target sequence is about 7 nucleotides to about 28 nucleotides in length and includes at least one region that is at least 100% complementary to the miR-183 seed sequence. In certain embodiments, a miR-183 target sequence contains a sequence with partial complementarity to SEQ ID NO: 11 and, thus, when aligned to SEQ ID NO: 11, there are one or more mismatches. In certain embodiments, a miR-183 target sequence comprises a sequence having at least 1, 2, 3, 4, 5, 6, 7, 8, 9, or 10 mismatches when aligned to SEQ ID NO: 11, where the mismatches may be non-contiguous. In certain embodiments, a miR-183 target sequence includes a region of 100% complementarity which also comprises at least 30% of the length of the miR-183 target sequence. In certain embodiments, the region of 100% complementarity includes a sequence with 100% complementarity to the miR-183 seed sequence. In certain embodiments, the remainder of a miR-183 target sequence has at least about 80% to about 99% complementarity to miR-183. In certain embodiments, the expression cassette or vector genome includes a miR-183 target sequence that comprises a truncated SEQ ID NO: 11, i.e., a sequence that lacks at least 1, 2, 3, 4, 5, 6, 7, 8, 9, or 10 nucleotides at either or both the 5' or 3' ends of SEQ ID NO: 1. In certain embodiments, the expression cassette or vector genome comprises a transgene and one miR-183 target sequence. In yet other embodiments, the expression cassette or vector genome comprises at least two, three or four miR-183 target sequences. (i) AGTGAATTCTACCAGTGCCATA (miR183, SEQ ID NO: 11); (ii) AGCAAAAATGTGCTAGTGCCAAA (miR-96, SEQ ID NO: 12).

In certain embodiments, the vector genome or expression cassette contains at least one miRNA target sequence that is a miR-182 target sequence. In certain embodiments, the vector genome or expression cassette contains an miR-182 target sequence that includes AGTGTGAGTTCTACCATTGCCAAA (SEQ ID NO: 13). In certain embodiments, the vector genome or expression cassette contains more than one copy (e.g., two or three copies) of a sequence that is 100% complementary to the miR-182 seed sequence. In certain embodiments, a miR-182 target sequence is about 7 nucleotides to about 28 nucleotides in length and includes at least one region that is at least 100% complementary to the miR-182 seed sequence. In certain embodiments, a miR-182 target sequence contains a sequence with partial complementarity to SEQ ID NO: 13 and, thus, when aligned to SEQ ID NO: 13, there are one or more mismatches. In certain embodiments, a miR-183 target sequence comprises a sequence having at least 1, 2, 3, 4, 5, 6, 7, 8, 9, or 10 mismatches when aligned to SEQ ID NO: 13, where the mismatches may be non-contiguous. In certain embodiments, a miR-182 target sequence includes a region of 100% complementarity which also comprises at least 30% of the length of the miR-182 target sequence. In certain embodiments, the region of 100% complementarity includes a sequence with 100% complementarity to the miR-182 seed sequence. In certain embodiments, the remainder of a miR-182 target sequence has at least about 80% to about 99% complementarity to miR-182. In certain embodiments, the expression cassette or vector genome includes a miR-182 target sequence that comprises a truncated SEQ ID NO: 13, i.e., a sequence that lacks at least 1, 2, 3, 4, 5, 6, 7, 8, 9, or 10 nucleotides at either or both the 5' or 3' ends of SEQ ID NO: 13. In certain embodiments, the expression cassette or vector genome comprises a transgene and one miR-182 target sequence. In yet other embodiments, the expression cassette or vector genome comprises at least two, three or four miR-182 target sequences.

The term "tandem repeats" is used herein to refer to the presence of two or more consecutive miRNA target sequences. These miRNA target sequences may be continuous, i.e., located directly after one another such that the 3' end of one is directly upstream of the 5' end of the next with no intervening sequences, or vice versa. In another embodiment, two or more of the miRNA target sequences are separated by a short spacer sequence.

As used herein, as "spacer" is any selected nucleic acid sequence, e.g., of 1, 2, 3, 4, 5, 6, 7, 8, 9 or 10 nucleotides in length which is located between two or more consecutive miRNA target sequences. In certain embodiments, the spacer is 1 to 8 nucleotides in length, 2 to 7 nucleotides in length, 3 to 6 nucleotides in length, four nucleotides in length, 4 to 9 nucleotides, 3 to 7 nucleotides, or values which are longer. Suitably, a spacer is a non-coding sequence. In certain embodiments, the spacer may be of four (4) nucleotides. In certain embodiments, the spacer is GGAT. In certain embodiments, the spacer is six (6) nucleotides. In certain embodiments, the spacer is CACGTG or GCATGC.

In certain embodiments, the tandem repeats contain two, three, four or more of the same miRNA target sequence. In certain embodiments, the tandem repeats contain at least two different miRNA target sequences, at least three different miRNA target sequences, or at least four different miRNA target sequences, etc. In certain embodiments, the tandem repeats may contain two or three of the same miRNA target sequence and a fourth miRNA target sequence which is different.

In certain embodiments, there may be at least two different sets of tandem repeats in the expression cassette. For example, a 3' UTR may contain a tandem repeat immediately downstream of the transgene, UTR sequences, and two or more tandem repeats closer to the 3' end of the UTR. In another example, the 5' UTR may contain one, two or more miRNA target sequences. In another example the 3' may contain tandem repeats and the 5' UTR may contain at least one miRNA target sequence.

In certain embodiments, the expression cassette contains two, three, four or more tandem repeats which start within about 0 to 20 nucleotides of the stop codon for the transgene. In other embodiments, the expression cassette contains the miRNA tandem repeats at least 100 to about 4000 nucleotides from the stop codon for the transgene.

In certain embodiments, the spacers between the miRNA target sequences are the same. As used herein, CDKL5 or hCDKL5 refers to isoform 1, unless otherwise specified. Isoforms 2-4 may be specified as: CDKL5-2GS or hCDKL5-2GS, CDKL5-3GS or hCDKL5-3GS, and CDKL5-4GS or hCDKL5-4GS. Expression cassettes and vector genomes with these isoforms may be constructed as described for isoform 1.

See, PCT/US19/67872, filed Dec. 20, 2019, now WO 2020/132455, which is incorporated by reference herein and U.S. Provisional Patent Applications No. 63/023,593, filed May 12, 2020; U.S. Provisional Patent Applications No. 63/038,488, filed Jun. 12, 2020; U.S. Provisional Patent Applications No. 63/043,562, filed Jun. 24, 2020; and U.S. Provisional Patent Applications No. 63/079,299, filed Sep. 16, 2020, U.S. Provisional Patent Application No. 63/152,042, filed Feb. 22, 2011, which are hereby incorporated by reference.

In certain embodiments, the Clade F AAV capsid is selected from an AAVhu68 capsid, an AAV9 capsid, an AAVhu31 capsid, an AAVhu32 capsid, or an engineered variant of one of these capsids (e.g., AAV-PHP.B). Nucleic acid sequences encoding AAVhu68 capsid protein, are utilized in the examples below for production of an AAV.hCDKL5 recombinant AAV (rAAV) carrying the vector genome. Additional details relating to AAVhu68 or AAV-PHP.B are provided in WO 2018/160582, and US 2015/0079038, each of which is incorporated herein by reference in its entirety. The Clade F vectors described herein are well suited for delivery of the vector genome comprising the hCDKL5 coding sequence to cells within the central nervous system, including brain, hippocampus, motor cortex, cerebellum, and motor neurons. These vectors may be used for targeting other cells within the central nervous system (CNS) and certain other tissues and cells outside the CNS. In certain embodiments, the AAV capsid for the compositions and methods described herein is chosen based on the target cell. In certain embodiment, the AAV capsid transduces a CNS cell and/or a PNS cell. In certain embodiments, the AAV capsid is selected from a cy02 capsid, a rh43 capsid, an AAV8 capsid, a rh01 capsid, an AAV9 capsid, an rh8 capsid, a rh10 capsid, a bb01 capsid, a hu37 capsid, a rh02 capsid, a rh20 capsid, a rh39 capsid, a rh64 capsid, an AAV6 capsid, an AAV1 capsid, a hu44 capsid, a hu48 capsid, a cy05 capsid a hull capsid, a hu32 capsid, a pi2 capsid, or a variation thereof. In certain embodiments, the AAV capsid is a Clade F capsid, such as AAV9 capsid, AAVhu68 capsid, hu31 capsid, hu32 capsid, or a variation thereof. See, e.g., WO 2005/033321 published Apr. 14, 2015, WO 2018/160582, and US 2015/0079038, each of which is incorporated herein by reference in its entirety. In certain embodiments, the AAV capsid is a non-clade F capsid, for example a Clade A, B, C, D, or E capsid. In certain embodiment, the non-Clade F capsid is an AAV1 or a variation thereof. In certain embodiment, the AAV capsid transduces a target cell other than the nervous system cells. In certain embodiments, the AAV capsid is a Clade A capsid (e.g., AAV1, AAV6, AAVrh91), a Clade B capsid (e.g., AAV 2), a Clade C capsid (e.g., hu53), a Clade D capsid (e.g., AAV7), or a Clade E capsid (e.g., rh10). In certain embodiments, the AAV capsid is a Clade A capsid, such as AAVrh91 capsid (nucleic acid sequence of SEQ ID NOs: 33 and 35). See, PCT/US20/030266, filed Apr. 29, 2020, now published WO2020/223231, which is incorporated by reference herein and US Provisional U.S. Patent Application No. 63/065,616, filed Apr. 29, 2019, which is hereby incorporated by reference. See also, U.S. Provisional Application No. 63/065,616, filed Aug. 14, 2020, and U.S. Provisional Patent Application No. 63/109,734, filed Nov. 4, 2020, which are incorporated herein by reference. Still, other AAV capsid may be chosen.

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, Molecular Evolution and Phylogenetics (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, J Virol, 2004 June; 78(10): 6381-6388, which identifies Clades A, B, C, D, E and F, and provides nucleic acid sequences of novel AAV, GenBank Accession Numbers AY530553 to AY530629. See, also, WO 2005/033321.

A rAAV is composed of an AAV capsid and a vector genome. An AAV capsid is an assembly of a heterogeneous population of vp1, a heterogeneous population of vp2, and a heterogeneous population of vp3 proteins. As used herein when used to refer to vp capsid proteins, the term "heterogeneous" or any grammatical variation thereof, refers to a population consisting of elements that are not the same, for example, having vp1, vp2 or vp3 monomers (proteins) with different modified amino acid sequences.

As used herein when used to refer to vp capsid proteins, the term "heterogeneous" or any grammatical variation thereof, refers to a population consisting of elements that are not the same, for example, having vp1, vp2 or vp3 monomers (proteins) with different modified amino acid sequences. The term "heterogeneous population" as used in connection with vp1, vp2 and vp3 proteins (alternatively termed isoforms), refers to differences in the amino acid sequence of the vp1, vp2 and vp3 proteins within a capsid. The AAV capsid contains subpopulations within the vp1 proteins, within the vp2 proteins and within the vp3 proteins which have modifications from the predicted amino acid residues. These subpopulations include, at a minimum, certain deamidated asparagine (N or Asn) residues. For example, certain subpopulations comprise at least one, two, three or four highly deamidated asparagines (N) positions in asparagine-glycine pairs and optionally further comprising other deamidated amino acids, wherein the deamidation results in an amino acid change and other optional modifications.

In certain embodiments, AAV capsids are provided which have a heterogeneous population of AAV capsid isoforms (i.e., VP1, VP2, VP3) which contain multiple highly deamidated "NG" positions. In certain embodiments, the highly deamidated positions are in the locations identified below, with reference to the predicted full-length VP1 amino acid sequence. In other embodiments, the capsid gene is modified such that the referenced "NG" is ablated and a mutant "NG" is engineered into another position.

As used herein, the terms "target cell" and "target tissue" can refer to any cell or tissue which is intended to be transduced by the subject AAV vector. The term may refer to any one or more of muscle, liver, lung, airway epithelium, central nervous system, neurons, eye (ocular cells), or heart.

As used herein, the term "vector genome" refers to a nucleic acid molecule which is packaged in a viral capsid, for example, an AAV capsid, and is capable of being delivered to a host cell or a cell in a patient. In certain embodiments, the vector genome is an expression cassette having inverted terminal repeat (ITR) sequences necessary for packaging the vector genome into the AAV capsid at the extreme 5' and 3' end and containing therebetween a CDLK5 gene as described herein operably linked to sequences which direct expression thereof. In certain embodiments, a vector genome may comprise at a minimum from 5' to 3', an AAV 5' ITR, coding sequence(s), and an AAV 3' ITR. In certain embodiments, the ITRs are from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. The vector genome is sometimes referred to herein as the "minigene".

As used herein, the term "host cell" may refer to the packaging cell line in which the rAAV is produced from the plasmid. In the alternative, the term "host cell" may refer to the target cell in which expression of the transgene is desired.

As indicated above, a rAAV is provided which has an AAV capsid which targets the desired cells and a vector genome which comprises, at a minimum, AAV ITRs required to package the vector genome into the capsid, a hCDKL5 coding sequence and regulatory sequences which direct expression therefor. In certain embodiments, the vector genome is a single-stranded AAV vector genome. In certain embodiments, a rAAV vector may be utilized in the invention which contains self-complementary (sc) AAV vector genome.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are about 145 base pairs (bp) in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences are from AAV2. A shortened version of the 5' ITR, termed AITR, has been described in which the D-sequence and terminal resolution site (trs) are deleted. In other embodiments, the full-length AAV 5' and 3' ITRs are used. In certain embodiments, the vector genome includes a shortened AAV2 ITR of 130 base pairs, wherein the external A elements is deleted. The shortened ITR is reverted back to the wild-type length of 145 base pairs during vector DNA amplification using the internal A element as a template. However, ITRs from other AAV sources may be selected. Where the source of the ITRs is from AAV2 and the AAV capsid is from another AAV source, the resulting vector may be termed pseudotyped. However, other configurations of these elements may be suitable.

In certain embodiments, vector genomes are constructed which comprise a 5' AAV ITR—promoter—optional enhancer—optional intron—hCDKL5 coding sequence—polyA—3' ITR. In certain embodiments, vector genomes are constructed which comprise a 5' AAV ITR—promoter—optional enhancer—optional intron—hCDKL5 coding sequence—optionally repeating miR detargetting sequences-polyA-3' ITR. In certain embodiments, vector genomes are constructed which comprise a 5' AAV ITR—promoter—optional intron—hCDKL5 coding sequence—optional enhancer—polyA—3' ITR. In certain embodiments, vector genomes are constructed which comprise a 5' AAV ITR—promoter—optional enhancer—optional intron—hCDKL5 coding sequence—optional enhancer—optionally repeating miR detargetting sequences—polyA—3' ITR. In certain embodiments, the ITRs are from AAV2. In certain embodiments, more than one promoter is present. In certain embodiments, the enhancer is present in the vector genome. In certain embodiments, more than one enhancer is present. In certain embodiments, an intron is present in the vector genome. In certain embodiments, the enhancer and intron are present. In certain embodiments, the polyA is an SV40 poly A (i.e., a polyadenylation (PolyA) signal derived from Simian Virus 40 (SV40) late genes). In certain embodiments, the polyA is a rabbit beta-globin (RBG) poly A. In certain embodiments, the vector genome comprises, at a minimum: a 5' AAV ITR—hSyn promoter—hCDKL5 coding sequence—poly A—3' ITR. In certain embodiments, the vector genome comprises, at a minimum, a 5' AAV ITR-CB7 promoter—hCDKL5 coding sequence—RBG poly A—3' ITR. In certain embodiments, the drg detargetting sequences are one, two, three, four or more miR183 sequences as described herein and are included in the expression cassette. In certain embodiments the hCDKL5 coding sequence is for CDKL5. In certain embodiments the hCDKL5 coding sequence is for CDKL5-2GS. In certain embodiments the hCDKL5 coding sequence is for CDKL5-3GS. In certain embodiments the hCDKL5 coding sequence is for CDKL5-4GS. Optionally, one or more of these vector genomes includes a WPRE element.

As used herein, a vector genome or a rAAV comprising the vector genome is illustrated herein as AAV.promoter (optional). Kozak (optional).intron (optional). CDKL5 coding sequence (e.g., hCDKL5, hCDKL5co, CDKL5, CDKL5co). miRNA (optional).polyA (optional).Stuffer (optional). In certain embodiments, a rAAV is illustrated herein as AAV capsid.promoter (optional). Kozak (optional).intron (optional). CDKL5 coding sequence. miRNA (optional) .polyA (optionl). Stuffer (optional). Optionally, one or more of these vector genomes includes a WPRE element.

In certain embodiments the vector genome comprises, at a minimum a 5' AAV ITR-Ubiquitin C promoter-hCDKL5 coding sequence—one, two, three, four or more miR183 sequences—RBG poly A—3' ITR. In certain embodiments the vector genome comprises, at a minimum a 5' AAV ITR—Chicken-beta actin hybrid promoter—hCDKL5 coding sequence—one, two, three, four or more miR183 sequences—RBG poly A-3' ITR. Optionally, one or more of these vector genomes includes a WPRE element.

Additionally, provided herein, is an rAAV production system useful for producing a rAAV as described herein. The production system comprises a cell culture comprising (a) a nucleic acid sequence encoding an AAV capsid protein; (b) the vector genome; and (c) sufficient AAV rep functions and helper functions to permit packaging of the vector genome into the AAV capsid. In certain embodiments, the vector genome is SEQ ID NOs: 1, 3, 5, 7, 9, 29 or 31. In certain embodiments, the cell culture is a human embryonic kidney 293 cell culture. In certain embodiments, the AAV rep is from a different AAV. In certain embodiments, wherein the AAV rep is from AAV2. In certain embodiments, the AAV rep coding sequence and cap genes are on the same nucleic acid molecule, wherein there is optionally a spacer between the rep sequence and cap gene. In certain embodiments, the spacer is atgacttaaaccaggt (SEQ ID NO: 15).

For use in producing an AAV viral vector (e.g., a recombinant (r) AAV), the vector genomes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, Adeno-associated virus as a gene therapy vector: Vector development, production and clinical applications, Adv. Biochem. Engin/Biotechnol. 99:119-145; Buning et al., 2008, Recent developments in adeno-associated virus vector technology, J. Gene Med. 10:717-733; and the references cited below, each of which is incorporated herein by reference in its entirety. As used herein, a gene therapy vector refers to a rAAV as described herein, which is suitable for use in treating a patient. For packaging a gene into virions, the ITRs are the only AAV components required in cis in the same construct as the nucleic acid molecule containing the gene. The cap and rep genes can be supplied in trans.

In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAVhu68 or AAVrh91 is provided. Such a cell culture contains a nucleic acid which expresses the AAVhu68 capsid protein in the host cell; a nucleic acid molecule suitable for packaging into the AAVhu68 capsid, e.g., a vector genome which contains AAV ITRs and a non-AAV nucleic acid sequence encoding a gene operably linked to regulatory sequences which direct expression of the gene in a host cell; and sufficient AAV rep functions and adenovirus helper functions to permit packaging of the vector genome into the recombinant AAVhu68, or AAVrh91 capsid. In one embodiment, the cell culture is composed of mammalian cells (e.g., human embryonic kidney 293 cells, among others) or insect cells (e.g., *Spodoptera frugiperda* (Sf9) cells). In certain embodiments, baculovirus provides the helper functions necessary for packaging the vector genome into the recombinant AAVhu68, or AAVrh91 capsid.

Optionally the rep functions are provided by an AAV other than hu68 or AAV-PHP.B. In certain embodiments, at least parts of the rep functions are from AAVhu68, or AAVrh91. In another embodiment, the rep protein is a heterologous rep protein other than AAVhu68rep, for example but not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. Any of these AAVhu68 or mutant AAV capsid sequences may be under the control of exogenous regulatory control sequences which direct expression thereof in a host cell.

In one embodiment, cells are manufactured in a suitable cell culture (e.g., HEK 293 or Sf9) or suspension. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV vector genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, Adenovirus-adeno-associated virus hybrid for large-scale recombinant adeno-associated virus production, Human Gene Therapy 20:922-929, the contents of each of which is incorporated herein by reference in its entirety. Methods of making and using these and other AAV production systems are also described in the following US patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in WO 2017/160360filed Dec. 9, 2016 and its priority documents, U.S. Patent Application Nos. 62/322,071, filed Apr. 13, 2016 and 62/226,357, filed Dec. 11, 2015 and entitled "Scalable Purification Method for AAV9", which is incorporated by reference herein. In certain embodiments, the purification of vector drug product (e.g., AAVrh91) include those described in more detail in WO2017/100674, filed Dec. 9, 2016, and its priority documents, U.S. Provisional Patent Application Nos. 62/266,351. Filed Dec. 9, 2015, and 62/322,083, filed Apr. 13, 2016 and titled "Scalable Purification Method for AAV1", which is incorporated herein by reference.

To calculate empty and full particle content, VP3 band volumes for a selected sample (e.g., in examples herein an iodixanol gradient-purified preparation where #of genome copies (GC)=#of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e., SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAVhu68 (or AAVrh91) particles having packaged genomic sequences from genome-deficient AAVhu68 (or AAVrh91) intermediates involves subjecting a suspension comprising recombinant AAVhu68 (or rh91) viral particles and AAVhu68 (or AAVrh91) capsid intermediates to fast performance liquid chromatography, wherein the AAVhu68 (or AAVrh91) viral particles and AAVhu68 intermediates are bound to a strong anion exchange resin equilibrated at a pH of about 10.2 (or about 9.8 for AAVrh91), and subjected to a salt gradient while monitoring eluate for ultraviolet absorbance at about 260 nanometers (nm) and about 280 nm. Although less optimal for rAAVhu68 and AAVrh91, the pH may be in the range of about 10 to 10.4. In this method, the AAV full capsids are collected from a fraction which is eluted when the ratio of A260/A280 reaches an inflection point. In one example, for the Affinity Chromatography step, the diafiltered product may be applied to an affinity resin (Life Technologies) that efficiently captures the AAVhu68 or AAVrh91 serotype. Under these ionic conditions, a significant percentage of residual cellular DNA and proteins flow through the column, while AAV particles are efficiently captured.

The rAAV.hCDKL5 is suspended in a suitable physiologically compatible composition (e.g., a buffered saline). This composition may be frozen for storage, later thawed and optionally diluted with a suitable diluent. Alternatively, the vector may be prepared as a composition which is suitable for delivery to a patient without proceeding through the freezing and thawing steps.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the gene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a gene to a host cell and protects these packaged genomic sequences from degradation (digestion) during nuclease incubation steps designed to remove contaminating nucleic acids which may be present from the production process.

IV. OTHER VECTOR

Provided herein is a vector comprising an expression cassette as described herein. In certain embodiments, the expression cassette comprises a nucleic acid sequence encoding a functional human cyclin dependent kinase like 5 (hCDKL5) under control of regulatory sequences which direct the hCDKL5 expression. In certain embodiments, the hCDKL5-coding sequence encodes a hCDKL5 protein comprising an amino acid sequence of [MKIPNIGNVMNK- FEILGVVGEGAYGVVLKCRHKETHEIVAIKKFKDSE- ENEEVKET TLRELKMLRTLKQENIVELKEAFRRRGKLYL- VFEYVEKNMLELLEEMPNGVPPEKV KSYIYQ- LIKAIHWCHKNDIVHRDIKPENLLISHNDVLKLCDFG- FARNLSEGNNANYT EYVATRWYRSPELLLGAPYGKSVDMWSVGCIL- GELSDGQPLFPGESEIDQLFTIQKV LGPLPSE- QMKLFYSNPRFHGLRFPAVNHPQSLERRYLGILNS- VLLDLMKNLLKLDPA DRYLTEQCLNHPTFQTQRLLDRSPSR- SAKRKPYHVESSTLSNRNQAGKSTALQSHHR SNSKDIQNLSVGLPRADEGLPANESFLNGNLAGASL- SPLHTKTYQASSQPGSTSKDL TNNNIPHLLSPKEAK- SKTEFDFNIDPKPSEGPGTKYLKSNSR- SQQNRHSFMESSQSKA GTLQPNEKQSRHSYIDTIPQSSRSPSYRTKAK- SHGALSDSKSVSNLSEARAQIAEPSTS RYFPSSCLD- LNSPTSPTPTRHSDTRTLLSPS- GRNNRNEGTLDSRRTTTRHSKTMEELK LPEHMDSSHSHSLSAPHESFSYGLGYT- SPFSSQQRPHRHSMYVTRDKVRAKGLDGSL SIGQG- MAARANSLQLLSPQPGEQLPPEMTVARSSVKETS- REGTSSFHTRQKSEGGVY HDPHSDDGTAPKENRHLYND- PVPRRVGSFYRVPSPRPDNSFHENNVSTRVSSLPSES SSGTNHSKRQPAFDPWKSPENISHSE- QLKEKEKQGFFRSMKKKKKKSQTVPNSDSPD LLTLQKSIHSASTPSSRPKEWRPEKIS- DLQTQSQPLKSLRKLLHLSSASNHPASSDPRF QPL- TAQQTKNSFSEIRIHPLSQASGGSSNIRQEPAPKGR- PALQLPGQMDPGWHVSSVT RSATEGPSYSEQLGAKSGPNGHPYNRTNRSRM- PNLNDLKETAL] (SEQ ID NO: 2), wherein the hCDKL5-coding sequence is a nucleic acid sequence of SEQ ID NO: 22 or which has at least about 95% identical to SEQ ID NO: 22 and encodes the protein of SEQ ID NO: 2. In certain embodiments, the hCDKL5-coding sequence encodes a hCDKL5-2GS protein comprising an amino acid sequence of [MKIPNIGNVMNKFEILGVVGEGAYGVVLKCRH- KETHEIVAIKKFKDSEENEEVKET TLRELKMLRTLKQENIVELKEAFRRRGKLYL- VFEYVEKNMLELLEEMPNGVPPEKV KSYIYQ- LIKAIHWCHKNDIVHRDIKPENLLISHNDVLKLCDFG- FARNLSEGNNANYT EYVATRWYRSPELLLGAPYGKSVDMWSVGCIL- GELSDGQPLFPGESEIDQLFTIQKV LGPLPSE- QMKLFYSNPRFHGLRFPAVNHPQSLERRYLGILNS- VLLDLMKNLLKLDPA DRYLTEQCLNHPTFQTQRLLDRSPSR- SAKRKPYHVESSTLSNRNQAGKSTALQSHHR SNSKDIQNLSVGLPRADEGLPANESFLNGNLAGASL- SPLHTKTYQASSQPGSTSKDL TNNNIPHLLSPKEAK- SKTEFDFNIDPKPSEGPGTKYLKSNSR- SQQNRHSFMESSQSKA GTLQPNEKQSRHSYIDTIPQSSRSPSYRTKAK- SHGALSDSKSVSNLSEARAQIAEPSTS RYFPSSCLD- LNSPTSPTPTRHSDTRTLLSPS- GRNNRNEGTLDSRRTTTRHSKTMEELK LPEHMDSSHSHSLSAPHESFSYGLGYT- SPFSSQQRPHRHSMYVTRDKVRAKGLDGSL SIGQG- MAARANSLQLLSPQPGEQLPPEMTVARSSVKETS- REGTSSFHTRQKSEGGVY HDPHSDDGTAPKENRHLYND- PVPRRVGSFYRVPSPRPDNSFHENNVSTRVSSLPSES SSGTNHSKRQPAFDPWKSPENISHSE- QLKEKEKQGFFRSMKKKKKKSQTTDSTNGE NPSIK- KSLFPLFNSKNHLKHSSSLKKLPVVTPPMVPNSD- SPDLLTLQKSIHSASTPSSR PKEWRPEKISDLQTQSQPLKSLRKLLHLSSASNH- PASSDPRFQPLTAQQTKNSFSEIRI HPLSQASGGSSNIRQEPAPKGR- PALQLPGQMDPGWHVSSVTRSATEGPSYSEQLGAK SGPNGHPYNRTNRSRMPNLNDLKETAL] (SEQ ID NO: 6), wherein the hCDKL5-coding sequence comprises a nucleic acid sequence of SEQ ID NO: 24 or a sequence which is at least about 95% identical to SEQ ID NO: 24 and encodes the protein of SEQ ID NO: 6. In certain embodiments, the hCDKL5-coding sequence encodes a hCDKL5-3GS protein comprising an amino acid sequence of [MKIP- NIGNVMNKFEILGVVGEGAYGVVLKCR HKETHEIVAIKKFKDSEENEEVKET TLRELKMLRTLKQENIVELKEAFRRRGKLYL- VFEYVEKNMLELLEEMPNGVPPEKV KSYIYQ- LIKAIHWCHKNDIVHRDIKPENLLISHNDVLKLCDFG- FARNLSEGNNANYT EYVATRWYRSPELLLGAPYGKSVDMWSVGCIL- GELSDGQPLFPGESEIDQLFTIQKV LGPLPSE- QMKLFYSNPRFHGLRFPAVNHPQSLERRYLGILNS- VLLDLMKNLLKLDPA DRYLTEQCLNHPTFQTQRLLDRSPSRNQAGK- STALQSHHRSNSKDIQNLSVGLPRAD EGL- PANESFLNGNLAGASLSPLHTKTYQASSQPGST- SKDLTNNNIPHLLSPKEAKSKT EFDFNIDPKPSEGPGTKYLKSNSR- SQQNRHSFMESSQSKAGTLQPNEKQSRHSYIDTI PQSSRSPSYRTKAKSHGALSDSKSVSNLSEARAQIAE- PSTSRYFPSSCLDLNSPTSPTP TRHSDTRTLLSPS- GRNNRNEGTLDSRRTTTRHSKT- MEELKLPEHMDSSHSHSLSAPH ESFSYGLGYT- SPFSSQQRPHRHSMYVTRDKVRAKGLDGSLSIGQG- MAARANSLQLL SPQPGEQLPPEMTVARSSVKETS- REGTSSFHTRQKSEGGVYHDPHSDDGTAPKENRH LYNDPVPRRVGSFYRVPSPRPDNSFH ENNVSTRVSSLPSESSSGTNHSKRQPAFDPW KSPEN- ISHSEQLKEKEKQGFFRSMKKKKKKSQTVPNSD- SPDLLTLQKSIHSASTPSSR PKEWRPEKIS- DLQTQSQPLKSLRKLLHLSSA SNHPASSDPRFQPLTAQQTKNSFSEIRI HPLSQASGGSSNIRQEPAPKGR- PALQLPGQMDPGWHVSSVTRSATEGPSYSEQLGAK SGPNGHPYNRTNRSRMPNLNDLKETAL] (SEQ ID NO: 8), wherein the hCDKL5-coding sequence comprises a nucleic acid sequence of SEQ ID NO: 25 or which is at least about 95% identical to SEQ ID NO: 25 and encodes the protein of SEQ ID NO: 8. In certain embodiments, the hCDKL5-coding sequence encodes a hCDKL5-4GS protein comprising an amino acid sequence of [MKIP- NIGNVMNKFEILGVVGEGAYGVVLKCRH- KETHEIVAIKKFKDSEENEEVKET TLRELKMLRTLKQENIVELKEAFRRRGKLYL- VFEYVEKNMLELLEEMPNGVPPEKV KSYIYQ- LIKAIHWCHKNDIVHRDIKPENLLISHNDVLKLCDFG- FARNLSEGNNANYT EYVATRWYRSPELLLGAPYGKSVDMWSVGCIL- GELSDGQPLFPGESEIDQLFTIQKV LGPLPSE- QMKLFYSNPRFHGLRFPAVNHPQSLERRYLGILNS- VLLDLMKNLLKLDPA DRYLTEQCLNHPTFQTQRLLDRSPSRNQAGK- STALQSHHRSNSKDIQNLSVGLPRAD EGL- PANESFLNGNLAGASLSPLHTKTYQASSQPGST- SKDLTNNNIPHLLSPKEAKSKT EFDFNIDPKPSEGPGTKYLKSNSR-SQQNRHSFMESSQSKAGTLQPNEKQSRHSYIDTI PQSSRSPSYRTKAKSHGALSDSKSVSNLSEARAQIAE-PSTSRYFPSSCLDLNSPTSPTP TRHSDTRTLLSPS-GRNNRNEGTLDSRRTTTRHSKT-MEELKLPEHMDSSHSHSLSAPH ESFSYGLGYT-SPFSSQQRPHRHSMYVTRDKVRAKGLDGSLSIGQG-MAARANSLQLL SPQPGEQLPPEMTVARSSVKETS-REGTSSFHTRQKSEGGVYHDPHSDDGTAPKENRH LYNDPVPRRVGSFYRVPSPRPDNSFHE NNVSTRVSSLPSESSSGTNHSKRQPAFDPW KSPEN-ISHSEQLKEKEKQGFFRSMKKKKKKSQTTDSTNGEN-PSIKKSLFPLFNSKNHL KHSSSLKKLPVVTPPMVPNSDSPDLLTLQKSIHSAS-TPSSRPKEWRPEKISDLQTQSQP LKSLRKLLHLSSAS-NHPASSDPRFQPLTAQQTKNSF-SEIRIHPLSQASGGSSNIRQEPA PKGRPALQLPGQMDPGWHVSSVTRSATEGPSYSEQL-GAKSGPNGHPYNRTNRSRMP NLNDLKETAL] (SEQ ID NO: 10), wherein the hCDKL5-coding sequence comprises a nucleic acid sequence of SEQ ID NO: 26 or which is at least about 95% identical to SEQ ID NO: 26 and encodes the protein of SEQ ID NO: 10.

In certain embodiments, the vector is a viral vector selected from a recombinant parvovirus, a recombinant lentivirus, a recombinant retrovirus, or a recombinant adenovirus; or a non-viral vector selected from naked DNA, naked RNA, an inorganic particle, a lipid particle, a polymer-based vector, or a chitosan-based formulation. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication. Such replication-defective viruses may be adeno-associated viruses (AAV), adenoviruses, lentiviruses (integrating or non-integrating), or another suitable virus source.

V. COMPOSITIONS

Provided herein is a composition comprising an rAAV or a vector as described herein and an aqueous suspension media. In certain embodiments, the suspension is formulated for intravenous delivery, intrathecal administration, or intracerebroventricular administration.

Provided herein are compositions containing at least one rAAV stock and an optional carrier, excipient and/or preservative. As used herein, a "stock" of rAAV refers to a population of rAAV. Despite heterogeneity in their capsid proteins due to deamidation, rAAV in a stock are expected to share an identical vector genome. A stock can include rAAV having capsids with, for example, heterogeneous deamidation patterns characteristic of the selected AAV capsid proteins and a selected production system. The stock may be produced from a single production system or pooled from multiple runs of the production system. A variety of production systems, including but not limited to those described herein, may be selected.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered vector genomes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. In one embodiment, the surfactant may be present in an amount up to about 0.0005% to about 0.001% (based on weight ratio, w/w %) of the suspension. In another embodiment, the surfactant may be present in an amount up to about 0.0005% to about 0.001% (based on volume ratio, v/v %) of the suspension. In yet another embodiment, the surfactant may be present in an amount up to about 0.0005% to about 0.001% of the suspension, wherein n % indicates n gram per 100 mL of the suspension.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Poloxamer 188 (also known under the commercial names Pluronic® F68 [BASF], Lutrol® F68, Synperonic® F68, Kolliphor® P188) which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In certain embodiments, the composition containing the rAAV.hCDKL5 is delivered at a pH in the range of 6.8 to 8, or 7.2 to 7.8, or 7.5 to 8. For intrathecal delivery, a pH above 7.5 may be desired, e.g., 7.5 to 8, or 7.8.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. The aqueous solution may have a pH of 7.2.

In another embodiment, the formulation may contain a buffered saline aqueous solution comprising 1 mM Sodium Phosphate ($Na_3PO_4$), 150 mM sodium chloride (NaCl), 3 mM potassium chloride (KCl), 1.4 mM calcium chloride ($CaCl_2$)), 0.8 mM magnesium chloride ($MgCl_2$), and 0.001% poloxamer (e.g., Kolliphor®) 188, pH 7.2. See, e.g., harvardapparatus.com/harvard-apparatus-perfusion-fluid.html. In certain embodiments, Harvard's buffer is preferred due to better pH stability observed with Harvard's buffer.

In certain embodiments, the formulation buffer is artificial CSF with Pluronic F68. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery. In one example, the composition is formulated for intravenous (iv) delivery.

VI. USES

Provided herein is a method of treating CDD, comprising administrating an effective amount of an rAAV or a vector as described herein to a subject in need thereof.

In certain embodiments, an "effective amount" herein is the amount which achieves amelioration of CDD symptoms and/or delayed CDD progression.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., brain, CSF, the liver (optionally via the hepatic artery), lung, heart, eye, kidney), oral, inhalation, intranasal, intrathecal, intratracheal, intraarterial, intraocular, intravenous, intramuscular, subcutaneous, intradermal, intraparenchymal, intracerebroventricular, intrathecal, ICM, lumbar puncture and other parenteral routes of administration. Routes of administration may be combined, if desired.

Dosages of the viral vector (for example, rAAV) depend primarily on factors such as the condition being treated, the age, weight and health of the patient, and can thus vary among patients. For example, a therapeutically effective human dosage of the viral vector is generally in the range of from about 25 to about 1000 microliters to about 100 mL of solution containing concentrations of from about $1\times10^{9}$ to $1\times10^{16}$ vector genome copies. In certain embodiments, a volume of about 1 mL to about 15 mL, or about 2.5 mL to about 10 mL, or about 5 mL suspension is delivered. In certain embodiments, a volume of about 1, about 2, about 3, about 4, about 5, about 6, about 7, about 8, about 9, about 10, about 11, about 12, about 13, about 14, or about 15 mL suspension is delivered. In certain embodiments, a dose of about $8.9\times10^{12}$ to $2.7\times10^{14}$ GC total is administered in this volume. In certain embodiments, a dose of about $1.1\times10^{10}$ GC/g brain mass to about 3.3x1011 GC/g brain mass is administered in this volume. In certain embodiments, a dose of about $3.0\times10^{9}$, about $4.0\times10^{9}$, about $5.0\times10^{9}$, about $6.0\times10^{9}$, about $7.0\times10^{9}$, about $8.0\times10^{9}$, about $9.0\times10^{9}$, about $1.0\times10^{10}$, about $1.1\times10^{10}$, about $1.5\times10^{10}$, about $2.0\times10^{10}$, about $2.5\times10^{10}$, about $3.0\times10^{10}$, about $3.3\times10^{10}$, about $3.5\times10^{10}$, about $4.0\times10^{10}$, about $4.5\times10^{10}$, about $5.0\times10^{10}$, about $5.5\times10^{10}$, about $6.0\times10^{10}$, about $6.5\times10^{10}$, about $7.0\times10^{10}$, about $7.5\times10^{10}$, about $8.0\times10^{10}$, about $8.5\times10^{10}$, about $9.0\times10^{10}$, about $9.5\times10^{10}$, about $1.0\times10^{11}$, about $1.1\times10^{11}$, about $1.5\times10^{11}$, about $2.0\times10^{11}$, about $2.5\times10^{11}$, about $3.0\times10^{11}$, about $3.3\times10^{11}$, about $3.5\times10^{11}$, about $4.0\times10^{11}$, about $4.5\times10^{11}$, about $5.0\times10^{11}$, about $5.5\times10^{11}$, about $6.0\times10^{11}$, about $6.5\times10^{11}$, about $7.0\times10^{11}$, about $7.5\times10^{11}$, about $8.0\times10^{11}$, about $8.5\times10^{11}$, about $9.0\times10^{11}$ GC per gram brain mass is administered in this volume.

The dosage is adjusted to balance the therapeutic benefit against any side effects and such dosages may vary depending upon the therapeutic application for which the recombinant vector is employed. The levels of expression of the transgene product can be monitored to determine the frequency of dosage resulting in viral vectors, preferably AAV vectors containing the minigene. Optionally, dosage regimens similar to those described for therapeutic purposes may be utilized for immunization using the compositions of the invention.

The replication-defective virus compositions can be formulated in dosage units to contain an amount of replication-defective virus that is in the range of about $1.0\times10^{0}$ GC to about $1.0\times10^{16}$ GC (to treat an subject) including all integers or fractional amounts within the range, and preferably $1.0\times10^{12}$ GC to $1.0\times10^{14}$ GC for a human patient. In one embodiment, the compositions are formulated to contain at least $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ GC per dose including all integers or fractional amounts within the range. In another embodiment, the compositions are formulated to contain at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per dose including all integers or fractional amounts within the range. In another embodiment, the compositions are formulated to contain at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per dose including all integers or fractional amounts within the range. In another embodiment, the compositions are formulated to contain at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range.

In one embodiment, for human application the dose can range from $1\times10^{10}$ to about $1\times10^{15}$ GC per kg body weight including all integers or fractional amounts within the range. In one embodiment, the effective amount of the vector is about $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ GC per kg body weight including all integers or fractional amounts within the range. In another embodiment, the effective amount of the vector is about $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per kg body weight including all integers or fractional amounts within the range. In another embodiment, the effective amount of the vector is about $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per kg body weight including all integers or fractional amounts within the range. In another embodiment, the effective amount of the vector is about $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per kg body weight including all integers or fractional amounts within the range. In another embodiment, the effective amount of the vector is about $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per kg body weight including all integers or fractional amounts within the range. In another embodiment, the effective amount of the vector is about $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per kg body weight including all integers or fractional amounts within the range. In another embodiment, the effective amount of the vector is about $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per kg body weight including all integers or fractional amounts within the range.

In one embodiment, for human application the dose can range from $1\times10^{10}$ to about $1\times10^{15}$ GC per gram (g) brain mass including all integers or fractional amounts within the range. In one embodiment, the effective amount of the vector is about $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ GC per gram (g) brain mass including all integers or fractional amounts within the range. In another embodiment, the effective amount of the vector is about $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per gram (g) brain mass including all integers or fractional amounts within the range. In another embodiment, the effective amount of the vector is about $1\times10^{11}$, $2\times10^{11}$. $3\times10^{11}$, $4\times10^{11}$, $5\times10^{11}$, $6\times10^{11}$, $7\times10^{11}$, $8\times10^{11}$, or $9\times10^{11}$ GC per gram (g) brain mass including all integers or fractional amounts within the range. In another embodiment, the effective amount of the vector is about $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per gram (g) brain mass including all integers or fractional amounts within the range. In another embodiment, the effective amount of the vector is about $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per gram (g) brain mass including all integers or fractional amounts within the range. In another embodiment, the effective amount of the vector is about $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per gram (g) brain mass including all integers or fractional amounts within the range. In another embodiment, the effective amount of the vector is about $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per gram (g) brain mass including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is between about 700 and 1000 μL.

In certain embodiments, the dose may be in the range of about $1\times10^9$ GC/g brain mass to about $1\times10^{12}$ GC/g brain mass. In certain embodiments, the dose may be in the range of about $1\times10^{10}$ GC/g brain mass to about $3\times10^{11}$ GC/g brain mass. In certain embodiments, the dose may be in the range of about $1\times10^{10}$ GC/g brain mass to about $2.5\times10^{11}$ GC/g brain mass. In certain embodiments, the dose may be in the range of about $5\times10^{10}$ GC/g brain mass.

In one embodiment, the viral constructs may be delivered in doses of from at least about least $1\times10^9$ GC to about $1\times10^{15}$, or about $1\times10^{11}$ to $5\times10^{13}$ GC. Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage may be adjusted to balance the therapeutic benefit against any side effects and such dosages may vary depending upon the therapeutic application for which the recombinant vector is employed.

The above-described recombinant vectors may be delivered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of about 6.8 to about 7.2 may be desired. However, other pHs within the broadest ranges and these subranges may be selected for other route of delivery.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna *magna*. In certain embodiment, a rAAV, vector, or composition as described herein is administrated to a subject in need via the intrathecal administration. In certain embodiments, the intrathecal administration is performed as described in US Patent Publication No. 2018-0339065 A1, published Nov. 29, 2019, which is incorporated herein by reference in its entirety.

As used herein, the terms "intracisternal delivery" or "intracisternal administration" refer to a route of administration for drugs directly into the cerebrospinal fluid of the cisterna *magna* cerebellomedularis, more specifically via a suboccipital puncture or by direct injection into the cisterna *magna* or via permanently positioned tube.

In certain embodiments, treatment of the composition described herein has minimal to mild asymptomatic degeneration of DRG sensory neurons in animals and/or in human patients, well-tolerated with respect to sensory nerve toxicity and subclinical sensory neuron lesions.

VII. APPARATUS AND METHOD FOR DELIVERY OF A PHARMACEUTICAL COMPOSITION INTO CEREBROSPINAL FLUID

In one aspect, the vectors provided herein may be administered intrathecally via the method and/or the device provided in this section and described in WO 2018/160582, which is incorporated by reference herein. Alternatively, other devices and methods may be selected. In certain embodiments, the method comprises the steps of CT-guided sub-occipital injection via spinal needle into the cisterna *magna* of a patient. As used herein, the term Computed Tomography (CT) refers to radiography in which a three-dimensional image of a body structure is constructed by computer from a series of plane cross-sectional images made along an axis. In certain embodiments, the apparatus is described in US Patent Publication No. 2018-0339065 A1, published Nov. 29, 2019, which is incorporated herein by reference in its entirety.

VIII. CDD

"Patient" or "subject", as used herein interchangeably, means a male or female mammalian animal, including a human, a veterinary or farm animal, a domestic animal or pet, and animals normally used for clinical research. In one embodiment, the subject of these methods and compositions is a human patient. In one embodiment, the subject of these methods and compositions is a male or female human. In certain embodiment, the subject of these methods and compositions is diagnosed with CDD and/or with symptoms of CDD.

The methods and compositions may be used for treatment of any of the stages of CDD. In certain embodiments, the patient is about 1, 2, 3, 4, 5, 6, 7, 8, 9, 10, 11 month(s) old, or about 1, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18 year(s) old. In certain embodiments, the patient is a toddler, e.g., 18 months to 3 years of age. In certain embodiments, the patient is from 3 years to 6 years of age, from 3 years to 12 years of age, from 3 years to 18 years of age, from 3 years to 30 years of age. In certain embodiments, patients are older than 18 years of age.

Symptoms in CDD include seizures that usually begin within the first 3 months of life, and can appear as early as the first week after birth. The types of seizures change with age, and may follow a predictable pattern. The most common types are generalized tonic-clonic seizures, which involve a loss of consciousness, muscle rigidity, and convulsions; tonic seizures, which are characterized by abnormal muscle contractions; and epileptic spasms, which involve short episodes of muscle jerks. Seizures occur daily in most people with CDKL5 deficiency disorder, although they can have periods when they are seizure-free. Seizures in CDKL5 deficiency disorder are typically resistant to treatment.

Development is impaired in children with CDKL5 deficiency disorder. Most have severe intellectual disability and little or no speech. The development of gross motor skills, such as sitting, standing, and walking, is delayed or not achieved. About one-third of affected individuals are able to walk independently. Fine motor skills, such as picking up small objects with the fingers, are also impaired; about half of affected individuals have purposeful use of their hands. Most people with this condition have vision problems (cortical visual impairment).

Other common features of CDKL5 deficiency disorder include repetitive hand movements (stereotypies), such as clapping, hand licking, and hand sucking; teeth grinding (bruxism); disrupted sleep; feeding difficulties; and gastrointestinal problems including constipation and backflow of acidic stomach contents into the esophagus (gastroesophageal reflux). Some affected individuals have episodes of irregular breathing. Distinctive facial features in some people with CDKL5 deficiency disorder include a high and broad forehead, large and deep-set eyes, a well-defined space between the nose and upper lip (philtrum), full lips, widely spaced teeth, and a high roof of the mouth (palate). Other physical differences can also occur, such as an unusually small head size (microcephaly), side-to-side curvature of the spine (scoliosis), and tapered fingers.

As described above, the terms "increase" "decrease" "reduce" "ameliorate" "improve" "delay" or any grammatical variation thereof, or any similar terms indication a change, means a variation of about 5 fold, about 2 fold, about 1 fold, about 90%, about 80%, about 70%, about 60%, about 50%, about 40%, about 30%, about 20%, about 10%, about 5% compared to the corresponding reference (e.g., untreated control or a subject in normal condition without CDD), unless otherwise specified.

In certain embodiments, the patient receives medications controlling some signs and symptoms associated with the CDD, such as seizures, muscle stiffness, or problems with breathing, sleep, the gastrointestinal tract or the heart.

In certain embodiments, a diuretic agent may be used in co-therapy in a subject in need thereof. Diuretic agent used may be acetazolamine (Diamox) or other suitable diuretics. In some embodiments, the diuretic agent is administered at the time of gene therapy administration. In some embodiments, the diuretic agent is administered prior to gene therapy administration. In some, embodiments the diuretic agent is administered where the volume of injection is 3 mL.

In certain embodiments, co-therapies may be utilized, which comprise co-administration of Cdk15-isoform 1, isoform 2, isoform 3, and/or isoform 4-expressing vectors, or various two- or three-way combinations thereof. Optionally, co-therapy may further comprise administration of another active agent. In certain embodiments, co-therapy may comprise enzyme replacement therapy.

Optionally, an immunosuppressive co-therapy may be used in a subject in need. Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent. In certain embodiments, the immunosuppressive therapy may be started 0, 1, 2, 3, 4, 5, 6, 7, or more days prior to or after the gene therapy administration. Such immunosuppressive therapy may involve administration of one, two or more drugs (e.g., glucocorticoids, prednelisone, micophenolate mofetil (MMF) and/or sirolimus (i.e., rapamycin)). Such immunosuppressive drugs may be administrated to a subject in need once, twice or for more times at the same dose or an adjusted dose. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week (7 days), about 60 days, or longer, as needed. In certain embodiments, a tacrolimus-free regimen is selected.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

The term "expression" is used herein in its broadest meaning and comprises the production of RNA or of RNA and protein. With respect to RNA, the term "expression" or "translation" relates in particular to the production of peptides or proteins. Expression may be transient or may be stable.

It is to be noted that the term "a" or "an", refers to one or more, for example, "an enhancer", is understood to represent one or more enhancer(s). As such, the terms "a" (or "an"), "one or more," and "at least one" is used interchangeably herein.

Throughout the specification, exponents are referred to using the term "e" followed by a numerical value (n). It will be understood with this refers to "x $10^n$"). For example, "3e9" is the same as $3\times10^9$ and "1e13" is the same as $1\times10^{13}$.

As described above, the term "about" when used to modify a numerical value means a variation of ±10%, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

IX. EXAMPLES

The following examples are illustrative only and are not intended to limit the present invention.

Several models for CDD have been developed and may selected for use in evaluating therapeutic effect. These following models are null for CDKL5 expression: g., a Cdk15-ko mouse having a deletion in exon 6 (Δ exon 6), Wang et al, Proceedings of the National Academy of Sciences December 2012, 109 (52) 21516-21521; DOI: 10.1073/pnas. 1216988110; a Cdk15-ko mouse having a deletion in exon 4 (A exon 4) (see, Amendola et al. (2014) Mapping Pathological Phenotypes in a Mouse Model of CDKL5 Disorder. PLOS ONE 9 (5): e91613. doi.org/10.1371/journal.pone.0091613 (2014); a Cdk15 (R59X knock-in) model (available form Jackson Laboratory; see, Tang et al (2019), Tang S, et al. Altered NMDAR signaling underlies autistic-like features in mouse models of CDKL5 deficiency disorder. Nat Commun. 2019; 10 (1): 2655. Published 2019 Jun. 14. doi: 10.1038/s41467-019-10689-w, and a Cdk15 (D471fs) model (Rodney Samaco, Baylor College of Medicine, Houston, TX).

In this study we show that restoring CDKL5 expression in the CNS of three CDD mouse models (Cdk15-ko (exon 6), Cdk15 (R59X). Cdk15 (D471fs)) significantly improves disease symptoms. We developed an AAV gene therapy vector comprised of the AAVhu68 capsid, and an expression cassette with the human synapsin promoter and a engineered human CDKL5 transgene. When the AAV-CDKL5 vector was administered to Cdk15 knock-out mice via neonatal injection into the lateral brain ventricle we detected robust expression in up to 50% of neurons throughout the brain. AAV administration and human CDKL5 expression were tolerated well. The human CDKL5 was mostly localized to the cytoplasm; protein expression and kinase activity persisted for over 4 months. We subjected cohorts of treated Cdk15-ko mice to a battery of neurobehavior tests and found significant improvement from untreated Cdk15-ko phenotype towards behavior outcomes observed in wildtype mice. We then repeated the same study in 2 different CDD mouse models that carry patient-derived frameshift mutations (Cdk15 (R59X) and CDKL5 (D471fs) models) instead of the gene knock-out. We obtained very similar results, thus reiterating the curative benefit of our CDKL5 gene therapy vector.

CDKL5 is expressed as at least four different isoforms in the human brain. We generated similar AAV gene therapy vectors for the three alternatively spliced isoforms which were all found to express and exhibit kinase activity in transduced mouse brains.

To test for expression of our AAV-CDKL5 gene therapy vector in a larger animal we conducted a study with rhesus macaques. Through infusion into the cerebrospinal fluid via the cisterna *magna*, we have been able to achieve vector distribution throughout the entire brain at 0.1 to 1 vector copies per diploid genome. Much higher vector transduction was observed in dorsal root ganglia (DRG). Accordingly, in situ hybridization with probes specific for the human CDKL5 sequence showed abundant expression in DRG neurons but much sparser expression in cortical grey matter neurons. CDKL5 administration and expression was generally tolerated well in all six rhesus macaques for 60 days, however, we noticed mild axonopathy of spinal white matter tracts.

In summary, we show promising evidence that CDKL5 gene therapy provides a lasting curative benefit to model mice and is tolerated well in non-human primates. Further optimization of this approach may eventually offer an option for clinical intervention in children affected by CDD.

Example 1. Materials and Methods

Plasmids. The amino acid sequences for four CDKL5 (cyclin-dependent kinase-like 5, Uniprot ID O76039) that express in human brain[1] were reverse translated into a DNA sequence. The coding sequence was further engineered, e.g., by considering codon frequencies found in the human genome, cryptic RNA splice sites and alternative reading frames. The engineered sequence was cloned into an AAV expression plasmid under the control of the human synapsin promoter[2]. The coding sequence is preceded by a Kozak sequence, followed by an WPRE enhancer cassette (Woodchuck Hepatitis Virus Posttranscriptional Regulatory Element), the SV40 poly A sequence, and framed by AAV2 inverted terminal repeats (ITR). To suppress expression in dorsal root ganglia (DRG), in some experiments the above plasmid was modified to contain four repeats of the miR183 binding site (agtgaattctaccagtgccata) (SEQ ID NO: 11) directly after the CDKL5 coding sequence and before the WPRE sequence. AAV CDKL5 vector was produced at the University of Pennsylvania Vector Core, using either as capsid PHP.B[3] for mouse studies or AAV9hu68[4] or AAVrh91 for mouse and non-human primate studies.

Mouse Studies. All studies involving mice were approved by the University of Pennsylvania IACUC. We obtained Cdk15-ko mice from Jackson Laboratories (B6.129(FVB)-Cdk15tm1.1Joez/J, strain #021967) and crossed heterozygous female ko mice with wt C57B16 males to obtain the following genotypes of littermates: male hemizygous Cdk15-ko (also referenced as KO mice or mice), male wt, female heterozygous Cdk15-ko and female wt. Mice received AAV Cdk15 vector (dose range $1\times10^{11}$ GC to $5\times10^{11}$ GC) or vehicle control (sterile phospho-buffered saline) at 18-21 days of age by retro-orbital injections in a total volume of 100 μl. Alternatively, mice were injected at day of birth intracerebroventricular with a dose of $1\times10^{10}$ GC to $5\times10^{10}$ GC in a total volume of 2 μl. Mice were housed mixed in regard of genotype and injection product, weighed and observed at least twice a week, and aged to 11 weeks for males or 14 week for females when they were subjected to behavior testing. We did not observer treatment-related morbidity.

Western Blotting and Tissue Staining. After euthanasia, one cortical hemisphere was flash frozen and subsequently protein lysates were generated using RIPA buffer. Western blotting was carried out with antibodies against human Cdk15 (S957D, University of Dundee, UK), EB2 (ab45767, Abcam) or EB2 phospo222 (pab01032-P, Covalab, UK). The other brain half was fixed overnight in formalin, embedded in paraffin and thin sections were processed for immunofluorescence staining with the same CDKL5 antibodies.

Behavior Testing. Mice underwent one test per day. Testing time of day, operator and environment was kept the same (60 dB white noise background and 1000 lumens incandescent indirect lighting). Mice were habituated in their home cages before each test for 30 minutes. For the Open Field Assay, a new cage with minimal amount of bedding was placed into an infrared beam array (MedAssociates, Inc.). A single mouse was added in the middle of the cage and the number of beam brakes over the next 30 minutes was automatically recorded, separated into beam brakes close to the ground (general activity) and 3 inches above ground (rearing activity). For the Elevated Zero Maze (EZM, Stoelting Co.), an elevated circular platform with two opposite enclosed quadrants and two open was used to allow uninterrupted exploration. A single mouse was place in the middle of an open quadrant and movement was video-recorded for 15 minutes. For the Y-Maze (Stoelting Co.), an enclosed platform containing three identical arms in the shape of a Y was used. A single mouse was placed in the arm closest to the operator and its movements were video-recorded for 5 minutes. For the Marble Burying Assay, a fresh cage was filled with 3 inches of AlphaDri bedding (Shepherd Specialty Papers) and gently compacted down. 12 solid-blue marbles were spaced equally onto the bedding and a single mouse placed in the middle of the cage. The number of marbles that were at least half covered by bedding was recorded after 30 minutes.

Data analysis. Data was graphed and analyzed using GraphPad Prims software. Video files were recorded in mp4 format at 20 fps and analyzed using Etho Vision XT software (version 14, Noldus Information Technology). For the Nest Building Assay, mice were single-house overnight in a new cage, supplied with a standardized 2×2 inch nestlet squares (cotton based). After 24 hours, the quality of the nest was scored on a scale of 1-5 and any remaining untouched nestlet material was weighed.

Non-human primate experiments. All studies involving non-human primates were approved by the University of Pennsylvania IACUC and carried out according to USDA regulations. Non-human primates (NHPs) for the species *Macaca* mulatta (rhesus macaques) were obtained from Covance Research Products, Inc. Quarantine and animal husbandry was performed according to Gene Therapy Program SOPs. In the month before AAV vector administration and throughout the study body weight, temperature, respiratory rate and heart rate was periodically monitored, and blood and CSF samples obtained. Whole blood was used for cell counts and differentials, and a clinical blood chemistry panel. CSF samples were used for blood cell counts and differentials, and total protein quantification. For AAV vector delivery into the CSF via puncture of the cisterna *magna*, anesthetized macaques were placed on a procedure table in the lateral decubitus position with the head flexed forward. Using aseptic technique, a 21-27 gauge, 1-1.5 inch Quincke spinal needle (Becton Dickinson) was advanced into the sub-occipital space until the flow of CSF is observed. The needle will be directed at the wider superior gap of the cisterna *magna* to avoid blood contamination and potential brainstem injury. Correct placement of needle puncture will be verified via myelography, using a fluoroscope. 1 mL of CSF was collected for baseline analysis, prior to dosing. After CSF collection, a leur access extension catheter was connected to the spinal needle to facilitate dosing of 1 ml Iohexol (Trade Name: Omnipaque 180 mg/mL, General Electric Healthcare) contrast media. After verifying needle placement, a syringe containing the test article (volume equivalent to 1 mL plus the volume of syringe and linker dead space) was connected to the flexible linker and injected over 30±5 seconds. The needle was removed, and direct pressure applied to the puncture site. AAVhu68.hSyn.Cdk15-1co and AAVhu68.hSyn.Cdk15-1co vector has injected at a dose of up to $3\times10^{13}$ GC/NHP. At study days 0, 14, 18, 41 and the last study day, a neurological assessment was given to all macaques for detailed evaluation of neurological function. Briefly, evaluation included posture and gait assessment, cranial nerve assessment, proprioceptive assessment and spinal/nerve reflexes. At study day 56, macaques were euthanized, and gross postmortem examination and necropsy was performed. 25 major tissues were harvested from each macaque in duplicate for either snap freezing or fixation in formalin. DNA or RNA was purified from snap-frozen tissues and used for vector biodistribution or transgene expression analysis, respectively. For vector biodistribution, genome copies (GC) per total DNA weight were determined using a TaqMan qPCR assay with probes directed again the polyA region of the transgene cassette and an internal standard. To quantify transgene expression, total RNA was used to generate cDNA via first strand synthesis with polyT oligonucleotides, followed by TaqMan qPCR with probes specific for the transgene that did not cross-react with the endogenous rhesus CDKL5 sequence. For histopathological analysis, macaque tissue was embedded into paraffin and these sections were stained with H&E solution or CDKL5 antibodies, respectively. Same spinal cord sections were incubated with Luxol Fast Blue to stain myelin. All stained tissues sections were reviewed by a board-certified veterinary pathologist, and abnormal findings verified by peer review.

REFERENCES

1. Hector, R. D. et al. Characterization of CDKL5 Transcript Isoforms in Human and Mouse. PloS one 11, e0157758, (2016).
2. Thiel, G., Greengard, P. & Sudhof, T. C. Characterization of tissue-specific transcription by the human synapsin I gene promoter. Proc Natl Acad Sci USA 88, 3431-3435, (1991).
3. Deverman, B. E. et al. Cre-dependent selection yields AAV variants for widespread gene transfer to the adult brain. Nat Biotechnol 34, 204-209, (2016).
4. Hinderer, C. et al. Severe Toxicity in Nonhuman Primates and Piglets Following High-Dose Intravenous Administration of an Adeno-Associated Virus Vector Expressing Human SMN. Human Gene Therapy 29, 285-298, (2018).

Example 2: Gene Therapy AAV Vector

Figure 1B:
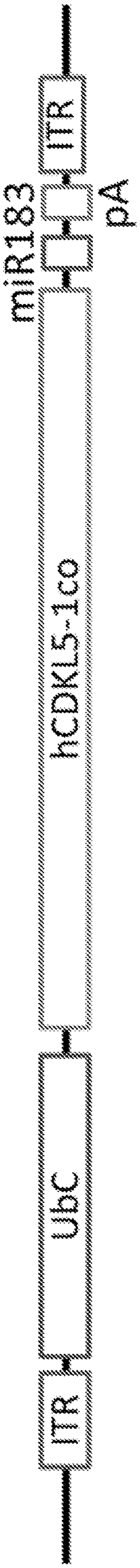
FIG. 1B shows an AAV vector design for an AAV CDKL5 vector genome comprising a 5'AAV ITR, and expression cassette comprising: ubiquitin C (UbC) promoter, an engineered human CDKL5 DNA coding sequence, a drg-detargetting miRNA, polyA, and an AAV 3'ITR.
Figure 1C:
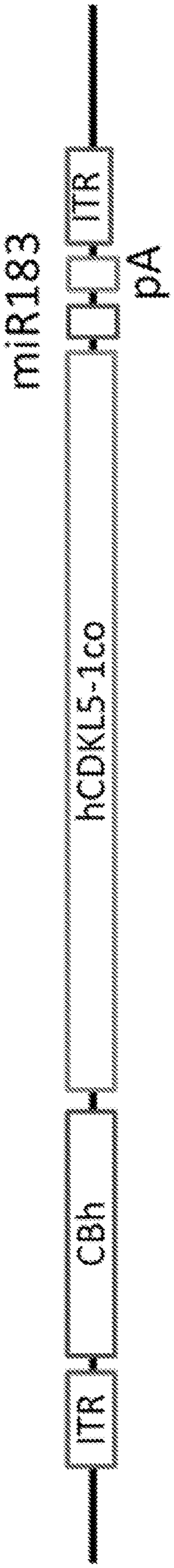
FIG. 1C shows an AAV vector design for an AAV CDKL5 vector genome comprising a 5'AAV ITR, and expression cassette comprising: a chicken beta-actin hybrid promoter (CBh), an engineered human CDKL5 DNA coding sequence, a drg-detargetting miRNA, polyA, and an AAV 3'ITR.
Figure 2A:
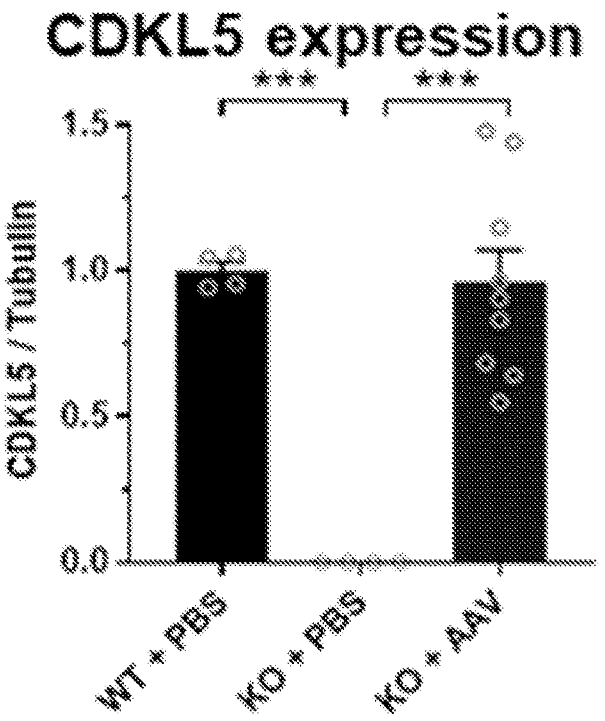
FIGS. 2A and 2B show analysis of mouse hippocampus, as assessed with anti-CDKL5 antibodies (S957D, University of Dundee, UK). Mice were treated with $5\times10^{10}$ GC AAV-hSyn-CDKL5-1co.WPRE via neonatal intracerebroventricular injection.
Figure 2B:
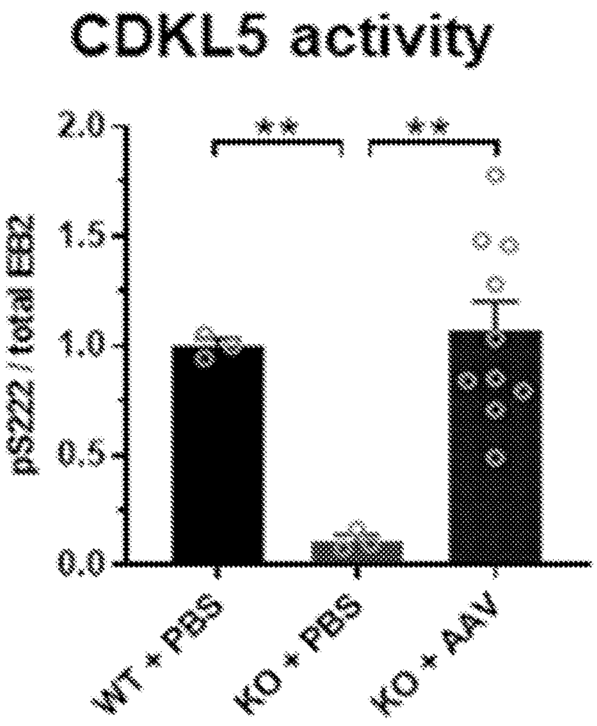
Figure 3:
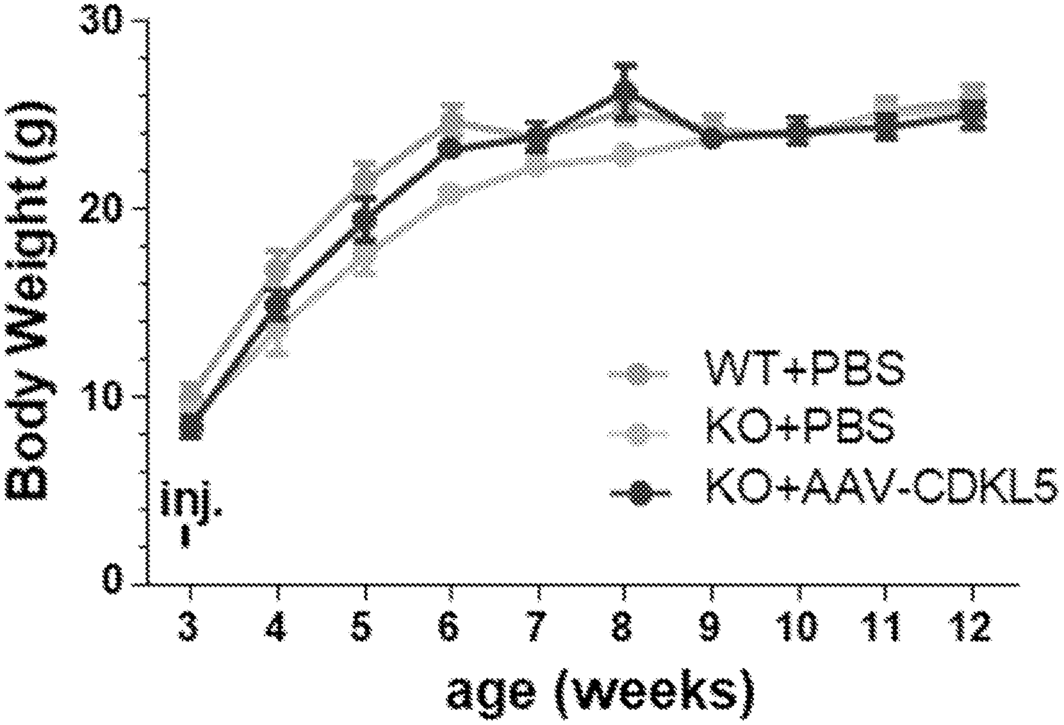
FIG. 3 provides a graph of mouse maturation and survival following injection of AAV-hSyn-hCDKL5-1co.WPRE in a CDD mouse model. All injected mice survived treatment, gained weight. They mice did not display any overt signs of adverse outcomes.
Figure 4:
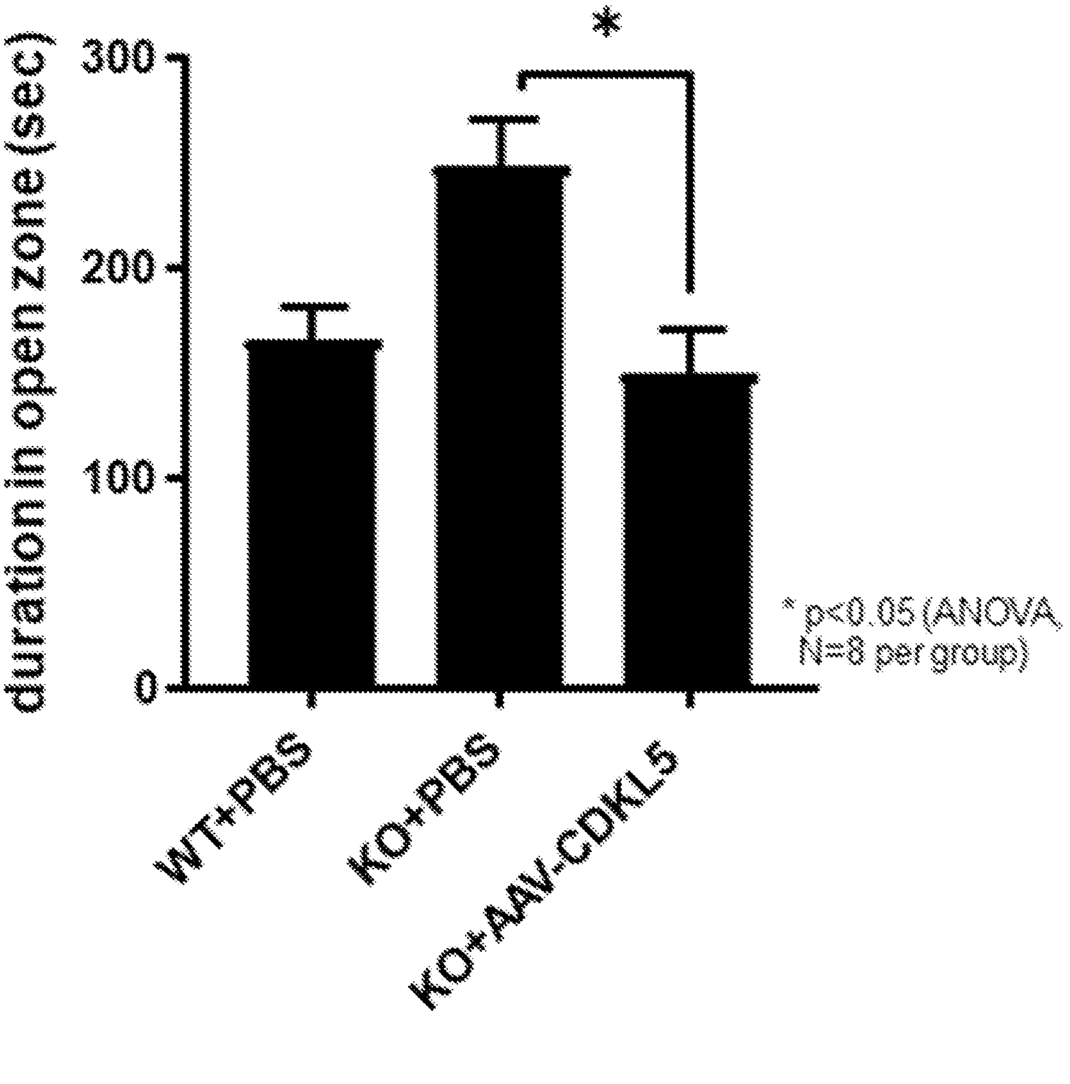
FIG. 4 provides results from a behavioral assessment in a CDD mice receiving AAV-hSyn-CDKL5-1co.WPRE. This figure charts results from the Elevated Zero Maze, which assesses the balance between risk taking, curiosity and anxiety. The first bar represents wt mice receiving PBS. Wt mice are curious but cautious and spend a limited time out in the open. The middle bar shows Cdk15-ko mice receiving PBS only, which showed decreased anxiety and spend more time out in the open, they entered the open zone more frequently. After AAV-CDKL5 treatment, behavior of Cdk15-ko mice reverts to wt behavior (for time in open zone and for entries from closed into open zone).
Figure 5A:
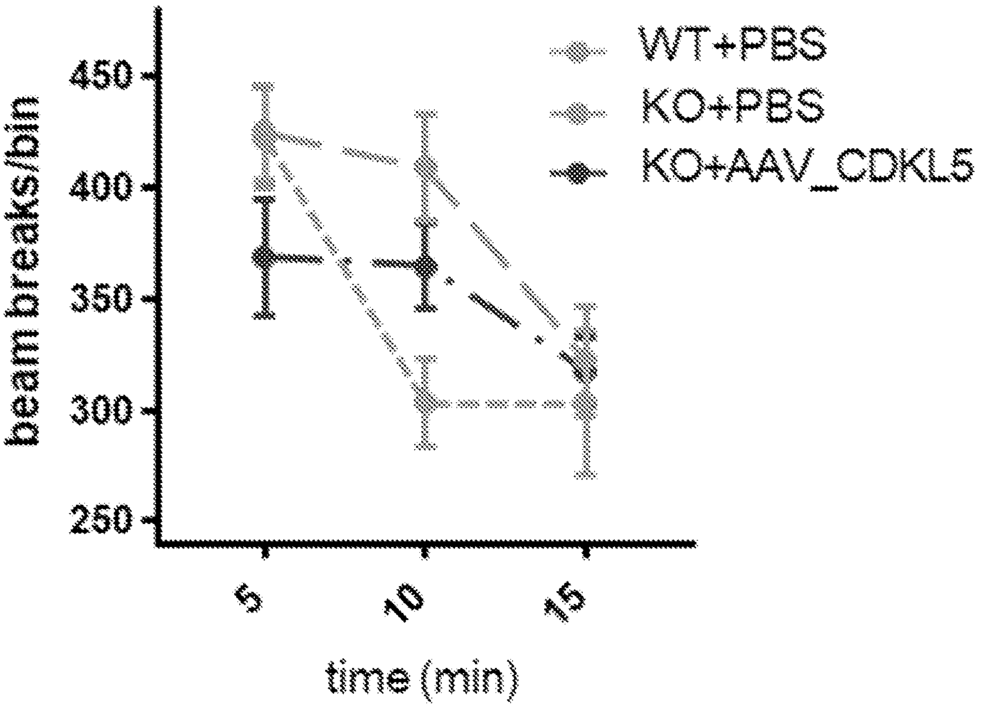
FIGS. 5A and 5B provide results from a behavioral assessment in a CDD mice receiving AAV-hSyn-CDKL5-1co.WPRE.
Figure 5B:
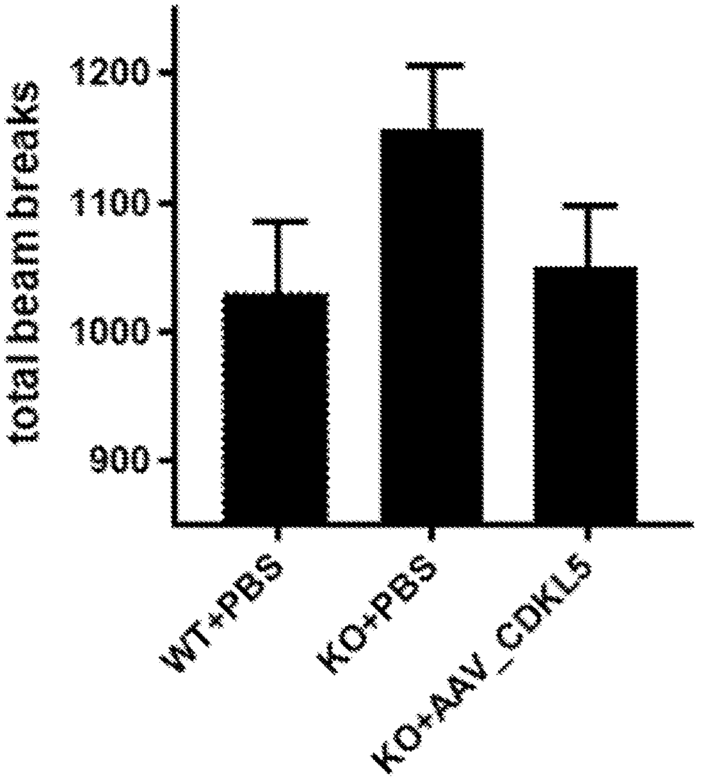
Figure 6:
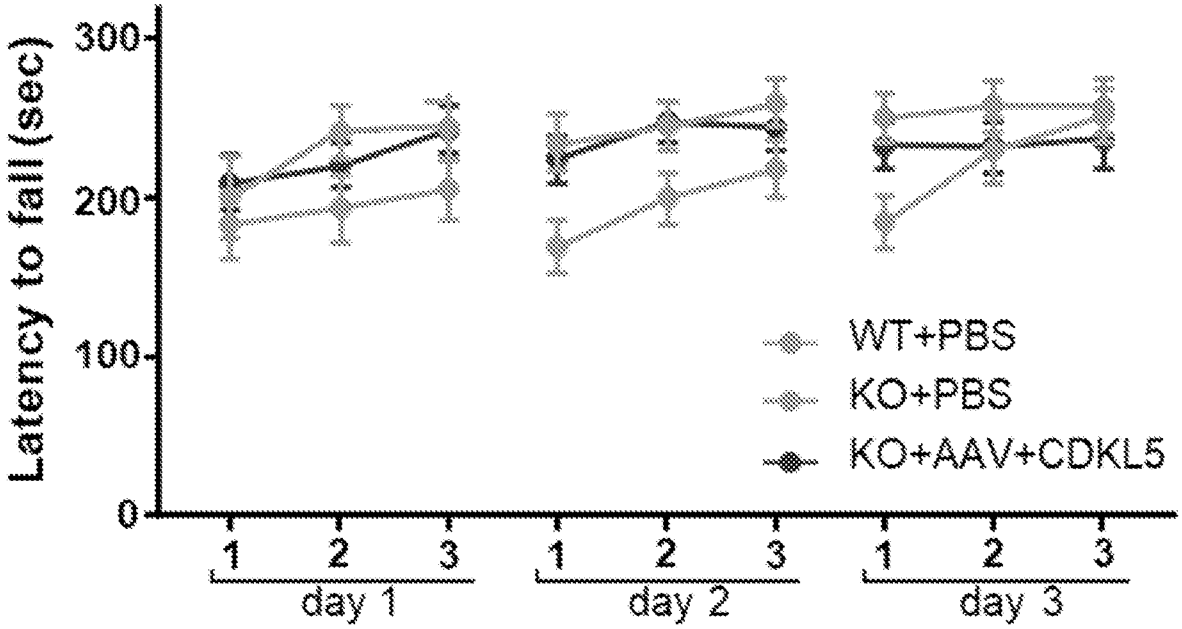
FIG. 6 shows a graph of measured latency to fall (sec) in a motor activity and agility assessment (rotarod) in mice over three consecutive days. The wild-type mice are observed to increase performance while learning over time. The Cdk15-ko mice show improved performance, compared to wt mice, likely due to the previously observed initial hyperactivity. After AAV-hSyn-CDKL5-1co. WPRE.treatment, behavior of Cdk15-ko mice does not revert to wt behavior.
Figure 7A:
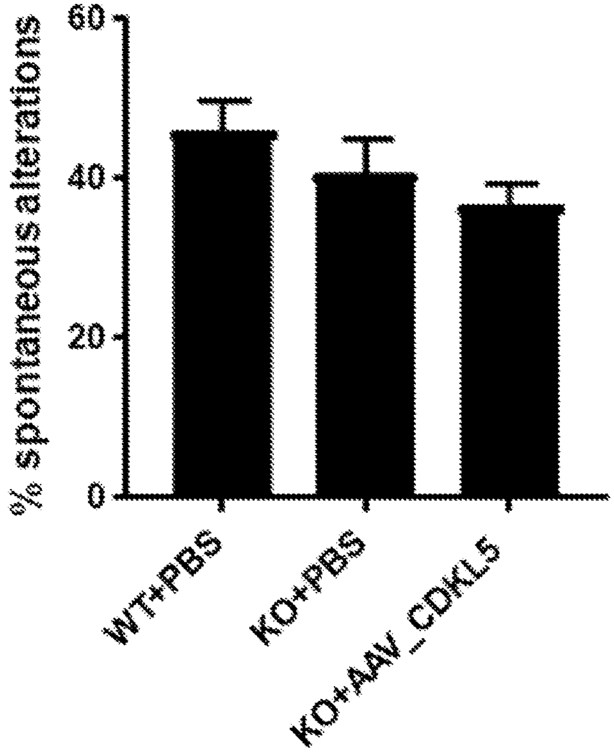
FIGS. 7A and 7B show results of hippocampal learning and memory (Y-maze).
Figure 7B:
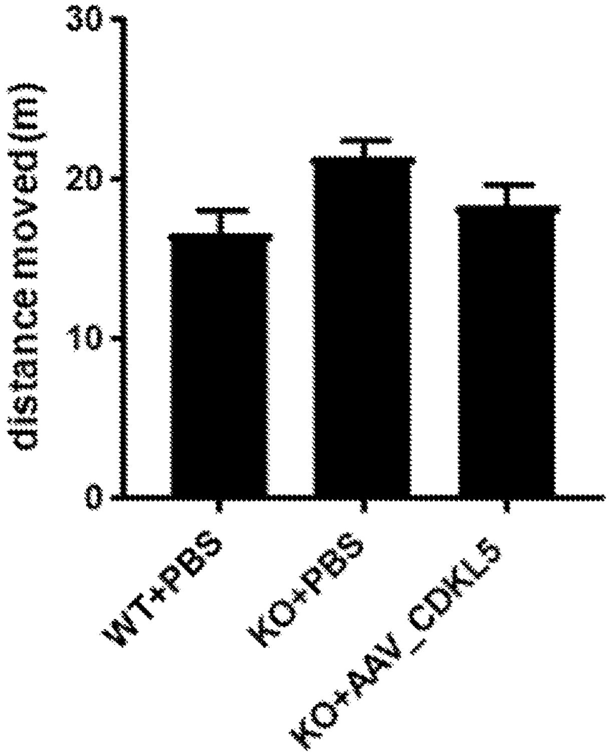

The expression construct between the ITRs is comprised of the human synapsin promoter (SEQ ID NO: 23), the engineered coding sequence for human CDKL5, isoform 1 (SEQ ID NO: 22), the WPRE expression enhancer (SEQ ID NO: 27) and SV40 poly A sequence (SEQ ID NO: 28) (FIG. 1A). Similarly, the alternative expression constructs contain engineered coding sequences for human CDKL5, isoform 2 (CDKL5-2GS or hCDKL5-2GS; SEQ ID NO: 24), 3 (CDKL5-3GS or hCDKL5-3GS; SEQ ID NO: 25) or 4 (CDKL5-4GS or hCDKL5-4GS; SEQ ID NO: 26), respectively, instead of isoform 1. All tested plasmids expressed well in mouse brain, showing minor differences in ability to phosphorylate EB2 (measurement of CDKL5 kinase activity). We found that the WPRE enhancer is required to obtain human CDKL5 expression levels in the mouse brain that resemble wildtype mouse Cdk15 expression (FIG. 2). CDKL5 was fully active, as determined by its ability to phosphorylate its endogenous target EB2 protein (FIG. 2). The expression and localization of CDKL5 was confirmed via IHC. We also generated an alternative expression construct by swapping the human synapsin with the human Ubiquitin C promoter (Ubc) (FIG. 1B) or with the chicken-beta actin hybrid promoter (FIG. 1C). The AAV vectors AAVrh91.UbC.CDKL5-1co.miR183 and AAVrh91.CBh.CDKL5-1co.miR183, in AAVrh91 capsid, were administered at a dose of $3\times10^{10}$ GC via neonatal ICV in Cdk15-ko mice and necropsy was performed at P14. Western blot analysis of mouse brain tissue confirmed the expression of CDKL5 following transduction with AAV vector genomes comprising UbC or CBh promoters. We observed expression of CDKL5 transgene in mouse brain following the transduction with AAVrh91.UbC.CDKL5-1co.miR183 and AAVrh91.CBh.CDKL5-1co.miR183. A higher CDKL5 expression per cell was observed in hippocampus of mouse brain after transduction with AAVrh91.UbC.CDKL5-1co.miR183. While, lower expression of CDKL5 per cell was observed in hippocampus of mouse brain after transduction with AAVrh91.CBh.CDKL5-1co.miR183, wherein. A higher expression of CDKL5 per cell was observed in cortex of mouse brain after transduction with AAVrh91.UbC.CDKL5-1co.miR183. A lower expression of CDKL5 per cell was observed in cortex of mouse brain after transduction with AAVrh91.CBh.CDKL5-1co.miR183. Furthermore, we compared CDKL5 expression in Cdk15-ko mouse brain following administration of AAVrh91.UbC.CDKL5-1co.miR183 ($3\times10^{10}$ GC, neonatal ICV) and AAVhu68.hSyn.CDKL5-1co.miR183 ($2.5\times10^{10}$ GC). Very similar expression patterns were observed in mouse brain following administration of the AAV as specified. A CDKL5 expression was observed in mouse brain after transduction either with AAVrh91.UbC.CDKL5-1co.miR183 (AAVrh91 capsid; Uiquitin C promoter) or with AAVhu68.hSyn.CDKL5-1co.miR183 (AAVhu68 capsid; Synapsin promoter). Additionally, varying doses of AAVrh91.UbC.CDKL5-1co.miR183 and AAVrh91.CBh.CDKL5-1co.miR183 at $1\times10^{10}$ GC, $3\times10^{10}$ GC, and $6\times10^{10}$ GC are examined in Cdk15-ko mice for behavior effects.

The AAV.UbC.CDKL5-1co.miR183 vector showed therapeutic utility in mice similar to when CDKL5 expression was driven by hSyn. The AAVrh91 capsid when used with AAV vector genome comprising an engineered nucleic acid sequence achieved a CDKL5 expression similar to that of AAVhu68. CDKL5 protein levels in mouse brain were higher with the Ubc promoter compared with the hSyn promoter.

Example 3: Pre-Clinical Therapeutic Benefit of CDKL5 Gene Therapy in CDD Mouse Model To test of the therapeutic benefit CDKL5 gene therapy on Cdk15 deficient mice, we treated cohort of juvenile Cdk15-ko (also referenced as KO mice or mice) and wild type (wt) littermates with $5\times10^{11}$ GC (5e11 gc) of AAV9-PHP.B-hSyn-hCDKL5-1co.WPRE vector by retro-orbital IV injection. All treatment groups continued to grow at the same rate and no treatment-related deaths were observed. At 10 weeks of age, mice were subjected to the battery of behavior testing. We observed a robust and statistically significant normalization for the treated group in the Elevated Zero Maze and Open Field Activity tests. There was a marginal improvement in the same group in the rotarod and Y-Maze test, and no improvement in thermal sensitivity.

Figure 9A:
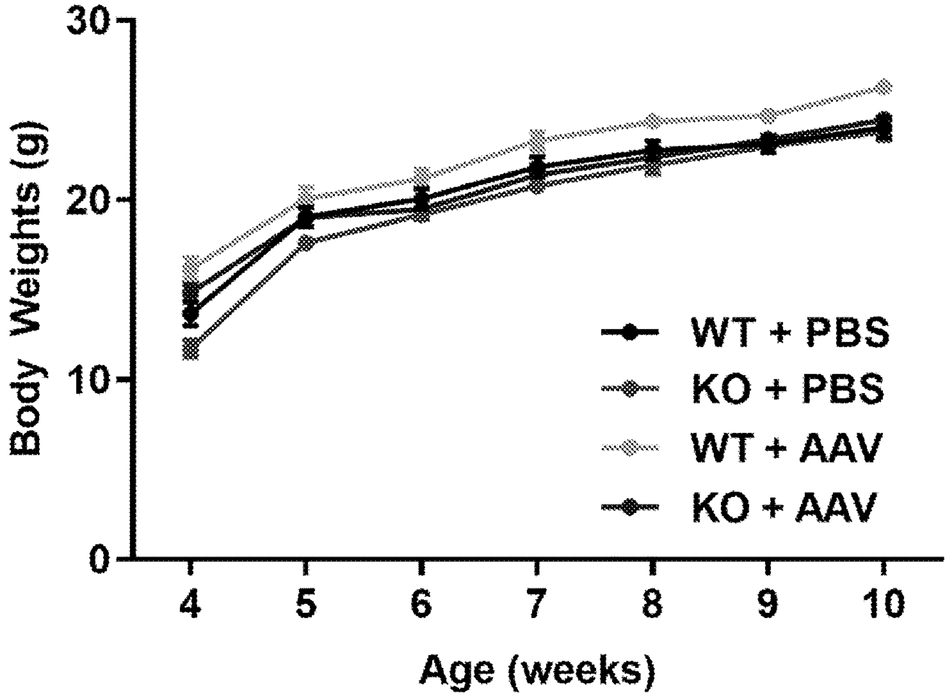
FIGS. 9A to 9F show therapeutic efficacy of the AAV.CDKL5 gene therapy in a mouse study comparing different vector doses ($5\times10^{10}$ GC, $2.5\times10^{10}$ GC, $1\times10^{10}$ GC, and $6\times10^{9}$ GC) in knock out and wild type mice.
Figure 9B:
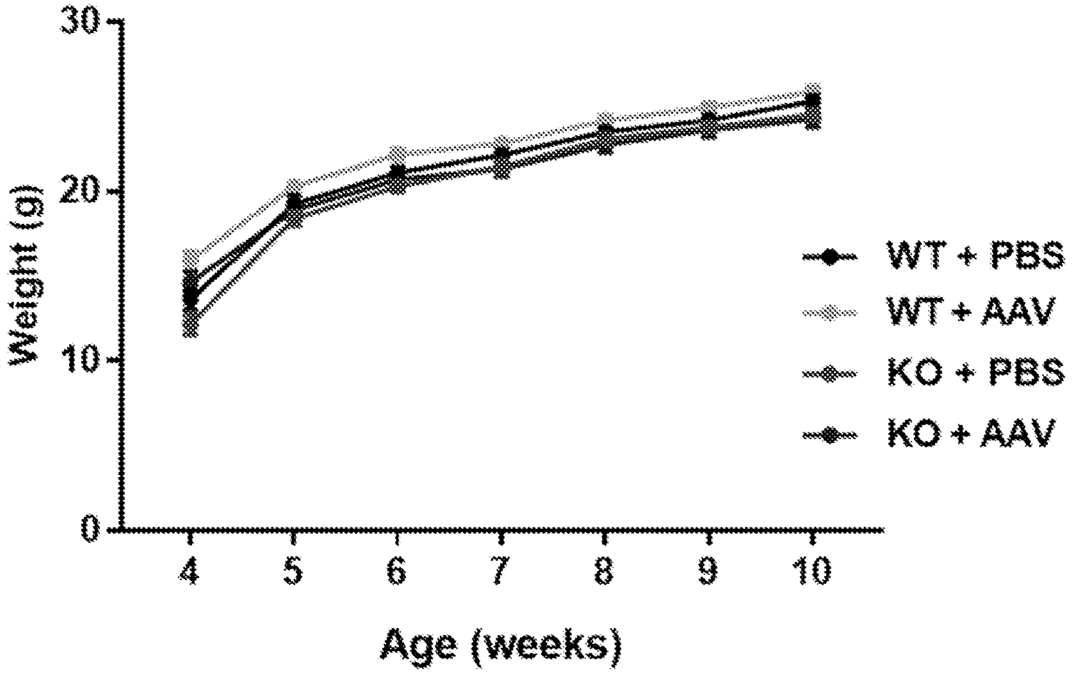
Figure 9C:
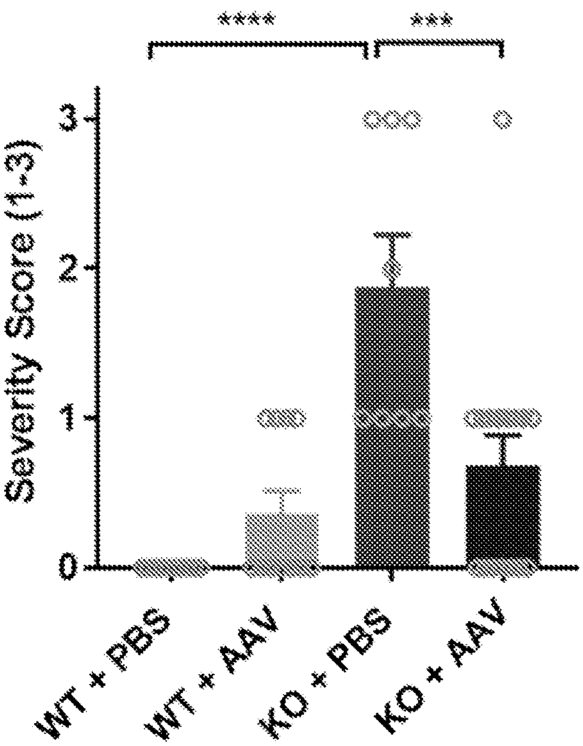
Figure 9D:
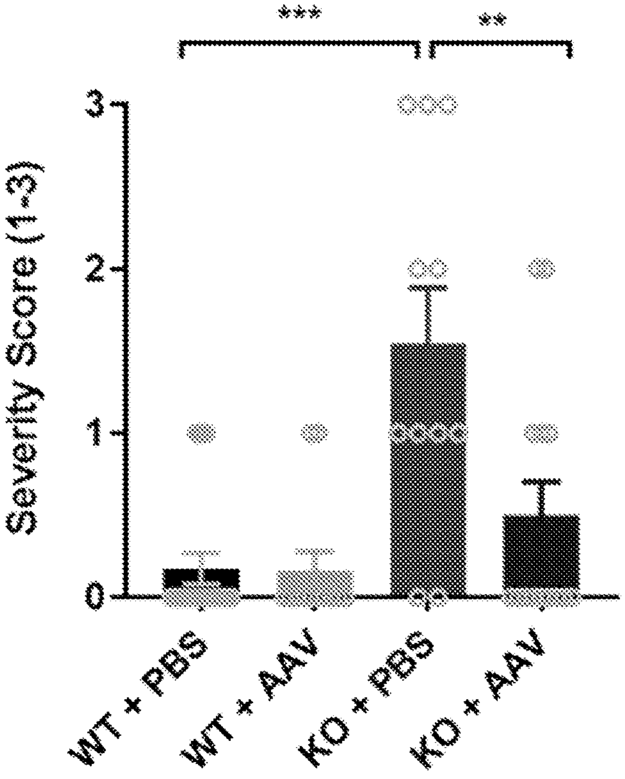
Figure 9E:
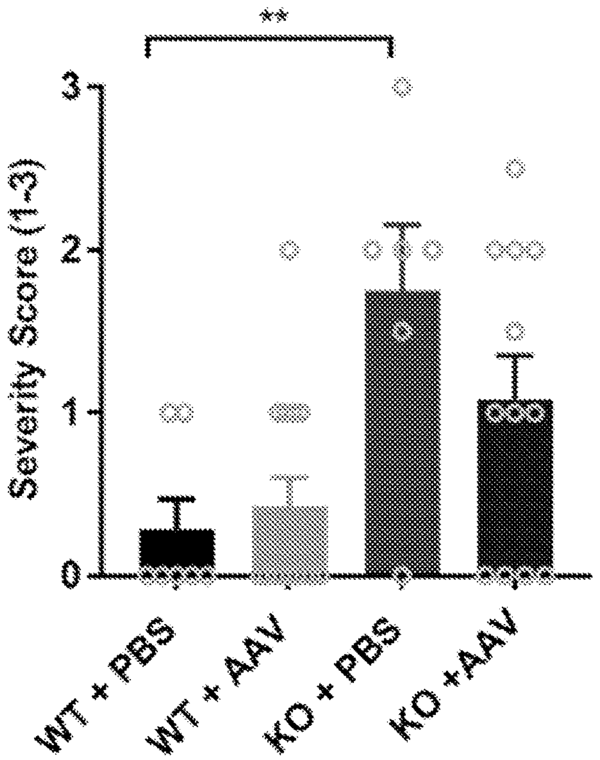
Figure 9F:
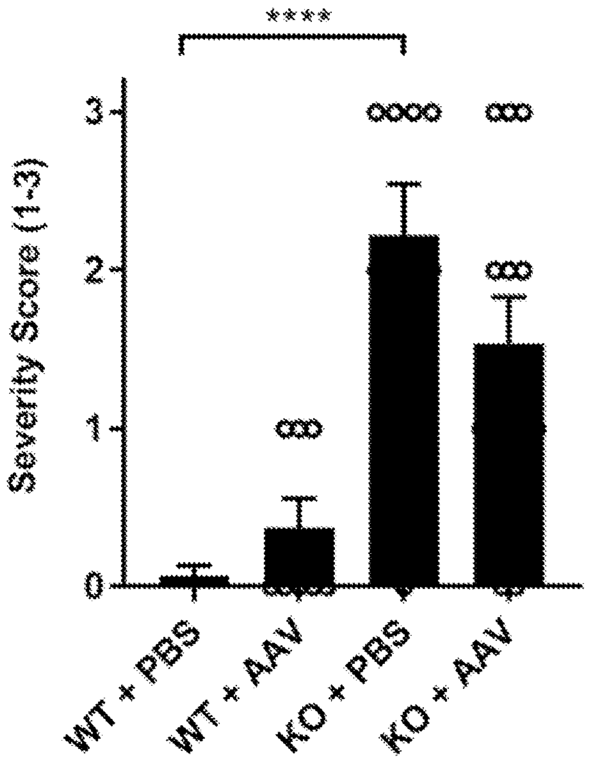
Figure 10A:
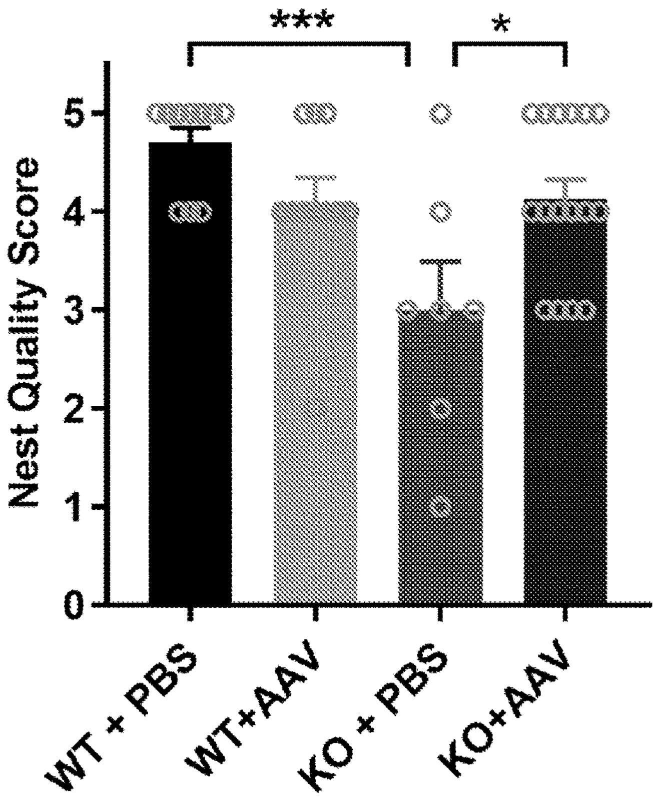
FIGS. 10A to 10E show therapeutic efficacy of the AAV.CDL5 gene therapy in the CDD ko mouse study.
Figure 10B:
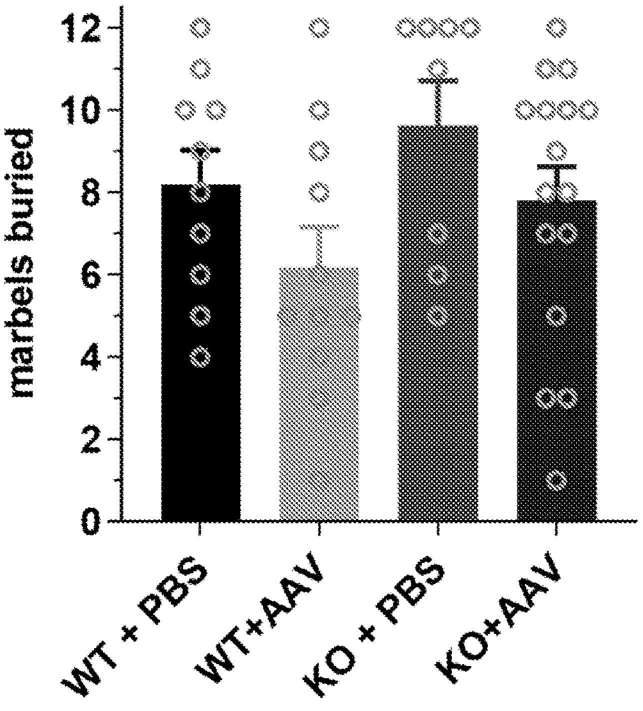
Figure 10C:
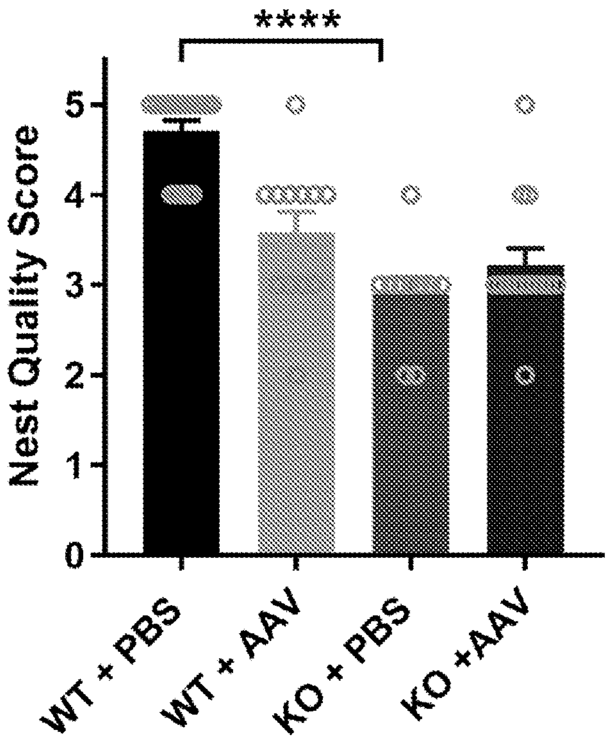
Figure 10D:
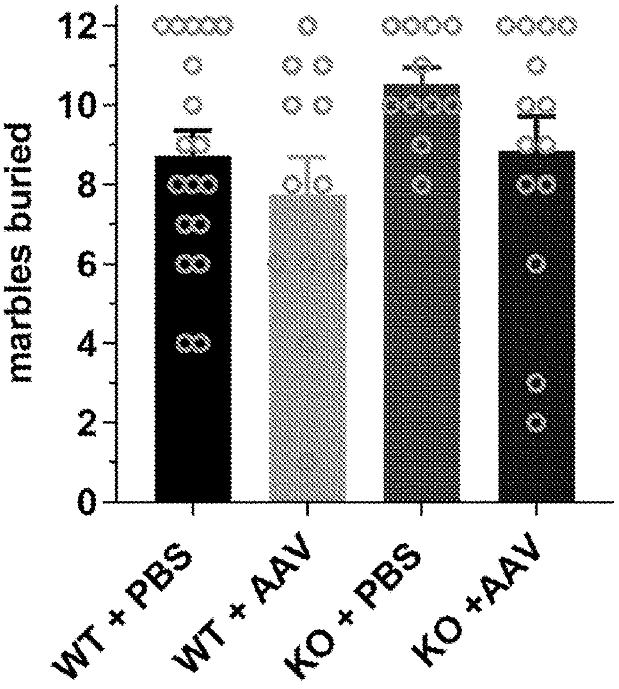
Figure 10E:
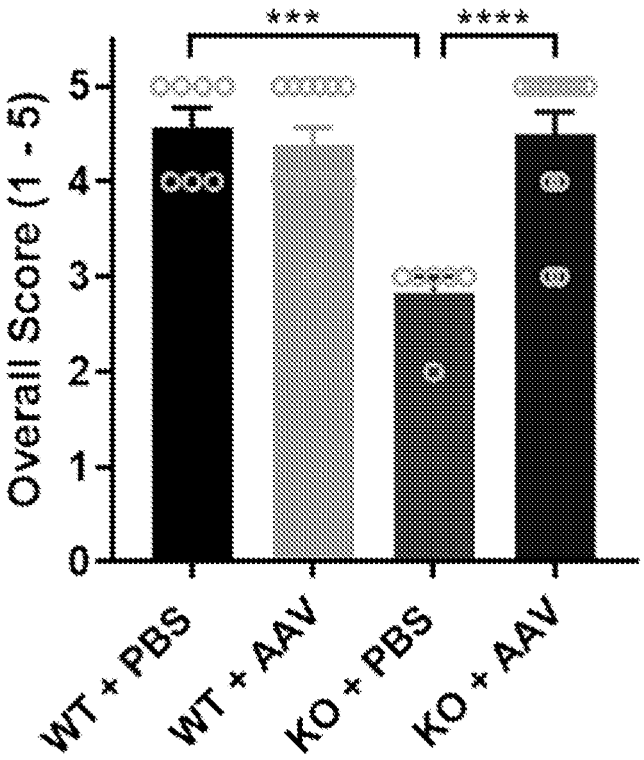
Figure 11A:
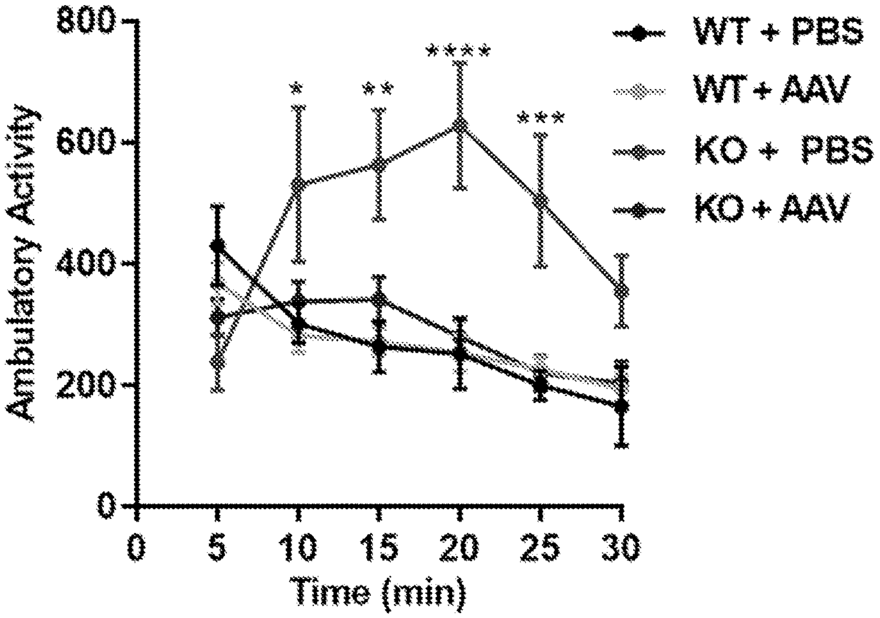
FIGS. 11A to 11F shows correction of hyperactivity in the ko mice receiving the AAV.CDKL5 treatment as assessed in the open field activity test.
Figure 11B:
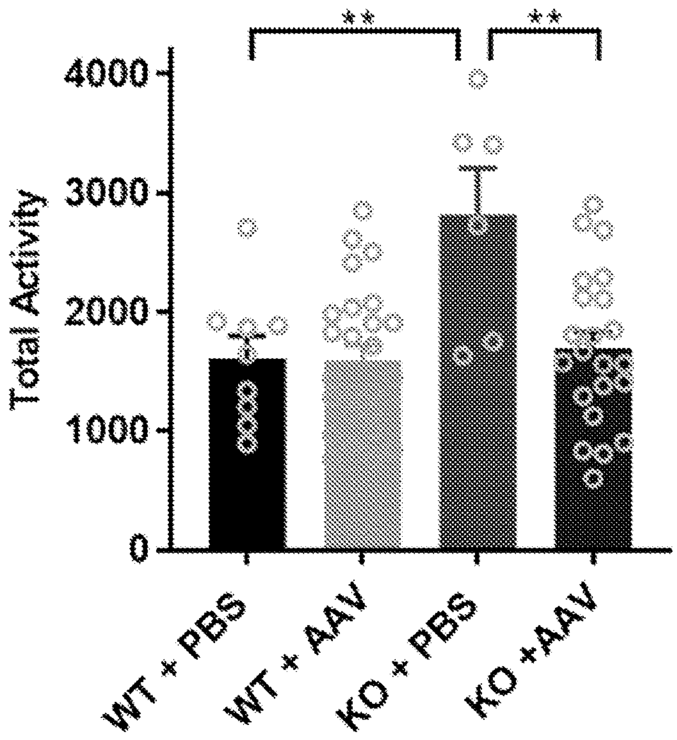
Figure 11C:
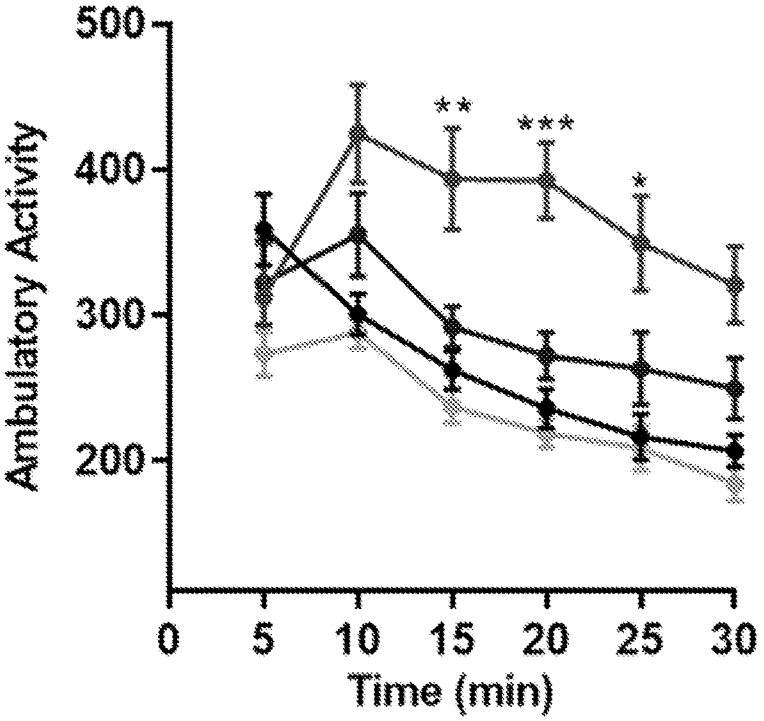
Figure 11D:
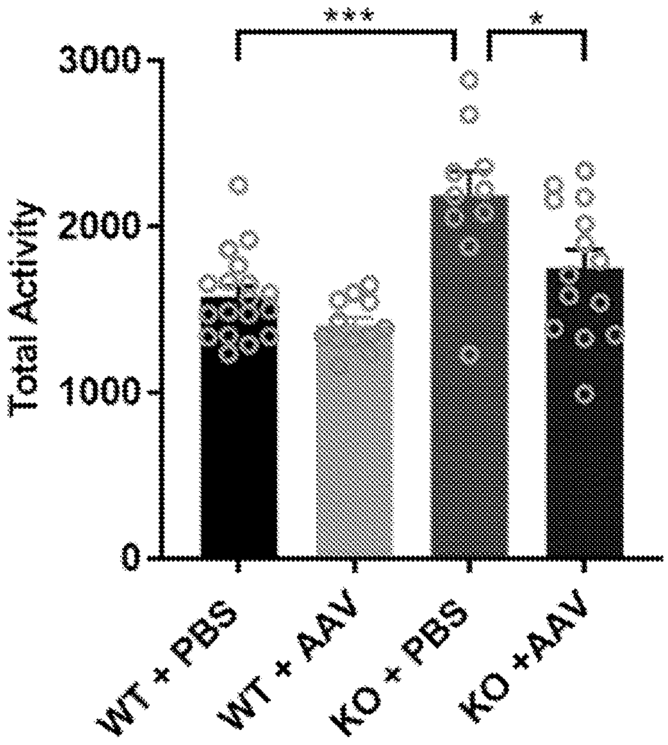
Figure 11E:
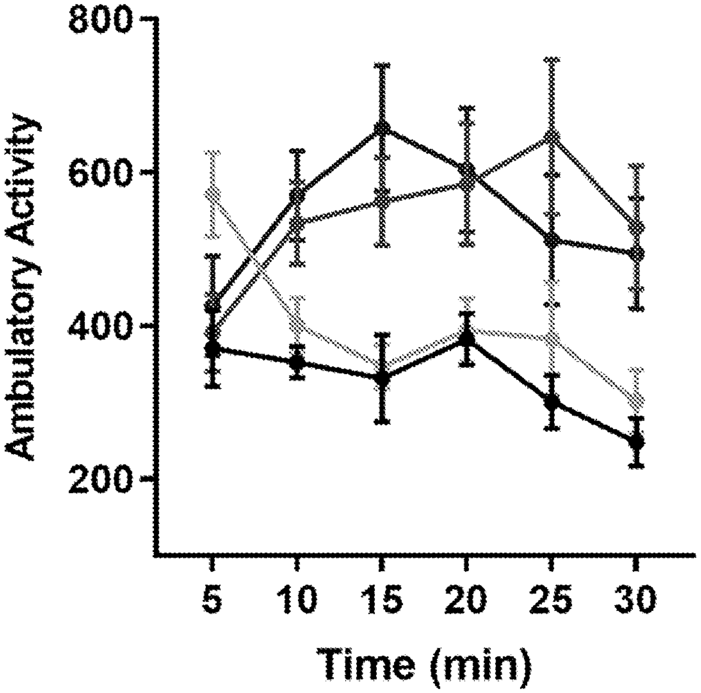
Figure 11F:
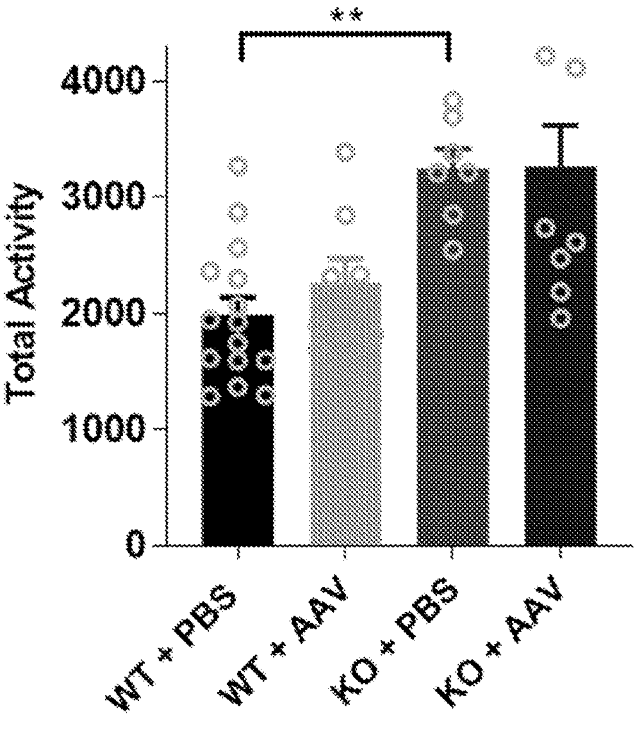

Given that Cdk15 is important for neurodevelopment, we wondered whether earlier administration of gene therapy might improve therapeutic outcome in mice. We next treated cohorts of neonatal Cdk15-ko or wt littermates with doses ranging $6\times10^{9}$ GC to $5\times10^{10}$ GC of AAVhu68-hSyn-hCDKL5-1co. WPRE vector per mouse by intraventricular (ICV) injection. Behavioral testing stated at 10 weeks of age or at 11 to 14 weeks, where indicated. Overall observation across all groups was that the treatment was well tolerated, there was no treatment related deaths, and normal weight gain (FIGS. 9A and 9B) and overall development was observed. A dose-dependent expression of CDKL5 transgene in Cdk15-ko mouse brain at a dose of $5\times10^{10}$ GC, a dose of $2.5\times10^{10}$ GC, and a dose of $1\times10^{10}$ GC was observed. At 10 weeks of age, KO mice show the characteristic hind limb clasping phenotype, which was substantially ameliorated in treated ko mice. Therapeutic efficacy of CDKL5 gene therapy was measured by hind limb clasping test. A dose dependent improvement was observed of the severity score in treated CDKL5-ko mice (FIGS. 9C-9F). Likewise, the persistent hyperactivity and rearing phenotype found in ko mice was normalized towards wildtype activity. Hippocampal learning and memory were highly improved in treated ko mice in the Y-Maze test (spontaneous alteration index). Therapeutic efficacy of CDKL5 gene therapy was further measured by open filed activity test, which measures for correction of hyperactivity in KO and AAV-treated mice. A dose-dependent resolution of hyperactivity in treated Cdk15-ko mice was observed (FIGS. 11A-11F). KO mice are poor nest-builders when overnight single-housed in a fresh cage and do not tear up all nesting material. Treated KO mice drastically improved their nest building capabilities in a dose-dependent manner (FIGS. 10A, 10C, 10E). Additional two other neurobehavior assays (marble burying and Y-Maze) showed a strong trend to improvement of phenotype in treated Cdk15-ko mice (FIGS. 10B and 10D). EEG phenotype was rescued in a preliminary collaborative study and may become useful as translational biomarker. Validation of outcomes of key assays (hindlimb clasping, ambulatory activity) are additionally performed with an independent experimental cohort. Larger cohort size (N=18/group) led to more robust statistical significance. Validation of outcomes of key assays (hindlimb clasping, ambulatory activity) with alternative CDD mouse models (R59X, D471fs) is also performed. In summary, CDKL5 gene therapy delivers a functional CDKL5 protein to mouse brain and has dose-dependent therapeutic effect for several neurobehavior outcomes in CDD male mouse models.

After finishing behavior testing, brains were harvested when the mice were about 3 months old. Western blotting revealed robust expression of human CDKL5 in Cdk15-ko brains, even 3 months after AAV administration. Lastly, human CDKL5 showed robust kinase activity when blotting for phosphorylated EB2 protein.

We also examined the outcome of CDKL5 gene therapy with an alternative CDD mouse model. Cdk15 (D471fs) carry a patient point mutation that leads to a premature stop codon. As in patients, no CDKL5 protein and highly reduced EB phosphorylation levels were found in the brains of these mice. Thus, Cdk15 (D471fs) share the absence of Cdk15 protein with the previously used Cdk15-ko mice, however, the genetic background is slightly different due the method of generation for the mouse models. Neonatal pups were injected at the same concentration as before ($5\times10^{10}$ GC, neoICV) and showed robust hCDKL5 protein expression and EB2 phosphorylation 3 months later. A small pilot cohort was subjected to behavior testing. AAV treatment was well tolerated and no morbidity was observed. Hind limb clasping was significantly corrected in treated mutant mice; likewise, the mutant phenotype in the Elevated Zero Maze test was corrected to wildtype behavior in treated mutant mice (In Open Zone, Open Zone Entries. Mutant mice show poor interaction and burying behavior with glass marbles arrange in a grid in a new cage, whereas wildtype mice typically burry almost all. Treated mutant mice show a strong correction of their behavior to wildtype mice. Significant improvement was observed in Cdk15-ko mice in treated group at higher dose of $5\times10^{10}$ GC/mouse.

We also examined the outcome of CDKL5 gene therapy with an alternative CDD mouse model. Cdk15 (R59X) carry a patient point mutation that introduces a premature stop codon. As in patients, no CDKL5 protein and highly reduced EB phosphorylation levels were found in the brains of these mice. Thus, Cdk15 (R59X) share the absence of Cdk15 protein with the previously used Cdk15-ko mice, however, the genetic background is slightly different due the method of generation for the mouse models. Neonatal pups were injected at the same concentration as before ($5\times10^{10}$ GC, neoICV) and showed robust hCDKL5 protein expression and EB2 phosphorylation 3 months later. A small pilot cohort was subjected to behavior testing. AAV treatment was well tolerated and no morbidity was observed. Hind limb clasping was significantly corrected in treated mutant mice.

Figure 14B:
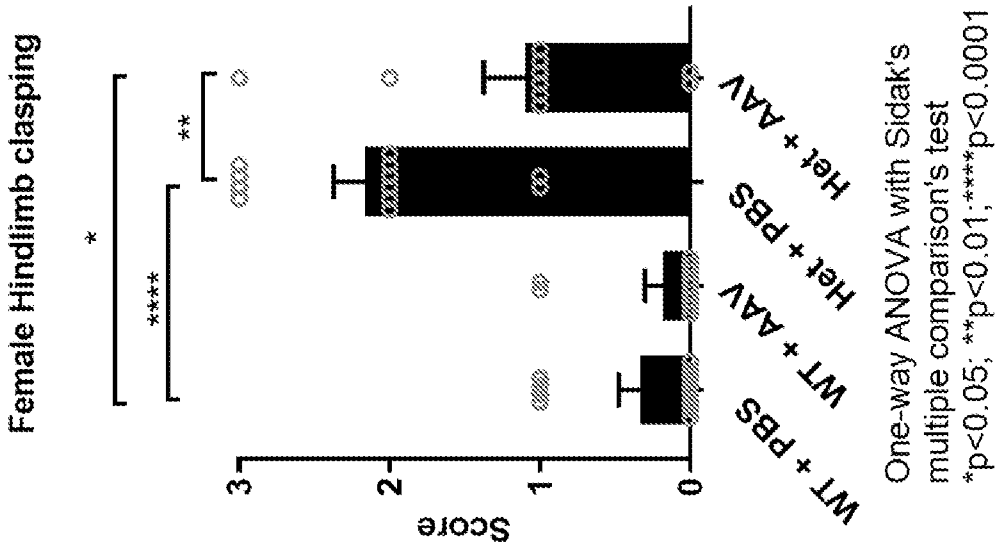
FIGS. 14A to 14C show gender specific results in hindlimb clasping following treating of knock-out mice with the AAV.CDKL5-isoform 1.
Figure 14A:
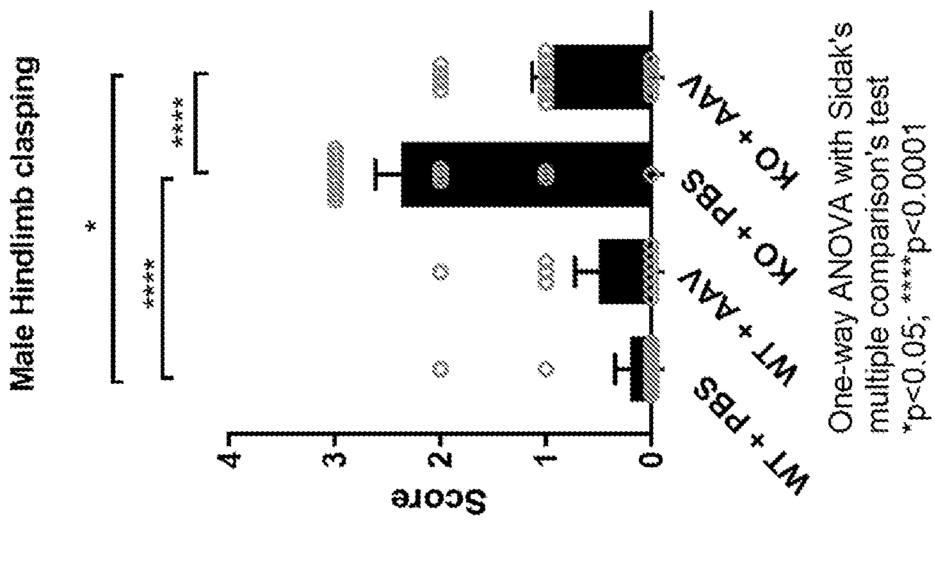
Figure 14C:
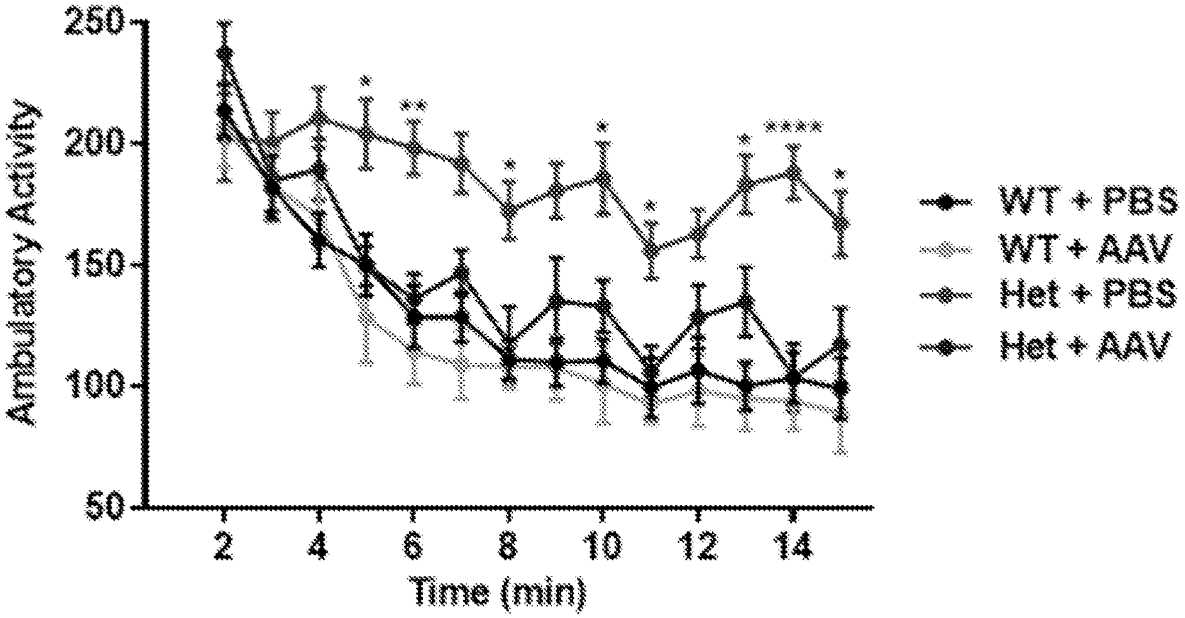
Figure 15A:
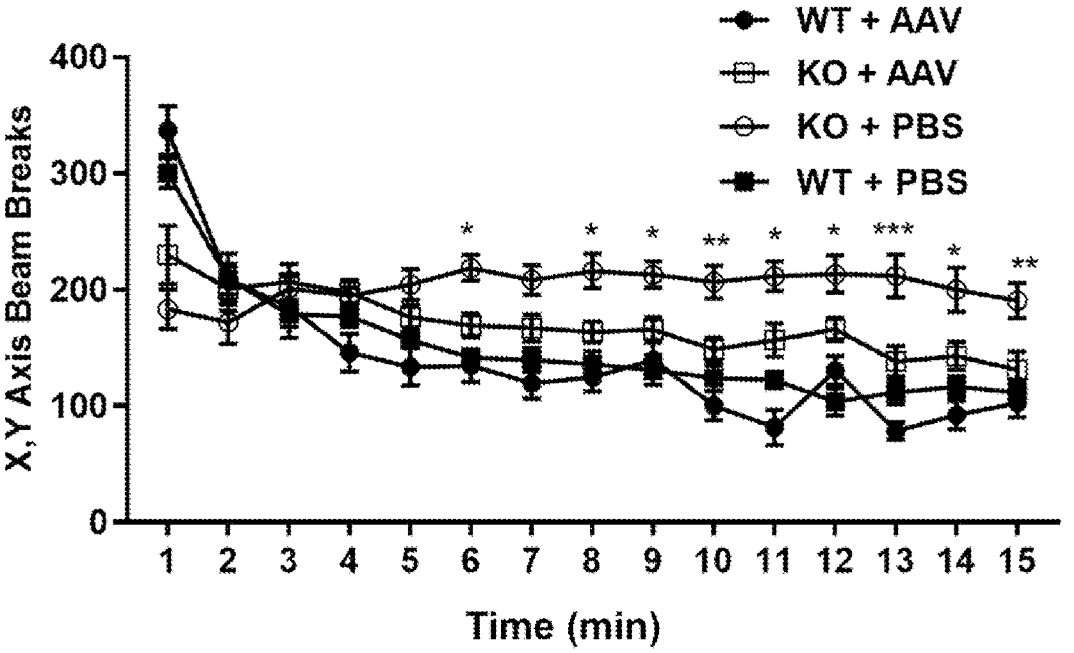
FIGS. 15A and 15B show gender specific results in open field-ambulatory activity in an open field assessment.
Figure 15B:
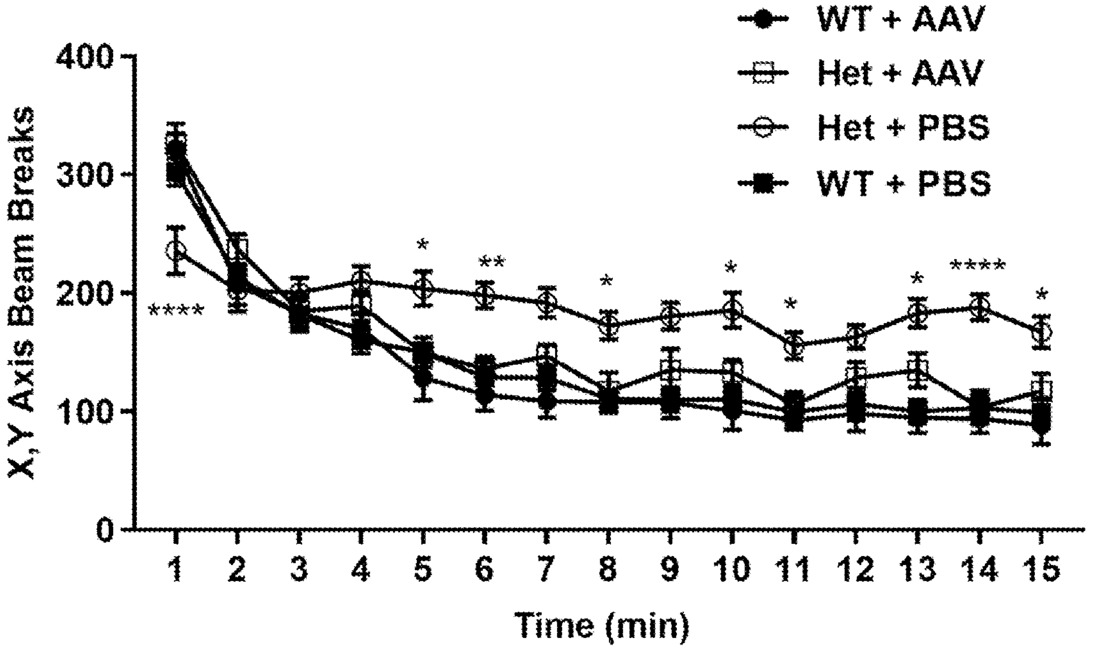
Figure 16A:
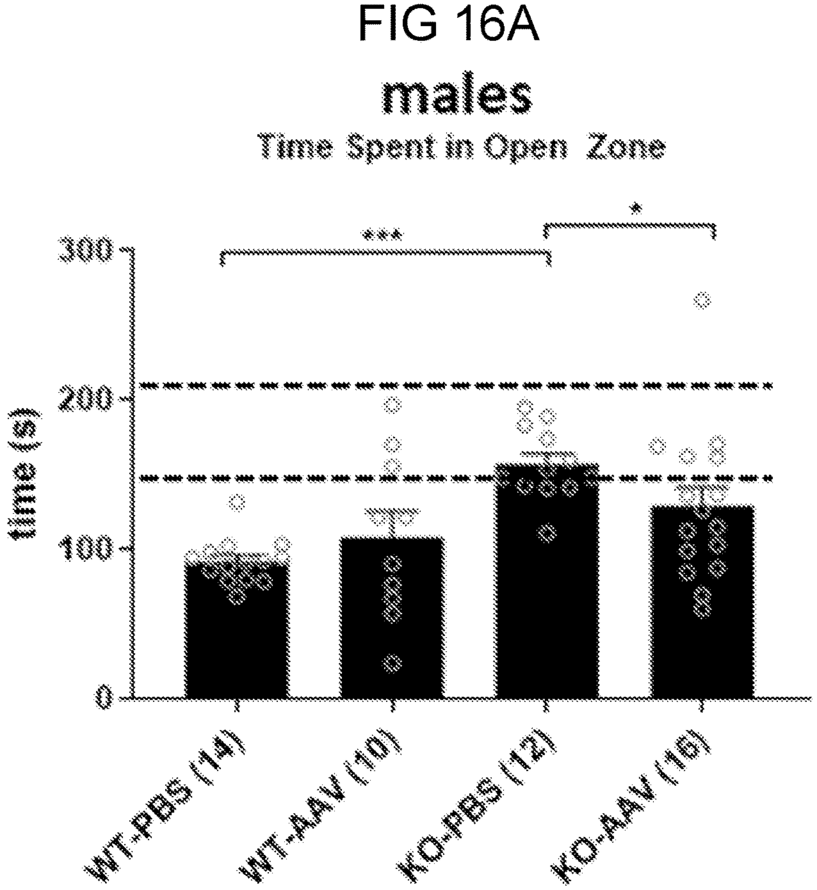
FIGS. 16A and 16B show gender differences in ko mice treated with the AAV.CDKL5-isoform 1 vector.
Figure 16B:
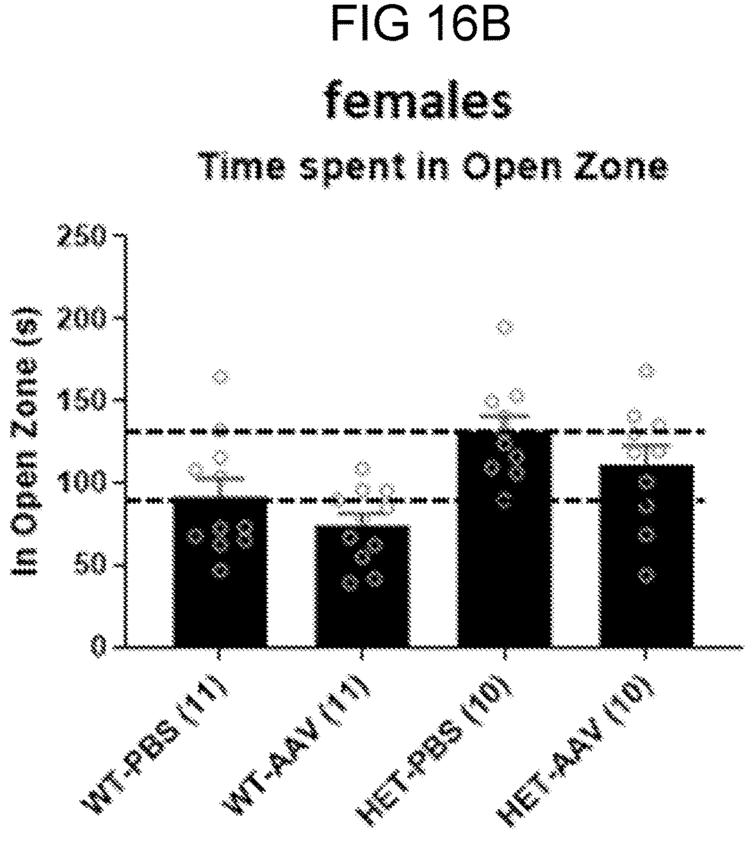

We also examined the outcome of CDKL5 gene therapy with alternative CDD mouse model in heterozygous female Cdk15-ko mice. Such model reflects most CDD patient (CDD females). Overall assessment showed that heterozygous female Cdk15-ko mouse neurobehavior phenotype is much milder, with later onset and thus makes robust assessment of a therapeutic outcome more difficult. However, a representative data for hindlimb clasping and ambulatory activity at high dose ($5\times10^{10}$ GC, neonatal ICV) shows significant improvement (FIGS. 14B and 14C).

Figure 19A:
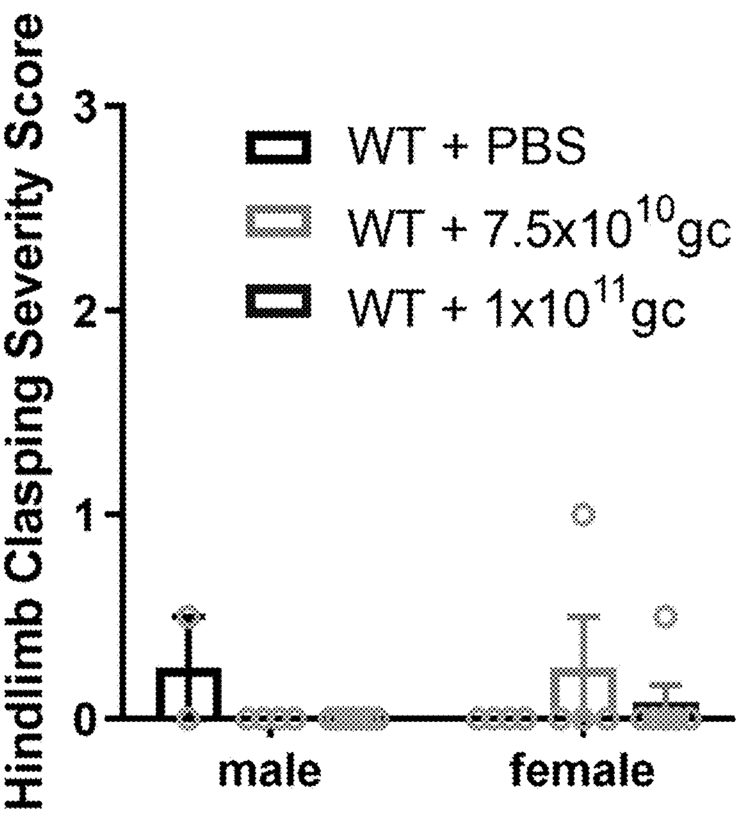
FIGS. 19A and 19B show results of a dose escalation studies measuring behavioral changes following CDKL5 gene therapy administration to WT mice.
Figure 19B:
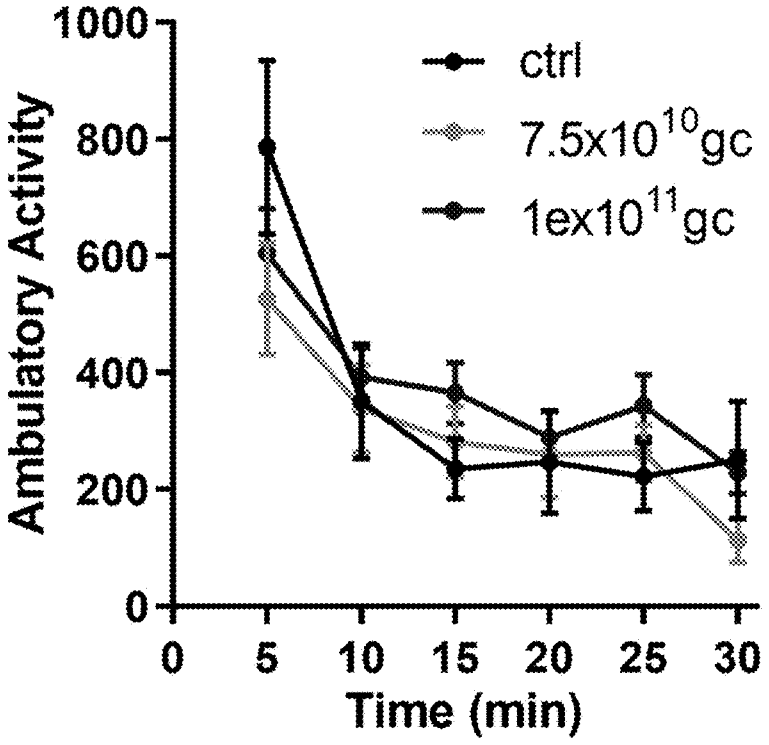

Additionally, we examined CDKL5 Gene therapy dose escalation in WT mice. WT (C57B16/J) mice were injected at $7.5\times10^{10}$ GC and $1\times10^{11}$ GC (i.e., 1.5× or 2× of previously highest used dose) via neonatal ICV. There was no overt effect observed on weight, development, and survival. Mice appeared normal and did not show hindlimb clasping or activity changes. There was no observed effects in pathologist review of CNS tissues (FIGS. 19A and 19B).

Example 4: Utility Human CDKL5 Isoforms 2-4

It has been shown that there are at last 4 detectable Cdk15 mRNA splice variants found in human and mouse brain, but it has not been established of isoforms 2-4 exist as stable proteins. Isoform 1 accounts for >85% of brain CDKL5.

We codon engineered coding sequences for human CDKL4 isoforms 2-4 and cloned the into the same AAV vector as before. AAV9-PHP.B vector coding for isoforms 1~4 was tail IV injected in adult Cdk15-ko mice and brains harvested after 2 weeks for Western Blot analysis. We found all four isoforms robustly expressing and displaying the expected gel migration patterns. The engineered sequence which yielded expression for isoforms 2-4 that closely resembled the amount of expression of isoform 1, were chosen for follow up. EB2 phosphorylation levels generated by isoform 2 were slightly higher, and by isoforms three or 4 slightly lower compared to isoform 1.

Figure 8A:
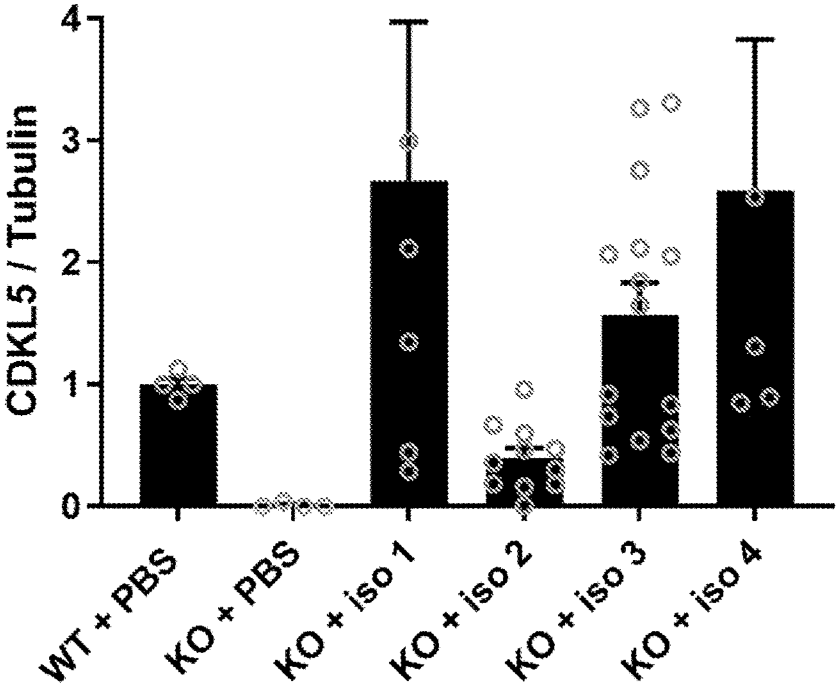
FIGS. 8A to 8D illustrate CDKL5 expression levels or activity levels for AAV.CDLK5 vector constructs for the expression isoform 1, isoform 2, isoform 3 or isoform 4.
Figure 8B:
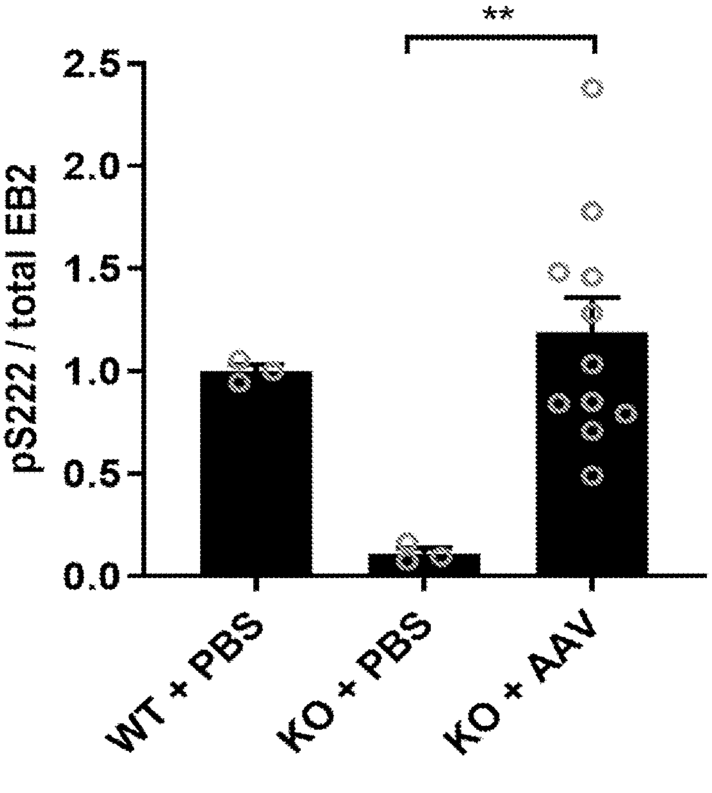
Figure 8C:
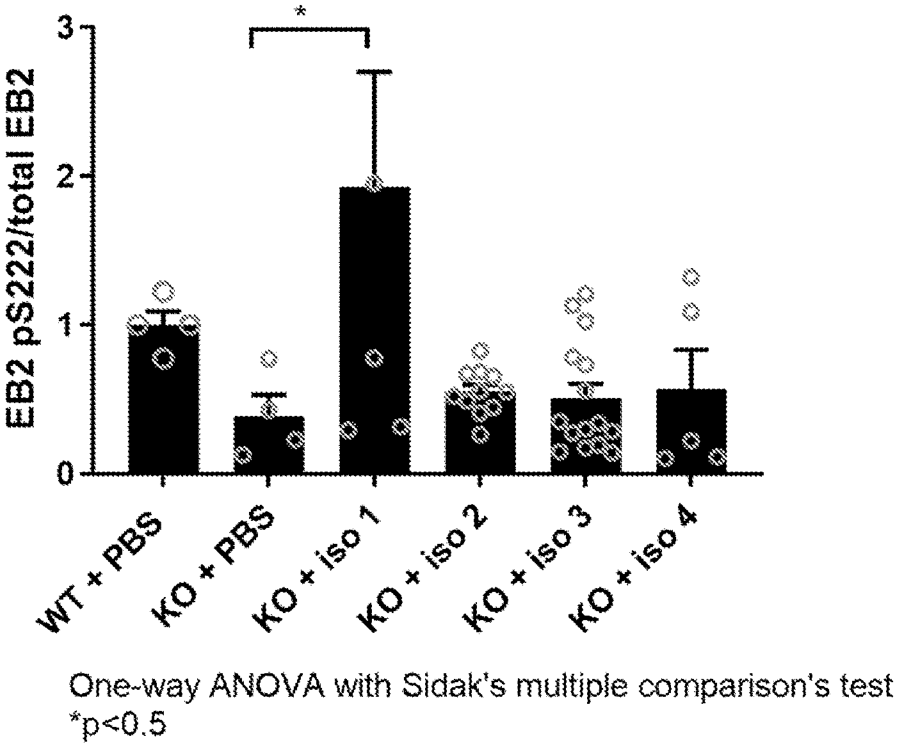
Figure 8D:
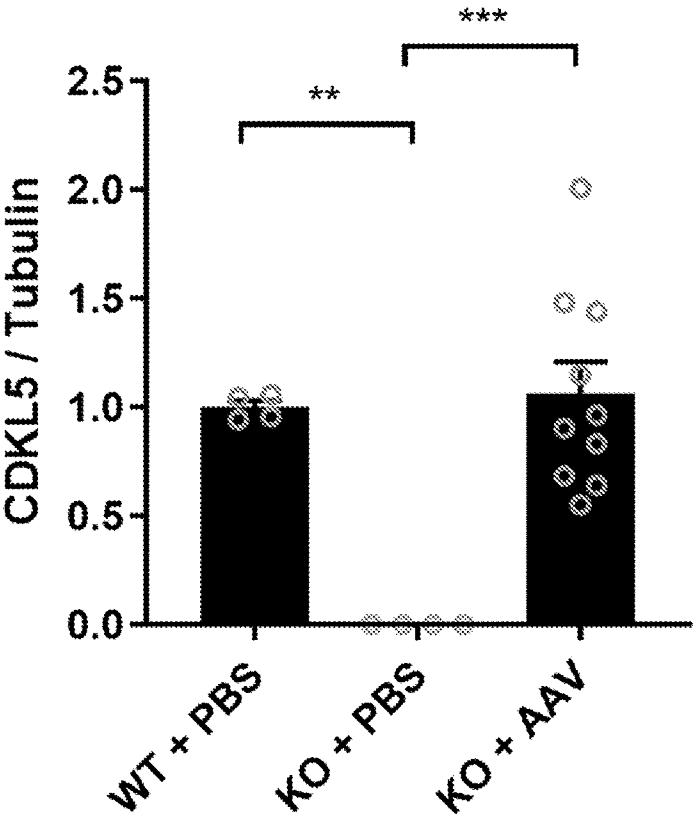
Figure 12:
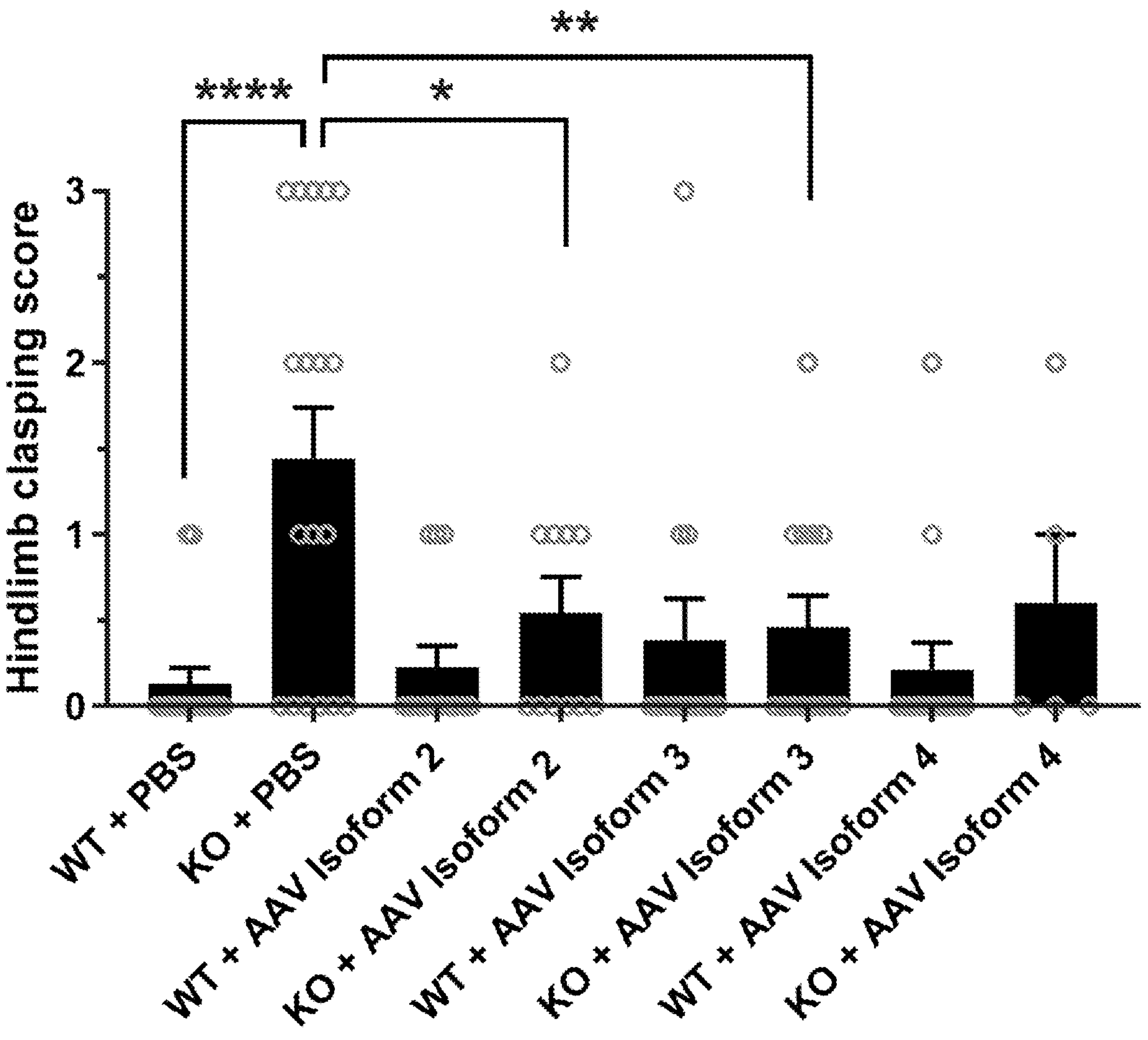
FIG. 12 illustrates that the expression of CDKL5 isoforms 2-4 provide significant correction of the hindlimb clasping phenotype when assessed at dose of $5\times10^{10}$ GC in ko mouse.
Figure 13A:
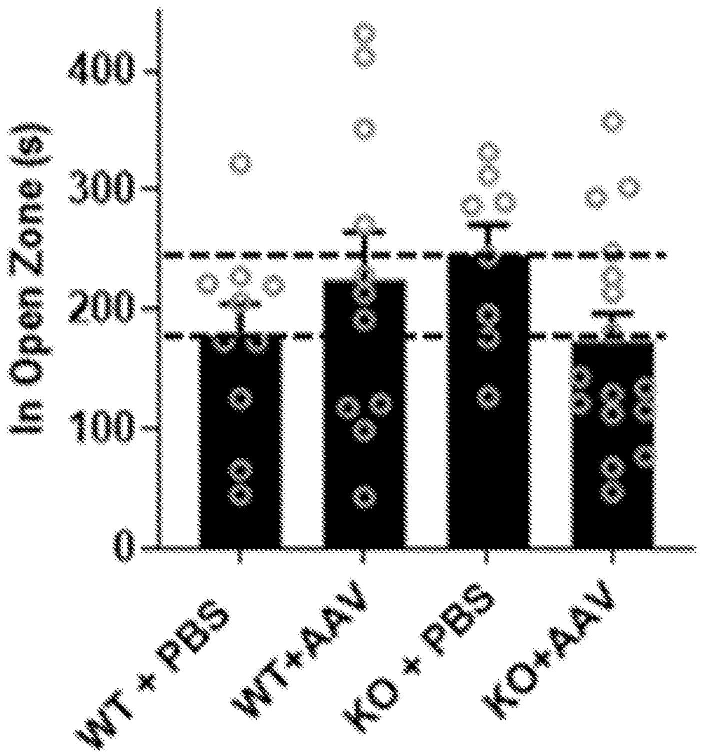
FIGS. 13A to 13D illustrate a strong trend for correction in KO mice treated with AAV.CDKL5-isoform 1.
Figure 13B:
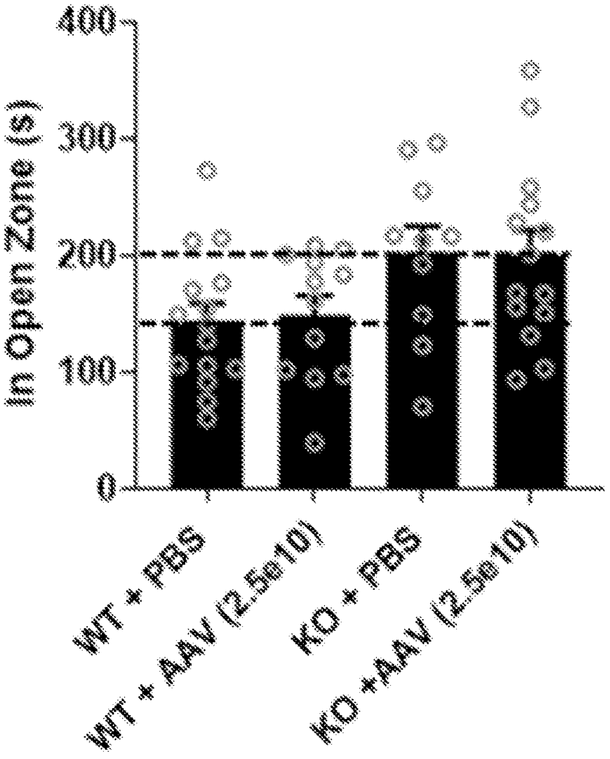
Figure 13C:
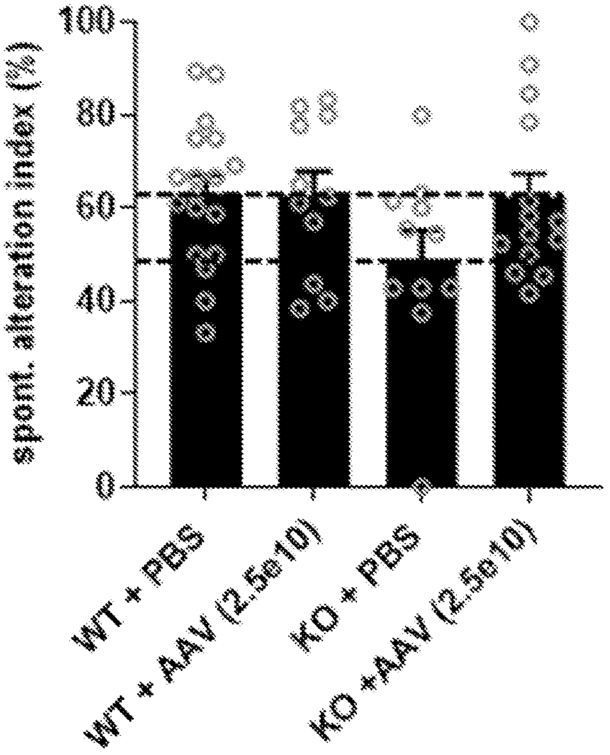
Figure 13D:
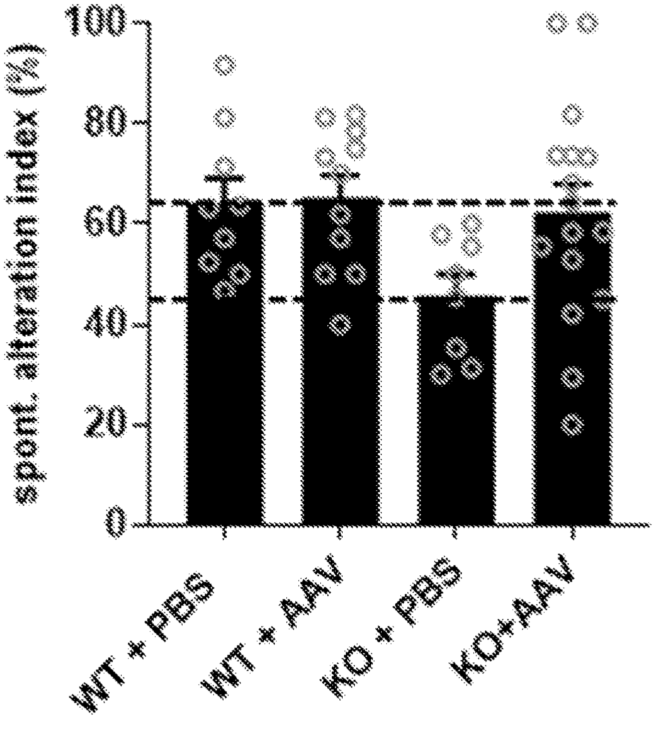

The three alternative CDKL5 isoforms have been injected in neonatal Cdkl5-ko mice to test how a potential therapeutic benefit compares to that of isoform 1. FIG. 12 shows significant correction of clasping phenotype with treatment by alternative CDKL5 isoforms (2, 3, and 4). FIGS. 8A to 8D provide CDKL5 expression levels or activity for AAV.CDLK5 vector constructs for the expression isoform 1, isoform 2, isoform 3 or isoform 4. FIG. 8A shows expression levels in knock-out mice injected with AAV vectors ($5\times10^{10}$ GC, neonatal ICV) expressing each one of these isoforms, as compared to a wild-type mouse injected with vehicle and a knock-out mouse injected with vehicle. FIG. 8B shows CDKL5 activity as determined using the pS222EB2 in a wild-type mouse injected with vehicle (PBS), a knock-out mouse injected with vehicle, or the AAV.CDKL5-1co. FIG. 8C shows CDKL5 activity as determined using the pS222EB2 for the groups in FIG. 8A. FIG. 8D shows CDKL5 expression levels for the groups in FIG. 8B.

In summary, all isoforms expressed as proteins and have comparable catalytic activity. Therapeutic outcome with isoforms 2, 3 or 4 in CDD mouse model are comparable to isoforms 1 when tested head-to-head ($5\times10^{10}$ GC, neonatal ICV). Overall, CDKL5 gene therapy with CDKL5 isoform 1 is a promising and safe approach in male CDD model mice with a significant therapeutic benefit.

Example 5: Pilot NHP Study for Toxicity and Safety Testing of hCDKL5 Gene Therapy We wanted to investigate the expression pattern and safety profile of the AAV-hSyn-CDKL5-1co.WPRE construct packaged in an AAVhu68 capsid in NHPs. Vector was generated using the vector genome described herein and production methods which have been previously described. See, e.g., WO 2018/160582, which is incorporated herein by reference. A group of six rhesus macaques (age 4-6 years old) was injected via the cisterna *magna* (ICM). We tested different conditions:

A. dose $1\times10^{14}$ GC, injected in 1 ml buffer
B. dose $1\times10^{14}$ GC, injected in 3 or 5 ml buffer
C. dose $3\times10^{14}$ GC, injected in 3 ml buffer
D. dose $1\times10^{14}$ GC, injected in 1 ml buffer, after 2 days of pre-treatment with the diuretic acetazolamine (Diamox®) to reduce CSF production.

Briefly, for non-human primate (NHP) study, the toxicity and safety testing of hCDKL5 gene therapy was performed using an AAVhu68-hSyn-Cdk15-1co-WPRE vector. In a preliminary study, three different doses were assessed, $3\times10^{12}$ GC/animal, $1\times10^{13}$ GC/animal and $3\times10^{13}$ GC/animal. For the pilot study, a dose of $1\times10^{14}$ GC/animal was selected, and two different volumes (3 mL and 5 mL) were assessed for delivery of the AAV vector to the cerebrospinal fluid (CSF) via cisternal *magna*. Other study arms used $1\times10^{14}$ GC/animal with a diuretic (e.g., a Diamox brand acetazolamide) or $3\times10^{14}$ GC/animal (subject).

Additionally, we tested a dose of $2\times10^{12}$, $1\times10^{13}$, and $3\times10^{13}$ GC/subject. Treatment with CDKL5 vector was well tolerated, no signs of changes in clinical blood chemistry was observed. Observations from cage-side neurological exams found no changes from baseline.

Necropsy was carried out 28 days after injection, followed by molecular analysis, histology and pathology review. Overall, no major transduction differences in main organs outside CNS were found (e.g., transduction of liver has likely already reach a maximum). No major transduction differences in spinal cord and DRGs (remain at very high transduction rates) were observed, however significant changes in brain tissues depending on the injection parameters became evident. The highest transduction increase of transduction was seen in the cortex. Diamox lead to a slight increase in transduction efficiency through the brain.

Figure 17:
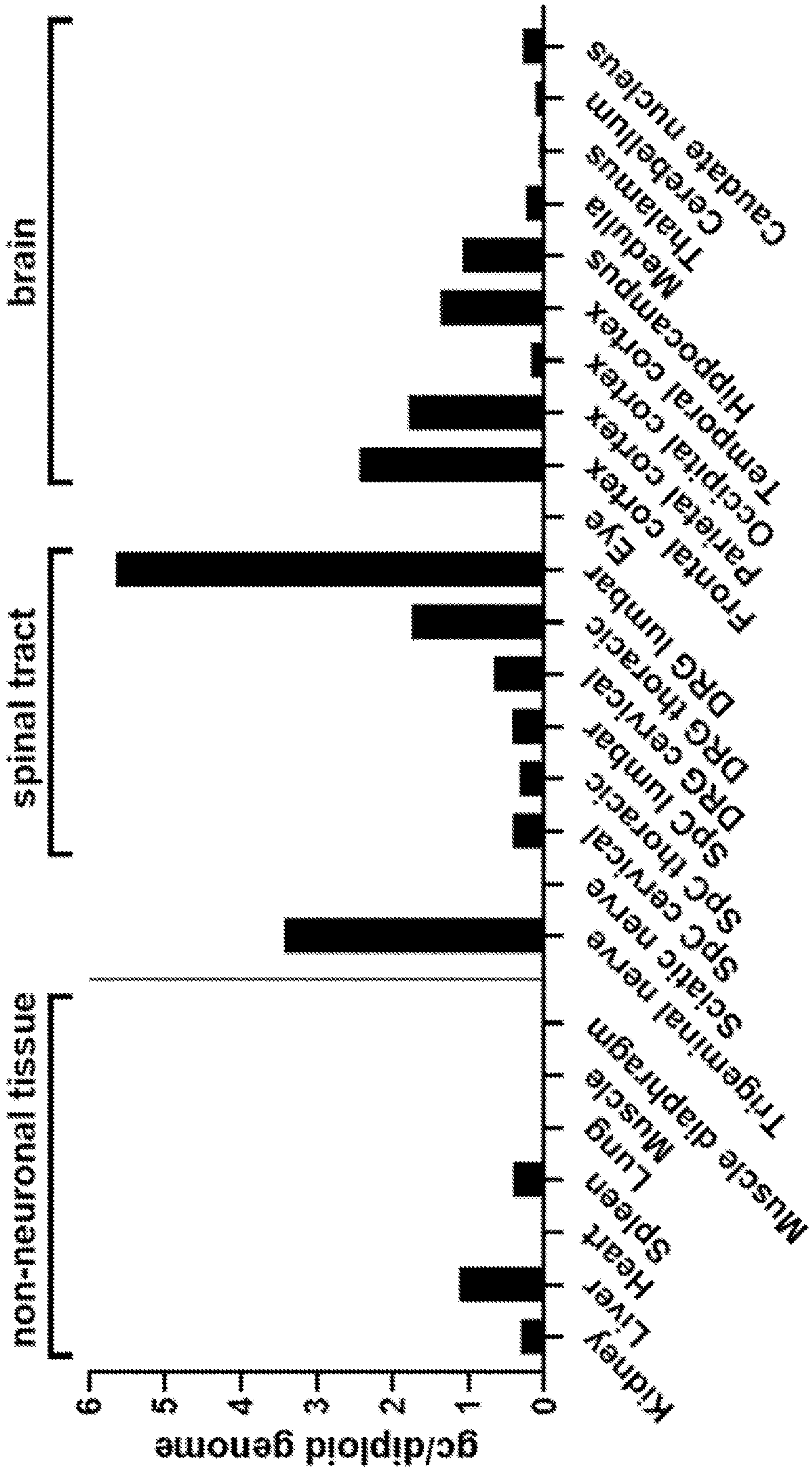
FIG. 17 provides vector distribution in various tissue samples from the NHP study (representative for the $1\times10^{14}$ GC dose). The graph provides rAAV.CDKL5 in gc/diploid genome for various non-neuronal tissue, spinal track, and brain tissue. Strong transduction of dorsal root ganglia (DRG) is observed. Moderate to low transduction of brain tissues is observed, with some leakage into non-neuronal tissues.
Figure 18:
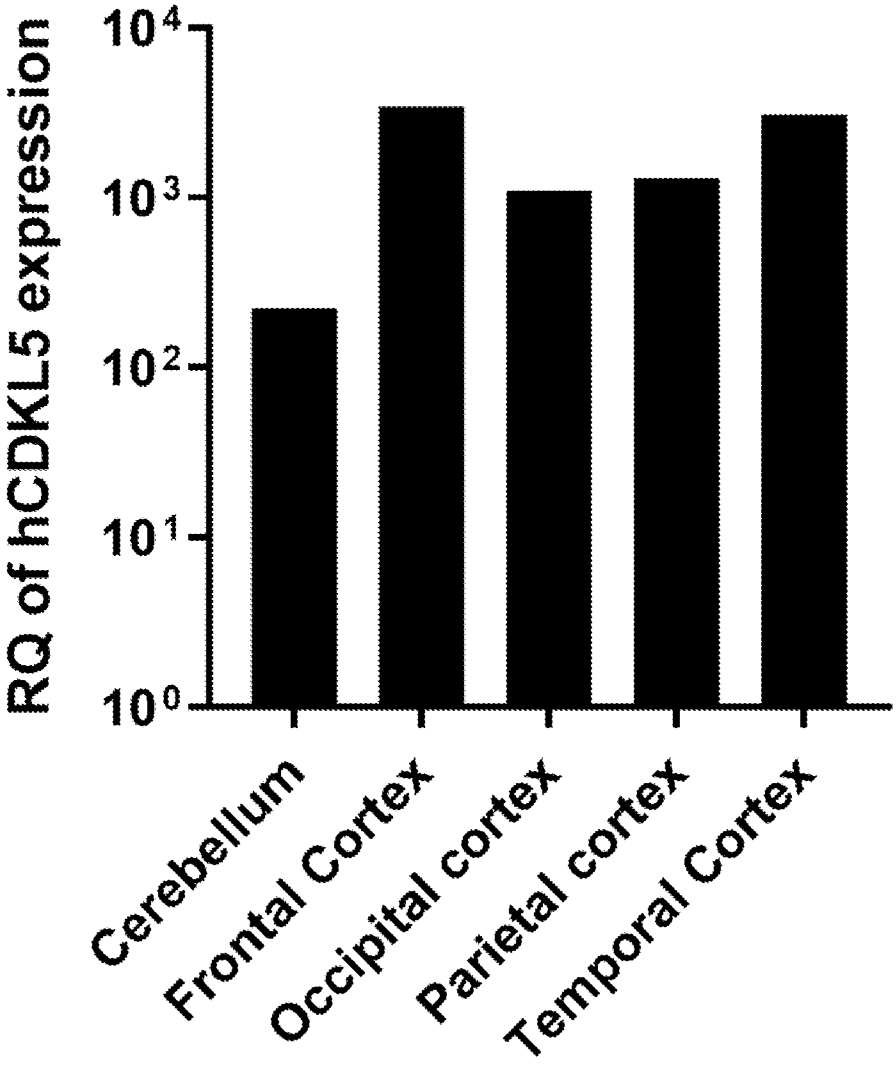
FIG. 18 provides results quantified hCDKL5 expression (measured by RT-qPCR) in the NHP study shown in cerebellum, frontal cortex, occipital cortex, parietal cortex, and temporal cortex.

FIG. 17 shows vector biodistribution for each NHP across non-neuronal tissue, spinal tract tissues and brain tissue. In FIG. 18, only the vector biodistribution data for brain is shown. The results show that there is an observed strong transduction of dorsal root ganglion tissue (DRGs), moderate to low transduction of brain tissues, and present transduction leakage into neuronal tissues. The pathology result indicated mild axonopathy in dorsal white matter tracts. Slight differences in hCDKL5 mRNA levels were observed. There is a trend for higher mRNA expression when a 3 ml injection volume was used. We also visualized hCDKL5 mRNA distribution by in-situ hybridization (ISH). Dorsal root ganglia (DRG) showed very strong mRNA expression across all six NHP. In the motor cortex small numbers of transduced neurons were observed (<10%). Occasionally, small clusters of transduced neurons were found. There was no significant difference in hCDKL5 mRNA positive neurons in the motor cortex across NHPs in this study.

A pathology review did not find any gross lesions across tissues and NHP. The NHP that had received the highest dose showed mild signs of inflammatory cell infiltration in the liver. Additionally, mild to moderate spinal cord axonopathy and DRG satellitosis in all NHPs.

Additionally, we examine vector expression and safety testing in NHPs of AAVrh91.UbC.CDKL5-1co.miR183 and AAVrh91.CBh.CDKL5-1co.miR183 vectors. Vectors are administered to *C. macaques* at a dose of $3\times01^{10}$ GC via ICM route. Pathology analysis and neuro-examination is performed to evaluate the effects of CDKL5 expression following AAV vector administration.

In conclusion, AAV-CDKL5 vector (SEQ ID NO: 1) examined in our studies can be used to achieve stable CDKL5 protein expression in neurons. AAV-CDKL5 gene therapy significantly improved the phenotype of a CDD mouse model. Additionally, AAV-CDKL5 vector can be efficiently delivered via the cisterna *magna* to non-human primates and expresses in throughout the CNS.

REFERENCES

1. Bahi-Buisson, N. et al. Key clinical features to identify girls with CDKL5 mutations. Brain 131, 2647-2661, (2008).
2. Fehr, S. et al. The CDKL5 disorder is an independent clinical entity associated with early-onset encephalopathy. Eur J Hum Genet 21, 266-273, (2013).
3. Kalscheuer, V. M. et al. Disruption of the serine/threonine kinase 9 gene causes severe X-linked infantile spasms and mental retardation. American journal of human genetics 72, 1401-1411, (2003).
4. Tao, J. et al. Mutations in the X-linked cyclin-dependent kinase-like 5 (CDKL5/STK9) gene are associated with severe neurodevelopmental retardation. American journal of human genetics 75, 1149-1154, (2004).
5. Weaving, L. S. et al. Mutations of CDKL5 cause a severe neurodevelopmental disorder with infantile spasms and mental retardation. American journal of human genetics 75, 1079-1093, (2004).
6. Hector, R. D. et al. Characterization of CDKL5 Transcript Isoforms in Human and Mouse. PloS one 11, e0157758, (2016).
7. Baltussen, L. L., et al. (2018). "Chemical genetic identification of CDKL5 substrates reveals its role in neuronal microtubule dynamics." EMBO Journal 37 (24).
8. Munoz, I. M., et al. (2018). "Phosphoproteomic screening identifies physiological substrates of the CDKL5 kinase." EMBO Journal.

All documents cited in this specification are incorporated herein by reference, as is U.S. Provisional Patent Application No. 63/016,036, filed Apr. 27, 2020, and U.S. Provisional Patent Application No. 63/091,032, filed Oct. 13, 2020, U.S. Provisional Application No. 63/109,608, filed Nov. 4, 2020. The Sequence Listing filed herewith, labelled "20-9196PCT_SeqListing_ST25.txt", and the sequences and text therein are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (rAAV) useful for treating CDKL5 deficiency disorder (CDD), wherein the rAAV comprises:

(a) an AAV capsid; and (b) a vector genome packaged in the AAV capsid of (a), wherein the vector genome comprises inverted terminal repeats (ITR) and a hCDKL5-coding sequence, which is a nucleic acid sequence encoding a functional human CDKL5 (hCDKL5), operably linked to sequences which regulate the hCDKL5 expression in central nervous system cells, and wherein the hCDKL5-coding sequence is nt 699 to 3581 of SEQ ID NO: 3 (SEQ ID NO: 22) or a sequence at least about 95% identical to nt 699 to 3581 of SEQ ID NO: 3 (SEQ ID NO: 22).

2. The rAAV according to claim 1, wherein the hCDLK5-coding sequence is less than 80% identical to any one of hCDKL5 transcript variants 1 to 3 (NM_001037343.1 (SEQ ID NO: 16), NM_NM_001323289.2 (SEQ ID NO: 17) and NM_003159.2 (SEQ ID NO: 18)).

3. The rAAV according to claim 1, wherein the functional hCDKL5 has an amino acid sequence of SEQ ID NO: 2.

4. The rAAV according to claim 1, wherein the regulatory sequences comprise a constitutive promoter.

5. The rAAV according to claim 1, wherein the regulatory sequences comprise a UbC promoter.

6. The rAAV according to claim 1, wherein the regulatory elements further comprise one or more of a Kozak sequence, an intron, an enhancer, a TATA signal and a polyA sequence.

7. The rAAV according to claim 1, wherein the regulatory elements further comprise a WPRE element.

8. The rAAV according to claim 1, wherein the vector genome further comprises four miR 183 targetting sequences operably linked to a 3' untranslated region of the hCDKL5 coding sequence, wherein the miR 183 targetting sequences downregulate expression in the dorsal root ganglia.

9. The rAAV according to claim 8, wherein at least one of the four miRNA target sequences for the expression cassette mRNA or DNA positive strand is (i) AGTGAATTC-TACCAGTGCCATA (miR183, SEQ ID NO: 11).

10. The rAAV according to claim 8, wherein the vector genome comprises: (i) a UbC promoter, (ii) hCDKL5-coding sequence comprising nucleic acid sequence of nt 699 to 3581 of SEQ ID NO: 3 (SEQ ID NO: 22), (iii) four miR183 targetting sequences operably linked to a 3' untranslated region of the hCDKL5 coding sequence, wherein the miR183 targetting sequences comprises AGTGAATTC-TACCAGTGCCATA (SEQ ID NO: 11), and (iv) a rabbit beta globin polyA signal sequence.

11. The rAAV according to claim 1, wherein the capsid is an AAVhu68 capsid, an AAV9 capsid, or AAVrh91 capsid.

12. A composition comprising a stock of rAAV according to claim 1 and an aqueous suspension media.

13. The composition according to claim 12, wherein the suspension is formulated for intravenous administration, intrathecal administration, intra-cisterna *magna* administration or intracerebroventricular administration.

14. A method of treating CDD, comprising administrating an effective amount of the rAAV according to claim 1 to a subject in need thereof.

15. An rAAV production system useful for producing the rAAV according to claim 1, wherein the production system comprises a cell culture comprising:

(a) a nucleic acid sequence encoding a Clade F capsid protein;

(b) a vector genome comprising a hCDKL5-coding sequence is nt 699 to 3581 of SEQ ID NO: 3 (SEQ ID NO: 22) or a sequence at least about 95% identical to nt 699 to 3581 of SEQ ID NO: 3 (SEQ ID NO: 22); and (c) sufficient AAV rep functions and helper functions to permit packaging of the vector genome into the Clade F capsid.

16. The rAAV production system according to claim 15, wherein the vector genome is SEQ ID NO: 1, SEQ ID NO: 29 or SEQ ID NO: 31.

17. The rAAV production system according to claim 15, wherein the cell culture is a human embryonic kidney 293 cell culture.

18. The rAAV according to claim 1, wherein the hCDKL5-coding sequence is at least 99% identical to nt 699 to 3581 of SEQ ID NO: 3 (SEQ ID NO: 22) encoding amino acid sequence of SEQ ID NO: 2.

19. The rAAV according to claim 1, wherein the hCDKL5-coding sequence is nt 699 to 3581 of SEQ ID NO: 3 (SEQ ID NO: 22) encoding amino acid sequence of SEQ ID NO: 2.

20. The rAAV according to claim 1, wherein the vector genome comprises nucleic acid sequence of SEQ ID NO: 29.

21. A vector comprising an expression cassette, wherein the expression cassette comprises a hCDKL5-coding sequence, which is a nucleic acid sequence encoding a functional human CDKL5 (hCDKL5), operably linked to sequences which regulate the hCDKL5 expression, and wherein the hCDKL5-coding sequence is SEQ ID NO: 22 or a sequence at least about 95% identical to SEQ ID NO: 22.

22. The vector according to claim 21, wherein the vector is a viral vector selected from a recombinant parvovirus, a recombinant lentivirus, a recombinant retrovirus, or a recombinant adenovirus; or a non-viral vector selected from naked DNA, naked RNA, an inorganic particle, a lipid particle, a polymer-based vector, or a chitosan-based formulation.

* * * * *